(12) United States Patent
Bibillo et al.

(10) Patent No.: US 12,221,634 B2
(45) Date of Patent: *Feb. 11, 2025

(54) METHODS OF cDNA PREPARATION

(71) Applicant: Bio-Rad Laboratories, Inc., Hercules, CA (US)

(72) Inventors: Arkadiusz Bibillo, Walnut Creek, CA (US); Pranav Patel, Pleasanton, CA (US)

(73) Assignee: BIO-RAD LABORATORIES, INC., Hercules, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/449,107

(22) Filed: Aug. 14, 2023

(65) Prior Publication Data

US 2024/0124856 A1    Apr. 18, 2024

Related U.S. Application Data

(63) Continuation of application No. 17/055,801, filed as application No. PCT/US2019/032701 on May 16, 2019, now Pat. No. 11,739,307.

(60) Provisional application No. 62/779,371, filed on Dec. 13, 2018, provisional application No. 62/672,480, filed on May 16, 2018.

(51) Int. Cl.
*C12N 9/12* (2006.01)

(52) U.S. Cl.
CPC .... *C12N 9/1276* (2013.01); *C12Y 207/07049* (2013.01); *C07K 2319/20* (2013.01)

(58) Field of Classification Search
None
See application file for complete search history.

(56) References Cited

U.S. PATENT DOCUMENTS

| | | | | |
|---|---|---|---|---|
| 11,739,307 B2 * | 8/2023 | Bibillo | | C12N 9/22 435/194 |
| 2004/0209276 A1 | 10/2004 | Smith et al. | | |
| 2006/0281079 A1 * | 12/2006 | Eickbush | | C12N 9/1276 435/6.13 |
| 2014/0363854 A1 * | 12/2014 | Smith | | C12N 9/1276 435/91.51 |
| 2015/0111789 A1 | 4/2015 | Betts et al. | | |
| 2017/0198285 A1 | 7/2017 | Betts et al. | | |

FOREIGN PATENT DOCUMENTS

WO    2005105142 A2    11/2005

OTHER PUBLICATIONS

Accession A0A0V0TAN8. Mar. 16, 2016. (Year: 2016).*
Jamburuthugoda et al. Nucleic Acids Res. Jul. 2014;42(13):8405-15.Epub Jun. 23, 2014 (Year: 2014).
Chica et al. Curr Opin Biotechnol. Aug. 2005; 16(4):378-84. (Year: 2005).
Singh et al. Curr Protein Pept Sci. 2017, 18, 1-11 (Year: 2017).
Thompson et al. Mob Genet Elements. May-Jun. 2011; 1 (1): 29-37 (Year: 2011).
Accession A0A0V0T7M5. Mar. 16, 2016 (Year: 2016).
(Korhonen, PK et al.) Retrovirus-related Pol polyprotein from type-2 retrotransposable element R2DM, partial [Trichinella murrelli]. Genbank entry (online). National Center for Biotechnology Information. Nov. 24, 2015 [retrieved on Nov. 26, 2019]. Retrieved from the Internet: <URL: https://www.ncbi.nlm.nih.gov/protein/KRX33447.1>; pp. 1-2.
(Korhonen, PK et al.) Retrovirus-related Pol polyprotein from type-2 retrotransposable element R2DM [Trichinella murrelli] Genbank entry (online). National Center for Biotechnology Information. Nov. 24, 2015 [retrieved on Nov. 26, 2019]. Retrieved from the Internet: <URL: https://www.ncbi.nlm.nih.gov/protein/KRX36111.1 >; pp. 1-2.
(Bibillo, A et al.) End-to-End Template Jumping by the Reverse Transcriptase Encoded by the R2 Retrotransposon. The Journal of Biological Chemistry. Apr. 9, 2004, Epub Jan. 28, 2004, vol. 279, No. 15; pp. 14945-14953; abstract; DOI: 10.1074/jbc.M310450200.
(Burke, WO et al.) The Domain Structure and Retrotransposition Mechanism of R2 Elements Are Conserved Throughout Arthropods. Molecular Biology and Evolution. Apr. 1999, vol. 16, No. 4; pp. 502-511; DOI: 10.1093/oxfordjournals.molbev.a026132.
Thomas H. Eickbush et al, "Integration, Regulation, and Long-Term Stability of R2 Retrotransposons", Microbiology Spectrum, (Apr. 1, 2015), vol. 3, No. 2, doi:10.1128/microbiolspec.MDNA3-0011-2014, XP055660172.
S. M. Christensen et al, "Role of the Bombyx mori R2 element N-terminal domain in the target-primed reverse transcription (TPRT) reaction", Nucleic Acids Research, GB, (Nov. 27, 2005), vol. 33, No. 20, doi:10.1093/nar/gki957, ISSN 0305-1048, pp. 6461-6468, XP055472140.

* cited by examiner

*Primary Examiner* — Christian L Fronda
(74) *Attorney, Agent, or Firm* — Sullivan & Worcester LLP; Thomas C. Meyers

(57) ABSTRACT

The present disclosure provides methods and systems for amplifying and analyzing nucleic acid samples. The present disclosure provides methods for preparing cDNA and/or DNA molecules and cDNA and/or DNA libraries using modified reverse transcriptases.

4 Claims, 31 Drawing Sheets

Specification includes a Sequence Listing.

KTAGRRNDLHDDRTA
SAHKTSRQKRRAEYARVQELYKKCRSRAAAEVIDGACGGVGHSLEEMETYWRPILERVSD
APGPTPEALHALGRAEWHGGNRDYTQLWKPISVEEIKASRFDWRTSPGPDGIRSGQWRAV
PVHLKAEMFNAWMARGEIPEILRQCRTVFVPKVERPGGPGEYRPISIASIPLRHFHSILA
RRLLACCPPDARQRGFICADGTLENSAVLDAVLGDSRKKLRECHVAVLDFAKAFDTVSHE
ALVELLRLRGMPEQFCGYIAHLYDTASTTLAVNNEMSSPVKVGRGVRQGDPLSPILFNVV
MDLILASLPERVGYRLEMELVSALAYADDLVLLAGSKVGMQESISAVDCVGROMGLRLNC
RKSAVLSMIPDGHRKKHHYLTERTFNIGGKPLRQVSCVERWRYLGVDFEASGCVTLEHSI
SSALNNISRAPLKPQQRLEILRAHLIPRFQHGFVLGNISDDRLRMLDVQIRKAVGQWLRL
PADVPKAYYHAAVQDGGLAIPSVRATIPDLIVRRFGGLDSSPWSVARAAKSDKIRKKLR
WAWKQLRFSRVDSTTQRPSVRLFWREHLASVDGRELRESTRTPTSTKWIRERCAQITG
RDFVQFVHTHINALPSRIRGSRGRGGESS

SUBSTITUTION: MOTIF-1

SUBSTITUTION: MOTIF 0

| | |
|---|---|
| Q101 TO N, S | R133 TO N, Y, K |
| L102 TO V, I | A134 TO L, M |
| W103 TO M, V | V135 TO T, S |
| K104 TO R, S, D | P136 TO S |
| P105 TO A | V137 TO A, Q |
| I106 TO L, V | H138 TO I, A |
| S107 TO T, V | L139 TO A, M, V |
| V108 TO N, L, S | K140 TO R, N, L |
| E109 TO D, Q, L | A141 TO DELETION |
| E110 TO D | E142 TO S, K, D |
| I111 TO V, M | M143 TO I, V |
| K112 TO I, R | F144 TO L, Y |
| R115 TO K, H | N145 TO D |
| F116 TO L, A | A146 TO L, V |
| D117 TO C, S, E | W147 TO F, L |
| R119 TO T, N | M148 TO L, V |
| T120 TO S | A149 TO L, F |
| S121 TO A | R150 TO T, H, K |
| P122 TO A | G151 TO R, E |
| G123 TO A | E152 TO R, N, D |
| P124 TO L | I153 TO V, C |
| D125 TO N, E | P154 TO A |
| G126 TO S, K | E155 TO K, P, Q, A, D |
| I127 TO M, V | I156 TO E, R, V |
| R128 TO T, K | L157 TO V, F |
| S129 TO L, H | R158 TO K, L, K |
| G130 TO K, S | Q159 TO L, M, H, N |
| Q131 TO D, R | C160 TO G, S, H |
| W132 TO L, A | R161 TO K |

FIG. 16

SUBSTITUTION: THUMB SUBUNIT

G403 TO D, S
G404 TO D, R, S
K405 TO Q, V, R
P406 TO V, Q, K
L407 TO V, M
R408 TO G, P, H, T, K
Q409 TO A, E, S
V410 TO M, L
S411 TO D, G, K
C412 TO L, H, A, R
V413 TO E, L, A, G
E414 TO G, H, Q, D
R415 TO T, E, Q, K
W416 TO Y, V, F
R417 TO K, H, T, G
Y418 TO F
L419 TO V, I
G420 TO A
V421 TO L, A, H
D422 TO R, W, N, T, P, E
F423 TO V, Y, I
E424 TO G, A, N, R, T, S, D
A425 TO S, H, G
S426 TO T, A, E
G427 TO A
C428 TO T, P, R, M
V429 TO C, I, E, A
T430 TO L, D, Q, R,

SUBSTITUTION: THUMB SUBUNIT

W492 TO L
L493 TO C, I
R494 TO V, K, G, N, A, M
L495 TO V
P496 TO K
A497 TO D, K, H
D498 TO G, S, E
V499 TO I, T, M
P500 TO S, C
K501 TO N, L, R, V
A502 TO G, D
Y503 TO F, K,
Y504 TO F, L
H505 TO Y
A506 TO T, S
A507 TO D, P, S, K
V508 TO T, Y, A
Q509 TO K, R, S, G
D510 TO Q, S, A, E
G511 TO A
G512 TO A
L513 TO M, K
A514 TO G, S
I515 TO L, V
P516 TO Q, L
S517 TO R, A, Q, E
V518 TO Y, L, F
R519 TO Q, E, S, G, K
T521 TO R, F, I
I522 TO A, V, G, S
P523 TO L
D524 TO R, F, E, M
L525 TO C, M, N
I526 TO R, K, V
V527 TO A, K, F, L
R528 TO K, A, S, H, Q
R529 TO A, K
F530 TO W, M, L
G531 TO A, N, D, E
G532 TO K, R, A, N
L533 TO Y, M, I
D534 TO N, K, G, E, L
S535 TO T, D, K, R, A
S536 TO T, N, P, C
P537 TO E, Q, A
W538 TO Y, R, D
S539 TO E, D, Q
V540 TO M, A, T, Y
A541 TO L, V
R542 TO K, Q, A, E
A543 TO V, M, E, R
A544 TO V, L, C, I
A545 TO R, G, L, V
K546 TO F, S, E, R

FIG. 18

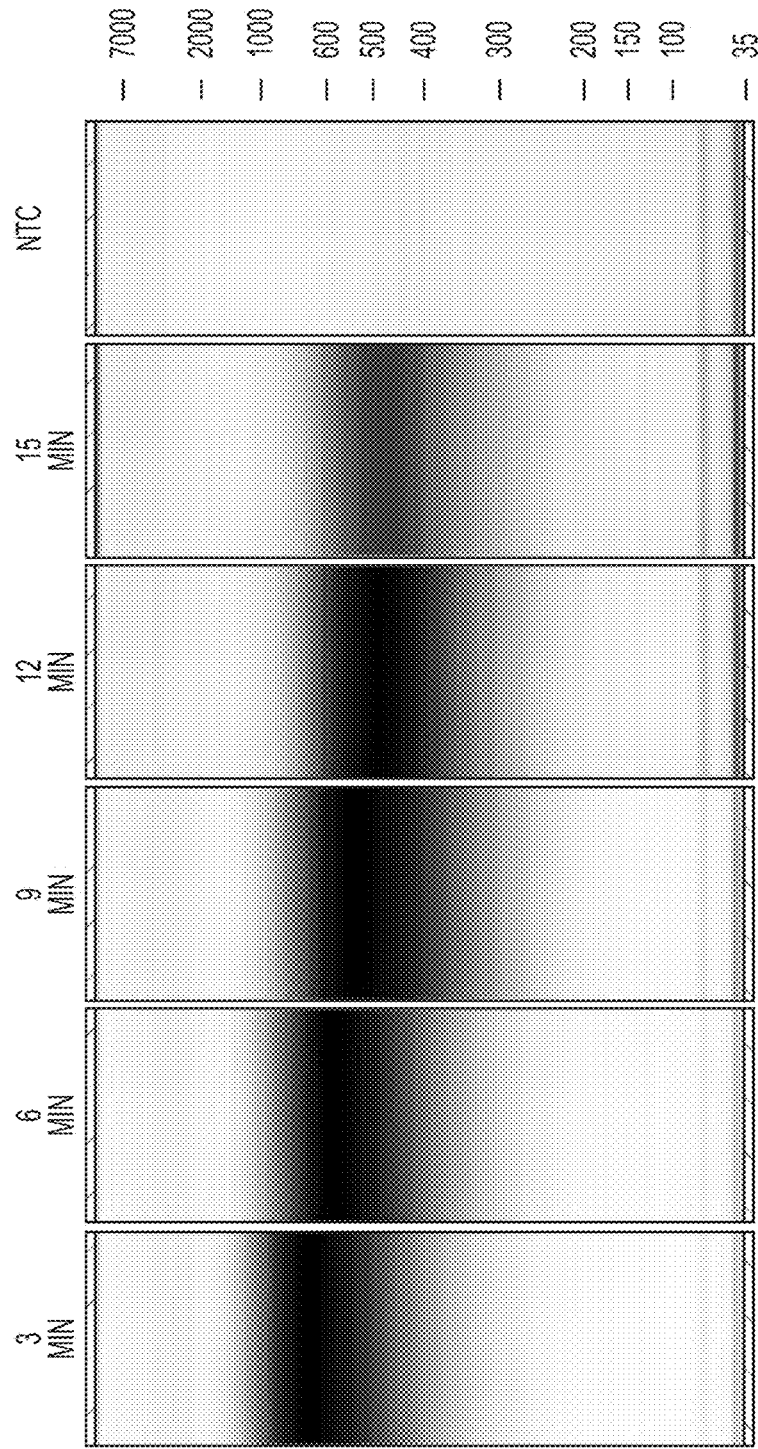
FIG. 25

SEQUENCE LISTING

```
Sequence total quantity: 67
SEQ ID NO: 1             moltype = AA  length = 805
FEATURE                  Location/Qualifiers
REGION                   1..805
                         note = Synthesized
source                   1..805
                         mol_type = protein
                         organism = synthetic construct
SEQUENCE: 1
CEPKRHQSPP PPKKRTTEEP KNRRQKIRSK YAQMQSLFKR DPKRVAAHLI KNQPLCNVSC   60
PIDAAESALR QRLSQRPGVD AAPFTSKCPQ YSKNILDPIF PEEVTLHLQK IKIHTLEGPD  120
GIKVSHLRSC DPDCRTTLIP KTDDPHPDAE DYRPITVASC LYRLFSKVVT RRLEDSLSLH  180
PRQKAFRSGT DGAFDNTSTL MTVIREAHNC GEELNIVSID LAKAFDNVNH TSITRALRMH  240
GLDDDSRTLI TQMVTGSSTI IKDGGALSNR IEINQGVRQG DPISPLLFNA VMDELVERLQ  300
LTGEGFKLKG VEVTTLAFAD DVTLISRSHR GIEKLLSITL DFLNERGLKL NINKCKGIRL  360
VRTPKTKSLV EDTSKPFTVP SYGEENQHIP MVPPGDLIKF LGVDITLNGK PHFDLAPLEC  420
TLERIRKAPL KPTQKLATVR DYLIPSLEYR LGVPGISRKI LESVDGAIRS AVKRFLHLPT  480
TGMNSMFLSM PIKKGGLGLR PLTTQHMARV AVGANNMMTS MDCLSRVVAD TTTLRKPLLS  540
ALEHFAVPAA TKSAIREGKQ NLLREEIAQL SETYHGSCLP SFKKGSLVNS WLRGTGGMRS  600
RDYITGLKLR FGVIETRSQK WKGRTPQNPD ALLCRHCGHL SGHRETAAHI SQKCPTTQAT  660
IIQRHNKIVN LVGDRAKREG FAVHVEPAIK SGDAVYKPDL VLVKDDTAHI LDVAAPWEKG  720
TTMHEKHERK ISKYTVLTED VKALFDVQTC TVGAIIIGAS SSWCPSNNRS LKACGLHMPK  780
KFKRLLCRVA LEGTCKIFQN FFTLT                                       805

SEQ ID NO: 2             moltype = AA  length = 898
FEATURE                  Location/Qualifiers
REGION                   1..898
                         note = Synthesized
source                   1..898
                         mol_type = protein
                         organism = synthetic construct
SEQUENCE: 2
CESKSHQPPP PRKKRTREEP KNRRQKIRSK YAQMQTLFKR DPKRVAAHLI RNQPLCNVSC   60
PIDAAESALR QRLSQRPGVD AAPITSKCPQ NSKNILDPIF PEEVTLHLQK MKIHTSAGPD  120
GIKVSHLRSC DPVCLAKAFN LFLLARHIPQ QLKDCRTTLI PKTDDPRPDA EDYRPITVAS  180
CLYRLFSKIV TRRLEDSLSL HPRQKAFRSG TDGAFDNTST LMTVIREAHN CGKELNIVSI  240
DLAKAFDTVN HTSITRALRM HGLDDESRTL ITEMVTGSST IIKGDGGALS NRIEINQGVR  300
QGDPISPLLF NAVMDELVER LERTGEGFKL KGVEVTTLAF ADDVTLISRS HRGMEKLLSI  360
TLDFLNERGL QLNINKCKGI RLVRTPKTKS LVEDTSKPFR VPSFGEENQH IPMVLPGDLI  420
KFLGIDITLN GKPHFDLAPL EDTLERIRKA PLKPAQKLAT VRDYLIPSLE YRLGVPGISR  480
KLLESVDGAI RLTVKRFLHL PLTGMNSMFL SMPVKEGGLG LRSLSTQHIA RLAVGTNSMS  540
ISTDTVSRVV ADTTTLRKPL LSALEHFAVP TATKSAIREG KRNLLRAEIA QLSETYQGSC  600
LPSFKHGSLV NTWLRGTSGM RSRDYITGLK LRFGVIETRS QKWRGRTPQN PDALLCRHCG  660
HSSGNRETAA HVSQKCLVTH ALIVQRHNKI VRLVGDRAKD EGFAVHVETA VKSGEEVYKP  720
DLILIKADTA HIIDVAVPWE KGTNMHEKHE RKTNKYAQLV DDVKALFGVQ NCTVGALVIG  780
ARSSWCTSND GSLKACGLHL PKKTDGEDLT TEADDSDAEP WQKPEHSPPH AKENTEDRNT  840
EEQSEPYTTP QTLRTSENPE IQRRRLHRT TTRRDCARRT DHNWTPERGT THPQKQGP    898

SEQ ID NO: 3             moltype = AA  length = 906
FEATURE                  Location/Qualifiers
REGION                   1..906
                         note = Synthesized
source                   1..906
                         mol_type = protein
                         organism = synthetic construct
SEQUENCE: 3
NCDGRNPPAP TNRRKRLPPP ARNRSERKRC NYASFQSLFK RDPKRIAAHL IKNQPLRNVS   60
CPIDVAESAL RQRLSQRPGI DAAPFKFKRP PNSECILSPI SADEVTLHLK LMSAETSAGL  120
DGVQVSHLRQ CDPMCLAKAF NCFLLARYIP PQLKDCRTTL IPKTDNPRPD ADDYRPITIA  180
```

```
SCIYRLFSKI  VTRRLENCIS  LHPRQKAFRS  GTDGAFDNIT  TLTTIVRDAH  KSGKELNIVC   240
VDLAKAFDTV  NHSSIDRALR  MHGLDANSRA  LIAQMVTGST  TVIKGDGGVL  SHKIEINQGV   300
RQGDPISPLL  FNSVMDELIE  RLEQSGVGYK  INNTEVVTLA  FADDVTLVSS  SHRGMEKLLS   360
ITHDFINERG  LKLNIRKCKG  IRFVRTPKTK  SLVQDTSKAF  KVRGSGEESS  CIPMAGPGEF   420
IKILGVPIAP  NGKPSFDIDT  LEGTLERIRK  APLKPAQKLA  IVRDYLIPSL  EYKLGVPGVG   480
RRVLDEVDAS  IRQTVKRFLH  LPHTGMNSMF  LTMPIKDGGL  GLRSLRTQHL  ARVAVGTNSM   540
MSSADPTSHT  IASMPQHQKP  LHAALQHFSV  PAATKDALKK  GKRQLLCAEI  AELTETYQGS   600
CLPTFRKRPV  GNSWLSGLNG  MRSRDFITGL  KLRFGVIETR  SQKWRGRTPQ  NPAVLLCRHC   660
GHSTGKRETA  AHISQKCPQT  KNLNIQRHNK  IVHLVAEHAR  REGFTVHVEH  ALKSDGQVYK   720
PDLILTKGNA  AHVLDVAVPW  ETGTDMHEHH  ERKVTKYCMI  SDDVKAHFGV  DSCTVGAIVV   780
GARSSWCASN  KTTLKACNTH  FTKRFKRLLC  RVALEGTCRP  LLSALEHPAV  PAATKSAIRE   840
DKQNLLREEI  GQLSETYRSS  CLPSFKKASL  VNSWLRGTSG  MRSRDYIAGL  KLRFGVIKTR   900
SQKWRG                                                                  906

SEQ ID NO: 4           moltype = AA  length = 827
FEATURE                Location/Qualifiers
REGION                 1..827
                       note = Synthesized
source                 1..827
                       mol_type = protein
                       organism = synthetic construct
SEQUENCE: 4
GAMRPEEERG  PKKGRKKKKP  EPSVPLNSKQ  RKRMAYRKVQ  QAYHKDPKRV  VAHLFHSQPL    60
ENVSCPVESG  EKALQARLGK  RPPADRAPFL  PKRAPLKNHL  LSPISAKEVS  EHLKQMNLAS   120
ASGPDGVKVS  HLRDIGPQCL  SKIFNTFLLE  RHIPQVLKDC  RTTLIPKVDN  PRPDAEDFRP   180
ITIGSCIYRL  FSKIVTSRLS  QLTPLNPRQK  AFRSGTDGAF  DNITVASLL   KLARKTGKEI   240
NLACIDLAKA  FDTVNHTSIT  RALHRHGVDS  ASIELVESMV  GEATTVIINS  DGTRSNVIKF   300
NRGVRQGDPI  SPLLFNLVLD  ELIDNLDQAR  CGFSITKEIQ  VSCVAFADDI  TLVSGSREGM   360
NNLLTITREF  LGERGLGINH  SKCKGIRFTK  VPKSKSLIID  TNPNCFLIRN  QQGTPEPIPM   420
AKPGEPLKTL  GINLTLEGNP  TFNYPELTRI  LNTIKHAPLK  PHQKVQIIRD  HLIPLLQYKL   480
GVPTFYRATL  NNIDKSIRLT  VKEILHLPTT  GLHNSYLYLP  LKEGGLGLKR  LATQYASRVG   540
LGLSNMATSD  DAVSRAVAGL  HLSLMDKAKN  CLGLSEISKE  AIKKAKEKLV  QAEIRTLLQC   600
HLGRSHSSFT  NDTISNSWMR  YPTFLSARNY  IMGIKLRAGI  IETRAQKWRG  RSPPHPTMLL   660
CRHCGARSRT  RETDIHVSQK  CLHNKKLILR  RHNCVVSTLG  RRATQQGFAV  YYEPCIKHGE   720
TVLKPDLVII  KGDTATIIDV  AVPWEQGTNL  REHNSRKISK  YQCLEREEAK  YFNVKTVKTG   780
SLVVGARGKW  SAGNDSTLKS  CGLHCSKRLK  KLLCTIALEG  TCAVFKH                  827

SEQ ID NO: 5           moltype = AA  length = 813
FEATURE                Location/Qualifiers
REGION                 1..813
                       note = Synthesized
source                 1..813
                       mol_type = protein
                       organism = synthetic construct
SEQUENCE: 5
LEPNRRRRGY  AKATRIALNA  PGKVRRRAEY  AAMQRQWKTK  RGLCAREALE  GTWKIPARTV    60
SLSDQEAFWR  PLMESQSKND  LREPAKVGET  LWGLLDPITP  DEVRQILGSM  SSKAPGPDGH   120
RLSDLRSIPI  DQICSHFNLW  LLAGYQPKAL  RMGESCLIPK  VKDASRPQQF  RPITLGSYVG   180
RCLHKCLASR  FERDLPISIR  QKAFRCMDGV  AENVMILRSV  LDDHKKRLAE  LNLVFLDVSK   240
AFDSVSHRSI  LHAVKRLGVP  PPLLKYVEEL  YADSETFLRG  SGELSPSIKV  RRGVKQGEPL   300
SPHLFNAVID  WALSSLDQSF  GVTVGEARVN  HLAFADDLVL  LSSSQPGLQR  LIDQLTTHLG   360
ESGLRVNSTK  SASIRIAVDG  KNKRWVVDPR  DSVHVGGVRI  PAVAVSGSYR  YLGVNISAAG   420
MRVDAADSLA  SKLANLSRAP  LKPQQRLYIL  CTHLLPSIYH  QLVLSSTSKK  FLKYLDRCVR   480
VAVRRWLRLP  KDTPKAYFHA  KCNDGGLGVP  ELQRVIPLQK  AGRWLKMTRS  QDPVVQAAVG   540
LEYFQKLLER  WSTPELYQWG  GGGITTSGHL  AVAQARSLYS  SVNGRGLRQS  GLVSTQPFWN   600
RSGCSLLSGR  NFIGAMQLRG  NLLATKLRAS  RGRPRVDISC  DCCRTPESSG  HILQVCPRTS   660
WGARIGRHDN  VAKLVARESA  KRHWKVIREP  AIPTPAGIRR  PDLVFSKGDT  AIVVDVTIVP   720
DNAELSDAHS  SKVSYYDNGA  IRGWVALNTG  ASHITFSSVN  NNWSDCMAEE  SKRMLKLGLG   780
LPNSIRGTIS  AVVLEKGFHM  YLCFKRGTFR  ASY                                  813

SEQ ID NO: 6           moltype = AA  length = 830
FEATURE                Location/Qualifiers
REGION                 1..830
                       note = Synthesized
source                 1..830
                       mol_type = protein
                       organism = synthetic construct
SEQUENCE: 6
NHERTTKQVP  ENNTPARRPF  KRRLHRVERY  KRFQRMYDLQ  RKRLAEEILD  GREAVTCNLK    60
KEEIKDHYDQ  VYGVSNDRVS  LDDCPRPPGA  NNTDLLKPFT  PTEVMDSLQG  MKNGAPGPDK   120
ITLPFLQKRL  KNGIHVSLAN  VFNLWQFSGR  IPECMKSNRS  VLIPKGKSNL  RDVRNWRPIT   180
ISSIVLRLYT  RILARRLERA  VQINPRQRGF  VPQAGCRDNI  FLLQSAMRRA  KRKGTLALGL   240
LDLSKAFDTV  GHKHLLTSLE  RFAVHPHFVR  IVEDMYSGCS  TSFRVGSQST  RPIVLMRGVK   300
QGDPMSPILF  NIALDPLLRQ  LEEESRGFMF  REGQAPVSSL  AYADDMALLA  KDHASLQSML   360
GTVDKFCSGN  GLGLNIAKSA  GLLIRGANKT  FTVNDCPSWL  VNGETLPMIG  PEQTYRYLGA   420
SICPWTGINS  GPVKPTLEKW  IANITESPLK  PHQRVDILCK  YALPRLFYQL  ELGTLNFKEL   480
KELDSMVKQA  VKRWCHLPAC  TADGLLYSRH  RDGGLAVVKL  ESLVPCLKIK  TNLRLVHSTD   540
PVISSLAESD  GLVGAIEGIA  QKAGLPIPTP  DQRSGTYHSN  WRDMERRSWE  RLALHGQGVE   600
LFKGSRSANH  WLPRPVGMKP  HHWVKCLAMR  ANVYPTKRGL  SRGNLSKNKD  SAKCRGCTSM   660
```

```
RETLCHLSGQ  CPKLKSMRIR  RHNKICEHLI  AEASFKGWKV  LQEPTLVTDN  GERRRPDLIF   720
HRDDKAVVVD  VTVRYEISKD  TLREAYASKV  RRYGCLTEQI  KDLTGATSVV  FHGFPMGARG   780
AWFPESSDVM  ADLNIRSKYF  EEFLCRRTIL  YTLDDLLWKSN NEQYLERLAP               830

SEQ ID NO: 7              moltype = AA   length = 821
FEATURE                   Location/Qualifiers
REGION                    1..821
                          note = Synthesized
source                    1..821
                          mol_type = protein
                          organism = synthetic construct
SEQUENCE: 7
NEGLQGNQRL  PKEKPMTARA  KMRHLRLLRY  RRLQELYKKD  RSLAAKQVLQ  DMLDSKPGRN    60
PEAVKYWAET  MGKESTGIDV  SVMTGRPRYR  DNVWSPIYPG  EVSAAVKLMD  SSGATGPDGF   120
SVRSLKCTPS  RVLAKVFNLF  LLEEKLPAFL  MTSRTVLVPK  VKEPKAPTDY  RPISVSSTLV   180
RLFHKILARR  LTLASGLDSR  QRGFVPVDGC  AENLVVLESA  IRSAKNYKRS  LFVASMDIKN   240
AFGSVAHEAI  FEALSKSGAP  DSFVTYVRNC  YDGFASVVKL  GRDTAQTTVR  QGVLQGDPLS   300
PILFNLVIDQ  IIRSLPETVG  VQLDANTKLN  SMAFADDLIL  LSSSEAGMRR  MLGVLAGVSS   360
KFGLIFHPGK  CKYLAMIWAG  KQKKMKIATD  LSFEIGGGFM  TPVGVTETWK  YLGAYLGQIG   420
IQPARLSLQT  FLERIAKSPL  KPQQKLYLIR  VHLLPKLIYP  LVMAPIRASM  LNKLDRMVRV   480
ALTGKDGILH  LPQSVPSAFF  YAPIGEGGLG  LMELRTSIPA  MVKARFERMM  NSTCHHVRAA   540
AKGAANSNRI  ALANRFLRKT  ADGIPVTSAK  LVKEYQAAKL  HGSFDGKPLS  EAGRVKGIHS   600
WTCDGRMVMT  GQAFCEALKI  RINALPCLSR  YNRGTEKPRE  CRAGCKTTES  LNHVLQVCPR   660
THDMRVARHD  KLVNRLGGYL  SQKGFEIHTE  PRIITSLGLR  KPDIIAIKGE  KGVVLDAQIG   720
GAANLNAAHD  AKMCYYSSSP  EIKEWVTGKG  APDVSYGACI  VSPQGIMSEE  SWKTLRGLGF   780
SKGMLNSLVV  TVMEQSTYVW  HVFNRSTASY  GWKRRRKRKW  D                        821

SEQ ID NO: 8              moltype = AA   length = 811
FEATURE                   Location/Qualifiers
REGION                    1..811
                          note = Synthesized
source                    1..811
                          mol_type = protein
                          organism = synthetic construct
SEQUENCE: 8
MAQNPCPKPP  PPAKNSRERR  DREYSRVQNF  YKKNRSACIN  SILDGNTRSQ  NVIPGLTKFW    60
TETFEKNSPP  DDEAPDQFVA  DEPRDMYKWI  TFYEMSQDYL  DSSTAPGVDG  FSAKQLRSMS   120
PRVLNKILNL  LLLSENLPNS  FKMHKTVLIP  KIDDPKSPGD  FRPITISPVL  ARLLNKILAA   180
RLSKLVPISQ  RQKAFLPVDG  CGENIFLLDY  ILRSSKKSSK  SVAMAVLDVK  KAFDSVSHHS   240
ILRALNEAKC  PINFINFVRN  SYDGCTTKLT  CGGTSFPDSV  RMNRGVKQGD  PLSPVLFNLI   300
IDSAIRKLPD  SIGYVIRDGL  KINCLAYADD  LILVASSRAG  LKTLLNIVAE  HLSRLGLDLN   360
AAKCHGLSII  ASGKAKTTYV  SAADSLDLDG  QPIKNLGVLD  TWTYLGIPFS  HLGRAEKVSP   420
DLTNLLNKLQ  KAPLKLQQKL  YAVRNFVIPR  ALHGLILSKT  NLKELNTLDR  AIRVFLRTLL   480
YLPKDTPLGF  FHSPIKSGGL  GITCFRTSVL  KCRLQRIARM  RSSCDGVIQA  VAESDIFADE   540
YAKLRDLIRI  NGNVLDTTES  IKRYWAQRLH  SSVDGKTLAY  MDYFPQGNLW  MSEDKVSQRS   600
YVFADCVKLR  INAIPTRVRV  SRGRPNKEMC  CRAKCFDSQR  MPAFESLNHI  TQVCPRTHGS   660
RIQRHDKIAK  FLFKNLNNCP  SRSVLYEPHF  VTVDGLRKPD  IIIYDDSHMV  VLDVQVVSDS   720
ANLEKEFECK  AKKYANDVAL  RSAMLIKYPF  IKSFSFVAAT  YNNRGLIAKS  SVQVLRQLGL   780
SPRSIMVSIL  ICLEGTLETW  RIFNQSTMNA  H                                    811

SEQ ID NO: 9              moltype = AA   length = 817
FEATURE                   Location/Qualifiers
REGION                    1..817
                          note = Synthesized
source                    1..817
                          mol_type = protein
                          organism = synthetic construct
SEQUENCE: 9
SDLEVTGRKR  VARGPRAIPV  LSKRKARRIE  YRRMQQLWRT  NMTKAAHKVL  DGDAGSLPHP    60
TLAAQLGFWK  PVLEAESVDL  AWPFAVGHPG  VAVGDLWSPI  TEGEVINIRL  PRTSSPGLDG   120
LTVHRWFTEV  PAILRATILN  IFMATGWVPP  RFRHSRTVLI  PKSSDLMDPA  YYRPISVSSV   180
ILRHFHKILA  RRVAACELLD  VRQRAFIAAD  GCAENVAVLS  AILFDARTNR  RQLHVITLDV   240
RKAFDTVSHN  AIRYVLSKHG  MPQIMVEYLS  TLYRTAAVRL  EVDGEFSDEI  LPGRGVRQGD   300
PLSPLLFNLI  MNEILAEVPD  QVGYCMMDRN  VNALAFADDL  VLIGATRDGA  QRSLERVMAA   360
LYRFGLELAP  AKCAAFSLVP  CGKTKRIKIL  TDPQFVAGDR  PIPQLGVLHT  VRYLGVRFGE   420
TGPVIQGVEL  LPLLERITRA  PLKPQQRLKI  LRTYLIPRYT  HNLVLGRVSY  SMLRKLDKQT   480
RAAVRRWLVL  PDDVPVAFFH  CPIKQGGLGI  QSFETAIPRL  TLLRLNRLKD  SQYEMARVVG   540
SSAWADRRMR  WCRFARRRDE  DWPSELHAKV  DGFELREAGN  VSVSTRWLDD  AMVHIPSSDW   600
LQYVKVWINA  LPTRIRTTRG  SRRLREDVNC  RGGCGVQETA  AHVVQQCFRT  HGGRIMRHDA   660
VASALAGELQ  RGGYNVHRER  VFRTREGVRK  PDILAAKGTH  GHVLDVQIIS  GARPLSDGHD   720
RKRSYYANNA  DLLARISALL  QVPVRNLDVS  TVTLSWRGVW  ARESAAVLTS  LGVSKAVLRG   780
ITTRVLKGSY  MNFSRFNQTT  ATCRGRANLR  MSGWGPP                              817

SEQ ID NO: 10             moltype = AA   length = 805
FEATURE                   Location/Qualifiers
REGION                    1..805
                          note = Synthesized
source                    1..805
                          mol_type = protein
```

```
                        organism = synthetic construct
SEQUENCE: 10
NTAKCPKGPR FRKTATHSGT NKQQRQQRYA RVQKLYKMNR KVAAKMVLEE TDKIQIKLPD    60
HDPMFKFWES EFKEGEGMPE RMPKDLKESP DLKAIWDPVT EEEVRKAKVA NNTAAGPDGI   120
QPKSWNRISL KYKTLIYNLL LYYEKVPHKL KVSRTVFIPK KKDGSSDPGE FRPLTICSVV   180
LRGFNKILVQ RLVSLYKYDE RQTAYLPIDG VGTNIHVLAA ILNDSNTKLS ELHVALLDIT   240
KAFNRLHHTS IIKSLVGKGF PYGFITFIRR MYTGLQTMMQ FEGHCKMTQV NRGVYQGDPL   300
SGPIFLLAIE KGLQALDKEV GYDIGDVRVN AGAYADDTDL VAGTRLGLQD NINRFSSTIK   360
QVGLEVNPRK SMTLSLVPSG KEKKMKVETG KPFRANDVPL KELSINDFWR YLGISYTNEG   420
PERLSLTIEQ DLERLTKAPL KPQQRIHMLN AYVIPKYQDK LVLSKTTAKG LKRTDRQIRQ   480
YVRRWLKLPH DVPIAYLHAP VKSGGLNIPC LQYWIPLLRV NRVNKITESQ RSVLAAVGKT   540
ALLTSTVYKC NQSLATLGGN PTMLAYRTYW EKELYAKVDG KDLQNARDDK ASTRWNGMLH   600
SDISGEDYLN YHKLRTNSVP TKVRTARGRP QKETSCRGGC KSTETLQHVV QQCHRTHGGR   660
TLRHDRIVGL LQHELRRDYN VLAKQELKTG IGLRKPDLVL IKDDTAHIVD VQVARCSKLN   720
ESHVRKRSKY DKKEIEVEVK SRYRVSKVMY EACTISYKGI WDKQSVMSMR RLGVSEYCLF   780
KIVTSTLRGT WLCWKRFNMI TSVRS                                        805

SEQ ID NO: 11              moltype = AA   length = 809
FEATURE                    Location/Qualifiers
REGION                     1..809
                           note = Synthesized
SITE                       63
                           note = misc_feature - Xaa can be any naturally occurring
                            amino acid
source                     1..809
                           mol_type = protein
                           organism = synthetic construct
SEQUENCE: 11
FWKPLTPNLA RVSLPSKDKV SRRRLRRADY GRVQRAWKRN RNTCLRDLLR DKRTESAPPE    60
ELXVPYWESV LRSGSSCTPG QRGRTAERTE LWDPVSSKEV EQALPPLGTA PGPDSFTPKD   120
FRAVPSAVWA CIFNIFMLCG RLPDYLLESR TTLIPKRDGA CNPEDFRPIT VSSVVVRCFH   180
KVIANRMSRH IQLDPRQKAF RSLDGCSEGV FLLDFILGHA RRNHRPVHLA SLDVAKAFDS   240
VSHAAILDVL RSFGVPDQMV EYIASVYAGS RTRLQGDGWQ SHAIHPTCGV KQGDPLSPMI   300
FNMVIDRLFT LFPRDTGVSV GDTVLNGMGY ADDLVLFATT PVGLQQLLDI TAEYLSQCGL   360
RVNAAKCFSV SLAIVPHEKK VVVATKHRFK CLGQPIPALK RSDQWKYLGV PFSPEGRLKI   420
DPLGRLKDEL EKLRRAPLKP QQRLYALRTV VVPGLYHLLV LGGTTISSLN RLDIAVRSTV   480
RKWLSLPHDV PNAYIHADAR DGGLSIPSYR WTVPRLRFHR LKALSVLCDG GGPDEMVACV   540
GDEIKRASAR LQDHGMNINT RNTYRVRFAR LLHTSNDGAP LKGSKKVEGQ HRWVTDGSLM   600
LSGRDYIACN WVRINSIPLR KRTARGRVRD TRCRAGCDST ETLHHVLQQC HRTHDMRIKR   660
HNACVKYLLD RQRSRGKTVF WEPHFHTAGG LLKPDSVILH DASTAVVVDA LVAGERSDLD   720
REHDRKVSKY EPLVDLVKDR YSVDKVIFSS LIISARGVWG GRSFRHLSKL RLLDISDAKV   780
LSTRVLLGGM GAVRVFNRRT AVSGRVNGW                                    809

SEQ ID NO: 12              moltype = AA   length = 809
FEATURE                    Location/Qualifiers
REGION                     1..809
                           note = Synthesized
source                     1..809
                           mol_type = protein
                           organism = synthetic construct
SEQUENCE: 12
EVFPAPPPRR ERRRKKTPNP APMRKREARR CEYGAAQSLW KRDRRHCITN ILNEMGPVNQ    60
PPRETMEPYW TRMMTTDGRT SPPSDKVPIK EDIWTPITGN DIKRSRIPRA SAPGPDGISA   120
RLYRSIPTTV IIRLFNLLLW CERLPEDLLL SRTIFLPKKT NASEPGDFRP ITIPPVLVRG   180
LHKILAKRLE TALDIDPRQR AFRSMDGCAD NTLLLDTLLR YHRKQYKSLY MASIDVSKAF   240
DAVTHPTIES TLISLGVPPP MIRYLGQVYA NSRTRIEGDG WTSKPVHPKR GVRQGDPLSP   300
ILFNAVTHRL LQRLPREVGA RLGNIPINAA AYADDLLLFA STSMGLQQMI DTMTDYLAEC   360
GMTINVEKSM TVAIRAAPHL KKTAVDASLS FSCGGRQLPS LKRTNKWRYL GVVFTPEGRA   420
QCRPAEVVAP LLGALTKAPL KPQQRLYALR TVVIPKLYHL LALGAVTIGT LNKTDRLVRG   480
ALRKWLALPH DTPNAYFHTS VRDGGLGIPA IRWTAPVQRR GRLLGVMKAL GQQGLDRFIQ   540
DELNTCKKRL TDHGVLLGTP EMVAKRWAQQ LYGSIDGAGL KDSAKTPHQH QWIADGSKFL   600
TGKDFINCNR ARIGALPTRS RTTRGRPQDR RCRGGCLAQE TLNHVLQCH RTHGQRIKRH   660
DAVVKYIARN MPRSGYEVHQ EPHYKTELGL RKPDLVAVLG QTAIIIDAQV VSEQTNLDDA   720
HTRKVAYYNE PATIRAIKAE HGVRTVKVTS ATLSWKGVWS PRSAEELRKL GFIRAGDAKV   780
VATRVLIGNI AAFRTFNATT SVEHRAGIG                                    809

SEQ ID NO: 13              moltype = AA   length = 823
FEATURE                    Location/Qualifiers
REGION                     1..823
                           note = Synthesized
source                     1..823
                           mol_type = protein
                           organism = synthetic construct
SEQUENCE: 13
SKEPAAHPPL PFGARRPPDK KRARRRWEYA AVQRAFRKNA ARCVNGLLDG TLLHQPPSIP    60
GLVEFWKDLF TAPCASSRPR SKEGLSPMLL ASSQPVSFRD LWAPITSEEA AAALPPRNSA   120
AGPDALTPAQ LRRLPHPVFL KILNLFLLAR SLPSRLLRAR TTLLPKKTSP ASPADFRPIT   180
VCSVLARAFH KVLAGRLMRY CVLDGRQRAF IPQDGMLHNS FLLDLAMAHS RRTACSLYVA   240
SLDVSKAFDS LDHGALSPVL RAHGLPVEFV EYVRGCYQAS TTVICGGGSS SDLVRPSKGV   300
```

```
RQGDPLSPIL FNLSIDLLLS RLPGYIGARI FSRRVNAAAF ADDILLFAET KGGLQELLST    360
ATSALGDLGL EVNPFKCFSL ALVASGREKK VKVDNSVIFR AGNKNIPALA MGDTFRYLGL    420
QFSTSGLSQF HPRQEVQEQL DIIKRAPLKP QQRLFALRSV ILPGTYHGLA LGRTRLGALK    480
SLDVCVRAAV RAWLRLPDDT PIGYFHAPVI YGGLGIPATR WLGPLLRRRR LASMEGLGVI    540
VDEPSQDILK REICRLDNYL KWDGDVIKTS YQLGRFWALR LHSSVDGAAL RRSAQTPGQH    600
SWVSNTRLML SGRDFLACVR ARISALPSRA RLLRGREGDT RCRAGCNASE TNNHVIQHCW    660
RSHEARVERH DAVALYMVRG LRRRGYDVHR ELHLRTSQGL KKPDIVAVSG TTAFVIDAQV    720
IGDHLDADRC HREKVEVYDQ QPVHTEIKRM FPEVQMITTT SATLNWRGVW SPASAKALIG    780
IGFNSNHLST MATRALLGSI MAARRFDSMT APRRRMMPRT GVG                     823

SEQ ID NO: 14            moltype = AA  length = 794
FEATURE                  Location/Qualifiers
REGION                   1..794
                         note = Synthesized
source                   1..794
                         mol_type = protein
                         organism = synthetic construct
SEQUENCE: 14
NRNDRPSSAT VPARRPRNRR ISRRQQYARC IKSLLDGTDE SALPNQSIME PYWRQVMTQP     60
SPSLCSNTVP RKGNMQEGVW SPITSRDLQV HKVPLTSSPG PDGITSQTAR SIPIGIMLRI    120
VNLILWCGDL PVPFRMARTI FIPKTVRANR PQDFRPISVP SIVVRQLNAI LASRLTAAVS    180
WDPRQRGFLP TDGCADNATI VDLVLRDHHK RYASCYIATL DVSKAFDSVA HDAVFNTVTA    240
YGAPKSFVDY VRRWYSGGGT YFNGGDWRSE EFVPARGVKQ GDPLSPVLFN LIIDRLLRSL    300
PKDIGVHVGN AKVNACAFAD DLMLFASTPK GLQELLNTTV KFLSSVGLTL NADKCFTISI    360
KGQPKQKVTV VEQRTFCIGR ARVQLKRSEE WKYLGIHFTA DGRARYNPSE DIGPKLERLM    420
QSPLKPQQKL FALRTVLVPQ LYHKLTLGSV ALGVLRKCDK LVRSFARKLL GLPLDVSVAF    480
YHAPHSCGGL GIPSVRWIAP MLRTKRLAGI NWPHLEQSEV ASAFLSEELR RARDRAKAGV    540
NELLSQPKID TYWADRLYTS VDGNGLREAR RYAPQHGWVS QPTRLMSGKA YRTGIQLRIN    600
ALPTRSRTTA GRHEMNRQCR AGCDAPSHNH VLQRCHRTHG SRVSRHNGVV SYLKKGLETR    660
GYTVYSEQSL HGQNRVYKPD IVAFRHDSTI VVDAQVVTDG LDLDRAHQSK VEIYNRQDLL    720
TTLRSVYRAR ENIEVVSATL NWRGIWSFQS ITRLRTLGIL TAGDSNVISS RVVSGRVYSF    780
KTFMFHAGFH RGMA                                                     794

SEQ ID NO: 15            moltype = AA  length = 802
FEATURE                  Location/Qualifiers
REGION                   1..802
                         note = Synthesized
source                   1..802
                         mol_type = protein
                         organism = synthetic construct
SEQUENCE: 15
SSGRKLPVKS RGARETVQKK MANPRVAKYK RFQRLFRSNR RKLASHIFDK ASLEQFGGSI     60
DEASDHLEKF LSRPRLESDS YSVINGNKSI GVAHPILAEE VELELKASRP TAVGPDGIAL    120
EDIKKLNSYD LASLFNLWLK AGDLPESVKA SRTIFLPKSD GTTIDISNCRP ITIASALYRL    180
FSKIITRRLA ARLELNVRQK AFRPEMNGVF ENSAILYALI KDAKARSKEI CITTLDDLAKA   240
FDTVPHSRIV RALRKNNVDP ESVDLISKML TGTTYAEIKG LQGKPITIRN GVRQGDPLSP    300
LLFSLFIDEI IGRLQACGPA YDFHGEKICI LAFADDLTLV ADNAAGMKIL LKAACDFLEE    360
SGMSLNAEKC RTLCISRSPR SRKTFVNPAA KFNISDWKTG ISSEEIPSLCA TDTFRFLGHT   420
FDGEGKIHID MEEIRSMLKS VRSAPLKPEQ KVALIRSHLL PRLQFLFSTA EADSRKAWLI    480
DSIIRGCVKE ILHSVKAGMC TEIFYIPSRD GGLGLTSLGE FSLFSRQKAL AKMAGSSDPL    540
SKRVAEFFME RWNIARDPKV TEAARRVYQK KRYQRFFQTY QSGGWNEFSG NTIGNAWLTN    600
GRARGRNYVM AVKFRSNTAA TRAENLRGRP GMKECRFCKS ATETLAHICQ KCPANHGLVI    660
QRHNAVVSFL GEVARKEGYQ VMIEPKVSTP VGALKPDLLL IKADTAFIVD VGIAWEGGRP    720
LKLVNKMKCD KYKIAIPAIL ETFHVGHAET YGVILGSRGC WLKSNDKALA SIGLNITRKM    780
KEHLSWLTFE NTIRIYNSFM KN                                            802

SEQ ID NO: 16            moltype = AA  length = 809
FEATURE                  Location/Qualifiers
REGION                   1..809
                         note = Synthesized
source                   1..809
                         mol_type = protein
                         organism = synthetic construct
SEQUENCE: 16
TKWRPSKPRL PPTYRANTSR KHLRRLQYGH IQTLYNRCRR DAANTVLDGR WRSPHTSSPF     60
SIPEFETFWK TIFTTPSTPD NRPVVPVLPT CPALLDPITP DEITWALKDM RNSAPGVDRL    120
SAQHFLNFDV PSLAGYLNMV LAFKFLPTNL SISRVTFIPK GASPQQPNDF RPISIAPVIT    180
RCLHKILAKR WMPLFPSSKL QFAFLQRDGC FEAINLLHSL LRHAHERHSG CSIALLDISR    240
AFDSVSHHSI LRAAHRFGAP DGLCQYLQRV YNGSTSLFNT VDCAPSRGVK QGDPLSPLLF    300
IMSLDEALES IETVSPVIVD GLPISYIAYA DDLVILAPNA DLLQKKLDKL ASLLQRSGLI    360
INTSKSMSID LIAGGHSKLT ALKPTVFKID GNQLQRLNVS DHFDFLGISF DYKGRSKMDH    420
VETLSAYLLN LTQAPLKPQQ RMSILRENLE PRLLYPLTIG VVHKCTLRQM DCLIRSSVRK    480
WLRLPSDTPT SFFHSSISTG GLGIPHLSSI IPLHRRKRAA KLLLSPCPII RWVSQSPSFS    540
NFLRICNLPI NVHRDLIHSF DEARCSWSKQ LHSTCDGRGL SMSSRNTVSH LWLRYPEHIF    600
PRLYINAIKL RGGLLSTKVR RSRGRQENAD LLCRGRCGHH ESIQHILQHC SLTHDIRCRR    660
HNDICRLVAS RLRRNNIRFF QEPCIPTPVS FCKPDFIIIR DSIAYVLDVS VCDDANVHLS    720
RQLKINKYGC STVVSSIYNF LNATGLRISS VRQTPLIITY RGLIDPLSTT SLRRLSFSSR    780
DISDLCVASI QGSMRIYNTY MRGTSPQDP                                     809
```

```
SEQ ID NO: 17             moltype = AA  length = 806
FEATURE                   Location/Qualifiers
REGION                    1..806
                          note = Synthesized
source                    1..806
                          mol_type = protein
                          organism = synthetic construct
SEQUENCE: 17
QHALDCFPRL WAPSRPRPNH PQPRSYRALR KAQYASLQRI LHTSPKDAAT HVLDGSWRLL    60
HQNRALPPDL HSFWTNVFRI PSFSDNRPVS ATQPELSLIS PITCEEVKKA IAGMGGTAPG   120
LDRLTPANLK SFGLKPLTGY LNLILCYGCP ASLAAARVTL IPKVPDATRP EQYRPLAVSS   180
VIVRCLHKIL AFRWASVLKL SSLQLAFMQR DGCLEATTIL QGVFRDAHSR RRPIAMAFLD   240
VSKAFDTVLH DSVFRAAAMY GAPPLLLRYL RKLYSQGTVT LGDIDILPKR GVRQGDPLSP   300
LLFILAMEEI LMAANPNDGY QLPSSTISTL AYADDLVLFA HSPGALGLKL ERVAAALRLA   360
GMEINAAKSI TFTISANTHN KNLCLENIAY TLDGVSIAAA DTETRVKYLG LHFNWKGQIS   420
YKDTARLAGY CQELTSAPLK PQQRIHILRQ VALPKLHHQL VLSSIHRRTL KAMDISCRHY   480
VRRWLKLPQD TSTAFFHAKI GDGGLGLTSL ATSIPLWRRT RLTKLITSEH PVVRDVVSIC   540
LTKALAVANE PVFVMGTVVS DKDEAAMAWK LAMYATLDCA DLQTIHETPE SSNWVVRPLR   600
MTPSLYIRGL QLRAGTLGTK SRQQRGRAQM DKLCRRGCGQ TETLPHILQS CPAAHAARCV   660
RHNRVAKSIA VSLRRKGYRV YEEPIIRTGT TYCKPDIIAC QDGLGFVIDV AVVSGHRLHE   720
SWDLKIAKYD TDFINTAIID CLPEDVEILS LIHQPAIISF KGVWFPPSAK RLKTLGLSAD   780
CLAGLGLVTI KGSLACFDMF MMGSNG                                       806

SEQ ID NO: 18             moltype = AA  length = 834
FEATURE                   Location/Qualifiers
REGION                    1..834
                          note = Synthesized
source                    1..834
                          mol_type = protein
                          organism = synthetic construct
SEQUENCE: 18
KENLKKRACK TLTRRIKPKK SKKHEYWKMQ QMYHRDRAGL AKLILEGEAR DICPIPLTRL    60
TTAFKEKWEK EDRFVSLGQF KSSCKAVNDI FASPISPEEV CKIRSKMKNK AATGLDGISK   120
TCLMRGDPKG INLANLFTAI LLNGYIPRAL KKNRTTLLPK TQDKRKLSDT SQWRPITIGS   180
TIQRLLSGVI NDRLKEACEI HPRQRGFISS PGCAENLMLL RELIALSKRE LKPLAVIFID   240
FAKAFDTVSH KHIKAVLQQR GVDKMIIDLI SNSYEGRTTI LKAKGSYSRE IRLKMGVKQG   300
DPLSPLLFNL AIDPLLCKLD KVGEGAIVDG IEITSLAFAD DIVLLSNSWS GMRKNLKILE   360
VFCELTGLTL NVMKCHGFFI DSMNRCLAIN ECPPWRLQQN DLHMIGSKEK EKYLGMEISP   420
WLGIIEPNIQ KMINIMLNNL TASLLKPSQK LELLRTYAVP KLTYMADNGM VTQTTLITTD   480
RKIRMTIKKW FHLNHATTDG LLYTGCKSGG MGLVKLARVI PRIQVNRILG LCNSEDSCTR   540
TMARKAHRPS EFRKIWKMGM GKKGGETTIQG ASDIRTPYWN TPKIHSDWRI NELDKWKKMK   600
TQGEGIEVFE NDKISNSWLR HPTLSNFSER DYILALKLRT NTYPMKAILA RGRMAKNKGT   660
KCRLCGYIKK TTKHVLGSCI GTRPNRMQRH NKICALLAKA ARQLGWETLT EHHLKMDNGK   720
TLVPDLIMMK DTRAIVADVT ICYETNQYSL RKAYEVKVKK YAPLELPIKE RWPGIKDVRI   780
HGFPLGTRGK WPSLNWRLLE ELDMDKSKRR KFASLLSKRS LLYTIDILKW FSKN         834

SEQ ID NO: 19             moltype = AA  length = 812
FEATURE                   Location/Qualifiers
REGION                    1..812
                          note = Synthesized
source                    1..812
                          mol_type = protein
                          organism = synthetic construct
SEQUENCE: 19
TRSAPSSTSS GKSTRNAKRL EKLKKYGYYQ HLYYNNKKKL VAEILDGETS GAKPPPMNLV    60
EDYYKNIWSR STIDDSPVNN IKTVNSDSIF APISRDEIKL ALSNTKKDSA AGPDSVTIKE   120
AKAIIDNLYV AYNIWLGVQG IPEQLKLNKT ILIPKGNSDL SLLKNWRPIT ISSIILRVYN   180
RLLAYRMNKV FKTNDKQVGF KPVNGCGINI SWLHSLLKHA RLNKNPIYAC LVDVSKAFDS   240
VSHQSIVRAL TMNGAPSLLV KLIMDQYTNI NTIITCSGSI SNKINISSGV KQGDPLSSLL   300
FNMVIDELFD VIKDQYGYTI DNIGTTNARC FADDLTLISS SRMGMNKLLE LTTEFFKERG   360
LNVNPSKCMS IGMSKGYKGK KSKIESEPLF SIADAQIPML GYIDKTTRYL GVNFTSIGAI   420
DAKRIKKDLH DTLDKLEHLK LKAQCKMDLL RTYMIPRFMF QLIHTELYPK LLIKMDILIR   480
KLAKRILHLP ISTSSEFFYL PFKEGGLQLT SLKEAVGLAK IKLHKKIMSS NDPMLCYLIE   540
SQRSRIIEHF MKDLKLGDSL TLNEMDNIKE CFMKEKRISF AQKIHGVGFE VFSSSPLTNQ   600
WINGEIKTMT TRTYINSIKL RTNTLETRVT TSRGLNIIKT CRRCHVADES LMHVLQYCSS   660
TKGLRYSRHH RICAKVANKL MKNGYGVYRE KSYPDPNNSG SYLRPDLIAV KDGHVIVLDV   720
TVVYEVTGAT FINAYQTKVN KYNTIMVQIE QMFNCVSGVL HGLVIGSRGS IHHSQLHIWH   780
QMGFSSTELK YVAIGCMEDS LRIMSTFSKA IL                                812

SEQ ID NO: 20             moltype = AA  length = 797
FEATURE                   Location/Qualifiers
REGION                    1..797
                          note = Synthesized
source                    1..797
                          mol_type = protein
                          organism = synthetic construct
SEQUENCE: 20
KSKSLPRLKR TGRAFHRREK YAICQKSLDK DFSGTISKIL DGVEISEAEV RPEMAKIEEV    60
YQQRLGNTSG ALPENTDTPV VEGLRFERKT APFDAQEVTR AIRESNKSTA AGPDRWFNGR   120
```

```
CLKNLDCETV AALFNLWRFK QKIPSALREN RTILLPKGGD LTDANNWRPL TIGSLLLRLY    180
AKSLTTRWSD APICERQKAF RPVDGCWENI NLLLGALKSA HKKRRQINLI SIDLAKAFDN    240
IQHGAIFNAM RRFGFSPSEI SVVKDLYTNV WTKISIGNEI SGPINISRGV KQGCPLSPFL    300
FNLVLDELIN ELQSSGYGYP VEGFKVPVLA YADDLILCGA TDYETKRMVE ITEKFFARQM    360
LAVNLKKCKA LRLLPVKGKR TLKVSSDPML WKGEQLPMVK SIDDFISYLG VKVSVTGKVI    420
WSVDQLRLWL DRVMKAPLKP DQKIGKIKEV LIGRLTYQLR LSEARVCELR RVTRMVRKAC    480
KQILHMQLGA PNAWAHLPLR KCGLGLPDFE LTIPLMRRAA CEKMKSSPDP VVANISEKIP    540
IYESGLTRGL DVRAAKRAIQ DKYEQAYLST QRGKLMNARW ISAVKPYWLH GGTGVVKAGE    600
YVSINKLVTR TIETRQFIHP GVTDPFETLKC RRCGKAVETD LHVLNECPFT RLAQCRRHNF    660
IADYLGKVLV DHGWEVWRER LVKKDLENFK PDLICRKGAE GAIIDVTVPY ESNEAVLQSK    720
ERFKEAKYAG LKGQVAELLN INGGVKVVGI AVGALGTILT STLEKAKGLG LDPVKVGKSL    780
QISALRGSGH VWKAFRS                                                   797

SEQ ID NO: 21          moltype = AA length = 69
FEATURE                Location/Qualifiers
REGION                 1..69
                       note = Synthesized
source                 1..69
                       mol_type = protein
                       organism = synthetic construct
SEQUENCE: 21
MPSVQEVEKL LHVLDRNGDG KVSAEELKAF ADDSKCPLDS NKIKAFIKEH DKNKDGKLDL    60
KELVSILSS                                                            69

SEQ ID NO: 22          moltype = DNA length = 210
FEATURE                Location/Qualifiers
misc_feature           1..210
                       note = Synthesized
source                 1..210
                       mol_type = other DNA
                       organism = synthetic construct
SEQUENCE: 22
atgccgtctg ttcaggaagt tgaaaaactg ctgcacgttc tggaccgtaa cggtgacggt    60
aaagtttctg cggaagaact gaaagcgttc gcggacgact ctaaatgccc gctggactct   120
aacaaaatca agcgttcat caaagaacac gacaaaaaca agacggtaa actggacctg    180
aaagaactgg tttctatcct gtcttcttag                                   210

SEQ ID NO: 23          moltype = DNA length = 220
FEATURE                Location/Qualifiers
misc_feature           1..220
                       note = Synthesized
source                 1..220
                       mol_type = other DNA
                       organism = synthetic construct
SEQUENCE: 23
ctgcagtaat acgactcact ataggatcct ctagagtcga cctgcaggca tgcaagcttg    60
gcactggccg tcgttttaca acgtcgtgac tgggaaaacc ctggcgttac ccaacttaat   120
cgccttgcag cacatccccc tttcgccagc tggcgtaata gcgaagaggc ccgcaccgat   180
cgcccttccc aacagttgcg cagcctgaat ggcgaatggc                         220

SEQ ID NO: 24          moltype = DNA length = 45
FEATURE                Location/Qualifiers
misc_feature           1..45
                       note = Synthesized
source                 1..45
                       mol_type = other DNA
                       organism = synthetic construct
SEQUENCE: 24
ctgcagtaat acgactcact ataggatcct ctagagtcga cctgc                   45

SEQ ID NO: 25          moltype = DNA length = 24
FEATURE                Location/Qualifiers
misc_feature           1..24
                       note = Synthesized
source                 1..24
                       mol_type = other DNA
                       organism = synthetic construct
SEQUENCE: 25
cagtcagtca gtcagtcagt gcca                                          24

SEQ ID NO: 26          moltype = RNA length = 38
FEATURE                Location/Qualifiers
misc_feature           1..38
                       note = Synthesized
source                 1..38
                       mol_type = other RNA
                       organism = synthetic construct
SEQUENCE: 26
cagtcagtca gtcagtcagt gccaaatgcc tcgtcatc                           38
```

```
SEQ ID NO: 27              moltype = DNA  length = 19
FEATURE                    Location/Qualifiers
misc_feature               1..19
                           note = Synthesized
source                     1..19
                           mol_type = other DNA
                           organism = synthetic construct
SEQUENCE: 27
tgatgacgag gcatttggc                                                          19

SEQ ID NO: 28              moltype = DNA  length = 23
FEATURE                    Location/Qualifiers
misc_feature               1..23
                           note = Synthesized
source                     1..23
                           mol_type = other DNA
                           organism = synthetic construct
SEQUENCE: 28
acactctttc cctacacgac gct                                                     23

SEQ ID NO: 29              moltype = DNA  length = 22
FEATURE                    Location/Qualifiers
misc_feature               1..22
                           note = Synthesized
source                     1..22
                           mol_type = other DNA
                           organism = synthetic construct
SEQUENCE: 29
gcgtcgtgta gggaaagagt gt                                                      22

SEQ ID NO: 30              moltype = DNA  length = 22
FEATURE                    Location/Qualifiers
misc_feature               1..22
                           note = Synthesized
source                     1..22
                           mol_type = other DNA
                           organism = synthetic construct
SEQUENCE: 30
cactctttcc ctacacgacg ct                                                      22

SEQ ID NO: 31              moltype = DNA  length = 45
FEATURE                    Location/Qualifiers
misc_feature               1..45
                           note = Synthesized
source                     1..45
                           mol_type = other DNA
                           organism = synthetic construct
SEQUENCE: 31
agcgtcgtgt agggaaagag tgtcactctt tccctacacg acgct                             45

SEQ ID NO: 32              moltype = DNA  length = 42
FEATURE                    Location/Qualifiers
misc_feature               1..42
                           note = Synthesized
source                     1..42
                           mol_type = other DNA
                           organism = synthetic construct
SEQUENCE: 32
acactttatg cttccggctc cactctttcc ctacacgacg ct                                42

SEQ ID NO: 33              moltype = DNA  length = 41
FEATURE                    Location/Qualifiers
misc_feature               1..41
                           note = Synthesized
source                     1..41
                           mol_type = other DNA
                           organism = synthetic construct
SEQUENCE: 33
taagttgggt aacgccaggc actctttccc tacacgacgc t                                 41

SEQ ID NO: 34              moltype = DNA  length = 33
FEATURE                    Location/Qualifiers
misc_feature               1..33
                           note = Synthesized
source                     1..33
                           mol_type = other DNA
                           organism = synthetic construct
SEQUENCE: 34
```

```
acactctttc ccactctttc cctacacgac gct                                33

SEQ ID NO: 35          moltype = DNA   length = 31
FEATURE                Location/Qualifiers
misc_feature           1..31
                       note = Synthesized
source                 1..31
                       mol_type = other DNA
                       organism = synthetic construct
SEQUENCE: 35
agcgtcgtgc actctttccc tacacgacgc t                                  31

SEQ ID NO: 36          moltype = DNA   length = 65
FEATURE                Location/Qualifiers
misc_feature           1..65
                       note = Synthesized
source                 1..65
                       mol_type = other DNA
                       organism = synthetic construct
SEQUENCE: 36
ttccaatgat acggcgacca ccganacngn canagctagc tcctcactct ttccctacac   60
gacgc                                                               65

SEQ ID NO: 37          moltype = DNA   length = 65
FEATURE                Location/Qualifiers
misc_feature           1..65
                       note = Synthesized
source                 1..65
                       mol_type = other DNA
                       organism = synthetic construct
SEQUENCE: 37
ggagctagct atgacagtat cggtggtcgc cgtatcatta cttcactctt tccctacacg   60
acgct                                                               65

SEQ ID NO: 38          moltype = DNA   length = 33
FEATURE                Location/Qualifiers
misc_feature           1..33
                       note = Synthesized
source                 1..33
                       mol_type = other DNA
                       organism = synthetic construct
SEQUENCE: 38
acactctttc cctacacgac gctcttccga tct                                33

SEQ ID NO: 39          moltype = DNA   length = 34
FEATURE                Location/Qualifiers
misc_feature           1..34
                       note = Synthesized
source                 1..34
                       mol_type = other DNA
                       organism = synthetic construct
SEQUENCE: 39
gtgactggag ttcagacgtg tgctcttccg atct                               34

SEQ ID NO: 40          moltype = DNA   length = 56
FEATURE                Location/Qualifiers
misc_feature           1..56
                       note = Synthesized
source                 1..56
                       mol_type = other DNA
                       organism = synthetic construct
SEQUENCE: 40
aatgatacgg cgaccaccga gatctacact aatcttaaca ctctttccct acacga       56

SEQ ID NO: 41          moltype = DNA   length = 50
FEATURE                Location/Qualifiers
misc_feature           1..50
                       note = Synthesized
source                 1..50
                       mol_type = other DNA
                       organism = synthetic construct
SEQUENCE: 41
caagcagaag acggcatacg agatattact cggtgactgg agttcagacg               50

SEQ ID NO: 42          moltype = DNA   length = 37
FEATURE                Location/Qualifiers
misc_feature           1..37
                       note = Synthesized
source                 1..37
```

```
                       mol_type = other DNA
                       organism = synthetic construct
SEQUENCE: 42
acactctttc cctacacgac gctcttccga tctaggg                              37

SEQ ID NO: 43         moltype = DNA   length = 38
FEATURE               Location/Qualifiers
misc_feature          1..38
                      note = Synthesized
source                1..38
                      mol_type = other DNA
                      organism = synthetic construct
SEQUENCE: 43
acactctttc cctacacgac gctcttccga tctcaggg                             38

SEQ ID NO: 44         moltype = DNA   length = 39
FEATURE               Location/Qualifiers
misc_feature          1..39
                      note = Synthesized
source                1..39
                      mol_type = other DNA
                      organism = synthetic construct
SEQUENCE: 44
acactctttc cctacacgac gctcttccga tcttctggg                            39

SEQ ID NO: 45         moltype = DNA   length = 34
FEATURE               Location/Qualifiers
misc_feature          1..34
                      note = Synthesized
source                1..34
                      mol_type = other DNA
                      organism = synthetic construct
SEQUENCE: 45
acactctttc cctacacgac gctcttccga tctg                                 34

SEQ ID NO: 46         moltype = DNA   length = 33
FEATURE               Location/Qualifiers
misc_feature          1..33
                      note = Synthesized
source                1..33
                      mol_type = other DNA
                      organism = synthetic construct
SEQUENCE: 46
acactctttc cctacacgac gctcttccga tct                                  33

SEQ ID NO: 47         moltype = DNA   length = 39
FEATURE               Location/Qualifiers
misc_feature          1..39
                      note = Synthesized
source                1..39
                      mol_type = other DNA
                      organism = synthetic construct
SEQUENCE: 47
acactctttc cctacacgac gctcttccga tctrgrgrg                            39

SEQ ID NO: 48         moltype = DNA   length = 39
FEATURE               Location/Qualifiers
misc_feature          1..39
                      note = Synthesized
source                1..39
                      mol_type = other DNA
                      organism = synthetic construct
SEQUENCE: 48
acactctttc cctacacgac gctcttccga tctrgrgrg                            39

SEQ ID NO: 49         moltype = DNA   length = 34
FEATURE               Location/Qualifiers
misc_feature          1..34
                      note = Synthesized
misc_feature          34
                      note = n is a, c, g, or t
source                1..34
                      mol_type = other DNA
                      organism = synthetic construct
SEQUENCE: 49
acactctttc cctacacgac gctcttccga tctn                                 34

SEQ ID NO: 50         moltype = DNA   length = 35
FEATURE               Location/Qualifiers
```

```
misc_feature                 1..35
                             note = Synthesized
misc_feature                 34..35
                             note = n is a, c, g, or t
source                       1..35
                             mol_type = other DNA
                             organism = synthetic construct
SEQUENCE: 50
acactctttc cctacacgac gctcttccga tctnn                               35

SEQ ID NO: 51                moltype = DNA   length = 33
FEATURE                      Location/Qualifiers
misc_feature                 1..33
                             note = Synthesized
source                       1..33
                             mol_type = other DNA
                             organism = synthetic construct
SEQUENCE: 51
acactctttc cctacacgac gctcttccga tct                                 33

SEQ ID NO: 52                moltype = DNA   length = 34
FEATURE                      Location/Qualifiers
misc_feature                 1..34
                             note = Synthesized
misc_feature                 34
                             note = n is a, c, g, or t
source                       1..34
                             mol_type = other DNA
                             organism = synthetic construct
SEQUENCE: 52
acactctttc cctacacgac gctcttccga tctn                                34

SEQ ID NO: 53                moltype = DNA   length = 32
FEATURE                      Location/Qualifiers
misc_feature                 1..32
                             note = Synthesized
source                       1..32
                             mol_type = other DNA
                             organism = synthetic construct
SEQUENCE: 53
acactctttc cctacacgac gctcttccga tc                                  32

SEQ ID NO: 54                moltype = DNA   length = 36
FEATURE                      Location/Qualifiers
misc_feature                 1..36
                             note = Synthesized
source                       1..36
                             mol_type = other DNA
                             organism = synthetic construct
SEQUENCE: 54
ccgtgactgg agttcagacg tgtgctcttc cgatct                              36

SEQ ID NO: 55                moltype = DNA   length = 61
FEATURE                      Location/Qualifiers
misc_feature                 1..61
                             note = Synthesized
misc_feature                 37..44
                             note = n is a, c, g, or t
source                       1..61
                             mol_type = other DNA
                             organism = synthetic construct
SEQUENCE: 55
ccgtgactgg agttcagacg tgtgctcttc cgatctnnnn nnnntttttt tttttttttt    60
t                                                                    61

SEQ ID NO: 56                moltype = DNA   length = 33
FEATURE                      Location/Qualifiers
misc_feature                 1..33
                             note = Synthesized
source                       1..33
                             mol_type = other DNA
                             organism = synthetic construct
SEQUENCE: 56
acactctttc cctacacgac gctcttccga tct                                 33

SEQ ID NO: 57                moltype = DNA   length = 59
FEATURE                      Location/Qualifiers
misc_feature                 1..59
                             note = Synthesized
```

```
source                     1..59
                           mol_type = other DNA
                           organism = synthetic construct
SEQUENCE: 57
aatgatacgg cgaccaccga gatctacacg tactgacaca ctctttccct acacgacgc    59

SEQ ID NO: 58              moltype = DNA   length = 53
FEATURE                    Location/Qualifiers
misc_feature               1..53
                           note = Synthesized
source                     1..53
                           mol_type = other DNA
                           organism = synthetic construct
SEQUENCE: 58
caagcagaag acggcatacg agatattact cggtgactgg agttcagacg tgt          53

SEQ ID NO: 59              moltype = AA   length = 829
FEATURE                    Location/Qualifiers
source                     1..829
                           mol_type = protein
                           organism = Bombyx mori
SEQUENCE: 59
KTAGRRNDLH DDRTASAHKT SRQKRRAEYA RVQELYKKCR SRAAAEVIDG ACGGVGHSLE   60
EMETYWRPIL ERVSDAPGPT PEALHALGRA EWHGGNRDYT QLWKPISVEE IKASRFDWRT  120
SPGPDGIRSG QWRAVPVHLK AEMFNAWMAR GEIPEILRQC RTVFVPKVER PGGPGEYRPI  180
SIASIPLRHF HSILARRLLA CCPPDARQRG FICADGTLEN SAVLDAVLGD SRKKLRECHV  240
AVLDFAKAFD TVSHEALVEL LRLRGMPEQF CGYIAHLYDT ASTTLAVNNE MSSPVKVGRG  300
VRQGDPLSPI LFNVVMDLIL ASLPERVGYR LEMELVSALA YADDLVLLAG SKVGMQESIS  360
AVDCVGRQMG LRLNCRKSAV LSMIPDGHRK KHHYLTERTF NIGGKPLRQV SCVERWRYLG  420
VDFEASGCVT LEHSISSALN NISRAPLKPQ QRLEILRAHL IPRFQHGFVL GNISDDRLRM  480
LDVQIRKAVG QWLRLPADVP KAYYHAAVQD GGLAIPSVRA TIPDLIVRRF GGLDSSPWSV  540
ARAAAKSDKI RKKLRWAWKQ LRRFSRVDST TQRPSVRLFW REHLHASVDG RELRESTRTP  600
TSTKWIRERC AQITGRDFVQ FVHTHINALP SRIRGSRGRR GGGESSLTCR AGCKVRETTA  660
HILQQCHRTH GGRLLRHNKI VSFVAKAMEE NKWTVELEPR LRTSVGLRKP DIIASRDGVG  720
VIVDVQVVSG QRSLDELHRE KRNKYGNHGE LVELVAGRLG LPKAECVRAT SCTISWRGVW  780
SLTSYKELRS IIGLREPTLQ IVPILALRGS HMNWTRFNQM TSVMGGGVG              829

SEQ ID NO: 60              moltype = RNA   length = 38
FEATURE                    Location/Qualifiers
misc_feature               1..38
                           note = Synthesized
source                     1..38
                           mol_type = other RNA
                           organism = synthetic construct
SEQUENCE: 60
cagtcagtca gtcagtcagt gccaaatgcc tcgtcatc                           38

SEQ ID NO: 61              moltype = DNA   length = 19
FEATURE                    Location/Qualifiers
misc_feature               1..19
                           note = Synthesized
source                     1..19
                           mol_type = other DNA
                           organism = synthetic construct
SEQUENCE: 61
tgatgacgag gcatttggc                                                19

SEQ ID NO: 62              moltype = DNA   length = 28
FEATURE                    Location/Qualifiers
misc_feature               1..28
                           note = Synthesized
source                     1..28
                           mol_type = other DNA
                           organism = synthetic construct
SEQUENCE: 62
gttaataacg aaatgagcag ccrgrgrg                                      28

SEQ ID NO: 63              moltype = DNA   length = 22
FEATURE                    Location/Qualifiers
misc_feature               1..22
                           note = Synthesized
source                     1..22
                           mol_type = other DNA
                           organism = synthetic construct
SEQUENCE: 63
cagggttatt gtctcatgag cg                                            22

SEQ ID NO: 64              moltype = DNA   length = 21
FEATURE                    Location/Qualifiers
```

```
misc_feature         1..21
                     note = Synthesized
source               1..21
                     mol_type = other DNA
                     organism = synthetic construct
SEQUENCE: 64
gccattcgcc attcaggctg c                                              21

SEQ ID NO: 65        moltype = DNA  length = 204
FEATURE              Location/Qualifiers
misc_feature         1..204
                     note = Synthesized
source               1..204
                     mol_type = other DNA
                     organism = synthetic construct
SEQUENCE: 65
acggccagtg aattgtaata cgactcacta tagggcgaat tgggtaccgc ctcgaggtcg    60
acggtatcga taagcttgat atcgaattcc tgcagcggat ccactagttc tagagcgcc   120
gccaccgcgg tggagctcca gcttttgttc cctttagtga gggttaattt cgagcttggc   180
gtaatcatgg tcatagctgt ttcc                                          204

SEQ ID NO: 66        moltype = DNA  length = 24
FEATURE              Location/Qualifiers
misc_feature         1..24
                     note = Synthesized
source               1..24
                     mol_type = other DNA
                     organism = synthetic construct
SEQUENCE: 66
acggccagtg aattgtaata cgac                                           24

SEQ ID NO: 67        moltype = DNA  length = 19
FEATURE              Location/Qualifiers
misc_feature         1..19
                     note = Synthesized
source               1..19
                     mol_type = other DNA
                     organism = synthetic construct
SEQUENCE: 67
ggaaacagct atgaccatg                                                 19
```

METHODS OF cDNA PREPARATION

RELATED APPLICATIONS

A "Sequence Listing XML" is submitted herewith in XML file format and (i) the name of the file is DGEN-002-Seqs.xml; (ii) the date of creation is Aug. 14, 2023; and (iii) the size of the file is 104,538 bytes and the material in the XML file is incorporated by reference.

BACKGROUND

A common technique used to study gene expression in living cells is to produce complementary deoxyribonucleic acid (cDNA) from a ribonucleic acid (RNA) molecule. This technique provides a means to study RNA from living cells which avoids the direct analysis of inherently unstable RNA. As a first step in cDNA synthesis, the RNA molecules from an organism are isolated from an extract of cells or tissues of the organism. After messenger RNA (mRNA) isolation, using methods such as affinity chromatography utilizing oligo dT (a short sequence of deoxy-thymidine nucleotides), oligonucleotide sequences are annealed to the isolated mRNA molecules and enzymes with reverse transcriptase activity can be utilized to produce cDNA copies of the RNA sequence, utilizing the RNA/DNA primer as a template. Thus, reverse transcription of mRNA is a key step in many forms of gene expression analyses. Generally, mRNA is reverse transcribed into cDNA for subsequent analysis by primer extension or polymerase chain reaction.

Reverse transcriptase has both an RNA-directed DNA polymerase activity and a DNA-directed DNA polymerase activity. The reverse transcription of RNA templates may require a primer sequence which is annealed to an RNA template in order for DNA synthesis to be initiated from the 3' OH of the primer. At room temperature, reverse transcriptase enzymes may allow formation of both perfectly matched as well as mismatched DNA/RNA hybrids. In some instances, a reverse transcriptase enzyme can produce large amounts of non-specific cDNA products as a result of such non-specific priming events. The products of non-specific reverse transcription can interfere with subsequent cDNA analyses, such as cDNA sequencing, real-time polymerase chain reaction (PCR), and alkaline agarose gel electrophoresis, among others. Non-specific cDNA templates produced by non-specific reverse transcriptase activity can present particular difficulties in applications such as real-time PCR. In particular, such non-specific cDNA products can give rise to false signals which can complicate the analysis of real-time PCR signals and products. Thus, the reduction of non-specific reverse transcriptase activity may result in greater specificity of cDNA synthesis. Currently, there are no reliable and easy to use methods for improving the specificity of reverse transcription. The present disclosure satisfies these and other needs.

Several approaches may be used for obtaining transcriptome data from single cells. A pioneer approach used reverse transcriptase and oligo-dT primers with a T7 phage RNA polymerase promoter sequence attached to the 5' end of the oligo-dT run. The resulting cDNA was transcribed into multiple copies of RNA which were then converted back to cDNA (Phillips, et al., Methods 10(3):283-288 (1996)). This often truncates the cDNA molecule, losing 5' sequences of the original mRNA, especially for relatively long transcripts, and requires multiple rounds of processing when starting with low quantity (LQ) of cells, further exacerbating cDNA truncation. A recent modification (Hashimshony, et al., Cell Rep. 2(3):666-673 (2012)) enables multiplex analyses, but this is still 3' end sequence biased. Other methods are based on PCR amplification of cDNA (Liu, et al., Methods Enzymol. 303:45-55 (1999), Ozsolak, et al., Genome Res. 20(4): 519-525 (2010), Gonzalez, et al., PLoS ONE. 5(12):e14418 (2010), Kanamori, et al., Genome Res. 21(7):1150-1159 (2011), Islam, et al., Genome Res. 21(7):1160-1167 (2011), Tang, et al., Nat. Methods. 6(5):377-382 (2009), Kurimoto, et al., Nucleic Acids Res. 34(5):e42 (2006), Qiu S, et al., Front Genet. 3:124 (2012)).

These approaches, however, may yield biased representations of sequences along the mRNA, and fail to give complete sequences for mRNAs (e.g., long mRNAs) because DNA templates (e.g., long DNA templates) are discriminated against even when a long PCR reaction is used.

SUMMARY

In some aspects, the disclosure provides a method for generating a non-naturally occurring enzyme comprising: a) expressing a heterologous sequence encoding said non-naturally occurring enzyme in a host, wherein said non-naturally occurring enzyme comprises: a first domain, such as a finger domain, derived from an R2 retrotransposon; a second domain, such as a thumb domain, derived from an R2 retrotransposon; a third domain, such as a palm domain, derived from an R2 retrotransposon; and an endonuclease domain derived from an R2 retrotransposon; b) purifying said non-naturally occurring enzyme from said host, thereby generating said non-naturally occurring enzyme. In some instances, said non-naturally occurring enzyme further comprises a fusion-tag molecule. In other instances, said fusion tag-molecule stabilizes said non-naturally occurring enzyme and said fusion-tag molecule is selected from the group consisting of: Fh8, MBP, NusA, Trx, SUMO, GST, SET, GB1, ZZ, HaloTag, SNUT, Skp, T7PK, EspA, Mocr, Ecotin, CaBP, ArsC, IF2-domain I, an 1F2-domain I derived tag, RpoA, SlyD, Tsf, RpoS, PotD, Crr, msyB, yjgD, rpoD, and His6. In other cases, said fusion-tag molecule is selected from the group consisting of: His-tag, His6-tag, Calmodulin-tag, CBP, CYD (covalent yet dissociable NorpD peptide), Strep II, FLAG-tag, HA-tag, Myc-tag, S-tag, SBP-tag, Softag-1, Softag-3, V5-tag, Xpress-tag, Isopeptag, SpyTag, B, HPC (heavy chain of protein C) peptide tags, GST, MBP, biotin, biotin carboxyl carrier protein, glutathione-S-transferase-tag, green fluorescent protein-tag, maltose binding protein-tag, Nus-tag, Strep-tag, and thioredoxin-tag. In some instances, at least one of said first domain, said second domain, said third domain, or said endonuclease domain, is derived from an arthropod. In some instances at least one of said first domain, said second domain, said third domain, or said endonuclease is derived from a vertebrate, an echinoderm, a flatworm, a hydra, or silkmoth. In some instances, said non-naturally occurring enzyme has at least 90% identity to SEQ ID NOs: 1-20. In some aspects, said host is selected from bacteria, yeast, algae, cyanobacteria, fungi, a plant cell, *E. coli*, or any combination thereof. In some instances, said non-naturally occurring enzyme comprises a mutagenized motif-1 sequence. In some instances, said mutagenized motif -1 sequence has an improved jumping activity as compared to a wild-type sequence. In some instances, said non-naturally occurring enzyme comprises a mutagenized motif 0 sequence. In some instances, said mutagenized motif 0 sequence has an improved jumping activity as compared to a wild-type sequence. In some instances, said non-naturally occurring enzyme comprises a mutagenized thumb sequence. In some instances, said mutagenized second domain sequence has an improved single-stranded priming efficiency or an improved processivity.

In some instances, the disclosure provides a non-naturally occurring enzyme, comprising (i) a first domain, such as a finger domain, from an R2 retrotransposon; (ii) a second domain, such as a thumb domain, derived from an R2 retrotransposon; (iii) a third domain, such as a palm domain, derived from an R2 retrotransposon; and (iv) an endonuclease domain derived from an R2 retrotransposon. In some instances, said non-naturally occurring enzyme has at least 80% identity to SEQ ID NOs: 1-20.

In some instances, the disclosure provides a method for simultaneously amplifying a ribonucleic acid (RNA) molecule and a deoxyribonucleic (DNA) molecule, comprising: (a) providing a reaction mixture comprising said RNA, DNA and non-naturally occurring enzymes, each of said non-naturally occurring enzymes comprising (i) a first domain, such as a finger domain, derived from a non-retroviral transposon or from an R2 retrotransposon; (ii) a second domain, such as a thumb domain, derived from an R2 retrotransposon; (iii) a third domain, such as a palm domain, derived from an R2 retrotransposon; and (iv) an endonuclease domain derived from an R2 retrotransposon; and (b) subjecting said reaction mixture to conditions sufficient to amplify said RNA and DNA, thereby yielding amplified products of said RNA and said DNA. In some instances, said DNA is complementary DNA derived from a subset of RNA in said reaction mixture.

In some instances, the disclosure provides a method for preparing a complementary deoxyribonucleic acid (cDNA) molecule comprising: (a) partitioning a cell and a non-naturally occurring reverse transcriptase, which cell comprises ribonucleic acid (RNA) molecules; (b) releasing said RNA molecules from said cell in said partition; and (c) in said partition, using said non-naturally occurring reverse transcriptase to synthesize a complementary deoxyribonucleic acid (cDNA) library from said RNA molecule, which non-naturally occurring transcriptase synthesizes said cDNA library at a processivity of 20 nucleotides or longer. In some instances, said non-naturally occurring reverse transcriptase has at least 80% identity to SEQ ID NOs: 1-20. In some instances, said partition further comprises: i) one or more acceptor nucleic acid molecules; and ii) a non-naturally occurring reverse transcriptase, wherein said non-naturally occurring reverse transcriptase has at least 80% identity to SEQ ID NOs: 1-20.

In some aspects, said partition is a reaction space or chamber that may be a droplet, a well, or a tube. In some instances, said droplet may be formed by bringing a first phase in contact with a second phase that is immiscible with the first phase, such as bringing an aqueous phase in contact with an oil phase.

In some instances, the disclosure provides, a method for processing a sample comprising various types of ribonucleic acids (RNAs), comprising using said RNA molecules to synthesize complementary deoxyribonucleic acid (cDNA) molecules in presence of ribosomal ribonucleic acid (rRNA) molecules blocked from transcription, such that less than 30% of said cDNA molecules comprise sequences from said rRNA molecules. In some instances, rRNA may not have been degraded and may be present during reverse transcription.

In some instances, the disclosure provides, a method for processing a mixture comprising ribonucleic acid (RNA) molecules, comprising: (a) in said mixture, fragmenting said RNA molecules to yield a plurality of RNA fragments; (b) bringing one or more single stranded nucleic sequences in contact with said plurality of RNA fragments, which one or more single-stranded nucleic acids sequences have complementarity with at least a subset of said RNA fragments, thereby providing one or more RNA fragment complexes comprising said one or more single-stranded nucleic acids sequences hybridized to said at least said subset of said RNA fragments; and (c) using a reverse transcriptase to synthesize at least one complementary deoxyribonucleic acid (cDNA) molecule from said RNA in presence of said one or more RNA fragment complexes.

In some instances, the disclosure provides a method for sequencing a single stranded nucleic acid molecule, comprising: (a) providing a reaction mixture comprising said single stranded nucleic acid molecule and a non-naturally occurring enzyme, wherein said non-naturally occurring enzyme comprises: a first domain, such as a finger domain, derived from an R2 retrotransposon; a second domain, such as a thumb domain, derived from an R2 retrotransposon; a third domain, such as a palm domain, derived from an R2 retrotransposon; and an endonuclease domain derived from an R2 retrotransposon, (b) subjecting said reaction mixture to conditions sufficient to use said non-naturally occurring enzyme to incorporate individual nucleotides into a growing strand complementary to said single stranded nucleic acid molecule, wherein incorporation of said individual nucleotides into said growing strand yields detectable signals; and (c) detecting said detectable signals, thereby sequencing said single stranded nucleic acid molecule. In some aspects, said single stranded nucleic acid molecule is an RNA molecule or a single stranded DNA molecule. In some aspects, said conditions sufficient to directly sequence said single stranded nucleic acid molecule comprise optic based single-molecule sequencing conditions. In some aspects, said conditions sufficient to directly sequence said single stranded nucleic acid molecule comprise microscopy based single-molecule sequencing conditions. In some aspects, said conditions sufficient to directly sequence said single stranded nucleic acid molecule comprise nanopore based single-molecule sequencing conditions. In some aspects, said conditions sufficient to directly sequence said single stranded nucleic acid molecule comprise field-effect transistors based single-molecule sequencing conditions.

In some aspects, the disclosure provides a method comprising: (a) preparing a complementary deoxyribonucleic acid (cDNA) molecule from one or more ribonucleic acid (RNAs), wherein said one or more ribonucleic acid (RNAs) are derived from an in situ tissue of a subject or from a fixed ex vivo tissue of said subject with a non-naturally occurring enzyme, wherein said non-naturally occurring enzyme comprises: a first domain, such as a finger domain, derived from an R2 retrotransposon; a second domain, such as a thumb domain, derived from an R2 retrotransposon; a third domain, such as a palm domain, derived from an R2 retrotransposon; and an endonuclease domain derived from an R2 retrotransposon; thereby generating a cDNA molecule from said in situ tissue of said subject or from said fixed ex vivo tissue of said subject; and (b) sequencing the said cDNA molecule generated in (a). In some aspects, said fixed ex vivo tissue of said subject is fixed in formaldehyde or in paraffin.

In some aspects, the disclosure provides a method for preparing a complementary deoxyribonucleic acid molecule comprising: (a) fragmenting a ribonucleic molecule to yield a plurality of RNA fragments; (b) removing a 3'-phosphate group, a 2'-phosphate group, and cyclic 2'3' phosphate from one or more of said RNA fragments, thereby generating one or more dephosphorylated fragmented RNAs; (c) adding a poly-A tail to said one or more dephosphorylated fragmented RNAs; (d) adding, to said one or more dephosphorylated fragmented RNAs: a primer adapter comprising an oligo-T sequence; an acceptor adapter; and a non-naturally occurring R2 enzyme having a processivity of 20 nucleotides or longer wherein said non-naturally occurring R2 enzyme reverse transcribes a sequence from said one or more dephosphorylated fragmented RNAs in a 3' to 5' order, wherein said R2 enzyme jumps to a 3'-end of said acceptor adapter upon reaching the 5' end of said one or more dephosphorylated fragmented RNAs. In some aspects, said acceptor adapter comprises a nucleotide analogue. In some aspects, said nucleotide analogue is at the 5' end of said acceptor adapter, of said primer adapter, or both. Some aspects further comprise removing one or more non-annealed primer-adapter of (d)(i) prior to adding said non-naturally occurring R2 enzyme. In some instances, said one or more non-annealed primer-adapter is removed with an immobilized poly A oligo. In some aspects, said acceptor adapter comprises a 3'-dideoxy nucleotide at the acceptor-adapter 3'-end.

In some aspects, the disclosure provides a method for preparing a complementary deoxyribonucleic acid molecule comprising: (a) fragmenting a ribonucleic (RNA) molecule to yield a plurality of fragmented RNA fragments; (b) adding, to said one or more fragmented RNAs: a primer adapter; an acceptor adapter; and a non-naturally occurring R2 enzyme having a processivity of 20 nucleotides or longer wherein said non-naturally occurring R2 enzyme primes the reverse transcription using a plurality of ssDNA primers that are not complementary to a template, wherein said R2 enzyme jumps to a 3'-end of said acceptor adapter upon reaching the 5' end of said fragmented RNAs.

In some aspects, the disclosure provides a method for preparing a complementary deoxyribonucleic acid molecule comprising: a) fragmenting a ribonucleic (RNA) molecule to yield a plurality of fragmented RNA fragments; b) adding, to said one or more fragmented RNAs: i. a primer adapter; ii. an acceptor adapter; and enzyme; wherein said enzyme primes the reverse transcription using a plurality of ssDNA primers that are not complementary to a template, wherein said enzyme jumps to a 3'-end of said acceptor adapter upon reaching the 5' end of said fragmented RNAs. In some instances, said enzyme is a non-naturally occurring R2 enzyme.

In some aspects, the disclosure provides a method for preparing a complementary deoxyribonucleic acid molecule comprising: a) adding to a non-fragmented ribonucleic (RNA) molecule: i. a primer adapter; ii. an acceptor adapter; and iii. an enzyme wherein said enzyme primes the reverse transcription using a plurality of ssDNA primers that are not complementary to a template, wherein said enzyme jumps to a 3'-end of said acceptor adapter upon reaching the 5' end of said fragmented RNAs. In some instances, said enzyme is a non-naturally occurring R2 enzyme.

In some aspects, the disclosure provides a method for depleting a plurality of ribonucleic acid (RNAs) from a sample, comprising: (a) synthesizing a complementary deoxyribonucleic acid (cDNA) molecule from a ribonucleic acid template from said sample, (b) incorporating a first adapter molecule to a 3' of said synthesized cDNA molecule and incorporating a second adapter molecule to a 5' end of said synthesized cDNA; (c) performing at most 10 cycles of a polymerase chain reaction (PCR) with a modified-oligo probe complementary to said rDNA sequence, wherein said modified-oligo probe is configured to permit binding of said probe to a solid support, thereby generating a hybridized product that is bound to said solid support in the reaction mixture; (d) removing the synthesized cDNA from said reaction mixture while the hybridized product is bound to said solid support, thereby depleting said plurality of ribonucleic acid (RNAs) from said sample.

In some aspects the disclosure provides a method for depleting a plurality of ribonucleic acid (RNAs) from a sample, comprising: a) synthesizing an asymmetric double stranded deoxyribonucleic acid molecule that is protected from enzymatic degradation at a first 5' end and unprotected at a second 5' end from a ribonucleic (RNA) molecule by adding to a reaction vessel comprising an RNA molecule i. a primer, wherein said primer comprises a modification at its 5' end that is configured to prevent enzymatic degradation by a 5' to 3' exonuclease; and ii. an enzyme; under conditions sufficient to allow for the synthesis of said asymmetric double stranded deoxyribonucleic acid molecule; (b) adding a 5' to 3' exonuclease to the product of step (a), thereby generating a ssDNA having a pre-determined polarity; and (c) depleting said plurality of RNAs from the product of said (b) by hybridizing one of more probes to said plurality of RNAs and performing a pull-down reaction.

In some aspects, the disclosure provides a method for preparing a sample for ribonucleic acid (RNA) sequencing, comprising: (a) individually labeling a plurality of single cells with a plurality of unique barcodes; (b) combining said plurality of single cells in a single pot; (c) performing an RNA sequencing reaction on said plurality of single cells; (d) selecting a cell of interest based on said RNA sequencing reaction and identifying a unique barcode associated with said cell of interest, wherein said selecting and said identifying are performed in a computer program product; (e) hybridizing a primer to said unique barcode associated with said cell of interest and performing an amplification reaction in said hybridized sample, thereby generating a plurality of amplicons.

In some aspects, the disclosure provides a method for preparing a sample for ribonucleic acid (RNA) sequencing, comprising: (a) dissociating a tissue sample in a lysis reaction, thereby generating a plurality of nucleic acid templates from said dissociated sample, wherein said nucleic acid templates comprise ribonucleic acid; (b) synthesizing a complementary deoxyribonucleic acid (cDNA) molecule from said plurality of nucleic acid templates from said dissociated sample, wherein said cDNA molecule is synthesized with a non-naturally occurring R2 enzyme having a processivity of 20 nucleotides or longer, wherein the synthesis is performed in the presence of one or more regents used in said lysis reaction or in the presence of a plurality of cell debris from said tissue sample.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications, and NCBI accession numbers mentioned in this specification are herein incorporated by reference to the same extent as if each individual publication, patent, patent application, or NCBI accession number was specifically and individually indicated to be incorporated by reference. To the extent publications and patents, patent applications, or NCBI accession numbers incorporated by reference contradict the disclosure contained in the specification, the specification is intended to supersede and/or take precedence over any such contradictory material.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative instances, in which the principles of the disclosure are utilized, and the accompanying drawings (also "Figure" and "FIG." herein), of which:

Figure 1A:
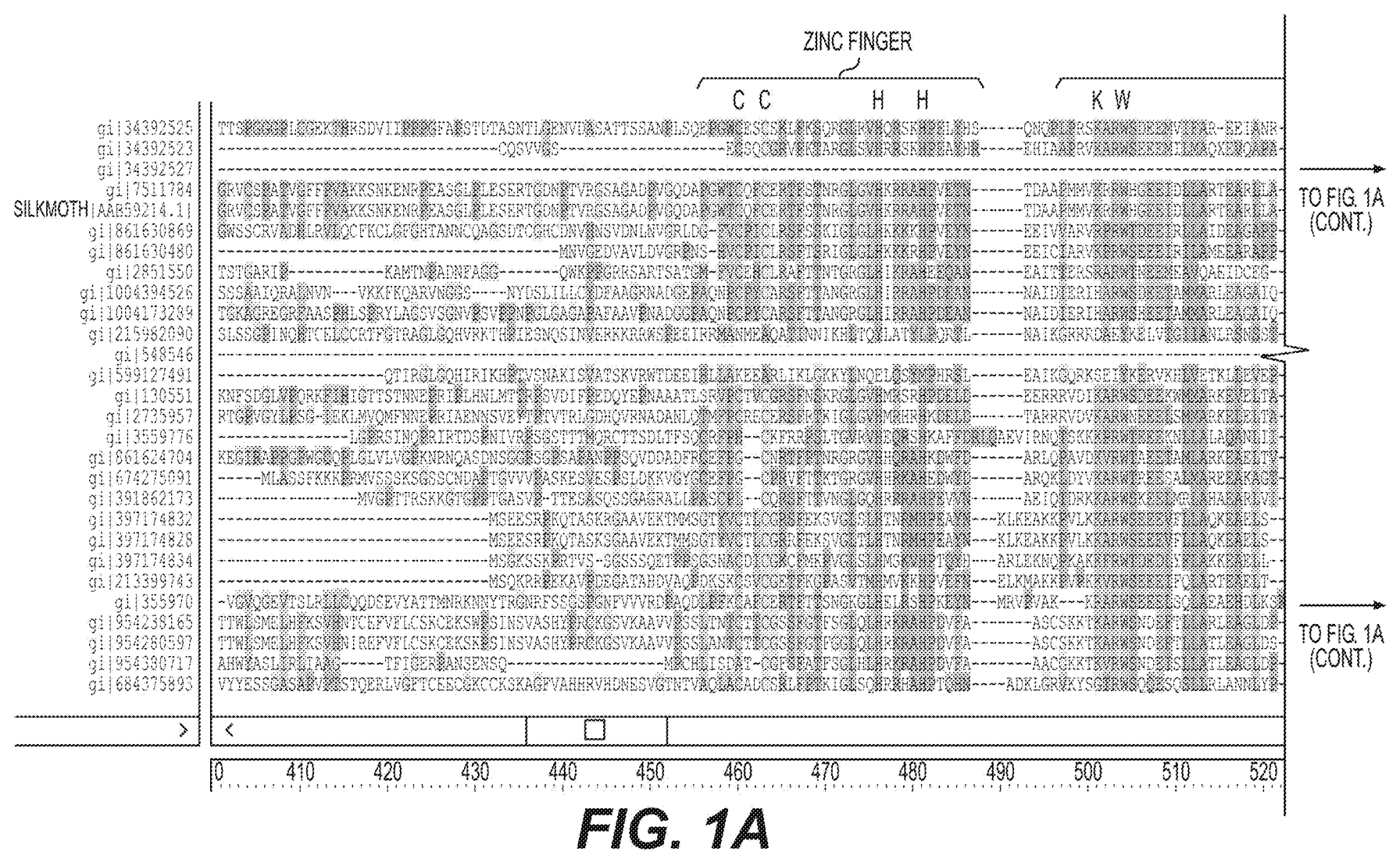
Figure 1A:
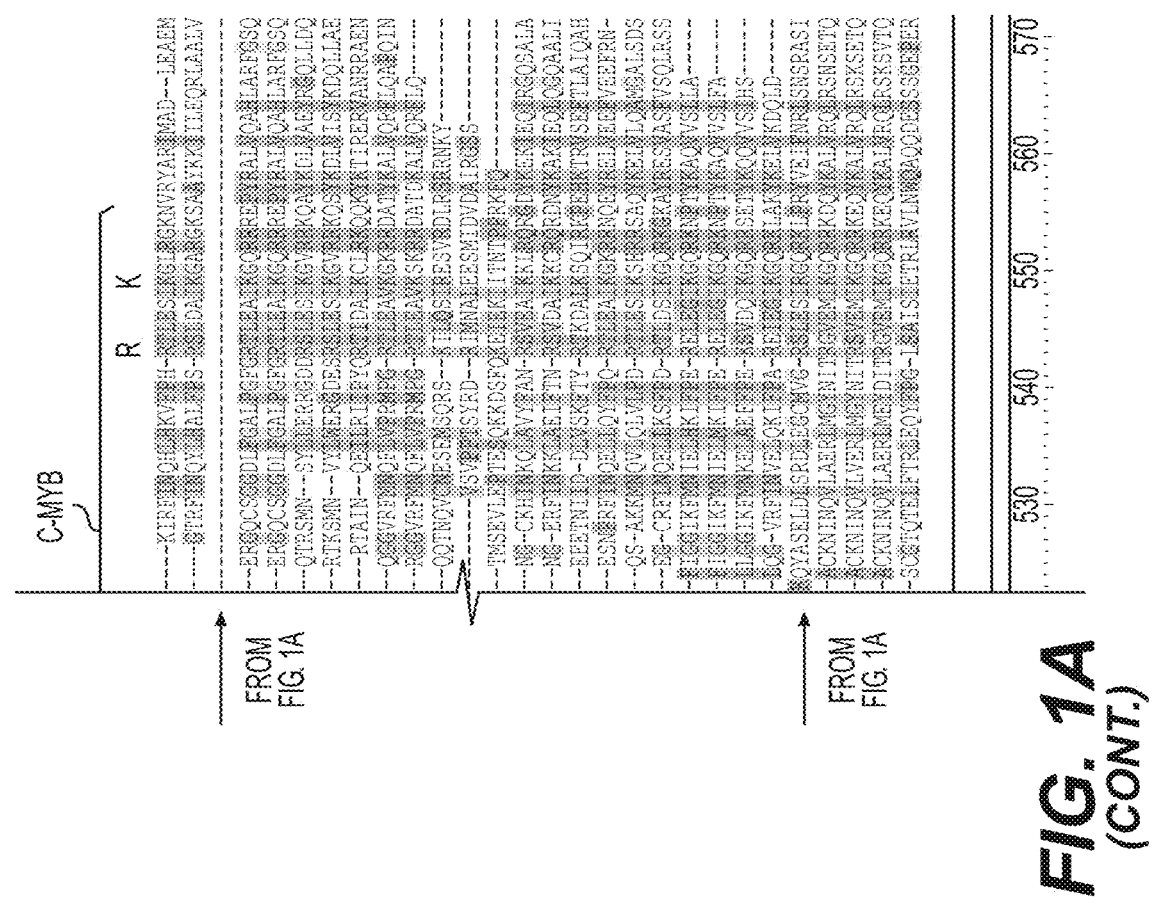
Figure 1B:
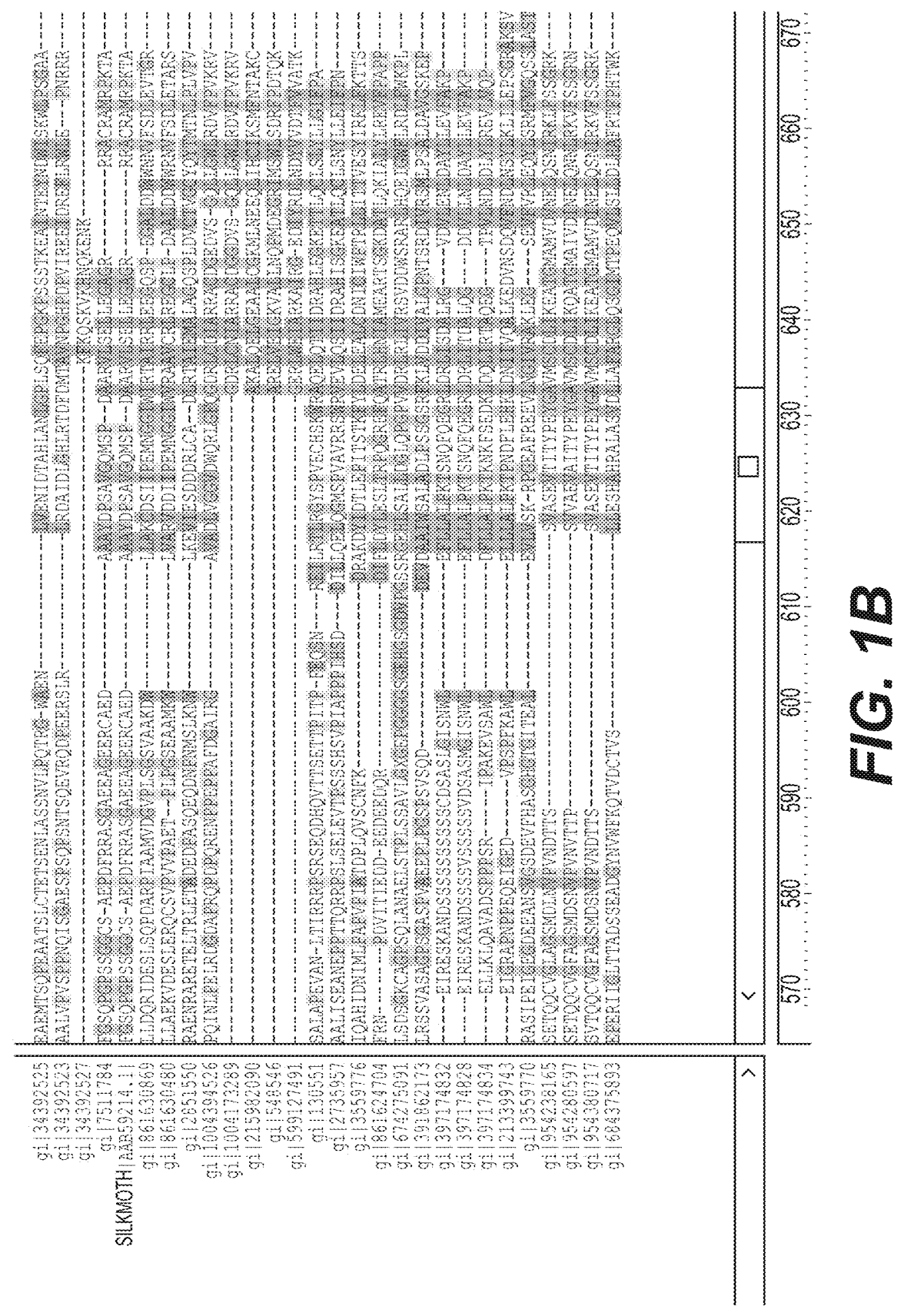

FIG. 1A illustrates the R2 N-terminal Domain. This figure illustrates the comparison of the conserved sequence motifs in the amino-terminal domains of the R2 elements. This figure also highlights the CCHH zinc finger and the KWRK c-myb DNA-binding motifs. The continuation of the N-terminal domain alignment is shown in FIG. 1B.

FIG. 1B illustrates the R2 N-terminal domain. This figure is a continuation of the alignment from Figure TA and as such, also illustrates the comparison of the conserved sequence in the N-terminal domains of R2 elements. The following sequences at the C-terminal are the RT and endonuclease domains, which are not shown in this figure.

FIG. 3 illustrates the R2 reverse transcriptase (RT) thumb domain. This figure illustrates the comparison of the conversed sequence motifs. The R2 RT thumb domain is subjected to engineering/mutagenesis in the method of the present disclosure.

FIG. 4 illustrates the R2 reverse transcriptase (RT) thumb domain. This figure is a continuation of FIG. 3 and illustrates a comparison of the conserved sequence motifs. The R2 RT thumb domain is subjected to engineering/mutagenesis in the method of the present disclosure.

FIG. 5B, however, illustrates a method in which an RCA product, which is rRNA complementary, is used instead of the circular ssDNA (DNA-sponge).

FIG. 14 illustrates the silkmoth R2 reference sequence (SEQ ID NO: 97).

FIG. 15 illustrates motif −1 point mutations.

FIG. 16 illustrates motif 0 point mutations.

FIG. 17 illustrates thumb subunit substitutions, continued in FIG. 18.

FIG. 18 illustrates thumb subunit substitutions. This figure is a continuation of FIG. 17.

FIG. 25 illustrates bioanalyzer traces in Example 25.

DETAILED DESCRIPTION

Figure 1C:
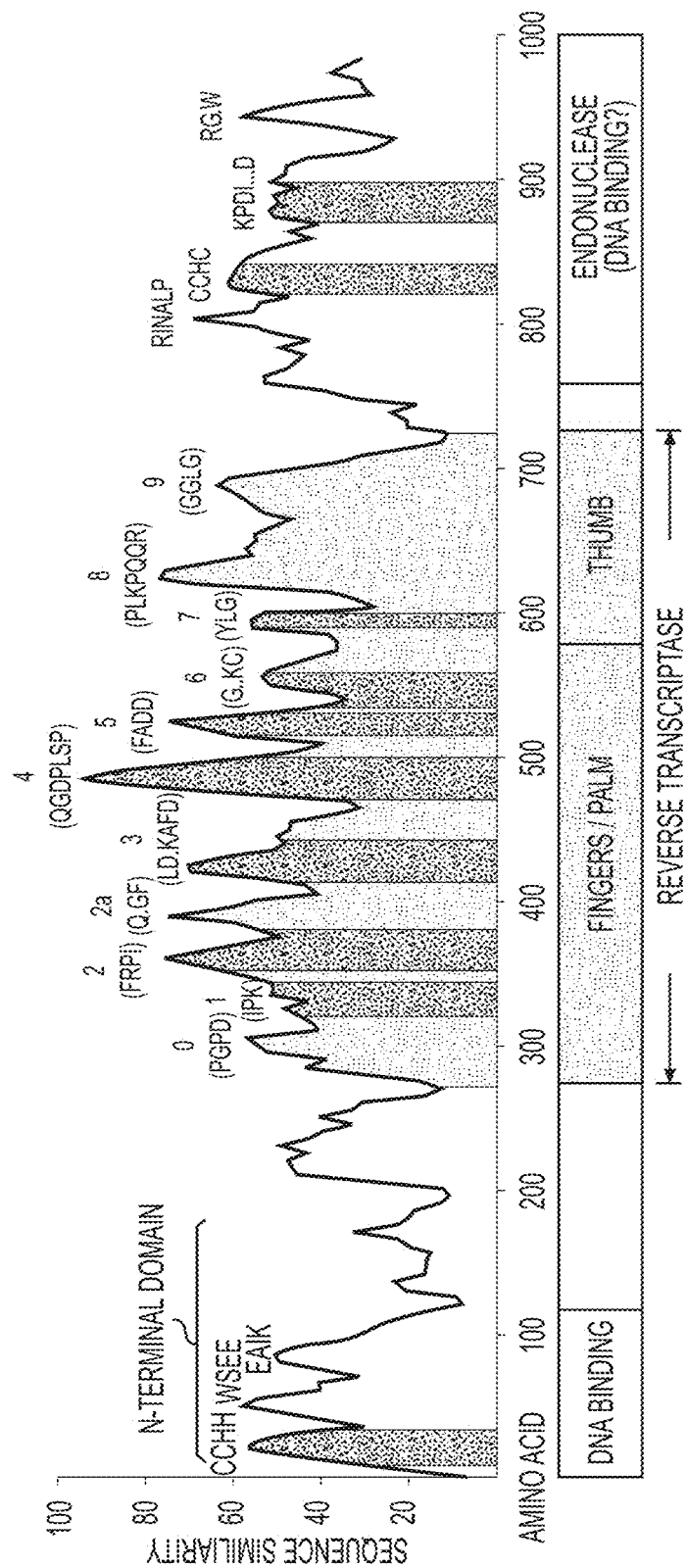
FIG. 1C illustrates a schematic diagram of the amino acid sequence similarity of nine arthropod R2 elements whereby the N-terminal domain is labeled.

While various embodiments of the disclosure have been shown and described herein, it will be obvious to those skilled in the art that such embodiments are provided by way of example only. Numerous variations, changes, and substitutions may occur to those skilled in the art without departing from the disclosure. It should be understood that various alternatives to the embodiments of the disclosure described herein may be employed.

Unless defined otherwise, all technical and scientific terms used herein have the same meaning as commonly understood by one of ordinary skill in the art to which the present disclosure belongs. In case of conflict, the present application including the definitions will control. Also, unless otherwise required by context, singular terms shall include pluralities and plural terms shall include the singular. All publications, patents and other references mentioned herein are incorporated by reference in their entireties for all purposes as if each individual publication or patent application were specifically and individually indicated to be incorporated by reference, unless only specific sections of patents or patent publications are indicated to be incorporated by reference. In order to further define the present disclosure, the following terms, abbreviations and definitions are provided.

The term "about" generally refers to variations in the numerical quantity that may occur, for example, through typical measuring and liquid handling procedures used for making concentrates or solutions in the real world; through inadvertent error in these procedures; through differences in the manufacture, source, or purity of the ingredients employed to make the compositions or to carry out the methods; and the like. The term "about" also encompasses amounts that differ due to different equilibrium conditions for a composition resulting from a particular initial mixture. Whether or not modified by the term "about", the claims include equivalents to the quantities. In some instances, the term "about" means within 10% of the reported numerical value, or within 5% of the reported numerical value, or within 20% of the reported numerical value.

The indefinite articles "a" and "an" preceding an element or component of the present disclosure are intended to be nonrestrictive regarding the number of instances, i.e., occurrences of the element or component. Therefore "a" or "an" should be read to include one or at least one, and the singular word form of the element or component also includes the plural unless the number is meant to be singular.

As used herein, "non-LTR retrotransposon" generally refers to naturally occurring proteins encoded by non-LTR retrotransposons and polypeptide fragments thereof which possess reverse transcriptase activity, as well as proteins or polypeptides derived therefrom which contain one or more amino acid substitutions that either enhance the reverse transcriptase activity thereof or have no deleterious effect thereon. A class of non-LTR retrotransposon is R2 proteins or polypeptides. Thus, as used herein, "R2 protein or R2 enzyme or polypeptide or a functional fragment thereof" refers to naturally occurring proteins encoded by R2 elements and polypeptide fragments thereof which possess reverse transcriptase activity, as well as proteins or polypeptides derived therefrom which contain one or more amino acid substitutions that either enhance the reverse transcriptase activity thereof or have no deleterious effect thereon.

As used herein, the terms "variant," "modified," "non-naturally occurring," and "mutant" are synonymous and refer to a polypeptide or enzyme differing from a specifically recited polypeptide or enzyme by one or more amino acid insertions, deletions, mutations, and substitutions, created using, e.g., recombinant DNA techniques, such as mutagenesis. Guidance in determining which amino acid residues may be replaced, added, or deleted without abolishing activities of interest, may be found by comparing the sequence of the particular polypeptide with that of homologous polypeptides, e.g., yeast or bacterial, and minimizing the number of amino acid sequence changes made in regions of high homology (conserved regions) or by replacing amino acids with consensus sequences. In some instances, the terms "derivative," "variant," "modified," "non-naturally occurring," and "mutant" are used interchangeably.

The terms "anneal", "hybridize" or "bind," generally refer to the combining of one or more single-stranded polynucleotide sequences, segments or strands, and allowing them to form a double-stranded molecule through base pairing. Two complementary sequences (e.g., ribonucleic acid (RNA) and/or deoxyribonucleic acid (DNA)) can anneal or hybridize by forming hydrogen bonds with complementary bases to produce a double-stranded polynucleotide or a double-stranded region of a polynucleotide.

As used herein the term "incorporating" when used with respect to the incorporation of an adapter may refer to the physical attachment of the adapter, to an extension of said adapter, or to the generation of a sequence that is complementary to an adaptor sequence in a nucleic acid molecule.

The term "subject" can be any animal which may benefit from the methods of the disclosure, including, e.g., humans and non-human mammals, such as primates, rodents, horses, dogs and cats. Subjects include without limitation a eukaryotic organism, a mammal such as a primate, e.g., chimpanzee or human, cow; dog; cat; a rodent, e.g., guinea pig, rat, mouse; rabbit; or a bird; reptile; or fish. Subjects specifically intended for treatment using the methods described herein include humans. A subject may be an individual or a patient.

As used herein, the term "primer extension reaction" generally refers to the denaturing of a double-stranded nucleic acid, binding of a primer to one or both strands of the denatured nucleic acid, followed by elongation of the primer(s).

As used herein, the term "reaction mixture" generally refers to a composition comprising reagents necessary to complete nucleic acid amplification (e.g., DNA amplification, RNA amplification), with non-limiting examples of such reagents that include primer sets having specificity for target RNA or target DNA, DNA produced from reverse transcription of RNA, a DNA polymerase, a reverse transcriptase (e.g., for reverse transcription of RNA), suitable buffers (including zwitterionic buffers), co-factors (e.g., divalent and monovalent cations), dNTPs, and other enzymes (e.g., uracil-DNA glycosylase (UNG)), etc). In some cases, reaction mixtures can also comprise one or more reporter agents.

As used herein, a "reporter agent" generally refers to a composition that yields a detectable signal, the presence or absence of which can be used to detect the presence of amplified product.

As used herein, the term "target nucleic acid" generally refers to a nucleic acid molecule in a starting population of nucleic acid molecules having a nucleotide sequence whose presence, amount, and/or sequence, or changes in one or more of these, are desired to be determined. A target nucleic acid may be any type of nucleic acid, including DNA, RNA, and analogues thereof.

The terms "polynucleotides", "nucleic acid", "nucleotides" and "oligonucleotides" can be used interchangeably. They can refer to a polymeric form of nucleotides of any length, either deoxyribonucleotides or ribonucleotides, fragments, or analogs thereof. The following are non-limiting examples of polynucleotides: coding or non-coding regions of a gene or gene fragment, loci (locus) defined from linkage analysis, exons, introns, messenger RNA (mRNA), transfer RNA, transfer-messenger RNA, ribosomal RNA, antisense RNA, small nuclear RNA (snRNA), small nucleolar RNA (snoRNA), micro-RNA (miRNA), small interfering RNA (siRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogues. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. A nucleic acid described herein can contain phosphodiester bonds. In some instances, the nucleic acids can be DNA (including, e.g., genomic DNA, mitochondrial DNA, and cDNA), RNA (including, e.g., mRNA and rRNA) or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc. A polynucleotide is intended to encompass a singular nucleic acid as well as plural nucleic acids. The polynucleotide may be composed of any polyribonucleotide or polydeoxyribonucleotide, which may be unmodified RNA or DNA or modified RNA or DNA. For example, polynucleotides may be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions.

The term "primer", as used herein, refers to an oligonucleotide, occurring naturally as in a purified restriction digest or produced synthetically that is characterized by an ability to be extended against a template oligonucleotide, so that an oligonucleotide whose sequence is complementary to that of at least a portion of the template molecule is linked to the primer, when all are placed in the presence of nucleotides at a suitable temperature and pH. However, the mere ability to be used in this fashion does not require that primers be fully extended against a template, and in some instances, primers are used only as a site for the addition of a small number of non-templated nucleotides. Primers such as primer hexamers having a length of at least 6 nucleotides long can be used. In some instances, a primer may be fluorescently labeled (e.g., 5'-/56FAM/TGATGACGAGG-CATTTGGC/3'). In some instances, primers have a length within the range of about 6 to about 100 nucleotides, or in some instances from about 10 to about 70 nucleotides. In some instances, larger primers can be used. In some instances, random primers may be used. In some instances, a primer may be a random primer. In some instances, one or more primer(s) may be one or more random primer(s).

The term "one or more primer(s)" can comprise any number of primers or random primers. For example, "one or more primer(s)" can include at least, at most, or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 20, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 primers or random primers. One or more primer(s) can include about 1 to about 2, about 1 to about 3, about 1 to about 4, about 1 to about 5, about 1 to about 6, about 1 to about 7, about 1 to about 8, about 1 to about 9, about 1 to about 10, about 1 to about 15, about 1 to about 20, about 1 to about 25, about 1 to about 30, about 1 to about 35, about 5 to about 15, about 3 to about 10, about 5 to about 20, about 10 to about 50, about 30 to about 100, or more than about 100 primers. One or more primer(s) can comprise any number of primers.

The term "random primer," as used herein, refers to a primer containing a random base sequence therein, and is intended to encompass primers whether they consist partially or wholly of random base sequences.

As used herein, "homologue" refers to a protein that is functionally equivalent i.e. has the same enzymatic activity as an enzyme having an amino acid sequence of the specified sequence identification number, but may have a limited number of amino acid substitutions, deletions, insertions or additions in the amino acid sequence. In order to maintain the function of the protein, the substitutions may be conservative substitutions, replacing an amino acid with one having similar properties.

The term "heterologous" refers to a molecule or activity derived from a source other than the referenced species whereas "homologous" refers to a molecule or activity derived from the host microbial organism. Accordingly, exogenous expression of an encoding nucleic acid of the present disclosure may use either or both a heterologous or homologous encoding nucleic acid.

The term "acceptor template," as used herein, generally refers to a nucleic acid molecule that is used to synthesize complementary DNA (cDNA) molecules. The acceptor nucleic acid may be modified. The acceptor nucleic acid molecule may be modified at the 3' end, for example to protect it from being mistaken as an RNA primer. The modification of the acceptor nucleic acid molecule may comprise a dideoxy 3' end. The modification may comprise a phosphorylated 3' end. In some instances, the phosphorylated 3' end of a polynucleotide or of an acceptor nucleic acid molecule, which typically has a hydroxyl group on its 3' end, can act as a 3' block because extension by an enzyme of the present disclosure, or of DNA polymerase for example may be inhibited or ligation by a ligase may be inhibited. Another non-limiting example of a 3' block includes the addition of a 3' C3 spacer (three-carbon spacer) to the 3' end of a polynucleotide which can function as an effective blocking agent against polymerase extension. Zhou, et al., Clin. Chem., 50: 1328-1335 (2004). Thus, the 3' end can be blocked by the addition of, for example, a C3 spacer, a phosphate, an amine group (NH2), or any other chemical modification that inhibits formation of a subsequent phosphodiester bond between the 3' end of the polynucleotide and another nucleotide.

An "overhang sequence," as used herein, generally refers to a single stranded region of nucleic acid extending from a double stranded region.

An "isolated" polynucleotide, as used herein, generally refers a polynucleotide that has been either removed from its natural environment, produced using recombinant techniques, or chemically or enzymatically synthesized. A polynucleotide can also be purified, i.e., essentially free from any other polynucleotides and associated cellular products or other impurities.

The term "polymerase" as used herein, generally refers to an enzyme that links individual nucleotides together into a strand, using another strand as a template. In some instances, the polymerase is a polymerase with editing capabilities. In some instances, the polymerase with editing capabilities may be 3' to 5' exonuclease, T4 DNA polymerase, exonuclease I, Phi29, Pfu, Vent, KOD, exonuclease III, and exonuclease T. Examples of polymerases can include a DNA polymerase, an RNA polymerase, an RNA-directed DNA polymerase, reverse transcriptase, a polypeptide having reverse transcriptase activity, or any variant thereof, a thermostable polymerase, a wild-type polymerase, a modified polymerase, E. coli DNA polymerase I, T7 DNA polymerase, bacteriophage T4 DNA polymerase PHI 29 (phi29) DNA polymerase, Taq polymerase, Tth polymerase, Tli polymerase, Pfu polymerase VENT polymerase, DEEP-VENT polymerase, EX-Taq polymerase, LA-Taq polymerase, Sso polymerase, Poc polymerase, Pab polymerase, Mth polymerase, ES4 polymerase, Tru polymerase, Tac polymerase, Tne polymerase, Tma polymerase, Tca polymerase, Tih polymerase, Tfi polymerase, Platinum Taq polymerases, Tbr polymerase, Tfl polymerase, Tth polymerase, Pfutubo polymerase, Pyrobest polymerase, Pwo polymerase, KOD polymerase, Bst polymerase, Sac polymerase, Klenow fragment, polymerase with 3' to 5' exonuclease activity, and variants, modified products and derivatives thereof. In some instances, the polymerase may be a reverse transcriptase or a modified reverse transcriptase of the present disclosure. In some instances, the polymerase is a single subunit polymerase. The polymerase can have high processivity, namely the capability of the polymerase to consecutively incorporate nucleotides into a nucleic acid template without releasing the nucleic acid template. In some cases a polymerase can be a polymerase described in PCT/US2017/061197, such as P2. PCT/US2017/061197 is incorporated herein in its entirety.

The term "reverse transcriptase" or RT, as used herein, generally refers to an enzyme with both an RNA-directed DNA polymerase and a DNA-directed DNA polymerase. RT refers to a group of enzymes having reverse transcriptase activity (e.g., that catalyze synthesis of DNA from an RNA template). In general, such enzymes include, but are not limited to, retroviral reverse transcriptase, retrotransposon reverse transcriptase, retroplasmid reverse transcriptases, retron reverse transcriptases, bacterial reverse transcriptases, group II intron-derived reverse transcriptase, and mutants, variants or derivatives thereof. Non-retroviral reverse transcriptases include non-long terminal repeat (LTR) retrotransposon reverse transcriptases, retroplasmid reverse transcriptases, retron reverse transcriptases, and group II intron reverse transcriptases. Further bacterial reverse transcriptases are described by Simon D & Zimmerly S (2008) "A diversity of uncharacterized retroelements in bacteria" Nucleic Acids Res 36(22):7219-7229, and Kojima, KK & Kanehisa, M (2008) "Systematic survey for novel types of prokaryotic retroelements based on gene neighborhood and protein architecture" Mol Biol Evol 25:1395-1404, which describe many classes of non-retroviral reverse transcriptases (i.e., retrons, group II introns, and diversity-generating retroelements among others). Reverse transcriptase has been used primarily to transcribe RNA into cDNA, which can then be cloned into a vector for further manipulation or used in various amplification methods such as polymerase chain reaction, nucleic acid sequence-based amplification (NASBA), transcription mediated amplification (TMA), self-sustained sequence replication (3SR), diverse primer extension reactions, 5'RACE, detection of chemical modifications or other techniques that require synthesis of DNA using an RNA template.

Reverse Transcriptases

Reverse transcriptase enzymes may be isolated from a large number of mobile genetic elements which are of retroviral and non-retroviral origin. Such mobile genetic elements are resident in the genomes of higher order species and play a function role in life cycle of these mobile genetic elements. Mobile genetic elements may encode genes for reverse transcriptase enzymes (reviewed in Howard M Temin, Reverse Transcription in the Eukaryotic Genome: Retroviruses. Pararetroviruses, Retrotransposons, and Retrotranscripts, Mol. Biol. Evol. 2(6):455-468). These elements include, but are not limited, to retrotransposons. Retrotransposons include the non-long terminal repeat (LTR) retrotransposon and LTR mobile elements (e.g., TY3, TY5, non-LTR, LINE-L1, R2, R1). (Reviewed by Cordaux and Batzer, Nature Reviews, October 2009, volume 10, pp 691-703.).

Retroelements, genetic elements that encode RTs, are divided into two major families denoted LTR-containing retroelements and non-LTR-containing retroelements (Xiong Y, Eickbush T H (1990) "Origin and evolution of retroelements based upon their reverse transcriptase sequences" EMBO J 9:3353-62). Non-LTR-retroelements are a diverse family of RT-encoding elements that includes retroplasmids, non-LTR-retrotransposons, retrons, and mobile group II introns.

The mutants of the present disclosure may be generated in accordance with any suitable method, including, but not limited to, methods described and exemplified herein. Mutations, such as substitutions, insertions, deletions, and/or side chain modifications, may be introduced into the nucleotide and amino acid sequences of the gene of interest using any suitable technique, including site-directed mutagenesis (Wu, ed., Meth. Enzymol. 217, Academic Press (1993)). The lambda red recombinase method may be used to "knock out" genes (Datsenko et al., PNAS USA 97: 6640-6645 (2000)). Permanent, marker-free, multiple gene disruptions may be created. Non-naturally occurring nucleotides and amino acids also may be used.

Methods of Expressing Non-Naturally Occurring Enzymes from a Host System

Non-naturally occurring enzymes, including R2 enzymes, can be difficult to manufacture, in part because of their size, structural complexity, and amino acid composition. In addition, R2 retroelements are multi-domain elements with molecular masses usually over 100 kD, which increases the challenges in manufacturing R2 enzymes recombinantly. Furthermore, naturally occurring R2 enzymes need to be expressed at low levels in host organisms largely because of their toxic effects to the host. In addition, naturally occurring R2 retroelements are believed to function as dimers.

In some aspects, the disclosure provides recombinantly manufactured enzymes comprising select sequences derived from an R2 retrotransposon and vectors comprising a nucleic acid sequence encoding the recombinantly manufactured enzymes disclosed herein. R2 retroelements are usually composed of three major domains (FIG. 1A, 1B, 1C): an N-terminal domain, a reverse transcriptase domain, and an endonuclease domain. The N-terminal domain may include zinc-finger and c-myb DNA binding motifs, which are believed to contribute to specific recognition and binding to target DNA (target primed reverse transcription mechanism (TPRT). The reverse transcriptase domain is responsible for copying R2 RNA template. Lastly, the endonuclease domain is responsible for specific cleavage of target DNA.

In some aspects, the disclosure provides non-naturally occurring enzymes that are phylogenetically related to one or more elements of an R2 retroelement. In some instances, the enzymes of the disclosure do not comprise the N-terminal domain of an R2 enzyme. In some aspects, the disclosure provides a method for generating a non-naturally occurring enzyme comprising: expressing a heterologous sequence encoding said non-naturally occurring enzyme in a host, wherein said non-naturally occurring enzyme comprises a first, a second, and a third domain derived from an R2 retrotransposon; such as for example, a palm, a finger, and a thumb domain derived from an R2 retrotransposon; an endonuclease domain derived from an R2 retrotransposon; and purifying said non-naturally occurring enzyme from said host, thereby generating said non-naturally occurring enzyme.

In some aspects, the disclosure provides non-naturally occurring enzymes whereby the N-terminal domain is removed. The N-terminal domain is believed to interfere with the expression and stability of R2 retroelements. As such, the removal of parts of the entire N-terminal or parts of the N-terminal is believed to improve the expression and stability of the R2 retroelement without necessarily affecting the disclosed enzyme's ability and performance in RNA library preparation for sequencing. In some aspects, the disclosure identifies the said N-terminal domain using sequence analysis of the R2 retrotransposon and other phylogenetically related R2 retroelements. In some instances, the enzyme of the disclosure is an enzyme that is phylogenetically related to one or more elements of an R2 retroelement and in some instances, the N-terminal domain is removed from said enzyme.

In some aspects, the disclosure provides non-naturally occurring enzymes comprising fusion-tag molecules, whereby the fusion-tag molecule stabilizes the non-naturally occurring enzymes disclosed herein. In some aspects, the fusion-tag molecules are selected from the group consisting of: Fh8, MBP, NusA, Trx, SUMO, GST, SET, GBT, ZZ, HaloTag, SNUT, Skp, T7PK, EspA, Mocr, Ecotin, CaBP, ArsC, IF2-domain I, an IF2-domain I derived tag, RpoA, SlyD, Tsf, RpoS, PotD, Crr, msyB, yjgD, rpoD, and His6.

In some aspects, the disclosure provides non-naturally occurring enzymes comprising fusion-tag molecules, whereby the fusion-tag molecule stabilizes the non-naturally occurring enzymes disclosed herein. In some aspects, the fusion-tag molecules are selected from the group consisting of: His-tag, His6-tag, Calmodulin-tag, CBP, CYD (covalent yet dissociable NorpD peptide), Strep II, FLAG-tag, HA-tag, Myc-tag, S-tag, SBP-tag, Softag-1, Softag-3, V5-tag, Xpress-tag, Isopeptag, SpyTag, B, HPC (heavy chain of protein C) peptide tags, GST, MBP, biotin, biotin carboxyl carrier protein, glutathione-S-transferase-tag, green fluorescent protein-tag, maltose binding protein-tag, Nus-tag, Strep-tag, and thioredoxin-tag.

In some aspects, the disclosure provides non-naturally occurring enzymes, whereby at least one of said palm and finger domain from an R2 retrotransposon, said thumb domain of an R2 retrotransposon, or said endonuclease domain of an R2 retrotransposon are derived from an arthropod.

In some aspects, the disclosure provides non-naturally occurring enzymes, whereby at least one of said palm and finger domain from an R2 retrotransposon, said thumb domain of an R2 retrotransposon, or said endonuclease domain of an R2 retrotransposon is derived from silkmoth.

In some aspects, the disclosure provides non-naturally occurring enzymes, whereby at least one of said palm and finger domain from an R2 retrotransposon, said thumb domain of an R2 retrotransposon, or said endonuclease domain of an R2 retrotransposon is derived from a vertebrate or an echinoderm.

In some aspects, the disclosure provides non-naturally occurring enzymes, whereby at least one of said palm and finger domain from an R2 retrotransposon, said thumb domain of an R2 retrotransposon, or said endonuclease domain of an R2 retrotransposon is derived from a flatworm or a hydra.

In some aspects, the disclosure provides non-naturally occurring enzymes with at least 80% identify to SEQ ID Nos: 1-20, with at least 81% identify to SEQ ID Nos: 1-20, with at least 82% identify to SEQ ID Nos: 1-20, with at least 83% identify to SEQ ID Nos: 1-20, with at least 84% identify to SEQ ID Nos: 1-20, with at least 85% identify to SEQ ID Nos: 1-20, with at least 86% identify to SEQ ID Nos: 1-20, with at least 87% identify to SEQ ID Nos: 1-20, with at least 88% identify to SEQ ID Nos: 1-20, with at least 89% identify to SEQ ID Nos: 1-20, with at least 90% identify to SEQ ID Nos: 1-20, with at least 91% identify to SEQ ID Nos: 1-20, with at least 92% identify to SEQ ID Nos: 1-20, with at least 93% identify to SEQ ID Nos: 1-20, with at least 94% identify to SEQ ID Nos: 1-20, with at least 95% identify to SEQ ID Nos: 1-20, with at least 96% identify to SEQ ID Nos: 1-20, with at least 97% identify to SEQ ID Nos: 1-20, with at least 98% identify to SEQ ID Nos: 1-20, with at least 99% identify to SEQ ID Nos: 1-20, with at least 100% identify to SEQ ID Nos: 1-20.

In some aspects, the disclosure provides non-naturally occurring enzymes wherein the host is selected from bacteria, yeast, algae, cyanobacteria, fungi, a plant cell, or any combination thereof. In some instances, the disclosure provides non-naturally occurring enzymes wherein the host is *E. coli*.

Figure 2:
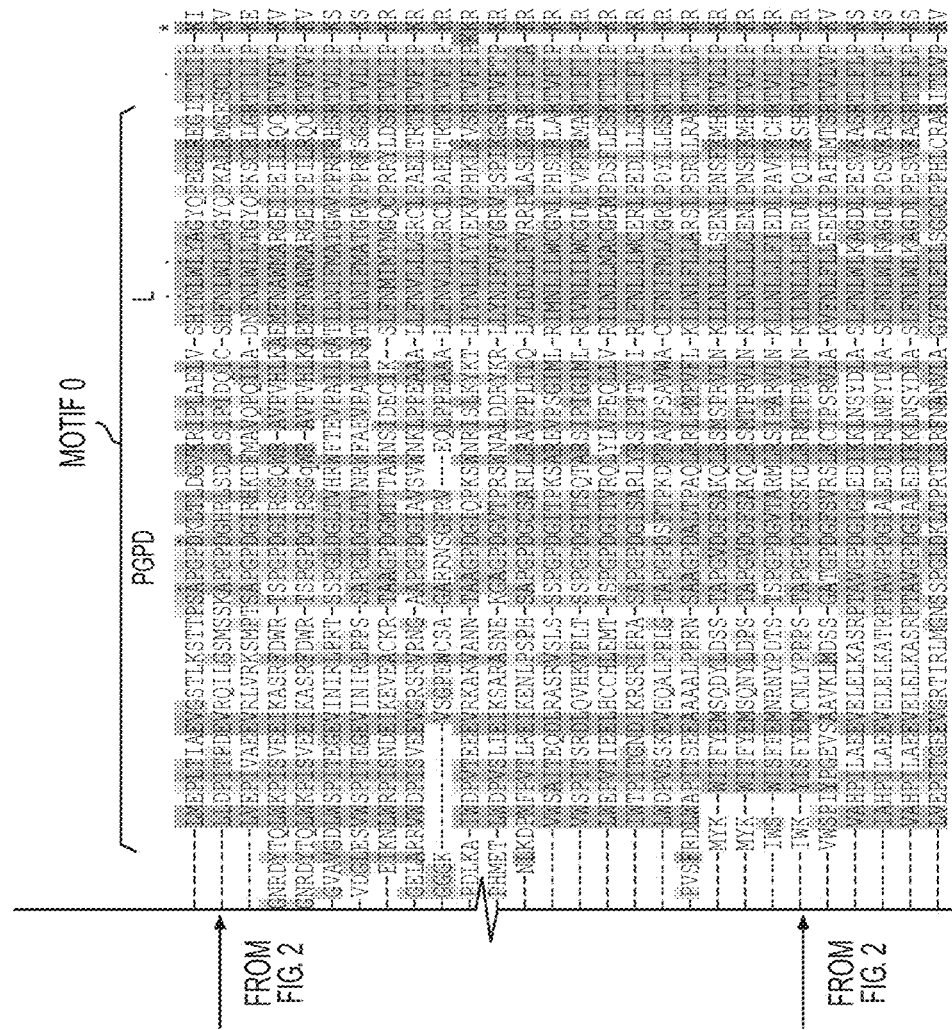
FIG. 2 illustrates the R2 reverse transcriptase. This figure illustrates the comparison of the conserved sequence motifs of the N-terminal portion of the reverse transcriptase R2 elements. This figure highlights motif −1 and motif 0. Both motifs are subjected to engineering/mutagenesis in the method of the present disclosure.
Figure 3:
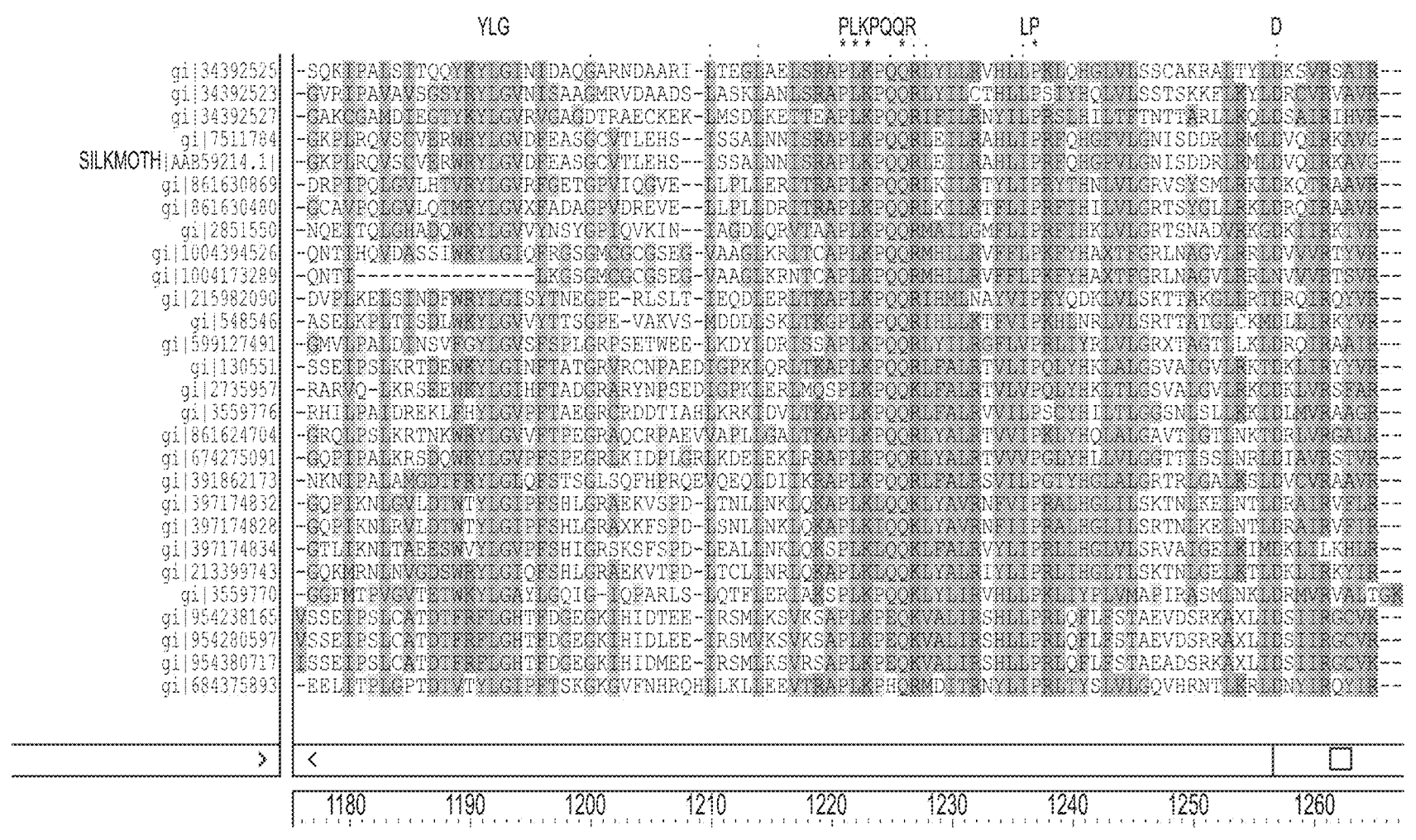
Figure 4:
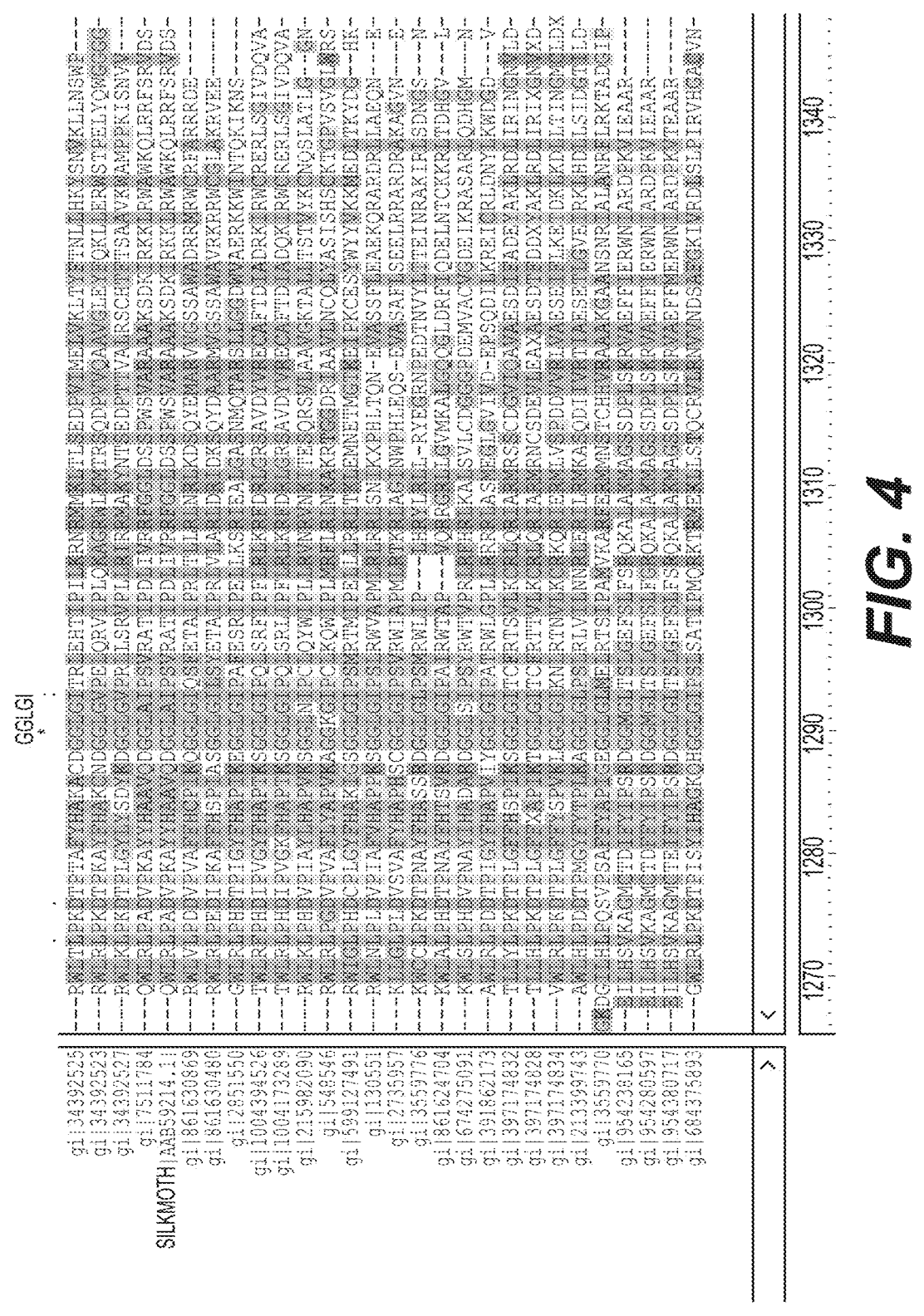
Figure 15:
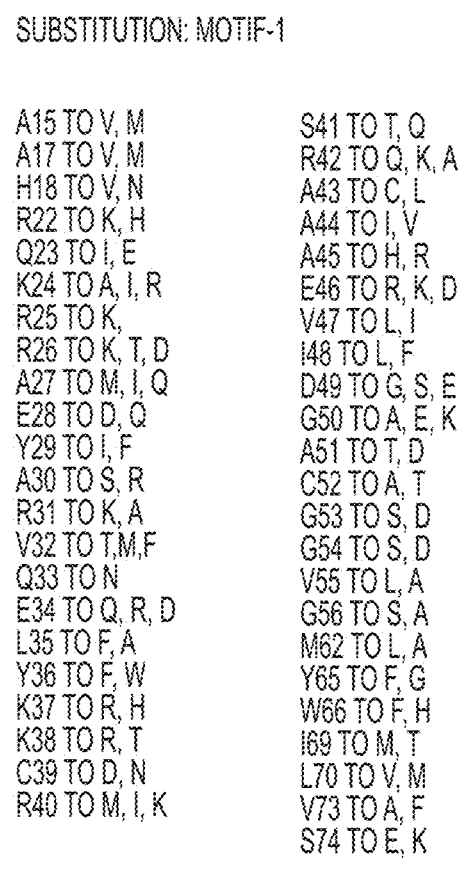

In some aspects, the disclosure provides a non-naturally occurring enzyme, which can comprise one or more amino acid mutations in motif-1, motif-0, and the thumb subunit (FIGS. 2, 3, and 4). Suitable amino acid modifications for improving a property of an R2 related enzyme can be conservative or non-conservative mutations. In some instances, motif-1 and motif-0 can be present in non-long terminal repeat (LTR) retrotransposons and telomerase, but not retroviral transposons and LTR retroelements. A mutation can be made such that the encoded amino acid is modified to a polar, non-polar, basic or acidic amino acid. FIGS. 15 and 16 disclose potential mutations in motif-1 or motif-0 that can improve one or more properties of an R2 enzyme derived from silkmoth, whereby the silkmoth R2 reference sequence is disclosed in FIG. 14. For instance, the following amino acid substitutions may be engineered in motif-1: A15→V15, A15→M15, A17→V17, A17→M17, H18→V18, H18→N18, R22→K22, R22→H22, Q23→I23, Q23→E23, K24→A24, K24→I24, K24→R24, R25→K25, R26→K26, R26→T26, R26→D26, A27→M27, A27→I27, A27→Q27, E28→D28, E28→Q28, Y29→I29, Y29→F29, A30→S30, A30→R30, R31→K31, R31→A31, V32→T32, V32→M32, V32→F32, Q33→N33, E34→Q34, E34→R34, E34→D34, L35→F35, L35→A35, Y36→F36, Y36→W36, K37→R37, K37→H37, K38→R38, K38→T38, C39→D39, C39→N39, R40→M40, R40→I40, R40→K40, S41→T41, S41→Q41, R42→Q42, R42→K42, R42→A42, A43→C43, A43→L43, A44→I44, A44→V44, A45→H45, A45→R45, E46→R46, E46→K46, E46→D46, V47→L47, V47→I47, I48→L48, I48→F48, D49→G49, D49→S49, D49→E49, G50→A50, G50→E50, G50→K50, A51→T51, A51→D51, C52→A52, C52→T52, G53→S53, G53→D53, G54→S54, G54→D54, V55→L55, V55→A55, G56→S56, G56→A56, M62→L62, M62→A62, Y65→F65, Y65→G65, W66→F66, W66→H66, I69→M69, I69→T69, L70→V70, L70→M70, V73→A73, V73→F73, S74→E74, S74→K74.

In some aspects, the disclosure provides a non-naturally occurring enzyme, which can comprise one or more amino acid mutations in motif-1, motif-0, and the thumb subunit (FIGS. 2, 3, and 4). A mutation can be made such that the encoded amino acid is modified to a polar, non-polar, basic or acidic amino acid. FIG. 16 discloses potential mutations in motif-0 that can improve one or more properties of an R2 enzyme derived from silkmoth, whereby the silkmoth R2 reference sequence is disclosed in FIG. 14. In some instances, the following amino acid substitutions may be engineered in motif-0: Q101→N101, Q101→S101, L102→V102, L102→I102, W103→M103, W103→V103, K104→R104, K104→S104, K104→D104, P105→A105, I106→L106, I106→V106, S107→T107, S107→V107, V108→N108, V108→L108, V108→S108, E109→D109, E109→Q109, E109→L109, E110→D110, I111→V111, I111→M111, K112→I112, K112→R112, R115→H115, F116→L116, F116→A116, D117→C117, D117→S117, D117→E117, R119→T119, R119→N119, T120→S120, S121→A121, P122→A122, G123→A123, P124→L124, D125→N125, D125→E125, G126→S126, G126→K126, I127→M127, I127→V127, R128→T128, R128→K128, S129→L129, S129→H129, G130→K130, G130→S130, Q131→D131, Q131→R131, W132→L132, W132→A132, R133→N133, R133→Y133, R133→K133, A134→L134, A134→M134, V135→T135, V135→S135, P136→S136, V137→A137, V137→Q137, H138→I138, H138→A138, L139→A139, L139→M139, L139→V139, K140→R140, K140→N140, K140→L140, A141→deletion, E142→S142, E142→K142, E142→D142, M143→I143, M143→V143, F144→L144, F144→Y144, N145→D145, A146→L146, A146→V146, W147→F147, W147→L147, M148→L148, M148→V148, A149→L149, A149→F149, R150→T150, R150→H150, R150→K150, G151→R151, G151→E151, E152→R152, E152→N152, E152→D152, I153→V153, I153→C153, P154→A154, E155→K155, E155→P155, E155→Q155, E155→A155, D155→D155, I156→E156, I156→R156, I156→V156, L157→V157, L157→F157, R158→K158, R158→L158, R158→K158, Q159→L159, Q159→M159, Q159→H159, Q159→N159, C160→G160, C160→S160, C160→H160, R161→K161.

In some aspects, the disclosure provides a non-naturally occurring enzyme, which can comprise one or more amino acid mutations in motif-1, motif-0, and the thumb subunit (FIGS. 2 and 3). A mutation can be made such that the encoded amino acid is modified to a polar, non-polar, basic or acidic amino acid. FIG. 17 discloses potential mutations in the thumb subunit that can improve one or more properties of an R2 enzyme derived from silkmoth, whereby the silkmoth R2 reference sequence is disclosed in FIG. 14. In some instances, the following amino acid substitutions may be engineered in the thumb subunit: G403→D403, G403→S403, G404→D404, G404→R404, G404→S404, K405→Q405, K405→V405, K405→R405, P406→V406, P406→Q406, P406→K406, L407→V407, L407→M407, R408→G408, R408→P408, R408→H408, R408→T408, R408→K408, Q409→A409, Q409→E409, Q409→S409, V410→M410, V410→L410, S411→D411, S411→G411, S411→K411, C412→I412, C412→H412, C412→A412, C412→R412, V413→E413, V413→L413, V413→A413, V413→G413, E414→G414, E414→H414, E414→Q414, E414→K414, W416→Y416, W416→V416, W416→F416, R417→K417, R417→H417, R417→T417, R417→G417, Y418→F418, L419→V419, L419→I419, G420→A420, V421→I421, V421→A421, V421→H421, D422→R422, D422→W422, D422→N422, D422→T422, D422→P422, D422→E422, F423→V423, F423→Y423, F423→I423, E424→G424, E424→A424, E424→N424, E424→R424, E424→T424, E424→S424, E424→D424, A425→S425, A425→H425, A425→G425, S426→T426, S426→A426, S426→E426, G427→A427, C428→T428, C428→P428, C428→R428, C428→C428→M428, V429→C429, V429→I429, V429→E429, V429→A429, T430→I430, T430→D430, T430→Q430, T430→R430, T430→T430→H430, S434→E434, S434→N434, I435→V435, I435→L435, I435→M435, S436→M436, S436→L436, S436→A436, S436→D436, S436→K436, S437→P437, S437→G437, S437→A437, S437→D437, S437→T437, A438→L438, A438→G438, A438→K438, A438→D438, A438→L438, L439→I439, L439→V439, N440→E440, N440→D440, N440→Q440, N440→K440, N441→E441, N441→R441, N441→A441, N441→Q441, I442→T442, I442→V442, S443→T443, S443→K443, S443→Q443, R444→A444, R444→C444, R444→S444, R444→Q444, R444→K444, A445→G445, A445→S445, P446→G446, L447→I447, K448→R448, P449→L449, Q450→E450, Q450→H450, Q451→E451, Q451→H451, L453→V453, L453→M453, E454→K454, E454→H454, E454→F454, E454→A454, E454→D454, I455→L455, I455→M455, I455→A455, L456→I456, R457→C457, R457→G457, R457→N457, R457→R457→K457, A458→N458, A458→T458, A458→V458, A458→S458, H459→Y459, H459→F459, H459→V459, L460→F460, L460→V460, I461→L461, I461→V461, P462→G462, R463→K463, R463→Q463, R463→G463, F464→Y464, F464→S464, F464→A464, F464→H464, Q465→T465, Q465→Y465, H466→Y466, H466→F466, G467→N467, G467→I467, G467→K467, G467→A467, F468→L468, F468→W468, V469→T469, V469→A469, V469→S469, V469→L469, L470→F470, L470→M470, L470→T470, G471→S471, G471→T471, G471→A471, N472→R472, N472→S472, N472→G472, R477→L477, R477→M477, R477→D477, R477→K477, L478→V478, L478→A478, R479→N479, R479→K479, R479→C479, R479→L479, R479→W479, M480→Q480, M480→K480, M480→T480, M480→R480, L481→G481, L481→T481, L481→M481, D482→N482, D482→E482, V483→S483, V483→K483, V483→R483, V483→L483, Q484→A484, Q484→I484, Q484→V484, Q484→M484, I485→T485, I485→V485, R486→K486, R486→L486, K487→A487, K487→T487, K487→Q487, K487→G487, K487→V487, K487→R487, A488→H488, A488→T488, A488→Y488, A488→S488, G490→R490, G490→K490, Q491→R491, Q491→T491, Q491→K491.

In some aspects, the mutagenized motif-1 sequence has an improved jumping activity compared to the wild-type sequence. In some aspects, the mutagenized motif-0 sequence has an improved jumping activity compared to the wild-type sequences. In some aspects, the mutagenized thumb domain sequence has an improved single-stranded priming efficiency compared to the wild-type sequences. In some instances, the mutagenized thumb domain sequence has an improved processivity compared to the wild-type sequences. Jumping efficiency, single-stranded priming efficiency, and processivity are essential parameters for the conversion efficiency of RNA samples to DNA library.

In some instances, a host cell may be selected from, and the modified or non-naturally occurring enzyme generated in, for example, bacteria, yeast, fungus or any of a variety of other organisms may be used as a host organism.

In some instances, the host is not particularly restricted and the enzymatic activity or activities may be incorporated into any suitable host organism using methods, for example, as described herein. In some instances, the host is selected from bacteria, yeast, algae, cyanobacteria, fungi, or a plant cell, or any combination thereof *E. coli* and *S. cerevisiae* are particularly useful host organisms since they are well characterized microorganisms suitable for genetic engineering. In some instances, the host is *E. coli*.

Each of the enzymes described herein may be attached to an additional amino acid sequence as long as it retains an activity functionally equivalent to that of the enzyme. As mentioned above, it is understood that each enzyme or a homologue thereof may be a (poly)peptide fragment as long as it retains an activity functionally equivalent to that of the enzyme.

In some instances, the enzyme is selected and/or engineered to exhibit high fidelity with low error rates. The fidelity of a nucleotide polymerase is typically measured as the error rate, i.e., the frequency of incorporation of a nucleotide in a manner that may violate the widely known Watson-Crick base pairing rules. The fidelity or error rate of a polymerase (e.g., DNA polymerase) may be measured using any suitable assay. See, for example, Lundburg et al., 1991 Gene, 108:1-6. The term "fidelity" can be used to refer to the accuracy of polymerization, or the ability of the polymerase to discriminate correct from incorrect substrates, (e. g., nucleotides) when synthesizing nucleic acid molecules (e. g. RNA or DNA) which are complementary to a template. The higher the fidelity of an enzyme, the less the enzyme misincorporates nucleotides in the growing strand during nucleic acid synthesis; that is, an increase or enhancement in fidelity results in a more faithful polymerase having decreased error rate (decreased misincorporation rate). In some instances, the misincorporation error rate is at most about 10-2, 10-4, 10-6, or 10-8.

In some aspects, the present disclosure relates to a non-naturally occurring or modified enzyme that can be readily expressed in a recombinant system in a functional form. In some instances, the non-naturally occurring or modified enzyme is an enzyme with reverse transcriptase activity. In some instances, the non-naturally occurring or modified enzyme is a modified reverse transcriptase. In some instances, the non-naturally occurring or modified enzyme is a modified non-retroviral reverse transcriptase. In some instances, the non-naturally occurring or modified enzyme is a modified non-LTR retrotransposon. In some instances, the non-naturally occurring or modified enzyme is a modified R2 reverse transcriptase, comprising mutations in an R2 Motif-1 or Motif-0. In some instances, a non-naturally occurring or modified enzyme or a modified polypeptide having reverse transcriptase activity can amplify a template nucleic acid molecule at a processivity of at least about 80% per base, of at least 81% per base, of at least 82% per base, of at least 83% per base, of at least 84% per base, of at least about 85% per base, of at least 86% per base, of at least 87% per base, of at least about 88% per base, of at least about 89% per base, of at least about 90% per base, of at least about 91% per base, of at least about 92% per base, of at least about 93% per base, of at least about 94% per base, of at least about 95% per base, of at least about 96% per base, of at least about 97% per base, of at least about 98% per base, of at least about 99% per base, of at least about 99.5% per base, or of about 100% per base.

In some instances, a non-naturally occurring or modified enzyme or a modified polypeptide having reverse transcriptase activity can amplify or is capable of amplifying a template nucleic acid molecule at a processivity measured at a temperature of between about 12° C. and about 40° C. In some instances, the temperature is between about 10° C. and about 35° C., between about 12° C. and about 30° C., between about 25° C. and about 40° C., or between about 12° C. and about 42° C. In some instances, the temperature is between about 8° C. to about 50° C., between about 2° C. to about 60° C., between about 8° C. to about 42° C., between about 6° C. to about 32° C., or between about 7° C. to about 35° C.

In some instances, a non-naturally occurring or modified enzyme or a modified polypeptide having reverse transcriptase activity can amplify or is capable of amplifying a template nucleic acid molecule at a processivity of at least about 80% per base at a temperature at about or at most about 4° C., at about or at most about 8° C., at about or at most about 12° C., at about or at most about 15° C., at about or at most about 20° C., at about or at most about 25° C., at about or at most about 30° C., at about or at most about 35° C., at about or at most about 40° C., or at about or at most about 42° C.; of at least about 85% per base at a temperature of about or at most about 12° C., at about or at most about 15° C., at about or at most about 20° C., at about or at most about 25° C., at about or at most about 30° C., at about or at most about 35° C., at about or at most about 40° C., at about or at most about 42° C., at about or at most about 45° C., at about or at most about 50° C.; of at least about 89% per base at a temperature at about or at most about 4° C., at about or at most about 8° C., at about or at most about 12° C., at about or at most about 15° C., at about or at most about 20° C., at about or at most about 25° C., at about or at most about 30° C., at about or at most about 35° C., at about or at most about 40° C., or at about or at most about 42° C.; of at least about 90% per base at a temperature of about or at most about 12° C., at about or at most about 15° C., at about or at most about 20° C., at about or at most about 25° C., at about or at most about 30° C., at about or at most about 35° C., at about or at most about 40° C., at about or at most about 42° C., at about or at most about 45° C., at about or at most about 50° C.; of at least about 91% per base at a temperature at about or at most about 4° C., at about or at most about 8° C., at about or at most about 12° C., at about or at most about 15° C., at about or at most about 20° C., at about or at most about 25° C., at about or at most about 30° C., at about or at most about 35° C., at about or at most about 40° C., or at about or at most about 42° C.; of at least about 85% per base at a temperature of about or at most about 12° C., at about or at most about 15° C., at about or at most about 20° C., at about or at most about 25° C., at about or at most about 30° C., at about or at most about 35° C., at about or at most about 40° C., at about or at most about 42° C., at about or at most about 45° C., at about or at most about 50° C.; of at least about 95% per base at a temperature at about or at most about 4° C., at about or at most about 8° C., at about or at most about 12° C., at about or at most about 15° C., at about or at most about 20° C., at about or at most about 25° C., at about or at most about 30° C., at about or at most about 35° C., at about or at most about 40° C., or at about or at most about 42° C.; of at least about 85% per base at a temperature of about or at most about 12° C., at about or at most about 15° C., at about or at most about 20° C., at about or at most about 25° C., at about or at most about 30° C., at about or at most about 35° C., at about or at most about 40° C., at about or at most about 42° C., at about or at most about 45° C., at about or at most about 50° C.; of at least about 99% per base at a temperature at about or at most about 4° C., at about or at most about 8° C., at about or at most about 12° C., at about or at most about 15° C., at about or at most about 20° C., at about or at most about 25° C., at about or at most about 30° C., at about or at most about 35° C., at about or at most about 40° C., or at about or at most about 42° C.; of at least about 85% per base at a temperature of about or at most about 12° C., at about or at most about 15° C., at about or at most about 20° C., at about or at most about 25° C., at about or at most about 30° C., at about or at most about 35° C., at about or at most about 40° C., at about or at most about 42° C., at about or at most about 45° C., at about or at most about 50° C.; of at least about 99.5% per base at a temperature at about or at most about 4° C., at about or at most about 8° C., at about or at most about 12° C., at about or at most about 15° C., at about or at most about 20° C., at about or at most about 25° C., at about or at most about 30° C., at about or at most about 35° C., at about or at most about 40° C., or at about or at most about 42° C.; of at least about 85% per base at a temperature of about or at most about 12° C., at about or at most about 15° C., at about or at most about 20° C., at about or at most about 25° C., at about or at most about 30° C., at about or at most about 35° C., at about or at most about 40° C., at about or at most about 42° C., at about or at most about 45° C., at about or at most about 50° C.; or of about 100% per base at a temperature at about or at most about 4° C., at about or at most about 8° C., at about or at most about 12° C., at about or at most about 15° C., at about or at most about 20° C., at about or at most about 25° C., at about or at most about 30° C., at about or at most about 35° C., at about or at most about 40° C., or at about or at most about 42° C.; of at least about 85% per base at a temperature of about or at most about 12° C., at about or at most about 15° C., at about or at most about 20° C., at about or at most about 25° C., at about or at most about 30° C., at about or at most about 35° C., at about or at most about 40° C., at about or at most about 42° C., at about or at most about 45° C., at about or at most about 50° C.

In some instances, the non-naturally occurring or modified enzyme or a modified polypeptide having reverse transcriptase activity can amplify or is capable of amplifying a template nucleic acid molecule at a processivity of at least about 80% per base at a temperature of at most about 35° C., of at least about 85% per base at a temperature of at most about 40° C., of at least about 88% per base at a temperature of at most about 35° C., of at least about 89% per base at a temperature of at most about 40° C., of at least about 90% per base at a temperature of at most about 35° C., of at least about 91% per base at a temperature of at most about 35° C., of at least about 92% per base at a temperature of at most about 40° C., of at least about 93% per base at a temperature of at most about 35° C., of at least about 94% per base at a temperature of at most about 40° C., of at least about 95% per base at a temperature of at most about 35° C., of at least about 96% per base at a temperature of at most about 40° C., of at least about 97% per base at a temperature of at most about 35° C., of at least about 98% per base at a temperature of at most about 40° C., of at least about 99% per base at a temperature of at most about 40° C., of at least about 99.5% per base at a temperature of at most about 40° C., or of about 100% per base at a temperature of at most about 40° C.

In some instances, the improved enzyme property is selected from at least one of the following: improved stability (e.g., improved thermostability), improved specific activity, improved protein expression, improved purification, improved processivity, improved strand displacement, improved template jumping, improved DNA/RNA affinity, improved single strand DNA priming, and improved fidelity. In some instances, a non-naturally occurring enzyme or a modified enzyme or a modified polypeptide having reverse transcriptase activity amplifies a template nucleic acid molecule. In some instances, the non-naturally occurring enzyme or the modified enzyme or the modified polypeptide having reverse transcriptase activity that amplifies a template nucleic acid molecule has a performance index greater than about 1, greater than about 2, greater than about 3, greater than about 4, greater than about 5, greater than about 6, greater than about 7, greater than about 8, greater than about 9, greater than about 10, greater than about 15, greater than about 20, greater than about 25, greater than about 30, greater than about 35, greater than about 40, greater than about 45, greater than about 50, greater than about 60, greater than about 70, greater than about 80, greater than about 90, or greater than about 100 for at least one enzyme property. In some instances, the enzyme property and/or the performance index is performed at a temperature equal to or lower than or at most about 50° C., equal to or lower than or at most about 42° C., equal to or lower than or at most about 40° C., equal to or lower than or at most about 39° C., equal to or lower than or at most about 38° C., equal to or lower than or at most about 37° C., equal to or lower than or at most about 36° C., equal to or lower than or at most about 35° C., equal to or lower than or at most about 34° C., equal to or lower than or at most about 33° C., equal to or lower than or at most about 32° C., equal to or lower than or at most about 31° C., equal to or lower than or at most about 30° C., equal to or lower than or at most about 29° C., equal to or lower than or at most about 28° C., equal to or lower than or at most about 27° C., equal to or lower than or at most about 26° C., equal to or lower than or at most about 25° C., equal to or lower than or at most about 23° C., equal to or lower than or at most about 20° C., equal to or lower than or at most about 15° C., equal to or lower than or at most about 13° C., equal to or lower than or at most about 12° C., equal to or lower than or at most about 10° C., equal to or lower than or at most about 8° C., equal to or lower than or at most about 4° C. In some instances, the non-naturally occurring enzyme or the modified enzyme (e.g., modified reverse transcriptase) or the modified polypeptide having reverse transcriptase activity exhibits a processivity for a given nucleotide substrate that is at least about 5%, at least about 10%, at least about 15%, at least about 20%, at least about 25%, at least about 30%, at least about 35%, at least about 37.5%, at least about 40%, at least about 45%, at least about 50%, at least about 60%, at least about 70%, at least about 75%, at least about 80%, at least about 90%, at least about 95%, at least about 100%, at least about 110%, at least about 125%, at least about 150%, at least about 170%, at least about 190%, at least about 200%, at least about 250%, at least about 500%, at least about 750%, at least about 1000%, at least about 5000%, or at least about 10000% higher than the processivity of a reference enzyme or a reference polypeptide for the same nucleotide substrate. In some instances, the non-naturally occurring enzyme is a non-naturally occurring reverse transcriptase enzyme. In some instances, the modified enzyme is a modified reverse transcriptase.

The present disclosure relates to processes and/or methods that require considerably less hands-on time, the protocol is much simpler to perform and requires a much shorter duration time than other methods used for RNA sequencing and/or liquid biopsy, for example. In some instances, the methods and processes of the present disclosure comprises a protocol that is less than about 2 hours and/or less than about 30 minutes of hands-on time. In some instances, the protocol is less than about 20 hours, less than about 15 hours, less than about 12 hours, less than about 11 hours, less than about 10 hours, less than about 9 hours, less than about 8 hours, less than about 7 hours, less than about 6 hours, less than about 5 hours, less than about 4 hours, less than about 3 hours, less than about 2.5 hours, less than about 2 hours, less than about 1.5 hours, less than about 1 hour, or less than about 30 minutes. In some instances, the hands-on time is less than about 5 hours, less than about 4 hours, less than about 3 hours, less than about 2.5 hours, less than about 2 hours, less than about 1.5 hours, less than about 1 hour, less than about 50 minutes, less than about 40 minutes, less than about 35 minutes, less than about 30 minutes, less than about 25 minutes, less than about 20 minutes, or less than about 15 minutes.

In some aspects, the disclosure provides a method for simultaneously amplifying a messenger ribonucleic (mRNA) molecule and a deoxyribonucleic (DNA) molecule. In some instances, said method comprises providing a reaction mixture comprising said mRNA, DNA and non-naturally occurring enzymes, each of said non-naturally occurring enzymes comprising (i) a palm and finger domain derived from an R2 retrotransposon; (ii) a thumb domain derived from an R2 retrotransposon; and (iii) an endonuclease domain derived from an R2 retrotransposon. In some instances, said method comprises subjecting said reaction mixture to conditions sufficient to amplify said mRNA and DNA, thereby yielding amplified products of said mRNA and said DNA. In some instances, said DNA is complementary DNA derived from a subset of mRNA in said reaction mixture.

In some instances, the non-naturally occurring or modified enzyme (e.g., non-naturally occurring or modified reverse transcriptase, non-naturally occurring or modified non-LTR retrotransposon, non-naturally occurring or modified R2 reverse transcriptase) or a modified polypeptide having reverse transcriptase activity exhibits a misincorporation error rate of equal to or less than about 50%, equal to or less than about 45%, equal to or less than about 40%, equal to or less than about 35%, equal to or less than about 30%, equal to or less than about 25%, equal to or less than about 20%, equal to or less than about 15%, equal to or less than about 10%, equal to or less than about 9%, equal to or less than about 8%, equal to or less than about 7%, equal to or less than about 6%, equal to or less than about 5%, equal to or less than about 4%, equal to or less than about 3%, equal to or less than about 2%, equal to or less than about 1%, equal to or less than about 0.01%, equal to or less than about 0.001%, equal to or less than about 0.0001%, equal to or less than about 0.00001%, equal to or less than about 0.000001%, or equal to or less than about 0.0000001%.

In some instances, the non-naturally occurring or modified enzyme (e.g., non-naturally occurring or modified reverse transcriptase, non-naturally occurring or modified non-LTR retrotransposon, non-naturally occurring or modified R2 reverse transcriptase) or a modified polypeptide having reverse transcriptase activity generates one or more nucleic acid (e.g., cDNA) molecule(s) complementary to a template at an error rate that is at least about 10000 times lower, at least about 1500 times lower, at least about 1000 times lower, at least about 500 times lower, at least about 100 times lower, at least about 95 times lower, at least about 90 times lower, at least about 85 times lower, at least about 80 times lower, at least about 75 times lower, at least about 70 times lower, at least about 65 times lower, at least about 60 times lower, at least about 55 times lower, at least about 50 times lower, at least about 45 times lower, at least about 40 times lower, at least about 35 times lower, at least about 30 times lower, at least about 25 times lower, at least about 20 times lower, at least about 15 times lower, at least about 10 times lower, at least about 9 times lower, at least about 8 times lower, at least about 7 times lower, at least about 6 times lower, at least about 5 times lower, at least about 4 times lower, at least about 3 times lower, at least about 2 times lower, or at least about 1 time lower than the unmodified or naturally occurring enzyme or unmodified polypeptide having reverse transcriptase activity.

In some instances, the sequencing error rate will be equal to or less than about 1 in 100,000 bases. In some instances, the error rate of nucleotide sequence determination is equal to or less than about 1 in 10 bases, 1 in 20 bases, 3 in 100 bases, 1 in 100 bases, 1 in 1000 bases, and 1 in 10,000 bases.

In some instances, the modified enzyme (e.g., modified reverse transcriptase), modified reverse transcriptase, non-naturally occurring enzyme, modified polypeptide having reverse transcriptase activity comprises at least one modification relative to the wild type, unmodified counterpart, or naturally occurring enzyme. In some instances, the modified non-LTR retrotransposon comprises at least one modification of a wild-type or unmodified non-LTR retrotransposon. In some instances, the modified R2 reverse transcriptase comprises at least one modification of a wild-type or unmodified R2 reverse transcriptase. In some instances, the modified reverse transcriptase comprises at least one modification of a wild-type or unmodified reverse transcriptase. In some instances, the modified polypeptide having reverse transcriptase activity comprises at least one modification of a wild-type or unmodified polypeptide having reverse transcriptase activity. In some instances, the modification comprises at least one truncation (e.g., N-terminal truncation, C-terminal truncation, and/or N- and C-terminal truncations). In some instances, the modification comprise(s) site-specific incorporation, and/or addition, and/or deletion, and/or substitution of amino acid(s) at positions of interest. In some instances, the modification enhances the biological properties of the modified enzyme or modified polypeptide relative to the wild-type or unmodified enzyme or polypeptide. In some instances, the modification improves at least one enzyme property of the modified enzyme or polypeptide relative to the wild-type or unmodified enzyme or polypeptide. In some instances, the modification(s) serve as a point of attachment for, e.g., labels and protein half-life extension agents, and for purposes of affixing the variants to the surface of a solid support. In some instances, the present disclosure is related to methods of producing cells capable of producing the modified enzymes (e.g., modified reverse transcriptase) or modified polypeptides, and of producing vectors containing DNA or RNA encoding the modified enzymes (e.g., modified reverse transcriptase) or modified polypeptides. In some instances, the truncation is based on a two-step process. In some instances, the first step for selecting a truncation includes analyzing the domains and motifs structure(s) and function(s) of a class of enzymes, or proteins, or polypeptides. In some instances, the enzymes, or proteins, or polypeptides are non-LTR retrotransposons, reverse transcriptases, R2 reverse transcriptase, LTR retrotransposons, R2 non-LTR retrotransposons, or any combination thereof. In some instances, the enzymes, or proteins, or polypeptides are from different organisms. In some instances, all the domains of the enzymes, or proteins, or polypeptides are present. In some instances, all the domains are present to ensure reverse transcriptase activity. In some instances, all the domains are present to ensure the unique properties essential for the present disclosure. In some instances, the domains responsible for reverse transcriptase activity are not modified. In some instances, the R2 domain does not comprise modifications. In some instances, the R2 domain may comprise modifications. In some instances, the truncated variants show expression level. In some instances, the truncated variants that show promising expression level are further subject to small adjustment(s) in the sequence (step two). In some instances, the small adjustment(s) in the sequence include deletion, insertion, and/or substitution of amino acid(s). In some instances, the deletion, insertion, and/or substitution of amino acid(s) may include one or several amino acid(s). In some instances, the deletion, insertion, and/or substitution of amino acid(s) further optimize expression and/or stability (e.g., thermostability).

In some instances, the modified enzyme (e.g., modified reverse transcriptase), modified reverse transcriptase, or modified polypeptides has an N-terminal truncation, a C-terminal truncation, or both, relative to the wild type or unmodified enzyme (e.g., wild-type reverse transcriptase) or wild-type or unmodified polypeptide. In some instances, the polymerase comprises an N-terminal truncation, a C-terminal truncation, or both. In some instances, the modified reverse transcriptase comprises N-terminal truncation, C-terminal truncation, or a combination of N-terminal and C-terminal truncation(s). In some instances, the modified enzyme comprises N-terminal truncation, C-terminal truncation, or a combination of N-terminal and C-terminal truncation(s). In some instances, the modified polypeptide comprises N-terminal truncation, C-terminal truncation, or a combination of N-terminal and C-terminal truncation(s). In some instances, the modified reverse transcriptase, modified enzyme, modified polypeptide, modified non-LTR retrotransposon, or modified R2 reverse transcriptase comprises a truncation of less than about 100 amino acid residues. In some instances, the modified reverse transcriptase, modified enzyme, modified polypeptide, modified non-LTR retrotransposon, or modified R2 reverse transcriptase comprises at least one of: (a) an amino-terminal truncation of less than about 400 amino acid residues and (b) a carboxyl-terminal truncation of less than about 400 amino acid residues. In some instances, the modified reverse transcriptase, modified enzyme, modified polypeptide, modified non-LTR retrotransposon, or modified R2 reverse transcriptase lacks up to: about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 30, about 50, about 75, about 100, about 120, about 150, about 175, about 200, about 220, about 250, about 275, about 280, about 290, about 300, about 325, about 350, about 375, about 380, about 390, about 400, or about 450 amino acids from the N-terminus, C-terminus, or both. In some instances, the modified reverse transcriptase, modified enzyme, modified polypeptide, modified non-LTR retrotransposon, or modified R2 reverse transcriptase may alternately or additionally have one or more internal deletions of up to: about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, or about 25 amino acids, about 30, about 50, about 75, about 100, about 120, about 150, about 175, about 200, about 220, about 250, about 275, about 280, about 290, about 300, about 325, about 350, about 375, about 380, about 390, or a total of about 450 amino acids. In some instances, the N-terminal truncation, C-terminal truncation, or both, may comprise deletions from about 1 to about 50 amino acids, from about 1 to about 25, from about 1 to about 70, from about 10 to about 50, from about 20 to about 30, from about 15 to about 100, from about 1 to about 150, from about 15 to about 60, from about 15 to about 40, from about 1 to about 10, from about 10 to 35, from about 50 to about 100, from about 20 to about 150, from about 200 to about 350, from about 25 to about 350, from about 150 to about 400, from about 50 to about 400, from about 50 to about 450, from about 200 to about 400, or from about 50 to about 350, or from about 50 to about 400 amino acids. In some instances, the N-terminal truncation removes at least about 5, at least about 10, at least about 15, at least about 20, at least about 25, at least about 30, at least about 35, at least about 40, at least about 50, at least about 60, at least about 65, at least about 70, at least about 75, at least about 80, at least about 90, at least about 95, at least about 100, at least about 120, at least about 130, at least about 140, at least about 150, at least about 175, at least about 200, at least about 220, at least about 250, at least about 275, at least about 300, at least about 325, at least about 350, at least about 375, or at least about 400 amino acids. In some instances, the C-terminal truncation removes at least about 5, at least about 10, at least about 15, at least about 20, at least about 25, at least about 30, at least about 35, at least about 40, at least about 50, at least about 60, at least about 65, at least about 70, at least about 75, at least about 80, at least about 90, at least about 95, at least about 100, at least about 120, at least about 130, at least about 140, at least about 150, at least about 175, at least about 200, at least about 220, at least about 250, at least about 275, at least about 300, at least about 325, at least about 350, at least about 375, or at least about 400 amino acids. In some instances, the N-terminal truncation lacks about 5, about 10, about 15, about 20, about 25, about 30, about 35, about 40, about 50, about 60, about 65, about 70, about 75, about 80, about 90, about 95, about 100, about 120, about 130, about 140, about 150, about 175, about 200, about 220, about 250, about 275, about 300, about 325, about 350, about 375, or about 400 amino acids. In some instances, the C-terminal truncation lacks about 5, about 10, about 15, about 20, about 25, about 30, about 35, about 40, about 50, about 60, about 65, about 70, about 75, about 80, about 90, about 95, about 100, about 120, about 130, about 140, about 150, about 175, about 200, about 220, about 250, about 275, about 300, about 325, about 350, about 375, or about 400 amino acids. In some instances, the N-terminal truncation lacks no more than about 5, no more than about 10, no more than about 15, no more than about 20, no more than about 25, no more than about 30, no more than about 35, no more than about 40, no more than about 50, no more than about 60, no more than about 65, no more than about 70, no more than about 75, no more than about 80, no more than about 90, no more than about 95, no more than about 100, no more than about 120, no more than about 130, no more than about 140, no more than about 150, no more than about 175, no more than about 200, no more than about 220, no more than about 250, no more than about 275, no more than about 300, no more than about 325, no more than about 350, no more than about 375, or no more than about 400 amino acids. In some instances, the C-terminal truncation lacks no more than about 5, no more than about 10, no more than about 15, no more than about 20, no more than about 25, no more than about 30, no more than about 35, no more than about 40, no more than about 50, no more than about 60, no more than about 65, no more than about 70, no more than about 75, no more than about 80, no more than about 90, no more than about 95, no more than about 100, no more than about 120, no more than about 130, no more than about 140, no more than about 150, no more than about 175, no more than about 200, no more than about 220, no more than about 250, no more than about 275, no more than about 300, no more than about 325, no more than about 350, no more than about 375, or no more than about 400 amino acids. In some instances, the truncation comprises an N-terminal truncation that removes at least about, at most about, or about 5, 10, 15, 20, 25, 30, 40, 50, 75, 100, 125, 150, 175, 200, 225, 250, 275, 300, 325, 350, 375, 400, 425, 450, 475, or 500 amino acids. In some instances, the truncation comprises a C-terminal truncation that removes at least about, at most about, or about 5, 10, 15, 20, 25, 30, 40, 50, 75, 100, 125, 150, 175, 200, 225, 250, 275, 300, 325, 350, 375, 400, 425, 450, 475, or 500 amino acids. In some instances, the N-terminal truncation, the C-terminal truncation, or both, may be more than about 500 amino acids, more than about 1000 amino acids, more than about 1500 amino acids, more than about 2000 amino acids, more than about 5000 amino acids, more than about 10000 amino acids, more than about 100000 amino acids, more than about 1000000 amino acids.

In some instances, truncations of regions which do affect functional activity of a protein or enzyme may be engineered. In some instances, truncations of regions which do not affect functional activity of a protein or enzyme may be engineered. A truncation may comprise a truncation of less than about 5, less than about 10, less than about 15, less than about 20, less than about 25, less than about 30, less than about 35, less than about 40, less than about 45, less than about 50, less than about 60, less than about 70, less than about 80, less than about 90, less than about 100, less than about 125, less than about 150, less than about 200, less than about 250, less than about 300, less than about 350, less than about 400 or more amino acids. A truncation may comprise a truncation of more than about 5, more than about 10, more than about 15, more than about 20, more than about 25, more than about 30, more than about 35, more than about 40, more than about 45, more than about 50, more than about 60, more than about 70, more than about 80, more than about 90, more than about 100, more than about 125, more than about 150, more than about 200, more than about 250, more than about 300, more than about 350, more than about 400 or more amino acids. A truncation may comprise of about 5%, about 10%, about 15%, about 20%, about 25%, about 30%, about 35%, about 40%, about 45%, about 50%, about 55%, about 60%, about 65%, about 70%, about 75%, about 80%, about 85%, about 87%, about 90%, about 92%, about 95% or about 100% of the polypeptide or enzyme.

In some instances, the variant or modified enzyme or modified protein may comprise one or more modification(s) at an amino acid position. In some instances, a variant, a mutant, or modified polypeptides or enzymes of the present disclosure may possess an increased activity, such as an increased RNA-dependent DNA polymerase activity or a DNA-dependent DNA polymerase activity, compared to the corresponding unmutated or unmodified or wildtype polymerase or as compared to one or more polymerases (e.g., RNA-dependent DNA polymerase, or a reverse transcriptase). In some instances, a polymerase or a reverse transcriptase having an increase in activity may be a modified polymerase or a modified reverse transcriptase that has at least about a 5% increase, at least about a 10% increase, at least about a 25% increase, at least about a 30% increase, at least about a 50% increase, at least about a 100% increase, at least about a 150% increase, at least about a 200% increase, at least about a 300% increase, at least about a 500% increase, at least about a 1,000% increase, at least about a 2,500% increase or at least about a 5,000% increase as compared to (1) the corresponding unmutated or wild-type enzyme; or (2) a particular polymerase (e.g., RNA-dependent DNA polymerase, reverse transcriptase) or a particular reverse transcriptase, or a group of polymerases, or a group of reverse transcriptases. In some instances, the modified polymerase or the modified reverse transcriptase of the present disclosure may have an increase in activity of from about 5% to about 5,000%, from about 5% to about 2,500%, from about 5% to about 1000%, from about 5% to about 500%, from about 5% to about 250%, from about 5% to about 100%, from about 5% to about 50%, from about 5% to about 25%, from about 25% to about 5,000%, from about 25% to about 2,500%, from about 25% to about 1,000%, from about 25% to about 500%, from about 25% to about 250%, from about 25% to about 100%, from about 100% to about 5,000%, from about 100% to about 2,500%, from about 100% to about 1000%, from about 100% to about 500%, or from about 100% to about 250%. An increase in RNA-dependent DNA polymerase activity and/or DNA-dependent DNA polymerase for a modified polymerase or modified reverse transcriptase of the present disclosure may also be measured according to relative activity compared to (1) the corresponding unmodified or wild-type enzyme; or (2) a particular polymerase (e.g., RNA-dependent DNA polymerase, reverse transcriptase) or a particular reverse transcriptase, or a group of polymerases, or a group of reverse transcriptases. In some instances, the increase in such relative activity is at least about 1.1, 1.2, 1.5, 2, 5, 10, 25, 50, 75, 100, 150, 200, 300, 500, 1,000, 2,500, 5,000, 10,000, or 25,000 fold when the activity of a modified polymerase or modified reverse transcriptase of the present disclosure is compared to (1) the corresponding unmutated or wild-type enzyme; or (2) a particular polymerase (e.g., RNA-dependent DNA polymerase, reverse transcriptase) or a particular reverse transcriptase, or a group of polymerases, or a group of reverse transcriptases. Thus a modified polymerase or modified reverse transcriptase of the present disclosure may have an increased RNA-dependent DNA polymerase and/or an increased DNA-dependent DNA polymerase activity of from about 1.1 fold to about 25,000 fold, from about 1.1 fold to about 10,000 fold, from about 1.1 fold to about 5,000 fold, from about 1.1 fold to about 2,500 fold, from about 1.1 fold to about 1,000 fold, from about 1.1 fold to about 500 fold, from about 1.1 fold to about 250 fold, from about 1.1 fold to about 50 fold, from about 1.1 fold to about 25 fold, from about 1.1 fold to about 10 fold, from about 1.1 fold to about 5 fold, from about 5 fold to about 25,000 fold, from about 5 fold to about 5,000 fold, from about 5 fold to about 1,000 fold, from about 5 fold to about 500 fold, from about 5 fold to about 100 fold, from about 5 fold to about 50 fold, from about 5 fold to about 25 fold, from about 50 fold to about 25,000 fold, from about 50 fold to about 5,000 fold, from about 50 fold to about 1,000 fold, from about 50 fold to about 500 fold, from about 50 fold to about 100 fold, from about 100 fold to about 25,000 fold, from about 1,000 fold to about 25,000 fold, from about 4,000 fold to about 25,000 fold, from about 10,000 fold to about 25,000 fold, from about 15,000 fold to about 25,000 fold, from about 1,000 fold to about 10,000 fold, from about 2,500 fold, to about 10,000 fold, from about 5,000 fold to about 10,000 fold, from about 7,500 fold to about 10,000 fold, from about 1,000 fold to about 15,000 fold, from about 2,500 fold, to about 15,000 fold, from about 5,000 fold to about 15,000 fold, from about 7,500 fold to about 15,000 fold, from about 10,000 fold to about 15,000 fold, or from about 12,500 fold to about 15,000 fold.

In some instances, the polypeptides, proteins, enzymes, modified enzymes (e.g., modified reverse transcriptase), modified polypeptides, non-naturally occurring enzymes, or variants comprise a fusion with, but not limited to, a protein, a domain, a fusion partner, a carrier protein, a target sequence, an antigenic determinant, or any combination thereof. In some instances, the reverse transcriptase or modified reverse transcriptase is fused to a protein, a domain, a fusion partner, a target sequence, an antigenic determinant, or any combination thereof. In some instances, the non-LTR retrotransposon or modified non-LTR retrotransposon is fused to a protein, a domain, a fusion partner, a target sequence, an antigenic determinant, or any combination thereof. In some instances, the modified LTR retrotransposon is fused to a protein, a domain, a fusion partner, a target sequence, an antigenic determinant, or any combination thereof. In some instances, the modified R2 non-LTR retrotransposon is fused to a protein, a domain, a fusion partner, a target sequence, an antigenic determinant, or any combination thereof. In some instances, the modified R2 reverse transcriptase is fused to a protein, a domain, a fusion partner, a target sequence, an antigenic determinant, or any combination thereof. In some instances, the modified reverse transcriptase is fused to a protein, a domain, a fusion partner, a target sequence, an antigenic determinant, or any combination thereof. In some instances, the variant is fused to a protein, a domain, a fusion partner, a target sequence, an antigenic determinant, or any combination thereof. In some instances, the polypeptide having reverse transcriptase activity is fused to a protein, a domain, a fusion partner, a target sequence, an antigenic determinant, or any combination thereof.

In some instances, the fused polypeptides, proteins, enzymes, modified enzymes (e.g., modified reverse transcriptase), modified polypeptides, non-naturally occurring enzymes, or variants thereof increase stability (e.g., increase thermostability), increase shelf life, increase active fraction(s), and/or improve purification compared to the wild-type counterpart, naturally occurring enzyme, or unfused polypeptides, proteins, enzymes, or variants thereof. In some instances, a modified reverse transcriptase comprises a fusion partner or a carrier protein. In some instances, the selection of the fusion protein, domain, fusion partner, target sequence, antigenic determinant, or any combination thereof is based on the mechanism causing reduced or increased stability (e.g., increased thermostability), reduced or increased shelf life, and/or reduced or increased expression level (Costa et al., "Fusion tags for protein solubility, purification and immunogenicity in *Escherichia coli*: the novel Fh8 system. Front Microbiol. 2014 Feb. 19; 5:63). In some instances, the fusion tags enhance the solubility of their partner proteins. In some instances, the fusion proteins form micelle-like structures. In some instances, the micelle-like structures are misfolded or unfolded proteins that are sequestered and protected from the solvent and/or the soluble protein domains face outward. In some instances, the fusion partners attract chaperones. In some instances, the fusion tag drives its partner protein into a chaperone-mediated folding pathway. In some instances, the MBP and/or N-utilization substance (NusA) are two fusion tags that present this mechanism. In some instances, the fusion partners have an intrinsic chaperone-like activity. In some instances, the hydrophobic patches of the fusion tag interact with partially folded passenger proteins, preventing self-aggregation, and promoting proper folding. In some instances, the solubility enhancer partners may play a passive role in the folding of their target proteins, reducing the chances for protein aggregation. In some instances, the fusion partners net charges. In some instances, the highly acidic fusion partners inhibit protein aggregation. In some instances, the fusion is with, but it is not limited to, Fh8, MBP, NusA, Trx, SUMO, GST, SET, GB1, ZZ, HaloTag, SNUT, Skp, T7PK, EspA, Mocr, Ecotin, CaBP, ArsC, IF2-domain I, an expressivity tag, an expressivity tag that is part of 1F2-domain I, RpoA, SlyD, Tsf, RpoS, PotD, Crr, msyB, yjgD, rpoD, His6, or any combination thereof. In some instances, the fusion enhances protein solubility and/or purification. In some instances, the Fh8 may act as an effective solubility enhancer partner and/or robust purification. In some instances, the Fh8 fusion tag has an amino acid sequence comprising MPSVQEVEKLLHVLDRNGDGKV-SAEELKAFADDSKCPLDSNKIKAFIKEHDKNKDGKL DLKELVSILSS (SEQ ID NO: 21). In some instances, the codon optimized sequence comprises ATGCCGTCTGTTCAGGAAGTT-GAAAAACTGCTGCACGTTCTGGACCGTAACGGTGA CGGTAAAGTTTCTGCGGAAGAACT-GAAAGCGTTCGCGGACGACTCTAAATGCCCGC TGGACTCTAACAAAATCAAAGCGTTCAT-CAAAGAACACGACAAAAACAAAGACGG TAAACTGGACCTGAAAGAACTGGTTTC-TATCCTGTCTTCTTAG (SEQ ID NO: 22). In some instances, an enzyme, or a modified enzyme (e.g., modified reverse transcriptase), or a protein (e.g., modified protein), or a polypeptide (e.g., modified polypeptide), or a variant, or a product, or a nucleic acid molecule, or a cDNA molecule, or a template, or an acceptor nucleic acid molecule, or a primer, or an RNA, or a DNA, or a fragment nucleic acid, or a degraded nucleic acid, of the present disclosure may comprise one or more tag(s). In some instances, the fragmented or degraded RNA or DNA, or a variant thereof may comprise one or more tag(s). In some instances, the R2 reverse transcriptase, or a variant thereof, may comprise one or more tag(s). In some instances, the non-LTR retrotransposon protein or polypeptide having reverse transcriptase activity, or a variant thereof, may comprise one or more tag(s). In some instances, the cDNA molecule may comprise one or more tag(s). In some instances, the tag may be captured on a solid support, facilitating the isolation of the enzyme, or protein, or polypeptide, or a variant, or a product of the present disclosure. In some instances, the tag may be biotin that can be recognized by avidin. The affinity tag may include multiple biotin residues for increased binding to multiple avidin molecules. In some instances, the tag may include a functional group such as an azido group or an acetylene group, which enables capture through copper(I) mediated click chemistry (see H. C. Kolb and K. B. Sharpless, Drug Discovery Today, 2003, 8(24), 1128-1137). In some instances, the tag may include an antigen that may be captured by an antibody bound on a solid support. In some instances, the tag may include, but is not limited to, His-tag, His6-tag, Calmodulin-tag, CBP, CYD (covalent yet dissociable NorpD peptide), Strep II, FLAG-tag, HA-tag, Myc-tag, S-tag, SBP-tag, Softag-1, Softag-3, V5-tag, Xpress-tag, Isopeptag, SpyTag, B, HPC (heavy chain of protein C) peptide tags, GST, MBP, biotin, biotin carboxyl carrier protein, glutathione-S-transferase-tag, green fluorescent protein-tag, maltose binding protein-tag, Nus-tag, Strep-tag, thioredoxin-tag, and combinations thereof. In some instances, the tagged molecule may be subjected to sequencing.

In some instances, a molecular barcode may be attached to any region of a molecule. For example, the molecular barcode may be attached to the 5' or 3' end of a polynucleotide (e.g., DNA, RNA). For example, the target-specific region of the molecular barcode comprises a sequence that is complementary to a sequence in the 5' region of the molecule. The target-specific region of the molecular barcode may also comprise a sequence that is complementary to a sequence in the 3' region of the molecule. In some instances, the molecular barcode is attached a region within a gene or gene product. For example, genomic DNA is fragmented and a sample tag or molecular identifier label is attached to the fragmented DNA. In other instances, an RNA molecule is alternatively spliced and the molecular barcode is attached to the alternatively spliced variants. In another example, the polynucleotide is digested and the molecular barcode is attached to the digested polynucleotide. In another example, the target-specific region of the molecular barcode comprises a sequence that is complementary to a sequence within the molecule.

In some instances the method of the present disclosure comprises introducing a biotin moiety or another affinity purification moiety to, for example, a nucleic acid molecule, such as DNA, RNA, or a combination of DNA and RNA. In some instances, the method further comprises immobilizing the affinity purification tagged nucleic acid molecule on a solid support. In some instances the solid support is a sepharose resin or magnetic beads having an affinity purification material, such as avidin, streptavidin, chitin, glutathione and the like, bound thereto.

In some instances, the enzyme, or protein, or polypeptide, or a variant, or a product of the present disclosure may be bound to a solid support. In some instances, the fragmented or degraded nucleic acid (e.g., RNA or DNA), or a variant thereof may be bound to a solid support. In some instances, the R2 reverse transcriptase, or a variant thereof, may be bound to a solid support. In some instances, the non-LTR retrotransposon protein or polypeptide having reverse transcriptase activity, or a variant thereof, may be bound to a solid support. In some instances, the cDNA molecule may be bound to a solid support. In some instances, the solid support may be glass, plastic, porcelain, resin, sepharose, silica, or other material. In some instances, the solid support may be a plate that is substantially flat substrates, gel, microbeads, magnetic beads, membrane, or other suitable shape and size. In some instances, the microbeads may have diameter between 10 nm to several millimeters. In some instances, the solid support may be non-porous or porous with various density and size of pores. In some instances the DNA and/or RNA fragment may be captured on a solid support, unwanted DNA and/or RNA may be washed away. In some instances, the DNA and/or RNA fragment may be released from the solid support, for example, by using restriction enzyme.

In some instances, the solid support may comprise the target nucleic acid binding region, wherein the target nucleic acid binding region comprises a sequence selected from the group consisting of a gene-specific sequence, an oligo-dT sequence, a random multimer, and any combination thereof. In some instances, the solid support further comprises a target nucleic acid or complement thereof. In some instances, the solid support comprises a plurality of target nucleic acids or complements thereof comprising from about 0.01% to about 100% of transcripts of a transcriptome of an organism or complements thereof, or from about 0.01% to about 100% of genes of a genome of an organism or complements thereof. In some instances, the cellular labels of the plurality of oligonucleotides comprise a first random sequence connected to a second random sequence by a first label linking sequence; and the molecular labels of the plurality of oligonucleotides comprise random sequences. In some instances, the solid support is selected from the group consisting of a polydimethylsiloxane (PDMS) solid support, a polystyrene solid support, a glass solid support, a polypropylene solid support, an agarose solid support, a gelatin solid support, a magnetic solid support, a pluronic solid support, and any combination thereof. In some instances, the plurality of oligonucleotides comprise a linker comprising a linker functional group, and the solid support comprises a solid support functional group; wherein the solid support functional group and linker functional group connect to each other. In some instances, the linker functional group and the solid support functional group are individually selected from the group consisting of C6, biotin, streptavidin, primary amine(s), aldehyde(s), ketone(s), and any combination thereof. In some instances, molecular labels of the plurality of oligonucleotides comprise at least 15 nucleotides.

In some instances, fusion partners may be removed from their target protein by enzymatic cleavage, chemical cleavage, and/or by using an in vivo cleavage strategy. In some instances, proteases may be used for tag removal. In some instances, the protease may be an endoprotease, serine protease, factor Xa, enterokinase, alpha-thrombin, a viral protease, tobacco etch virus (TEV), the human rhinovirus 3C protease, SUMO protease, exoprotease, metallocarboxypeptidase, or aminopeptidase. In some instances, a fusion tag may be removed by two purification steps. In some instances, the initial affinity purification step includes (e.g., via a histidine tag located at the N-terminal of the fusion protein), the purified fusion protein mixed in solution with the endoprotease (e.g., a his-tagged protease) to cleave off the tag. The cleaved target protein may be recovered in the flow-through sample after a second affinity purification step, in which the cleaved fusion tag and the added protease are collected in the eluted sample.

In some instances, the modified enzyme, modified reverse transcriptase, non-naturally occurring enzyme, or modified polypeptide having reverse transcriptase activity of the present disclosure shows activity, is capable of template jumping, and/or generate a nucleic acid molecule (e.g., cDNA molecule) without thermal cycling. In some instances, the modified reverse transcriptase, modified enzyme, non-naturally occurring enzyme, or the modified polypeptide having reverse transcriptase activity of the present disclosure shows activity, is capable of template jumping, and/or generate a nucleic acid, cDNA molecule at a temperature ranging from about 25° C. to about 42° C., from about 12° C. to about 42° C., from about 8° C. to about 50° C., from about 4° C. to about 60° C., from about 27° C. to about 35° C., from about 28° C. to about 33° C., from about 29° C. to about 32° C., from about 30° C. to about 37° C., from about 26° C. to about 38° C., from about 30° C. to about 37° C., from about 25° C. to about 32° C., from about 29° C. to about 31° C., from about 27° C. to about 38° C., from about 29° C. to about 38° C. In some instances, the non-naturally occurring enzyme, modified reverse transcriptase, modified enzyme, or modified polypeptide having reverse transcriptase activity of the present disclosure shows activity, is capable of template jumping, and/or generate a nucleic acid molecule (e.g., cDNA molecule) at about 30° C., or at about 35° C., or at about 25° C. In some instances, the modified enzyme, modified reverse transcriptase, non-naturally occurring enzyme, or modified polypeptide having reverse transcriptase activity of the present disclosure shows activity, is capable of template jumping, and/or generate a nucleic acid molecule (e.g., cDNA molecule) at a temperature equal to less than about 38° C., equal to less than about 42° C., equal to less than about 50° C., equal to less than about 60° C., equal to less than about 35° C., equal to less than about 30° C., equal to less than about 28° C., equal to less than about 25° C., equal to less than about 20° C., equal to less than about 12° C., equal to less than about 8° C., or equal to less than about 4° C. In some instances, the modified enzyme, modified reverse transcriptase, non-naturally occurring enzyme, or modified polypeptide having reverse transcriptase activity of the present disclosure shows activity, is capable of template jumping, and/or generate a nucleic acid molecule (e.g., cDNA molecule) at a temperature equal to less than about 36° C. In some instances, the modified enzyme, modified reverse transcriptase, non-naturally occurring enzyme, or modified polypeptide having reverse transcriptase activity of the present disclosure shows activity, is capable of template jumping, and/or generate a nucleic acid molecule (e.g., cDNA molecule) at room temperature. In some instances, the modified enzyme, modified reverse transcriptase, non-naturally occurring enzyme, or modified polypeptide having reverse transcriptase activity of the present disclosure shows activity, is capable of template jumping, and/or generate a nucleic acid molecule (e.g., cDNA molecule) at a temperature of at about or of at most about 8° C., at about or of at most about 12° C., at about or of at most about 20° C., at about or of at most about 25° C., at about or of at most about 28° C., at about or of at most about 30° C., at about or of at most about 31° C., at about or of at most about 32° C., at about or of at most about 33° C., at about or of at most about 34° C., at about or of at most about 35° C., at about or of at most about 36° C. at about or of at most about 39° C., at about or of at most about 40° C., at about or of at most about 41° C., at about or of at most about 42° C., at about or of at most about 50° C., at about or of at most about 55° C., at about or of at most about 60° C. In some instances, the modified enzyme, modified reverse transcriptase, non-naturally occurring enzyme, or modified polypeptide having reverse transcriptase activity of the present disclosure shows activity, is capable of template jumping, and/or generate a nucleic acid molecule (e.g., cDNA molecule) at a temperature equal to or less than about any temperature between about 42° C. to about 80° C., or between about 35° C. to about 80° C., or between about 30° C. to about 50° C., or between about 8° C. to about 50° C., or between about 12° C. to about 42° C.

In some instances, a modified enzyme, modified reverse transcriptase, modified polypeptide having reverse transcriptase activity, or a non-naturally occurring enzyme of the present disclosure has at least one altered characteristic relative to an unmodified or naturally occurring enzyme. In some instances, the altered characteristic enables the modified enzyme, modified reverse transcriptase, non-naturally occurring enzyme, or modified polypeptide having reverse transcriptase activity to generate a nucleic acid molecule and/or a complementary deoxyribonucleic acid (cDNA) molecule from a template nucleic acid molecule without thermal cycling. In some instances, a modified enzyme, modified reverse transcriptase, modified polypeptide having reverse transcriptase activity, or a non-naturally occurring enzyme of the present disclosure is capable of generating one or more copies of the nucleic acid molecule or cDNA molecule at an error rate of at most about 0.5%, of at most about 1%, of at most about 1.5%, of at most about 2%, of at most about 2.5%, of at most about 3%, of at most about 3.5%, of at most about 4%, of at most about 4.5%, of at most about 5%, of at most about 6%, of at most about 7%, of at most about 8%, of at most about 9%, of at most about 10%, of at most about 15%, of at most about 20%, of at most about 25%, of at most about 30%, of at most about 40%, of at most about 45%, of at most about 50%, of at most about 60%, of at most about 65%, of at most about 70%, of at most about 75%, or of at most about 80%. In some instances, the modified enzyme, modified reverse transcriptase, modified polypeptide having reverse transcriptase activity, or the non-naturally occurring enzyme of the present disclosure is a variant of any one of the sequences disclosed herein. In some instances, the modified enzyme, modified reverse transcriptase, modified polypeptide having reverse transcriptase activity, or the non-naturally occurring enzyme of the present disclosure is a variant of any one of the sequences provided in SEQ ID Nos: 1-20. In some instances, a modified enzyme, modified reverse transcriptase, modified polypeptide having reverse transcriptase activity, or a non-naturally occurring enzyme of the present disclosure has at least one altered characteristic that improves enzyme property relative to an unmodified or a naturally occurring enzyme. In some instances, the at least one altered characteristic that improves enzyme property comprises at least one of increased/improved stability (e.g., increased/improved thermostability), increased/improved specific activity, increased/improved protein expression, increased/improved purification, increased/improved processivity, increased/improved strand displacement, increased/improved template jumping, improved single strand DNA priming, and increased/improved fidelity.

In one embodiment, the present disclosure relates to a non-naturally occurring enzyme that subjects a template nucleic acid molecule to reverse transcription to generate a complementary deoxyribonucleic acid (cDNA) product and amplification of the cDNA product at a processivity of at least about 80%, at least about 85%, at least about 87%, at least about 90%, at least about 92%, at least about 95%, at least about 96%, at least about 97%, at least about 98%, at least about 99%, or at least about 99.5% per base as measured at about 12° C., about 15° C., about 20° C., about 25° C., about 30° C., about 32° C., about 35° C., about 40° C.

In some instances, the non-naturally occurring enzyme has a performance index greater than about 1.0 for at least one enzyme property. In some instances, enzyme property is at least one of the group consisting of improved stability (e.g., improved thermostability), specific activity, protein expression, purification, processivity, strand displacement, template jumping, increased DNA/RNA affinity, and fidelity.

In one embodiment, the present disclosure relates to a non-naturally occurring enzyme that subjects a template nucleic acid molecule to reverse transcription to generate a complementary deoxyribonucleic acid (cDNA) product, a nucleic acid product, and amplification of the cDNA product in a time period of about 3 hours or less and/or at a performance index greater than about 1.0 for at least one enzyme property selected from the group consisting of improved stability (e.g., improved thermostability), specific activity, protein expression, purification, processivity, strand displacement, template jumping, increased DNA/RNA affinity, and fidelity. In some instances, the temperature is from about 25° C. to about 40° C. (e.g., about 28° C., about 30° C., about 32° C., about 35° C., or about 37° C.). In some instances, the temperature is from about 8° C. to about 50° C. (e.g., about 8° C., about 20° C., about 42° C., about 45° C., or about 50° C.).

In one embodiment, the present disclosure relates to a non-naturally occurring enzyme that subjects a template nucleic acid molecule to reverse transcription to generate a complementary deoxyribonucleic acid (cDNA) product and amplification of the cDNA product in a time period of 3 hours or less (e.g., 2.5 hours or less, 2 hours or less, 1.5 hours or less, 1 hour or less, or 30 minutes or less) and/or at a processivity for a given nucleotide substrate that is at least about 5%, at least about 10%, at least about 20%, at least about 30%, at least about 40%, at least about 50%, at least about 60%, at least about 70%, at least about 80%, at least about 85%, at least about 88%, at least about 90%, at least about 95%, or at least about 98% higher than the processivity of a reference enzyme for the same nucleotide substrate.

In one embodiment, the present disclosure relates to a non-naturally occurring enzyme that subjects a template nucleic acid molecule to reverse transcription to generate a nucleic acid product and amplification of the nucleic acid product in a time period of 3 hours or less (e.g., 2.5 hours or less, 2 hours or less, 1.5 hours or less, 1 hour or less, or 30 minutes or less) and/or at a processivity for a given nucleotide substrate that is at least about 5%, at least about 10%, at least about 20%, at least about 30%, at least about 40%, at least about 50%, at least about 60%, at least about 70%, at least about 80%, at least about 85%, at least about 88%, at least about 90%, at least about 95%, or at least about 98% higher than the processivity of a reference enzyme for the same nucleotide substrate.

In one embodiment, the present disclosure provides a method of amplifying a nucleic acid molecule, comprising subjecting the nucleic acid molecule to nucleic acid amplification using a modified reverse transcriptase. In some instances, the reverse transcriptase is capable of amplifying the nucleic acid molecule at processivity of at least about 80%, at least about 88%, at least about 90%, at least about 95%, or at least about 98% per base at about 4° C., about 8° C., about 12° C., about 30° C., about 28° C., about 29° C., about 32° C., about 35° C., about 37° C., about 42° C., about 50° C., or higher than about 42° C.

Methods of Preparing RNA Libraries

In some aspects, the disclosure provides a method for preparing a complementary deoxyribonucleic acid (cDNA) molecule comprising: partitioning a cell and a non-naturally occurring reverse transcriptase, which cell comprises ribonucleic acid (RNA) molecules; releasing said RNA molecules from said cell in said partition; and in said partition, using said non-naturally occurring reverse transcriptase to synthesize a complementary deoxyribonucleic acid (cDNA) library from said RNA molecule, which non-naturally occurring transcriptase synthesizes said cDNA library at a processivity of 20 nucleotides or longer per continuous run, whereby processivity is defined as the number of reaction enzymes generated in one continuous run without dissociation. In some aspects, the processivity of the enzyme is about 15 nucleotides, 16 nucleotides, 17 nucleotides, 18 nucleotides, 19 nucleotides, 20 nucleotides per second, 21 nucleotides, 22 nucleotides, 23 nucleotides, 24 nucleotides, 25 nucleotides, 26 nucleotides, 27 nucleotides, 28 nucleotides, 29 nucleotides, 30 nucleotides, or more.

In some aspects, said non-naturally occurring reverse transcriptase has at least 80% identity to SEQ ID NOs: 1-20. In some aspects said partition further comprises: one or more acceptor nucleic acid molecules; and a non-naturally occurring reverse transcriptase, wherein said non-naturally occurring reverse transcriptase has at least 80% identity to SEQ ID NOs: 1-20.

Methods currently used to conduct library preparation for single cell and low input methods include various confinement methods, such as emulsion-based techniques, nanofabrication-based techniques, cell-sorting techniques, and serial dilution-based techniques. Library preparation for single cell and low input methods includes many challenges including but not limited to a risk of artifact amplification due to an excess of reaction reagents such as oligo adapters and primers rather than the RNA sample in itself. Achieving quality library preparation requires high RNA to DNA conversion efficiency and low oligo adapter-adapter products.

In some aspects, the disclosure provides a method for preparing a complementary deoxyribonucleic acid (cDNA) molecule for single cell or low RNA sample input, whereby the RNA sample input is from 5 to 50 pg, from 10 to 50 pg, from 15 to 50 pg, from 20 to 50 pg, from 25 to 50 pg, from 30 to 50 pg, from 35 to 50 pg, from 40 to 50 pg, from 45 to 50 pg.

In some aspects, the disclosure provides an enzymatic platform for preparing a complementary deoxyribonucleic acid (cDNA) molecule for single cell or low RNA sample input, which provides the necessary high RNA-sample-library conversion efficiency. In some instances, the method disclosed herein provides a relatively simple protocol with a small number of steps, assuring a small amount of sample loss.

In some aspects, the disclosure provides an enzymatic platform for preparing a complementary deoxyribonucleic acid (cDNA) molecule for single cell or low RNA sample input that is not only limited to target poly-adenylated ribonucleic acid (RNA) from cells. In some instances, the enzymatic platform disclosed herein captures non-polyadenylated RNA, such as micro RNA (miRNA), non-coding RNA (ncRNA), long intergenic noncoding RNA (lincRNA), long non-coding RNA (lnRNA). In some instances, the enzymatic platform disclosed herein captures the full transcriptome, and thus, including but not limited to messenger RNA (mRNA), ribosomal RNA (rRNA), transfer RNA (tRNA), microRNA (miRNA), small interfering RNA (siRNA), small nucleolar RNA (snoRNA), piwi-interacting RNA (piRNA), tRNA-derived small RNA (tsRNA), and small rDNA-derived RNA (srRNA).

In one embodiment, the present disclosure relates to a method for preparing a concatemer of nucleic acid molecules. In some instances, the method comprises processing ends of a plurality of double-stranded nucleic acid molecules. In some instances, the method comprises adding a first plurality of adaptor molecules to the plurality of double stranded nucleic acid molecules. In some instances, the first plurality of adaptor molecules comprise one or more overhang sequences. In some instances, at least two of the one or more overhang sequences are complementary to each other. In some instances, the method provides a first plurality of adaptor connected double-stranded nucleic acid molecules. In some instances, the method comprises adding a polymerizing enzyme (e.g., adding a polymerase enzyme to the first plurality of adaptor connected double-stranded nucleic acid molecules). In some instances, adding a polymerase enzyme is in the absence of a primer. In some instances, the method does not comprise adding a primer. In some instances, the polymerizing enzyme forms a first set of adaptor connected double-stranded nucleic acid concatemers. In some instances, forming a first set of adaptor connected double-stranded nucleic acid concatemers is by joining two or more adaptor connected double-stranded nucleic acid molecules by the one or more overhang sequences. In some instances, the method comprises adding a second plurality of adaptor molecules to the first set (e.g., first adaptor molecules). In some instances, the second plurality of adaptor molecules comprises one or more overhang sequences. In some instances, at least two of the one or more overhang sequences are complementary to each other. In some instances, the method provides a second set of adaptor connected double-stranded nucleic acid molecules. In some instances, any one of the previous instances can be repeated with a set of adaptor molecules to yield a concatemer comprising a predetermined average length.

In one embodiment, the present disclosure relates to a method for preparing a concatemer of nucleic acid molecules. In some instances, the method comprises subjecting at least one nucleic acid molecule and/or a plurality of double-stranded nucleic acid molecules to end-repair. In some instances, the method comprises adding at least one or a plurality of adaptor molecules to the at least one nucleic acid molecule and/or the plurality of double-stranded nucleic acid molecules. In some instances, adding at least one or a (first) plurality of adaptor molecules to the at least one nucleic acid molecule and/or the plurality of double stranded nucleic acid molecules comprises ligation. In some instances, adding at least one or a (first) plurality of adaptor molecules to the at least one nucleic acid molecule and/or the plurality of double stranded nucleic acid molecules comprises a reverse transcriptase (e.g., R2 reverse transcriptase, or a modified reverse transcriptase). In some instances, In some instances, the at least one or a plurality of adaptor molecules comprise one or more overhang sequences. In some instances, at least two overhang sequences are complementary to each other (e.g., thereby providing a (first) plurality of adaptor connected double-stranded nucleic acid molecules). In some instances, the at least one or a plurality of adaptor molecules comprise a sequence (e.g., overhang sequence) that attaches/ligates to the 3' end of the nucleic acid molecule and/or a sequence (e.g., overhang sequence) that attaches/ligates to the 5' end of the nucleic acid molecule. In some instances, the nucleic acid molecule comprises adaptors on both the 3' and the 5' end. In some instances, the adaptor that binds to the 3' end is complementary to the adaptor that binds to the 5' end. In some instances, the sequence of the adaptors is unknown. In some instances, the sequence of the adaptors is pre-determined. In some instances, the adaptor serves as a template and/or as a primer. In some instances, the adaptor that binds to the 3' end of one nucleic acid molecule can bind to an adaptor on the 5' end of another nucleic acid molecule. In some instances, the method further comprises adding a polymerase enzyme to the adaptor connected to a nucleic acid molecule. In some instances, the method further comprises adding a polymerase to the (first) plurality of adaptor connected double-stranded nucleic acid molecules. In some instances, the polymerase is added in the absence of a primer. In some instances, the polymerase enzyme forms a first set of adaptor connected double-stranded nucleic acid concatemers by joining two or more adaptor connected double-stranded nucleic acid molecules by the one or more overhang sequences. In some instances, the polymerase permits that the adaptor connected to the nucleic acid molecule form concatemers. In some instances, the method comprises adding a second plurality of adaptor molecules to the first set. In some instances, the second plurality of adaptor molecules comprise one or more overhang sequences. In some instances, the at least two overhang sequences are complementary to each other. In some instances, a second set of adaptor connected double-stranded nucleic acid molecules is formed. In some instances, the concatemer length or the number of attached templates can be determined, for example, by tagging the adaptors with modified nucleotides (e.g., by introducing methylated nucleotides or by inserting dUTP). In some instances the length of the concatemer can be regulated based on the ratio between modified/unmodified adaptors. In some instances the adaptor sequences can serve as a homology priming location (annealed to the homology spot ssDNA fragments serve as template and primer). In some instances, the method comprises amplifying the concatemers by PCR or isothermal reaction. In some instances, the reaction in the PCR undergoes a selected number of cycles (the more cycles, the longer the concatemer) or time (isothermal amplification). In some instances, the reaction is stopped and the (long) dsDNA concatemers are ligated with two unique dsDNA adaptors. In some instances, the length of the concatemer can be manipulated. In some instances, the length of the concatemer can be determined at least based on the number of PCR cycles, and/or the amount of time (e.g., in an isothermal amplification), and/or based on the modified nucleotide present in the adaptor. In some instances, the adaptor comprises a unique molecular identifier sequence (UMI). In some instances, the polymerase enzyme joins two or more adaptor connected double-stranded nucleic acid molecules in a PCR or isothermal amplification reaction. In some instances, the adaptor comprises at least one modified nucleotide.

In some instances, the method for preparing a nucleic acid library and/or a complementary cDNA library comprises preparing the library in at most about 1 hour, at most about 2 hours, at most about 3 hours, at most about 4 hours, at most about 5 hours, at most about 7 hours, at most about 10 hours, at most about 15 hours, or at most about 20 hours.

In one embodiment, the present disclosure relates to methods and processes that enable the discovery of novel markers and mutations for cancer, and/or provides approaches for precision medicine. In some instances, the methods and processes disclosed herein provides for higher sensitivity to capture minor allele in ctDNA of <0.10% (available current methods have sensitivity >1%). In some instances, the methods and/or processes of the present disclosure comprise a 1-pot (e.g., single vessel), 1-step protocol, and the library is prepared from a sample in an amount of time that is equal to or less than about 2 hours.

The present disclosure relates to methods for preparing a complementary deoxyribonucleic acid (cDNA) molecule. In some instances, the method comprises annealing a primer to a template nucleic acid molecule, thereby generating an annealed template nucleic acid molecule. In some instances, the method further comprises mixing, in the presence of nucleotides, the annealed template nucleic acid molecule, a one or more acceptor nucleic acid molecules, and a modified reverse transcriptase. In some instances, the modified reverse transcriptase generates a plurality of continuous complementary deoxyribonucleic acid molecules. In some instances, the plurality of continuous complementary deoxyribonucleic acid molecules are prepared in at most about 2 hours. In some instances, the plurality of continuous complementary deoxyribonucleic acid molecules is generated by having the modified reverse transcriptase reverse transcribe a sequence of the annealed template nucleic acid molecule. In some instances, the modified reverse transcriptase then migrates to an acceptor nucleic acid molecule (e.g., one or more acceptor nucleic acid molecules). In some instances, the reverse transcriptase (e.g., modified reverse transcriptase) is able to reverse transcribe a sequence of the template and/or the acceptor nucleic acid molecule at a temperature of from about 12° C. to about 42° C. In some instances, the reverse transcriptase (e.g., modified reverse transcriptase) is able to reverse transcribe a sequence of the template and/or the acceptor nucleic acid molecule at a temperature of from about 8° C. to about 50° C. (e.g., about 8° C., about 15° C., about 20° C., about 25° C., about 30° C., about 35° C., about 40° C., about 45° C., about 48° C.). In some instances, the reverse transcriptase (e.g., modified reverse transcriptase) is able to reverse transcribe a sequence of the template and/or the acceptor nucleic acid molecule at a temperature of at most about 4° C., at most about 8° C., at most about 15° C., at most about 20° C., at most about 25° C., at most about 30° C., at most about 35° C., at most about 40° C., at most about 45° C., or at most about 48° C. In some instances, reverse transcription occurs at an error rate of at most about 5%. In some instances, the reverse transcriptase (e.g., modified reverse transcriptase) is capable of reverse transcribing the template and/or the acceptor nucleic acid molecule at an error rate of at most about 45%, at most about 40%, at most about 35%, at most about 30%, at most about 25%, at most about 20%, at most about 15%, at most about 10%, at most about 8%, at most about 7%, at most about 6%, at most about 5%, at most about 4%, at most about 3%, at most about 2%, or at most about 1%. In some instances, the reverse transcriptase (e.g., modified reverse transcriptase) can migrate from the template to the acceptor nucleic acid molecule independently of sequence identity between the template and the acceptor nucleic acid molecule. In some instances, the method is prepared in a single vessel. In some instances, the template nucleic acid molecule is a fragmented DNA template, a fragmented RNA template, a non-fragmented DNA template, a non-fragmented RNA template, or a combination thereof. In some instances, the method further comprises adding a tag to a template nucleic acid molecule, thereby generating a plurality of tagged continuous complementary deoxyribonucleic acid molecules. In some instances, the method further comprises performing a polymerase chain reaction amplification reaction, thereby forming one or more amplicons.

The present disclosure relates to methods for preparing a complementary deoxyribonucleic acid (cDNA) molecule using a modified reverse transcriptase. In some instances, the method for preparing a cDNA molecule is via template jumping. In some instances, the modified reverse transcriptase has an improved enzyme property compared to a naturally occurring or unmodified or wild type enzyme (e.g., wild type reverse transcriptase). In some instances, the method for preparing a cDNA molecule comprises: (a) annealing a primer to a template; and (b) mixing, in the presence of nucleotides (e.g., dNTPs), the template annealed to the primer with a modified reverse transcriptase and an acceptor nucleic acid molecule (e.g., acceptor RNA, DNA, or a combination thereof) under conditions sufficient to generate a cDNA molecule complementary to the template and/or to the acceptor nucleic acid molecule. In some instances, the enzyme (e.g., modified reverse transcriptase) generates a continuous cDNA molecule by migrating from the template to the acceptor nucleic acid molecule. In some instances, template jumping is independent of sequence identity between the template and the acceptor nucleic acid molecule. In some instances, step (a) and step (b) are done at the same time. In some instances, step (a) comprises step (b) (e.g., step (a) and step (b) are merged into one step). In some instances, at least one of step (a) and/or step (b) further comprises addition of a hot start thermostable polymerase. In some instances, the method of the present disclosure is performed in a single tube. In some instances, the method of the present disclosure further comprises a polymerase chain reaction (PCR) amplification reaction. In some instances, the PCR amplification reaction is performed in a single tube (e.g., the same one tube from steps (a) and (b)). In some instances, all the steps of the method of the present disclosure are performed in a single tube.

The present disclosure relates to a method for preparing a concatemer of nucleic acid molecules for sequencing. In some instances, the method comprises ligating a nucleic acid molecule with a first adaptor. In some instances, the method further comprises amplifying the ligated nucleic acid molecule by performing a nucleic acid amplification reaction to form a concatemer. In some instances, the amplification reaction is performed in the absence of a primer. In some instances, the method further comprises ligating the concatemer with a second adaptor. In some instances, the adaptor(s) (first and/or second adaptor) is/are designed to allow recombination or homology based annealing and extension of molecules (e.g., nucleic acid molecules, and/or a template, and/or a primer, and/or an acceptor). In some instances, the nucleic acid amplification reaction is polymerase chain reaction (PCR) or isothermal amplification. In some instances, the first adaptor comprises a unique molecular identifier (UMI) sequence. In some instances, the first adaptor serves as a primer. In some instances, the first adaptor comprises single stranded nucleic acid. In some instances, the single stranded nucleic acid comprises single stranded DNA (ssDNA). In some instances, the second adaptor comprises double stranded nucleic acid. In some instances, the double stranded nucleic acid comprises double stranded DNA (dsDNA). In some instances, the first adaptor is different from the second adaptor. In some instances, the first adaptor comprises two or more adaptors. In some instances, the second adaptor comprises two or more adaptors. In some instances, both ends of the nucleic acid molecule comprise an adaptor. In some instances, only one end of the nucleic acid molecule comprises an adaptor. In some instances, both the 3' and the 5' ends of a nucleic acid molecule comprise an adaptor.

The present disclosure relates to methods for preparing a complementary deoxyribonucleic acid (cDNA) molecule using a modified reverse transcriptase. In some instances, the method for preparing a cDNA molecule is via template jumping. In some instances, the modified reverse transcriptase has an improved enzyme property compared to a naturally occurring or unmodified or wild type enzyme (e.g., wild type reverse transcriptase). In some instances, the method for preparing a cDNA molecule comprises mixing, in the presence of nucleotides (e.g., dNTPs), a primer, a template, a modified reverse transcriptase and an acceptor nucleic acid molecule (e.g., acceptor RNA, DNA, or a combination thereof) under conditions sufficient to generate a cDNA molecule complementary to the template and/or to the acceptor nucleic acid molecule. In some instances, the method comprises addition of a hot start thermostable polymerase (e.g., to the mixing step). In some instances, the method of the present disclosure is performed in a single tube. In some instances, the method of the present disclosure further comprises a polymerase chain reaction (PCR) amplification reaction. In some instances, the PCR amplification reaction is performed in a single tube (e.g., the same one tube as the mixing step). In some instances, all the steps of the method of the present disclosure is performed in a single tube (single vessel).

In some instances, the method for preparing a cDNA molecule comprises: (a) annealing one or more primer(s) to a template; and (b) mixing, in the presence of nucleotides (e.g., dNTPs), the template annealed to one or more primer(s) with a modified reverse transcriptase and an acceptor nucleic acid molecule (e.g., acceptor RNA, DNA, or a combination thereof) under conditions sufficient to generate a cDNA molecule complementary to the template and/or to the acceptor nucleic acid molecule. In some instances, the method for preparing a cDNA molecule is via template jumping. In some instances, step (a) and step (b) are done at the same time. In some instances, step (a) comprises step (b) (e.g., step (a) and step (b) are merged into one step). In some instances, at least one of step (a) and/or step (b) further comprises addition of a hot start thermostable polymerase. In some instances, the method of the present disclosure is performed in a single tube. In some instances, the method of the present disclosure further comprises a polymerase chain reaction (PCR) amplification reaction. In some instances, the PCR amplification reaction is performed in a single tube (e.g., the same one tube used in or from steps (a) and (b)). In some instances, all the steps of the method of the present disclosure is performed in a single tube (i.e. one-pot or single pot).

In some instances, the method for preparing a cDNA molecule comprises mixing, in the presence of nucleotides (e.g., dNTPs), one or more primer(s), a template, a modified reverse transcriptase, and an acceptor nucleic acid molecule (e.g., acceptor RNA, DNA, or a combination thereof) under conditions sufficient to generate a cDNA molecule complementary to the template and/or to the acceptor nucleic acid molecule. In some instances, the method for preparing a cDNA molecule is via template jumping. In some instances, the method comprises addition of a hot start thermostable polymerase (e.g., to the mixing step). In some instances, the method of the present disclosure is performed in a single tube. In some instances, the method of the present disclosure further comprises a polymerase chain reaction (PCR) amplification reaction. In some instances, the PCR amplification reaction is performed in a single tube (e.g., the same one tube as the mixing step). In some instances, all the steps of the method of the present disclosure is performed in a single tube.

ssDNA Sponges for RNA Depletion

Ribosomal RNAs can make up as much as 80% or more of the total RNA in a sample. It is often desirable to separate mRNA from rRNA because rRNA can adversely affect the quantitative analysis of mRNA. One approach to separating rRNA from the other RNA biotypes, including mRNA, miRNA, lncrna, and lincRNA is to deplete the rRNA from the sample. One example is the hybridization of rRNA molecules using oligonucleotides, for example, oligonucleotides homologous to the 5.8S rRNA, 17S rRNA, 18S rRNA, or 28S rRNA in the case of eukaryotic rRNAs, or to the 5S rRNA, 16S rRNA, or 23S rRNA in the case of bacterial rRNA. The oligonucleotides are designed such that they can be "captured" and the hybridization product removed from the sample. For example, the oligonucleotides may be immobilized on a surface such as a column or a bead. MICROBExpress (Registered Trademark) and MICROBEnrich (Registered Trademark) (Ambion, Austin, Tex.) are examples of commercially available kits for the depletion of rRNA. Methods and compositions for the depletion or rRNA from a sample are described in U.S. application Ser. No. 10/029,397, which is incorporated by reference. The poly(A) tail at the 3' end of most eukaryotic mRNAs can be used to separate these molecules away from rRNA and other non-mRNA species that lack this poly(A) tail.

Rather than removing the rRNA from samples, in some instances, the method of the present disclosure contemplates blocking the RNA from any potential amplification or additional reaction. In some instances, the disclosure provides a method for processing a sample comprising messenger ribonucleic acid (mRNA), ribosomal ribonucleic acid (rRNA) molecules, microRNAs (miRNA), long non-coding RNAs (lncRNA), long intergenic noncoding RNAs (lincRNA), and other RNA biotypes, including comprising using said mRNA molecules or other RNA biotypes, including miRNA, lncRNA, and lincRNA, to synthesize complementary deoxyribonucleic acid (cDNA) molecules in presence of said rRNA molecules blocked from transcription, such that less than 30% of said cDNA molecules comprise sequences from said rRNA molecules.

In some aspects, the disclosure provides a method for processing a sample comprising messenger ribonucleic acid (mRNA) and ribosomal ribonucleic acid (rRNA) molecules; comprising using said mRNA molecules to synthesize complementary deoxyribonucleic acid (cDNA) molecules in presence of said rRNA molecules blocked from transcription, such that less than 30% of said cDNA molecules comprise sequences from said rRNA molecules.

Figure 5A:
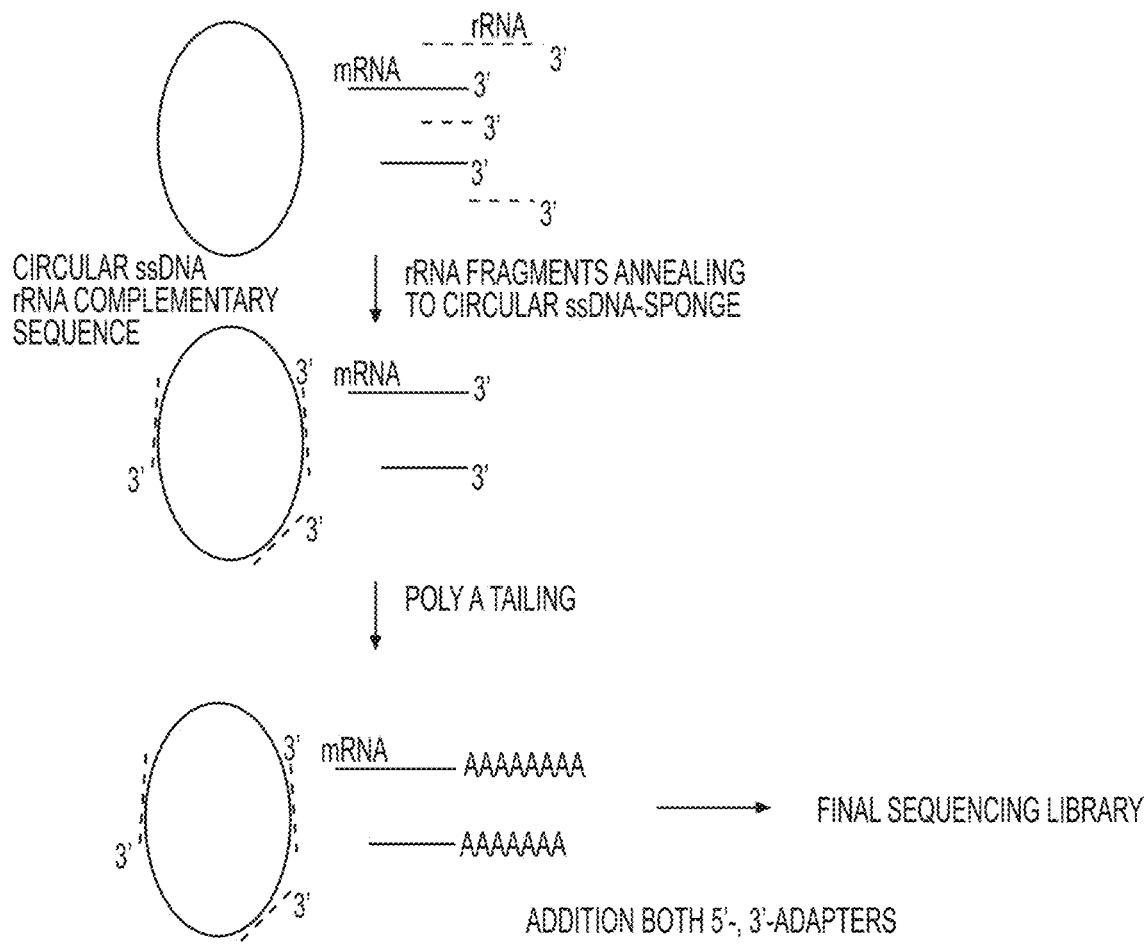
FIG. 5A illustrates a method for rRNA sequence depletion as described in the present disclosure whereas the rRNA depletion is integrated into the process of sample preparation. This figure illustrates the different steps of the procedure whereby during or right after RNA sample fragmentation, the ssDNA (DNA-sponge), which is complementary to rRNA, is included in the library preparation reaction. DNA-sponges are large ssDNA fragments that are at least partially complementary to a sequence of an rRNA subunit.
Figure 5B:
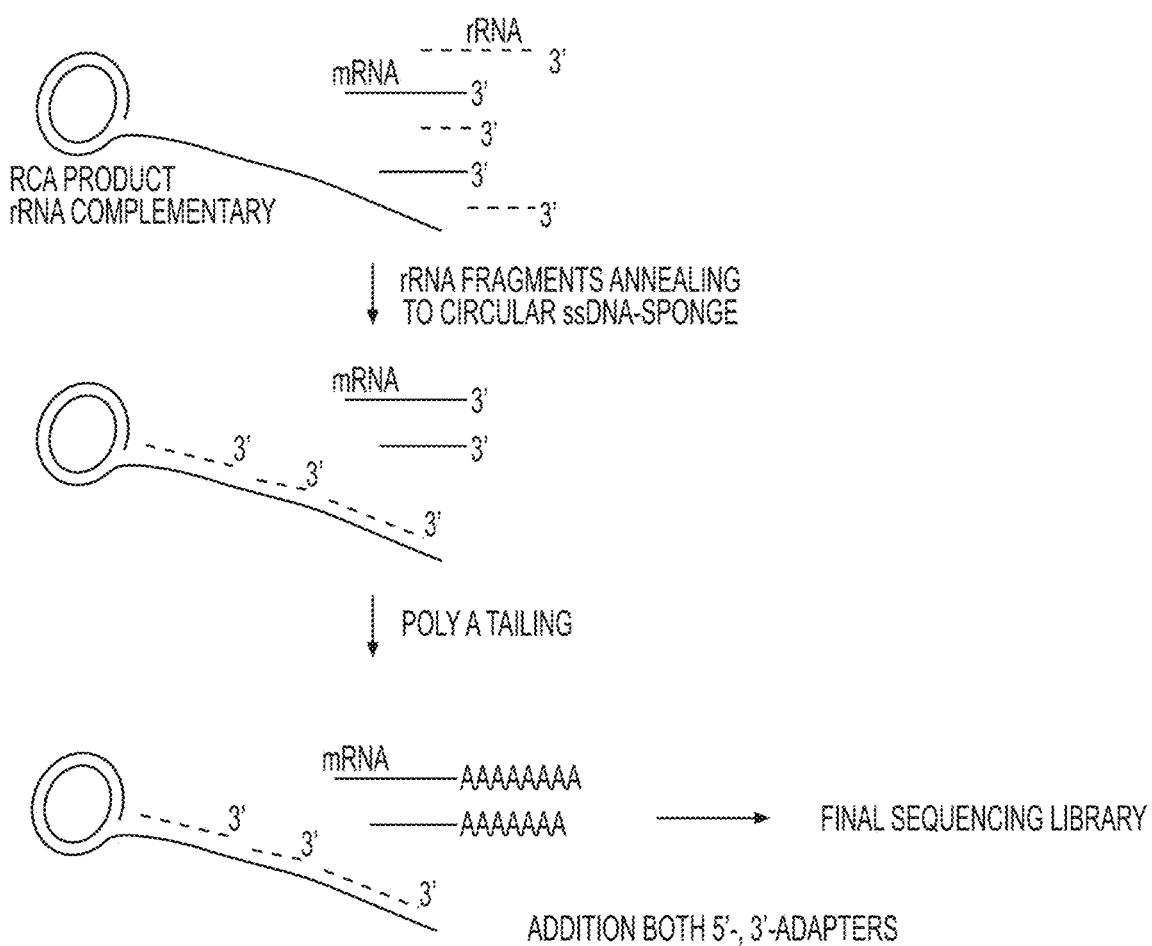
FIG. 5B illustrates a method for rRNA sequence depletion as described in the present disclosure and illustrated in FIG. 5A.
Figure 6:
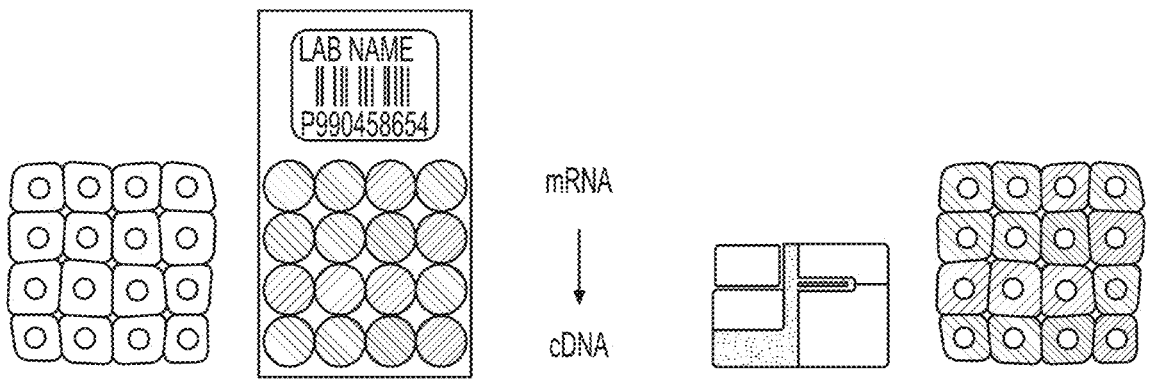
FIG. 6 illustrates the ability of in situ RNA-seq to allow genome-wide profiling of gene expression in situ in fixed cells and tissues. This figure illustrates the steps of in situ RNA-seq whereby RNA is converted into cDNA and either directly sequenced using single-molecule method or converted to a sequencing library. This figure also illustrates the spatial-specific barcoding technique in which a glass plate with printed barcoded primer oligonucleotide is used.

In some aspects, the disclosure provides a method for processing a mixture comprising a messenger ribonucleic acid (mRNA) and a ribosomal ribonucleic (rRNA) molecule, comprising: in said mixture, fragmenting said ribosomal ribonucleic (rRNA) molecule to yield a plurality of rRNA fragments; bringing one or more single stranded nucleic sequences in contact with said plurality of rRNA fragments, which one or more single-stranded nucleic acids sequences have complementarity with at least a subset of said rRNA fragments, thereby providing one or more rRNA fragment complexes comprising said one or more single-stranded nucleic acids sequences hybridized to said at least said subset of said rRNA fragments; and using a reverse transcriptase to synthesize at least one complementary deoxyribonucleic acid (cDNA) molecule from said mRNA in presence of said one or more rRNA fragment complexes (FIGS. 5 and 6).

In some aspects, the complementary to rRNA ssDNA (DNA-sponge) has a linear form with blocked 3' ends. In some instances, the DNA-sponge has a circular form. In some instances, the DNA-sponge is concatemerized. FIG. 5 illustrates a DNA-sponge with a circular form, whereas FIG. 5B illustrates a rolling-circle amplification (RCA) product. This figure illustrates the function of the DNA-sponge, which is to anneal to rRNA fragments. The annealing of the rRNA fragments to large complementary ssDNA make the 3'-end of the rRNA fragment not available to Poly A polymerase or to 3'-priming by R2 enzyme. As such, rRNA fragments without available 3'-ends will not be converted to the sequencing library, as illustrated in FIG. 5.

Direct RNA and ssDNA Sequencing with R2 Enzyme

In some aspects, the disclosure provides a method for sequencing a single stranded nucleic acid molecule, comprising providing a reaction mixture comprising said single stranded nucleic acid molecule and a non-naturally occurring enzyme, wherein said non-naturally occurring enzyme comprises a finger domain derived from an R2 retrotransposon, a plain domain derived from an R2 retrotransposon, a thumb domain derived from an R2 retrotransposon; and an endonuclease domain derived from an R2 retrotransposon. In some instances, the method disclosed herein comprises subjecting said reaction mixture to conditions sufficient to use said non-naturally occurring enzyme to incorporate individual nucleotides into a growing strand complementary to said single stranded nucleic acid molecule, wherein incorporation of said individual nucleotides into said growing strand yields detectable signals. In some instances, the method disclosed herein comprises detecting said detectable signals, thereby sequencing said single stranded nucleic acid molecule.

In some aspects, the disclosure provides a method for sequencing a single stranded nucleic acid molecule, wherein the said single stranded nucleic acid molecule is an RNA molecule. In some instances, the method disclosed herein is for sequencing a single stranded nucleic acid molecule, wherein the single stranded nucleic acid molecule is a single stranded DNA molecule.

In some aspects, the disclosure provides a method for sequencing a single stranded nucleic acid molecule, wherein said conditions sufficient to directly sequence said single stranded nucleic acid molecule comprise optic based single-molecule sequencing conditions.

In some aspects, the disclosure provides a method for sequencing a single stranded nucleic acid molecule, wherein said conditions sufficient to directly sequence said single stranded nucleic acid molecule comprise microscopy based single-molecule sequencing conditions.

In some aspects, the disclosure provides a method for sequencing a single stranded nucleic acid molecule, wherein said conditions sufficient to directly sequence said single stranded nucleic acid molecule comprise nanopore based single-molecule sequencing conditions.

In some aspects, the disclosure provides a method for sequencing a single stranded nucleic acid molecule, wherein said conditions sufficient to directly sequence said single stranded nucleic acid molecule comprise field-effect transistors based single-molecule sequencing conditions.

Common single-molecule sequencing techniques are based on long-reads, whereby several kb fragments are read in one continuous read. In some aspects, the disclosure provides a method whereby the enzyme disclosed herein is capable of efficient template jumping, whereby a large number of templates can be sequenced in a single continuous sequencing run.

In Situ RNAseq with Non-Naturally Occurring Enzymes

Unlike in situ RNA-sequencing, conventional RNA-sequencing profiles gene expression over the whole transcriptome, yet still lacks spatial context. In situ RNA sequencing, however, allows genome-wide profiling of gene expression in situ in fixed cells and fixed tissue (FIG. 6).

In some aspects, the disclosure provides a method comprising preparing a complementary deoxyribonucleic acid (cDNA) molecule from one or more ribonucleic acid (RNAs), wherein said one or more ribonucleic acid (RNAs) are derived from an in situ tissue of a subject or from a fixed ex vivo tissue of said subject with a non-naturally occurring enzyme, wherein said non-naturally occurring enzyme comprises a palm and finger domain derived from an R2 retrotransposon, a palm domain derived from an R2 retrotransposon, a thumb domain derived from an R2 retrotransposon, and an endonuclease domain derived from an R2 retrotransposon; thereby generating a cDNA molecule from said in situ tissue of said subject or from said fixed ex vivo tissue of said subject; and sequencing the said cDNA molecule generated in with the non-naturally occurring enzyme disclosed herein.

In some aspects, the disclosure provides a method comprising preparing a complementary deoxyribonucleic acid (cDNA) molecule from one or more ribonucleic acid (RNAs), wherein said one or more ribonucleic acid (RNAs) are derived from an in situ tissue of a subject or from a fixed ex vivo tissue of said subject with a non-naturally occurring enzyme, wherein said fixed ex vivo tissue of said subject is fixed in formaldehyde.

In some aspects, the disclosure provides a method comprising preparing a complementary deoxyribonucleic acid (cDNA) molecule from one or more ribonucleic acid (RNAs), wherein said one or more ribonucleic acid (RNAs) are derived from an in situ tissue of a subject or from a fixed ex vivo tissue of said subject with a non-naturally occurring enzyme, wherein said fixed ex vivo tissue of said subject is fixed and embedded in paraffin.

In some aspects, the method disclosed herein consists of cDNA that is tagged with a barcode, including but not limited to spatial information (FIG. 6). The said cDNA can then be converted to a sequencing library. In some instances, the spatial-specific barcoding technique consists of using a glass plate with oligonucleotide primers that are printed in a spatial-specific manner. In some instances, the primer used in the method disclosed herein is a specifically-barcoded polyT oligonucleotide. In some aspects, the method disclosed herein is highly sensitive and can operate with very low sample input. In some aspects, the method disclosed herein has a protocol where a random primer is used. In some instances, the method disclosed herein has a protocol where a specific primer is used.

In some instances, a biological sample has been purified. In some instances, a biological sample has not been purified. In some instances, the nucleic acid of a biological sample has not been extracted when the biological sample is provided to a tube. For example, the RNA or DNA in a biological sample may not be extracted from the biological sample when providing the biological sample to a tube. In some instances, a target nucleic acid (e.g., a target RNA or target DNA) present in a biological sample may not be concentrated prior to providing the biological sample to a reaction vessel (e.g., a tube). Any suitable biological sample that comprises nucleic acid may be obtained from a subject.

In some instances, nucleic acid from a biological sample obtained from a subject is amplified. In some cases, the biological sample is obtained directly from the subject. In some instances, a biological sample obtained directly from a subject refers to a biological sample that has been further processed after being obtained from the subject. In some instances, a biological sample obtained directly from a subject refers to a biological sample that has not been further processed after being obtained from the subject, with the exception of any approach used to collect the biological sample from the subject for further processing. For example, blood is obtained directly from a subject by accessing the subject's circulatory system, removing the blood from the subject (e.g., via a needle), and entering the removed blood into a receptacle. The receptacle may comprise reagents (e.g., anti-coagulants) such that the blood sample is useful for further analysis. In another example, a swab may be used to access epithelial cells on an oropharyngeal surface of the subject. After obtaining the biological sample from the subject, the swab containing the biological sample can be contacted with a fluid (e.g., a buffer) to collect the biological fluid from the swab.

The present disclosure relates to methods of detecting, diagnosing, and/or prognosing a disease (e.g., cancer) in a subject comprising: (a) obtaining sequence information of a nucleic acid sample (e.g., a cell-free nucleic acid sample) derived from a subject and (b) using the sequence information derived from step (a) to detect circulating tumor nucleic acid in the sample. In some instances, obtaining sequence information according to step (a) comprises using one or more adaptor(s). In some instances, the one or more adaptor(s) comprises a molecular barcode. An adaptor can comprise one or more end modifications. An adaptor can comprise one 5' phosphate. An adaptor can comprise two 5' phosphates. An adaptor can comprise one 3' hydroxyl. An adaptor can comprise two 3' hydroxyls. An adaptor can lack a 3' hydroxyl.

In some instances, the molecular barcode comprises a randomer sequence. In some instances, the method is capable of detecting cell-free nucleic acid that is less than or equal to about 0.75%, 0.50%, 0.25%, 0.1%, 0.9%, 0.8%, 0.7%, 0.6%, 0.5%, 0.4%, 0.3%, 0.2%, 0.1%, 0.05%, 0.01%, 0.009%, 0.008%, 0.007%, 0.006%, 0.005%, 0.004%, 0.003%, 0.002%, 0.001%, 0.0005%, or 0.00001%, 1%, 1.75%, 1.5%, 1.25%, 2%, 3%, 4%, 5%, 6%, 8%, 9%, 10%, 11%, 12%, 13%, 14% 15%, 16%, 17%, 18%, 19%, 20%, 22%, 25%, 27%, 30%, 32%, 35%, 40%, 45%, 50%, 55%, 60%, 65%, 70%, 75%, 80%, 85%, 90%, 95%, or 100% of total cell-free nucleic acid. In some instances, the method is capable of detecting circulating tumor nucleic acid that is less than or equal to about 0.75%, 0.50%, 0.25%, 0.1%, 0.9%, 0.8%, 0.7%, 0.6%, 0.5%, 0.4%, 0.3%, 0.2%, 0.1%, 0.05%, 0.01%, 0.009%, 0.008%, 0.007%, 0.006%, 0.005%, 0.004%, 0.003%, 0.002%, 0.001%, 0.0005%, or 0.00001%, 1%, 1.75%, 1.5%, 1.25%, 2%, 3%, 4%, 5%, 6%, 8%, 9%, 10%, 11%, 12%, 13%, 14%, 15%, 16%, 17%, 18%, 19%, 20%, 22%, 25%, 27%, 30%, 32%, 35%, 40%, 45%, 50%, 55%, 60%, 65%, 70%, 75%, 80%, 85%, 90%, 95%, or 100% of total circulating nucleic acid. In some instances, the method is capable of detecting a percentage of circulating tumor nucleic acid (ct nucleic acid) that is less than or equal to 1.75%, 1.5%, 1.25%, 1%, 0.75%, 0.50%, 0.25%, 0.1%, 0.9%, 0.8%, 0.7%, 0.6%, 0.5%, 0.4%, 0.3%, 0.2%, 0.1%, 0.05%, 0.01%, 0.009%, 0.008%, 0.007%, 0.006%, 0.005%, 0.004%, 0.003%, 0.002%, 0.001%, 0.0005%, or 0.00001% of the total cell-free nucleic acid. In some instances, the sequence information comprises information related to at least about 1, 2, 3, 4, 5, 6, 7, 8, 9, 10, 15, 20, 25, 30, 35, 40, 50, 70, 80, 100, 200, or 300 genomic regions. In some instances, the sequence information comprises information related to partially all, mostly all, or all genome sequencing. In some instances, concentrations as low as 50 ng of cfDNA may provide for full genome sequencing.

In some instances, the method of the present disclosure may be used to determine the presence of a disease (e.g., cancer) in a subject. In some instances, determining the presence of cancer in a subject comprises obtaining a sample from a subject and detecting a nucleic acid molecule (e.g., nucleic acid fragment) in the sample according to any of the methods described herein. In some instances, determining the presence of a disease (e.g., cancer) in a subject comprises amplifying and/or sequencing the nucleic acid molecule. In some instances, the presence of a nucleic acid molecule is indicative of cancer. In some instances, the presence of a nucleic acid molecule is indicative of a prenatal condition. In some instances, the nucleic acid molecule and/or template comprises an unknown sequence. In some instances, the sample is a biological sample. In some instances, the biological sample comprises circulating tumor DNA. In some instances, the biological sample comprises a tissue sample.

In some instances, the method of the present disclosure comprises detecting an amplicon generated by the amplification primers, wherein the presence of the amplicon determines whether the modified reverse transcriptase is present in the sample.

In some instances, the method of the present disclosure comprises providing a prenatal diagnosis based on the presence or absence of a nucleic acid molecule (e.g., cDNA molecule).

Preparations of RNA Libraries for Sequencing

In some aspects, the disclosure provides a method for preparing a complementary deoxyribonucleic acid (cDNA) molecule comprising fragmenting a ribonucleic acid (RNA) molecule to yield a plurality of RNA fragments; removing a 3'-phosphate, a 2'-phosphate, and a cyclic 2'3'-phosphate group from one or more of said RNA fragments, thereby generating one or more dephosphorylated fragmented rRNAs; adding a poly-A tail to said one or more dephosphorylated fragmented RNAs; adding, to said one or more dephosphorylated fragmented RNAs: a primer adapter comprising an oligo-T sequence, a poly-T and another adapter sequence compatible with major sequencing technologies; an acceptor adapter; and a non-naturally occurring R2 enzyme having a processivity of 20 nucleotides or longer.

In some aspects, the disclosure provides a method for preparing a complementary deoxyribonucleic acid (cDNA) molecule, comprising a non-naturally occurring R2 enzyme, wherein said non-naturally occurring R2 enzyme reverse transcribes a sequence from said one or more dephosphorylated fragmented RNAs in a 3' to 5' order, wherein said R2 enzyme jumps to a 3'-end of said acceptor adapter upon reaching the 5' end of said one or more dephosphorylated fragmented RNAs.

Figure 9:
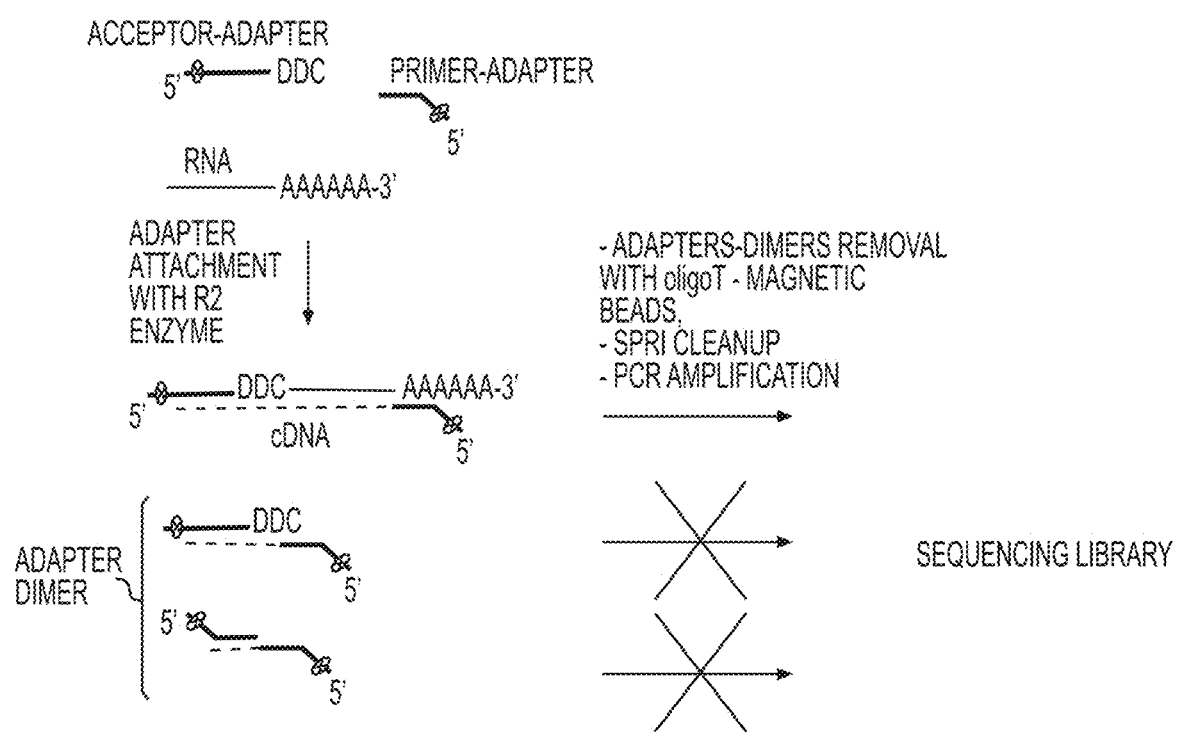
FIG. 9 illustrates the library product and adapter-dimer artifacts that can be generated in the reaction with the R2 enzyme. The adapter dimers artifacts including acceptor extension are prevented by 3'-dideoxy nucleotide at the acceptor-adapter 3'-end (alternatively different extension blockers can be applied like 3'phospho-dNTP, 3'amino-dNTP). The artifacts primed by primer-adapter (including poly-T sequence) are removed from the reaction with oligo-A attached to magnetic beads. The artifacts are primed without annealing (template primer duplex formation) so the primer sequence remained single-stranded.

In some aspects, the method disclosed herein consists of acceptor-adapter that comprises a nucleotide analogue (FIG. 9). In some instances, the said nucleotide analogue is at the 5' end of said acceptor-adapter. In some instances, the said acceptor-adaptor comprises a 3'-dideoxy nucleotide at the acceptor-adapter 3'-end.

Figure 10:
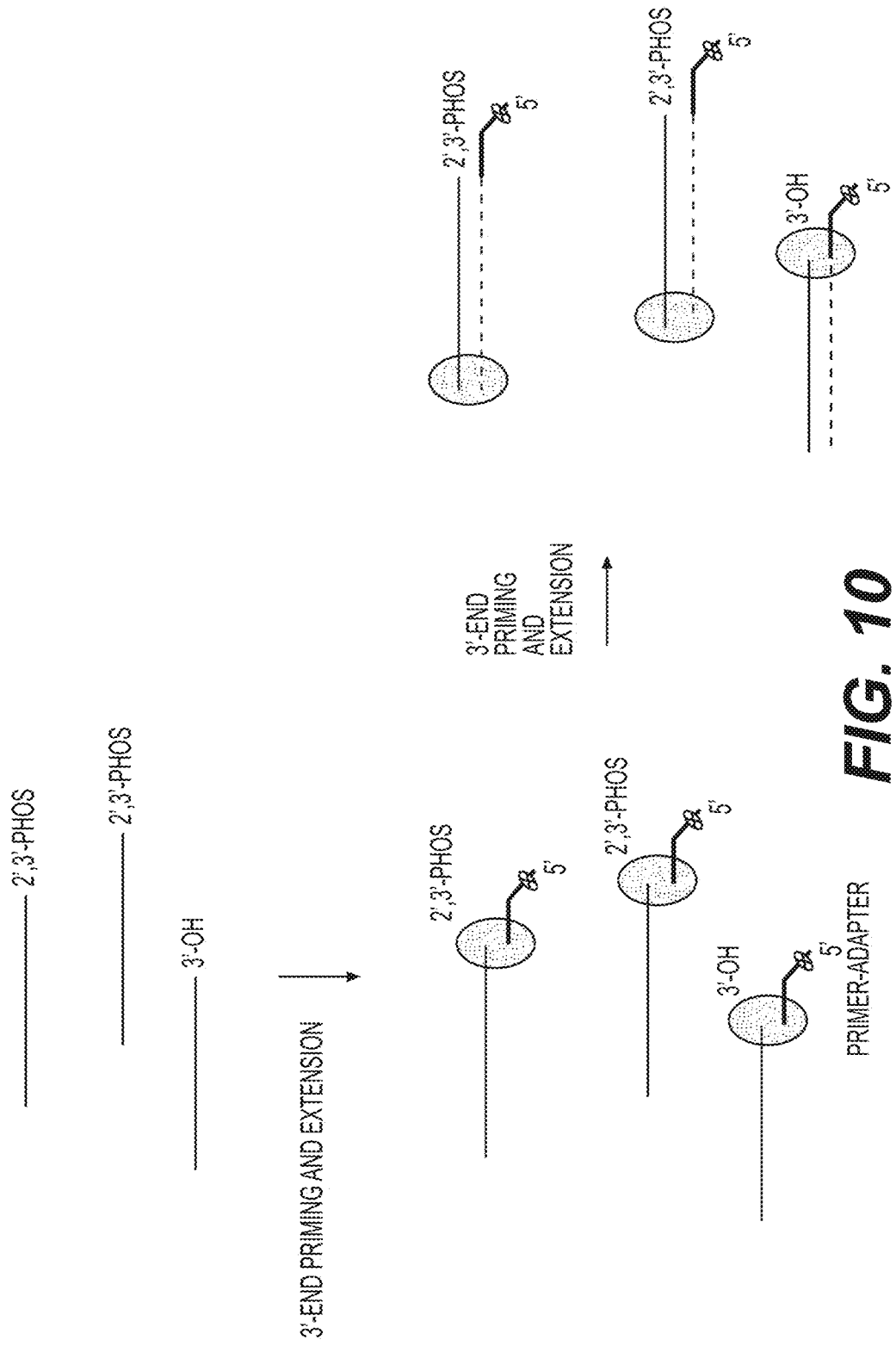
FIG. 10 illustrates 3'-end priming and extension with ssDNA primer-adapter and R2. In this mechanism, extension is primed on the 3'-end of the template by ssDNA primer without complementary sequence annealing to the template. This figure illustrates that the library products are a full length copy of the template.
Figure 11:
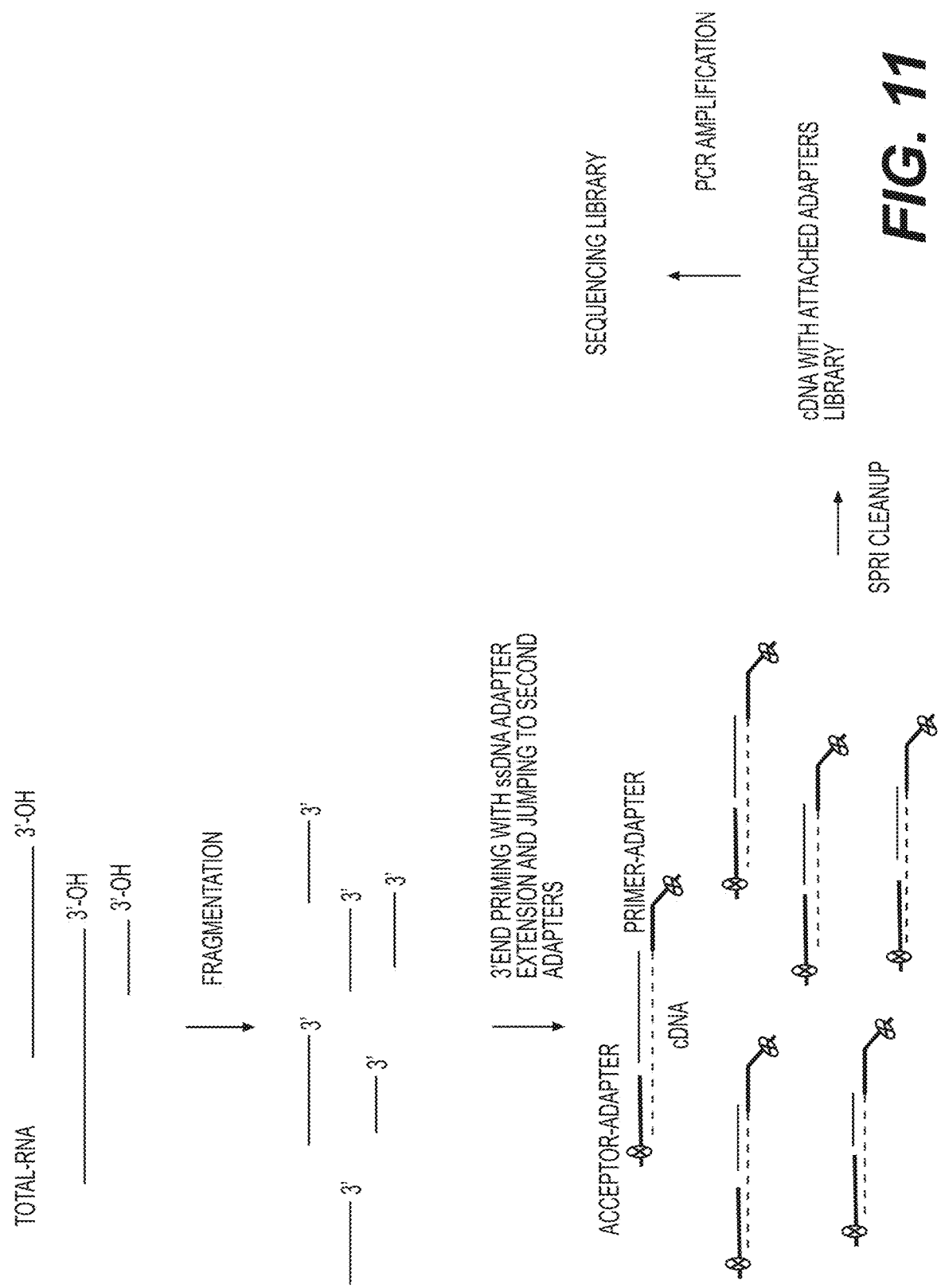
FIG. 11 illustrates a method of random priming by random fragmentation. This figure illustrates the first step, whereby the RNA sample is fragmented. This figure also illustrates the second step, whereby the RNA sample is mixed with primer-adapter (ssDNA), R2 enzyme, and acceptor-adaptor (ssDNA or RNA). The figure illustrates the third step, the cleanup by solid phase reversible immobilization (SPRI), whereby size selection is used to remove some adapter-adapter dimer artifacts. The figure illustrates the last step, which is a polymerase chain reaction (PCR) amplification using primer complementary to both the primer- and the acceptor-adapter.
Figure 12:
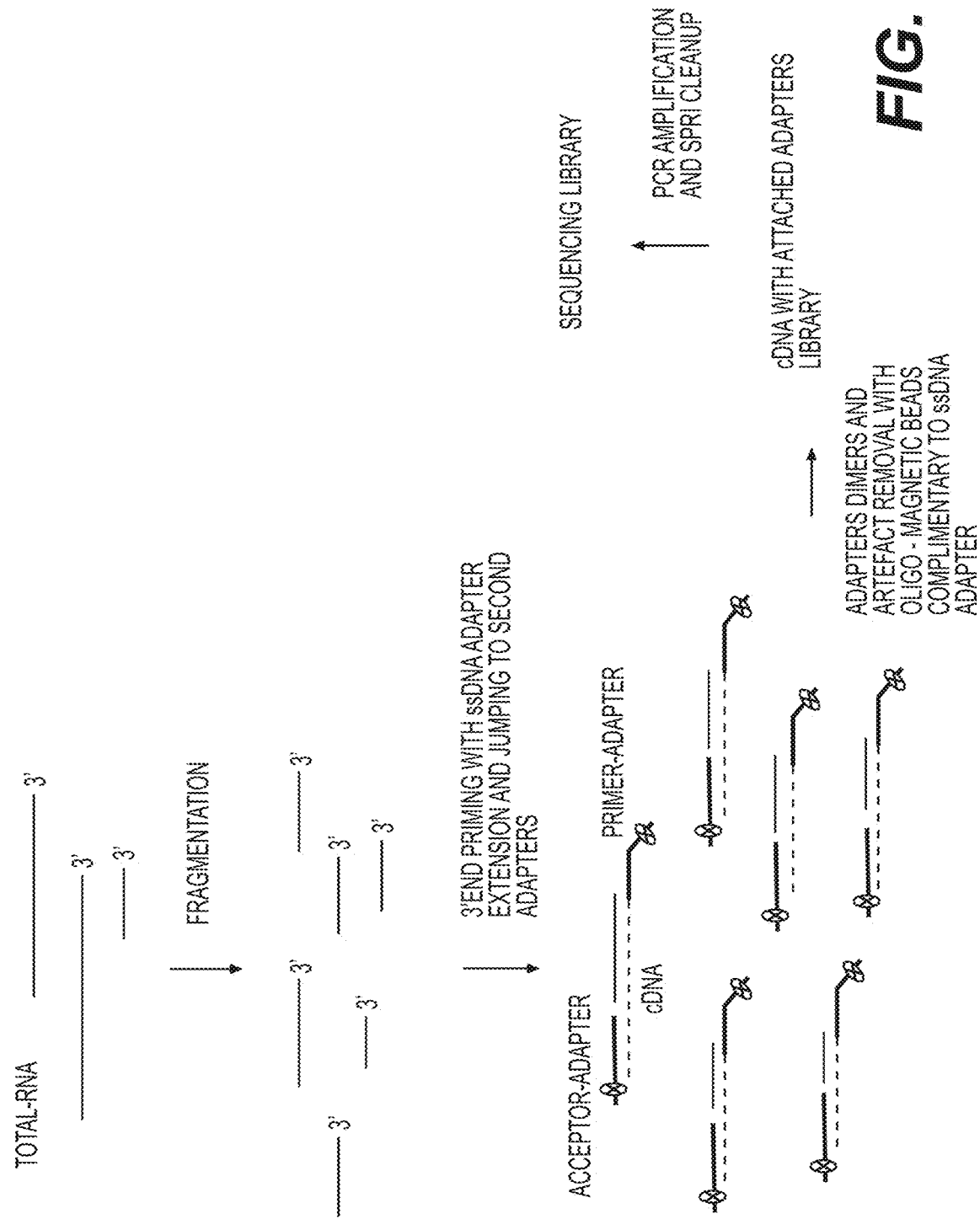
FIG. 12 illustrates the same method described in FIG. 11, however, with a different cleanup reaction. This figure illustrates the fragmentation step, the 3'-end priming, and finally the cleanup reaction, whereby adapter dimers and artifacts are removed with oligo-magnetic beads complementary to the ssDNA adapter.
Figure 13:
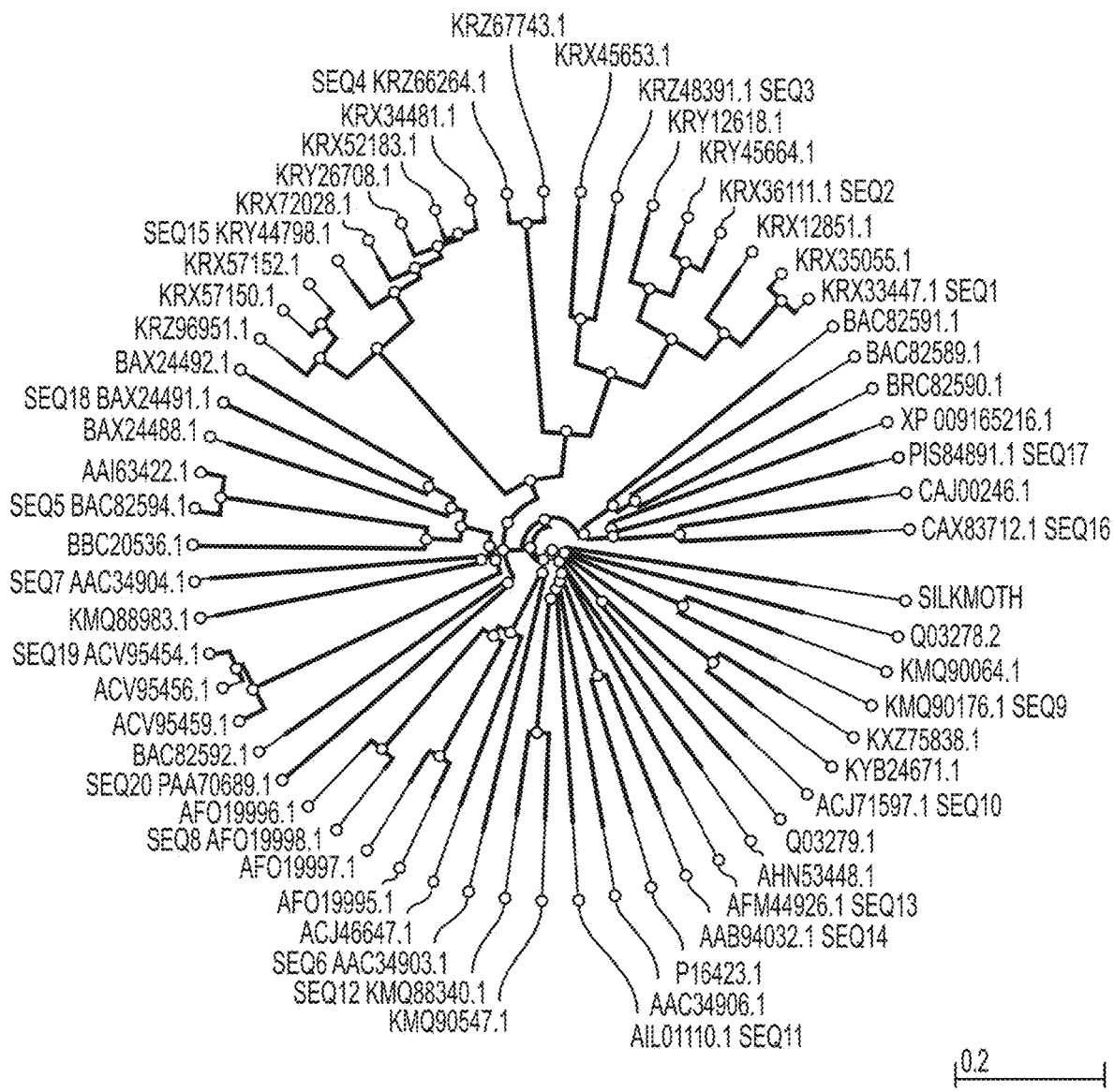
FIG. 13 illustrates a phylogenic tree, which highlights the inferred evolutionary relationships between non-LTR retro-elements and silkmoth, here with a minimum 27% identity to silkmoth, and R2 retrotransposon focused on fragments of RT-endonuclease.
Figure 19:
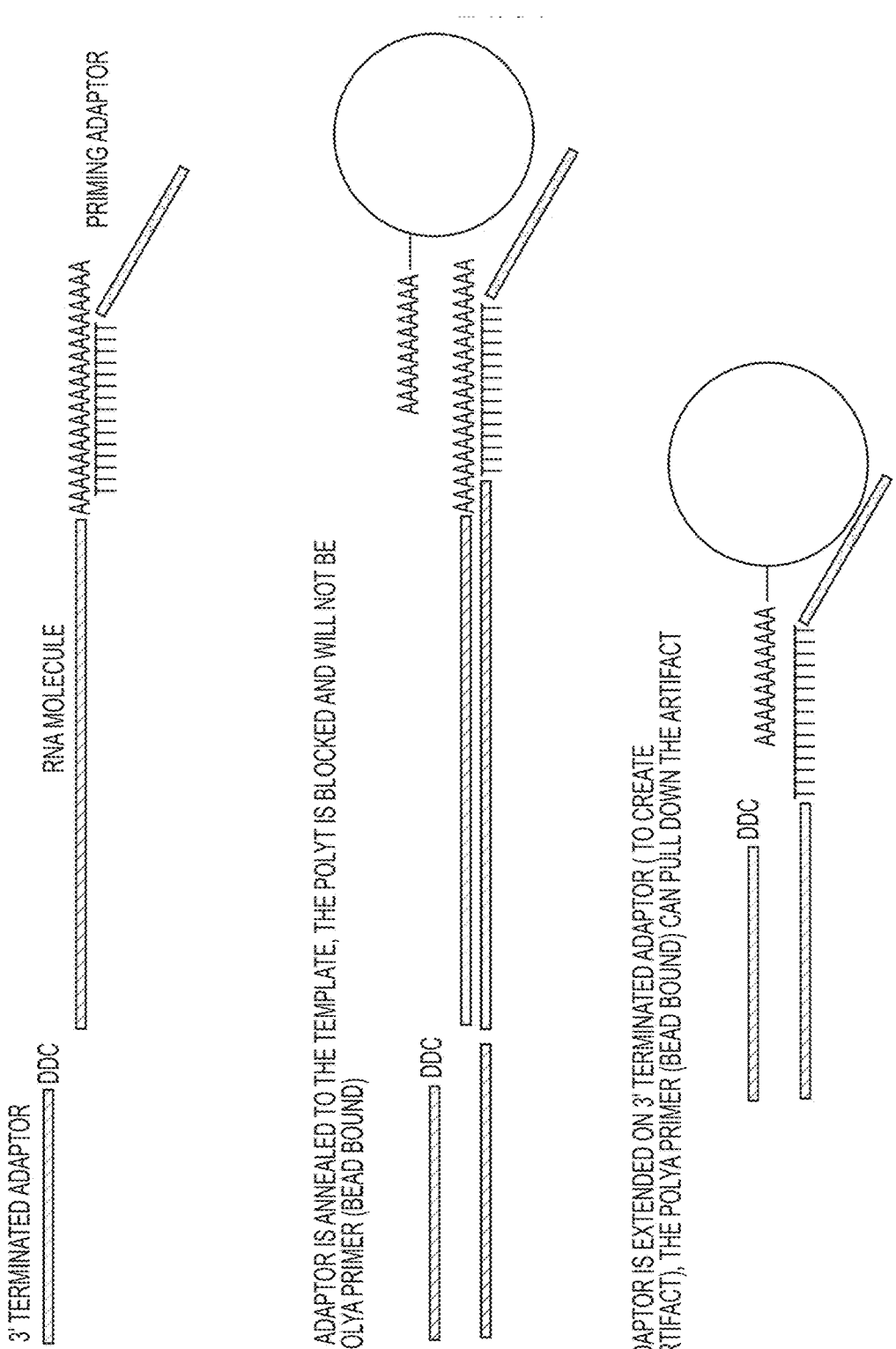
FIG. 19 illustrates a method to remove specific artifacts.
Figure 20:
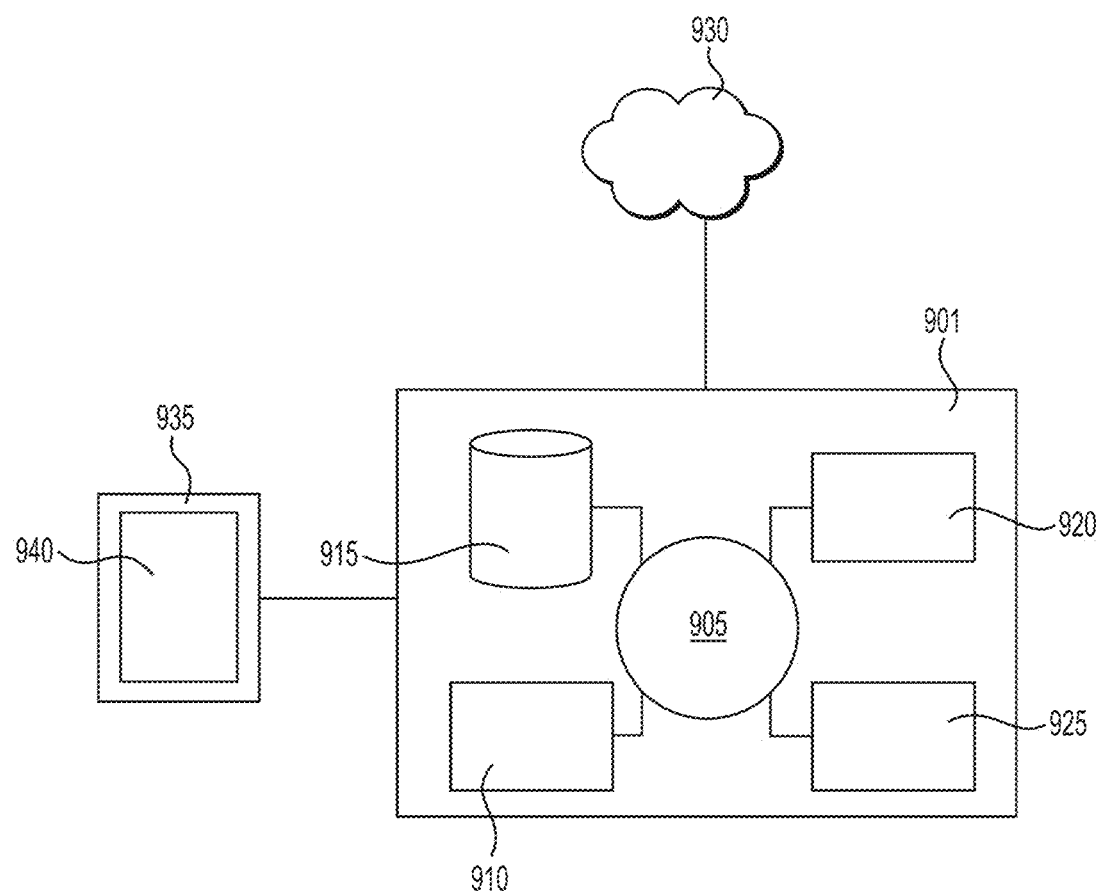
FIG. 20 illustrates a computer system that is programmed or otherwise configured to implement methods provided herein.

In some aspects, the method disclosed herein comprises a non-naturally occurring R2 enzyme, wherein said non-naturally occurring R2 enzyme reverse transcribes a sequence from said one or more fragmented RNAs in a 3' to 5' order, wherein said R2 enzyme jumps to a 3'-end of said acceptor adapter upon reaching the 5' end of said one or more fragmented RNAs (FIGS. 10, 11, and 12).

In some instances, a primer may comprise an adaptor sequence. In some instances, the 5' tail sequence of a primer comprises a sequence which does not hybridize to a target (the adaptor sequence). The adapter sequence may be selected such that it is the same in a variety of primers which have different 3' target binding sequences (i.e., a "universal" 5' tail sequence). The adapter sequence is compatible with major sequencing technologies including but not limited to, Illumina, Ion Torrent, PacBio, and Roche 454. This allows a single reporter probe sequence to be used for detection of any desired target sequence, which is an advantage in that synthesis of the reporter probe is more complex due to the labeling. In some instances, a primer may comprise an RNA primer. In some instances, a primer may comprise a DNA primer. In some instances, a primer may comprise an R2 RNA primer. In some instances, a primer may comprise one or more random primer(s).

The present disclosure relates to methods for preparing a nucleic acid molecule comprising: mixing, in the presence of nucleotides (e.g., dNTPs), a fragment or degraded template (e.g., a nucleic acid fragment), a primer, a modified reverse transcriptase, and an acceptor nucleic acid molecule under conditions sufficient to generate a nucleic acid molecule. In some instances, the acceptor nucleic acid molecule comprises a modified nucleotide. In some instances, the primer extension stops at the modified nucleotide. In some instances, the modified reverse transcriptase comprises at least one improved enzyme property relative to a wild type, naturally occurring, or unmodified reverse transcriptase. In some instances, the primer is an RNA primer. In some instances, the primer is an engineered primer (e.g., engineered RNA primer). In some instances, the primer has been optimized. In some instances, the primer is an optimized and/or engineered primer (e.g., optimized and/or engineered RNA primer). In some instances, the primer is RNA R2 primer. In some instances, the method for preparing a nucleic acid molecule is via template jumping. In some instances, the mixing step of the method of the present disclosure further comprises addition of a hot start thermostable polymerase. In some instances, the method of the present disclosure is performed in a single tube. In some instances, the method of the present disclosure further comprises a polymerase chain reaction (PCR) amplification reaction. In some instances, the PCR amplification reaction is performed in the same single tube. In some instances, all the steps of the method of the present disclosure is performed in a single tube.

The present disclosure relates to methods for preparing a nucleic acid molecule comprising: mixing, in the presence of nucleotides (e.g., dNTPs), a fragment or degraded template (e.g., a nucleic acid fragment), a donor complex, a modified reverse transcriptase, and an acceptor nucleic acid molecule under conditions sufficient to generate a nucleic acid molecule. In some instances, the acceptor nucleic acid molecule comprises a modified nucleotide. In some instances, the primer extension stops at the modified nucleotide. In some instances, the modified reverse transcriptase comprises at least one improved enzyme property relative to a wild type or naturally occurring or unmodified reverse transcriptase. In some instances, the donor complex comprises a template and a primer. In some instances, the donor complex is a donor R2 complex. In some instances, the donor R2 complex comprises an RNA R2 primer. In some instances, the method for preparing a nucleic acid molecule is via template jumping. In some instances, the mixing step of the method of the present disclosure further comprises addition of a hot start thermostable polymerase. In some instances, the method of the present disclosure is performed in a single tube. In some instances, the method of the present disclosure further comprises a polymerase chain reaction (PCR) amplification reaction. In some instances, the PCR amplification reaction is performed in the same single tube (e.g., the same single tube used to prepare a nucleic acid molecule). In some instances, all the steps of the method of the present disclosure is performed in a single tube.

The present disclosure relates to methods for preparing a complementary deoxyribonucleic acid (cDNA) library using a modified reverse transcriptase. In some instances, the method for preparing a cDNA library uses template jumping. In some instances, the modified reverse transcriptase has an improved enzyme property compared to a naturally occurring or wild type or unmodified enzyme (e.g., wild type reverse transcriptase). In some instances, the method for preparing a cDNA library comprises: (a) annealing a primer or one or more primer(s) to a template; and (b) mixing, in the presence of nucleotides (e.g., dNTPs), the template annealed to the primer or the template annealed to one or more primer(s) with a modified reverse transcriptase and an acceptor nucleic acid molecule (e.g., acceptor RNA, DNA, or a combination thereof) under conditions sufficient to generate a cDNA molecule complementary to the template and/or to the acceptor nucleic acid molecule. In some instances, the method for preparing a cDNA library comprises mixing, in the presence of nucleotides (e.g., dNTPs), a primer or one or more primer(s), a template, a modified reverse transcriptase, and an acceptor nucleic acid molecule (e.g., acceptor RNA, DNA, or a combination thereof) under conditions sufficient to generate a cDNA molecule complementary to the template and/or to the acceptor nucleic acid molecule. In some instances, the enzyme (e.g., modified reverse transcriptase) generates a continuous cDNA molecule by migrating from the template to the acceptor nucleic acid molecule. In some instances, template jumping is independent of sequence identity between the template and the acceptor nucleic acid molecule. In some instances the method further comprises amplifying the cDNA molecule to generate a cDNA library. In some instances, step (a) and step (b) are done at the same time. In some instances, step (a) comprises step (b) (e.g., step (a) and step (b) are merged into one step). In some instances, the mixing step or at least one of step (a) and/or step (b) further comprises addition of a hot start thermostable polymerase. In some instances, the method of the present disclosure is performed in a single tube. In some instances, the method of the present disclosure further comprises a polymerase chain reaction (PCR) amplification reaction. In some instances, the PCR amplification reaction is performed in a single tube (e.g., the same one tube used in or from the mixing step, or in or from steps (a) and (b)). In some instances, all the steps of the method of the present disclosure is performed in a single tube.

The present disclosure relates to methods for preparing a cDNA and/or DNA library comprising: mixing, in the presence of nucleotides (e.g., dNTPs), a fragment or degraded template (e.g., a nucleic acid fragment), a primer, a modified reverse transcriptase, and an acceptor nucleic acid molecule under conditions sufficient to generate a nucleic acid (e.g., cDNA and/or DNA) molecule. In some instances, the acceptor nucleic acid molecule comprises a modified nucleotide. In some instances, the primer extension stops at the modified nucleotide. In some instances, the modified reverse transcriptase comprises at least one improved enzyme property relative to a wild type or unmodified reverse transcriptase. In some instances, the primer is an RNA R2 primer. In some instances, the method further comprises amplifying the nucleic acid (e.g., cDNA and/or DNA) molecule to generate a cDNA library. In some instances, the method for preparing a cDNA and/or DNA and/or nucleic acid molecule is via template jumping.

The present disclosure relates to methods for preparing a cDNA and/or DNA library comprising: mixing, in the presence of nucleotides (e.g., dNTPs), a fragment or degraded template (e.g., a nucleic acid fragment), a donor complex, a modified reverse transcriptase, and an acceptor nucleic acid molecule under conditions sufficient to generate a nucleic acid (e.g., cDNA and/or DNA) molecule. In some instances, the acceptor nucleic acid molecule comprises a modified nucleotide. In some instances, the primer extension stops at the modified nucleotide. In some instances, the modified reverse transcriptase comprises at least one improved enzyme property relative to a wild type or unmodified reverse transcriptase. In some instances, the donor complex comprises a template and a primer. In some instances, the donor complex is a donor R2 complex. In some instances, the donor R2 complex comprises an RNA R2 primer. In some instances, the method further comprises amplifying the nucleic acid (e.g., cDNA and/or DNA) molecule to generate a cDNA and/or DNA library. In some instances, the method for preparing a cDNA and/or DNA and/or nucleic acid molecule is via template jumping.

In some instances, the method of the present disclosure may comprise a donor complex. In some instances, the donor complex comprises a template and a primer. In some instances, the method of the present disclosure may comprise a template. In some instances, the template is a fragmented and/or degraded template. In some instances, the template is not fragmented. In some instances, the template is RNA, DNA, or a combination of DNA and RNA. In some instances, the RNA is mRNA. In some instances, the template is mRNA.

The present disclosure relates to methods for preparing a library for sequencing comprising: (a) obtaining a sample with cell-free nucleic acid from a subject; and (b) adding a modified reverse transcriptase enzyme, a template (e.g., a nucleic acid template), nucleotides, an acceptor nucleic acid molecule, and one or more primer(s) to the nucleic acid. In some instances, the method further comprises conducting an amplification reaction on the cell-free nucleic acid (cf nucleic acid) derived from the sample to produce a plurality of amplicons. In some instances, the amplification reaction comprises 35 or fewer amplification cycles. In some instances, the method comprises producing a library for sequencing. In some instances, the library comprises a plurality of amplicons. In some instances, the modified reverse transcriptase is capable of template jumping and/or comprises at least one improved enzyme property relative to a wild type or unmodified reverse transcriptase. In some instances, the nucleic acid is DNA, RNA, or a combination of RNA and DNA.

The present disclosure relates to a method for preparing a complementary deoxyribonucleic acid (cDNA) molecule using template jumping, comprising mixing, in a single tube, a primer or one or more primer(s), a messenger RNA (mRNA) template, nucleotides, a modified reverse transcriptase, an acceptor nucleic acid molecule, and a catalytic metal under conditions sufficient to generate a continuous cDNA molecule. In some instances, the continuous cDNA molecule is complementary to the mRNA template and/or to the acceptor nucleic acid molecule. In some instances, the modified reverse transcriptase comprises at least one improved enzyme property relative to a wild type or unmodified reverse transcriptase. In some instances, a continuous cDNA molecule is produced. In some instances, the modified reverse transcriptase undergoes migration from the template to the acceptor nucleic acid molecule.

The present disclosure relates to a method for preparing a library for sequencing comprising mixing, in a single tube, a cell-free nucleic acid, a modified reverse transcriptase enzyme, a template, nucleotides, an acceptor nucleic acid molecule, a catalytic metal, and one or more primer(s) under conditions sufficient to generate a library. In some instances, the modified reverse transcriptase comprises at least one improved enzyme property relative to a wild type or unmodified reverse transcriptase.

In some instances, the nucleic acid molecule comprises an unknown nucleic acid sequence. In some instances, the template comprises an unknown nucleic acid sequence. In some instances, the migration from the template to the acceptor nucleic acid molecule is independent of sequence identity between the template and the acceptor nucleic acid molecule. In some instances, the acceptor nucleic acid molecule comprises a modified nucleotide that may cause primer extension to stop. In some instances, the cell-free nucleic acid is cell-free DNA (cfDNA), circulating tumor DNA (ctDNA), and/or formalin-fixed, paraffin-embedded DNA (FFPE DNA), or combinations thereof.

In some instances, a hot start thermostable polymerase may be added to a method of the present disclosure at or prior to any step of the method and/or at the same time that a mixing step takes place. For example, a hot start thermostable polymerase may be added at the same time that the modified reverse transcriptase is added to the reaction. The hot start thermostable polymerase may be added at the same time that the acceptor nucleic acid molecule is added, and/or at the same time that the template, and/or primer, and/or reverse transcriptase, and/or nucleotides is added to the reaction tube. In some instances, the hot start thermostable polymerase is added prior to the start of the PCR reaction. In some instances, the hot start thermostable polymerase is added prior to or at the same time as the RT reaction. In some instances, the hot start thermostable polymerase is hot start taq polymerase. Amplification of target nucleic acids can occur on a bead. In some instances, amplification does not occur on a bead. Amplification can be by isothermal amplification, e.g., isothermal linear amplification. In some instances, a hot start PCR can be performed wherein the reaction is heated to 95° C. e.g., for two minutes prior to addition of a polymerase or the polymerase can be kept inactive until a first heating step in cycle 1. Hot start PCR can be used to minimize nonspecific amplification.

In some instances, the PCR amplification is performed at a temperature sufficient to inactivate the reverse transcriptase enzyme. In some instances, the PCR amplification is performed at a temperature sufficient to activate the hot start thermostable polymerase.

The present disclosure relates to methods of amplifying a cell-free nucleic acid molecule from a sample. In some instances, the sample is a biological sample. In some instances, the cell-free nucleic acid molecule is subjected to nucleic acid amplification comprising a reverse transcriptase (e.g., modified reverse transcriptase). In some instances, the cell-free nucleic acid molecule is subjected to nucleic acid amplification comprising a reverse transcriptase (e.g., modified reverse transcriptase) under conditions that amplify the nucleic acid molecule at a specified processivity. In some instances the processivity is of at least about 80% per base, at least about 81% per base, at least about 82% per base, at least about 83% per base, at least about 84% per base, at least about 85% per base, at least about 86% per base, at least about 87% per base, at least about 88% per base, at least about 89% per base, at least about 90% per base, at least about 91% per base, at least about 92% per base, at least about 93% per base, at least about 94% per base, at least about 95% per base, at least about 96% per base, at least about 97% per base, at least about 98% per base, at least about 99% per base, or at least about 100% per base. In some instances, the processivity is performed at a temperature of about or at most about or at least about 12° C., of about or at most about or at least about 13° C., of about or at most about or at least about 14° C., of about or at most about or at least about 15° C., of about or at most about or at least about 16° C., of about or at most about or at least about 17° C., of about or at most about or at least about 18° C., of about or at most about or at least about 19° C., of about or at most about or at least about 20° C., of about or at most about or at least about 21° C., of about or at most about or at least about 22° C., of about or at most about or at least about 23° C., of about or at most about or at least about 24° C., of about or at most about or at least about 25° C., of about or at most about or at least about 26° C., of about or at most about or at least about 27° C. of about or at most about or at least about 28° C., of about or at most about or at least about 29° C., of about or at most about or at least about 30° C., of about or at most about or at least about 31° C., of about or at most about or at least about 32° C., of about or at most about or at least about 33° C., of about or at most about or at least about 34° C., of about or at most about or at least about 35° C., of about or at most about or at least about 36° C., of about or at most about or at least about 37° C., of about or at most about or at least about 38° C., of about or at most about or at least about 39° C., of about or at most about or at least about 40° C., of about or at most about or at least about 45° C., of about or at most about or at least about 50° C., of about or at most about or at least about 60° C., of about or at most about or at least about 70° C., of about or at most about or at least about 80° C., of about or at most about or at least about 8° C. In some instances the processivity is of at least about 80% per base, at least about 81% per base, at least about 82% per base, at least about 83% per base, at least about 84% per base, at least about 85% per base, at least about 86% per base, at least about 87% per base, at least about 88% per base, at least about 89% per base, at least about 90% per base, at least about 91% per base, at least about 92% per base, at least about 93% per base, at least about 94% per base, at least about 95% per base, at least about 96% per base, at least about 97% per base, at least about 98% per base, at least about 99% per base, or at least about 100% per base, at a temperature of about or at most about or of at least about 30° C., or of about or at most about or of at least about 12° C., of about or at most about or of at least about 45° C., of about or at most about or of at least about 35° C. In some instances, the reverse transcriptase is a non-LTR retrotransposon or a modified non-LTR retrotransposon. In some instances, the reverse transcriptase is an R2 reverse transcriptase or a modified R2 reverse transcriptase. In some instances, the reverse transcriptase is an R2 non-LTR retrotransposon or a modified R2 non-LTR retrotransposon.

The present disclosure relates to methods for preparing a complementary deoxyribonucleic acid (cDNA) library and/or a DNA library from a plurality of single cells. In some instances, the method comprises the steps of: releasing nucleic acid from each single cell to provide a plurality of individual nucleic acid samples. In some instances, the nucleic acid in each individual nucleic acid sample is from a single cell. In some instances, the method further comprises annealing the nucleic acid template to one or more primer(s). In some instances, the method further comprises mixing the nucleic acid template annealed to one or more primer(s) with an acceptor template (or an acceptor nucleic acid molecule) and a modified reverse transcriptase, in the presence of nucleotides, under conditions effective for producing a cDNA and/or a DNA molecule. In some instances, the modified reverse transcriptase is capable of template jumping and/or comprises at least one improved enzyme property relative to a wild type or unmodified reverse transcriptase. In some instances, the method further comprises amplifying the cDNA molecule and/or DNA molecule to generate a cDNA and/or DNA library.

The present disclosure relates to methods of detecting a nucleic acid molecule. In some instances, the method comprises mixing a sample comprising a nucleic acid molecule with an acceptor template (or an acceptor nucleic acid molecule), a modified reverse transcriptase, a primer, and nucleotides, under conditions effective for generating a nucleic acid molecule. In some instances, the modified reverse transcriptase comprises at least one improved enzyme property relative to a wild type or unmodified reverse transcriptase. In some instances, the acceptor template (or an acceptor nucleic acid molecule) comprises at least one modified nucleotide. In some, the modified nucleotide may cause primer extension to stop. In some instances, the method further comprises amplifying the nucleic acid molecule.

The present disclosure relates to any method disclosed herein wherein the methods may further comprise detecting at least one amplicon generated by the amplification primers. In some instances, the presence of at least one amplicon indicates the presence of at least one modified reverse transcriptase in a sample.

In some instances, any of the methods of the present disclosure does not comprise a purification step. In some instances, any of the methods of the present disclosure comprises at least one purification step. In some instances, any of the methods of the present disclosure comprises at least two purification steps. In some instances, any of the methods of the present disclosure comprises at least three, at least four, at least five, at least six, at least seven, at least eight, at least nine, at least ten, at least fifteen, or at least twenty purification steps.

The present disclosure relates to a method for preparing a library for sequencing.

In some instances, the modified reverse transcriptase is a modified non-retroviral reverse transcriptase. In some instances, the modified reverse transcriptase is a modified non-LTR retrotransposon. In some instances, the modified reverse transcriptase is a modified R2 reverse transcriptase.

In some instances, the sample is a biological sample. In some instances, the biological sample comprises a circulating tumor DNA. In some instances, the biological sample comprises a tissue sample. In some instances, the nucleic acid is from a sample. In some instances, the sample is a liquid biopsy sample. In some instances, a sample may be an RNA sample. In some instances, an RNA sample may be used for various purposes, including but not limited to PCR, ligation, transcriptome analysis, microarray analysis, northern analysis, and cDNA library construction. In some instances, the present disclosure is directed to methods for amplifying cDNA libraries from low quantities of cells and/or single cells in suitable quantity and quality for transcriptome analysis through, for example, sequencing or microarray analysis.

In some instances, the nucleic acid and/or a template is of an unknown sequence. In some instances, the nucleic acid and/or a template is RNA, DNA, or a combination of RNA and DNA. In some instances, the RNA is mRNA. In some instances, the mRNA comprises internal priming. In some instances, the nucleic acid may be a fragmented nucleic acid and/or a degraded nucleic acid. In some instances, the template may be a fragmented template and/or a degraded template. In some instances, the nucleic acid may be a non-fragmented nucleic acid and/or a non-degraded nucleic acid. In some instances, the template may be a non-fragmented template and/or a non-degraded template. In some instances, the nucleic acid and/or template is indicative of a disease. In some instances, the nucleic acid and/or template is indicative of cancer. In some instances, the nucleic acid is equal to or less than about 0.01 micromolar. In some instances, the nucleic acid is between about 0.1 nM to about 100 nM. In some instances, the nucleic acid is equal to or less than about 500 femtomolar.

In some instances, the RNA is obtained from a source selected from the group consisting of single cells, cultured cells, tissues, RNA transcription-based amplified RNA (such as TTR-amplified RNA or other DNA-dependent RNA polymerase transcribed RNA), RNA-promoter-driven transcribed RNA, aRNA, aRNA-amplified RNA, single-cell mRNA library, isolated mRNA, RNA contained within cells, and combinations of RNA sources. In some instances, the RNA is prepared from a plurality of fixed cells, wherein said fixed cells are protected from RNA degradation and also subjected to permeabilisation for enzyme penetration. In some instances, the fixed cells are obtained from fixative-treated cultural cells, frozen fresh tissues, fixative-treated fresh tissues or paraffin-embedded tissues on slides.

In some instances, the RNA molecule can be the product of in vitro synthesis or can have been isolated from cells or tissues (Ausubel, et. al., Short Protocols in Molecular Biology, 3rd ed., Wiley, 1995). Cells and tissues suitable for use in obtaining RNA useful in the practice of the present disclosure may include both animal cells and plant cells. In some instances, the cells include mammalian cells and insect cells. RNA may also be isolated from prokaryotic cells such as bacteria.

In some instances, the template is RNA, DNA, or a combination of RNA and DNA. In some instances, the template may be a fragmented template and/or a degraded template. In some instances, the template is not degraded and/or fragmented. In some instances, the RNA is mRNA. In some instances, the template is an RNA template. In some instances, the template is a DNA template. In some instances, the template is a DNA and/or RNA template. In some instances, the template is a mixture of DNA and RNA. In some instances, the RNA comprises any type of RNA (e.g., one or more of rRNA, tRNA, mRNA, lncRNA, lincRNA, miRNA, and/or snRNA). In some instances the RNA comprises a mixture of at least one type of RNA. In some instances, the DNA can comprise a mixture of, or at least one of, genomic DNA or nuclear DNA, mitochondrial DNA, Y-line DNA, autosomal DNA, ribosomal DNA, or a combination thereof. In some instances, the template is a polymer of any length. In some instances, the template is from about 20 bases to about 100 bases, from about 30 bases to about 500 bases, from about 30 bases to about 1000 bases, from about 50 bases to about 300 bases, about 100 bases to about 600 bases, about 200 bases to about 800 bases, about 200 bases to about 600 bases, about 100 bases to about 2000 bases, about 100 bases and about 2500 bases, about 200 bases to about 5000 bases, about 200 bases to about 1000 bases, about 200 to about 10000 bases. In some instances, the template is at least about 10 bases, at least about 20 bases, at least about 30 bases, at least about 40 bases, at least about 50 bases, at least about 60 bases, at least about 70 bases, at least about 80 bases, at least about 90 bases, at least about 100 bases, at least about 150 bases, at least about 200 bases, at least about 250 bases, at least about 300 bases, at least about 350 bases, at least about 400 bases, at least about 450 bases, at least about 500 bases, at least about 550 bases, at least about 600 bases, at least about 650 bases, at least about 700 bases, at least about 750 bases, at least about 800 bases, at least about 850 bases, at least about 900 bases, at least about 950 bases, at least about 1000 bases, at least about 1100 bases, at least about 1200 bases, at least about 1300 bases, at least about 1400 bases, at least about 1500 bases, at least about 1700 bases, at least about 2000 bases, at least about 2200 bases, at least about 2500 bases, at least about 2700 bases, at least about 3000, at least about 3500 bases, at least about 4000 bases, at least about 4500 bases, at least about 5000 bases, at least about 10,000 bases, or at least about 50,000 bases. In some instances, the template is about or at least about or at most about 10 bases, about or at least about or at most about 20 bases, about or at least about or at most about 30 bases, about or at least about or at most about 40 bases, about or at least about or at most about 50 bases, about or at least about or at most about 60 bases, about or at least about or at most about 70 bases, about or at least about or at most about 80 bases, about or at least about or at most about 90 bases, about or at least about or at most about 100 bases, about or at least about or at most about 150 bases, about or at least about or at most about 200 bases, about or at least about or at most about 250 bases, about or at least about or at most about 300 bases, about or at least about or at most about 350 bases, about or at least about or at most about 400 bases, about or at least about or at most about 450 bases, about or at least about or at most about 500 bases, about or at least about or at most about 550 bases, about or at least about or at most about 600 bases, about or at least about or at most about 650 bases, about or at least about or at most about 700 bases, about or at least about or at most about 750 bases, about or at least about or at most about 800 bases, about or at least about or at most about 850 bases, about or at least about or at most about 900 bases, about or at least about or at most about 950 bases, about or at least about or at most about 1000 bases, about or at least about or at most about 1100 bases, about or at least about or at most about 1200 bases, about or at least about or at most about 1300 bases, about or at least about or at most about 1400 bases, about or at least about or at most about 1500 bases, about or at least about or at most about 1700 bases, about or at least about or at most about 2000 bases, about or at least about or at most about 2200 bases, about or at least about or at most about 2500 bases, about or at least about or at most about 2700 bases, about or at least about or at most about 3000, about or at least about or at most about 3500 bases, about or at least about or at most about 4000 bases, about or at least about or at most about 4500 bases, about or at least about or at most about 5000 bases, about or at least about or at most about 10,000 bases, or about or at least about or at most about 50,000 bases. In some instances, the template DNA may be a double-stranded DNA template (dsDNA template) or a single-stranded DNA template (ssDNA template). In some instances, the template RNA may be a double-stranded RNA template (dsRNA template) or a single-stranded RNA template (ssRNA template).

In some instances, the template is from a single cell. In some instances, the template is from a plurality of cells. In some instances, the template comprises low copy number DNA, or RNA, or a combination of DNA and/or RNA. In some instances, low copy number refers to samples that contain equal to or less than about 250 picograms (e.g. 100 picograms) of for example the template and/or DNA and/or RNA and/or a mixture of DNA and RNA. In some instances, the RNA can comprise at least one of messenger RNA (mRNA), transfer RNA, transfer-messenger RNA, ribosomal RNA, antisense RNA, small nuclear RNA (snRNA), small nucleolar RNA (snoRNA), micro-RNA (miRNA), small interfering RNA (siRNA), long non-coding RNA (lncRNA), long intervening noncoding (lincRNA), or any combination thereof. In some instances, the template is from a sample. In some instances, the total amount of template is the total amount of template in a sample. In some instances, the total amount of template is the total amount of template in a reaction mixture. In some instances, the total amount of template is the total amount of template in one pot (e.g., single vessel). In some instances, the total amount of the template is from about 1 femtomolar (fM) to about 100 micromolar, from about 40 femtomolar to about 0.01 micromolar, from about 50 femtomolar to about 500 femtomolar, from about 50 femtomolar to about 0.01 micromolar, from about 50 femtomolar to about 0.1 micromolar, from about 50 femtomolar to about 500 picomolar, from about 50 femtomolar to about 500 nanomolar, from about 50 femtomolar to about 500 micromolar, from about 50 femtomolar to about 1 picomolar, from about 40 femtomolar to about 1 nanomolar, from about 1 femtomolar to about 1 picolomar, from about 0.0001 micromolar to about 0.01 micromolar, from about 0.0001 micromolar to about 0.1 micromolar, or from about 0.1 nM to about 100 nM. In some instances, the total about of template is equal to or at least about or lower than about 1000 micromolar, equal to or at least about or lower than about 500 micromolar, equal to or at least about or lower than about 250 micromolar, equal to or at least about or lower than about 100 micromolar, equal to or at least about or lower than about 50 micromolar, equal to or at least about or lower than about 25 micromolar, equal to or at least about or lower than about 10 micromolar, equal to or at least about or lower than about 1 micromolar, equal to or at least about or lower than about 0.1 micromolar, equal to or at least about or lower than about 0.01 micromolar, equal to or at least about or lower than about 0.001 micromolar, equal to or at least about or lower than about 0.0001 micromolar, equal to or at least about or lower than about 2000 nanomolar, equal to or at least about or lower than about 500 nanomolar, equal to or at least about or lower than about 250 nanomolar, equal to or at least about or lower than about 200 nanomolar, equal to or at least about or lower than about 50 nanomolar, equal to or at least about or lower than about 25 nanomolar, equal to or at least about or lower than about 20 nanomolar, equal to or at least about or lower than about 2 nanomolar, equal to or at least about or lower than about 0.2 nanomolar, equal to or at least about or lower than about 0.01 nanomolar, equal to or at least about or lower than about 0.001 nanomolar, equal to or at least about or lower than about 0.0001 nanomolar, equal to or at least about or lower than about 3000 picomolar, equal to or at least about or lower than about 500 picomolar, equal to or at least about or lower than about 250 picomolar, equal to or at least about or lower than about 300 picomolar, equal to or at least about or lower than about 50 picomolar, equal to or at least about or lower than about 25 picomolar, equal to or at least about or lower than about 30 picomolar, equal to or at least about or lower than about 3 picomolar, equal to or at least about or lower than about 0.3 picomolar, equal to or at least about or lower than about 0.01 picomolar, equal to or at least about or lower than about 0.001 picomolar, equal to or at least about or lower than about 0.0001 picomolar, equal to or at least about or lower than about 5000 femtomolar, equal to or at least about or lower than about 500 femtomolar, equal to or at least about or lower than about 250 femtomolar, equal to or at least about or lower than about 50 femtomolar, equal to or at least about or lower than about 25 femtomolar, equal to or at least about or lower than about 10 femtomolar, equal to or at least about or lower than about 1 femtomolar, equal to or at least about or lower than about 0.1 femtomolar, equal to or at least about or lower than about 0.01 femtomolar, equal to or at least about or lower than about 0.001 femtomolar, equal to or at least about or lower than about 0.0001 femtomolar.

In some instances, the template may be present in any nucleic acid sample of interest, including but not limited to, a nucleic acid sample isolated from a single cell, a plurality of cells (e.g., cultured cells), a tissue, an organ, or an organism (e.g., bacteria, yeast, or the like). In some instances, the nucleic acid sample is isolated from a cell(s), tissue, organ, and/or the like of a mammal (e.g., a human, a rodent (e.g., a mouse), or any other mammal of interest). In some instances, the nucleic acid sample is isolated from a source other than a mammal, such as bacteria, yeast, insects (e.g., *Drosophila*), amphibians (e.g., frogs (e.g., *Xenopus*)), viruses, plants, or any other non-mammalian nucleic acid sample source.

In some instances, the template is optimized. In some instances, the acceptor template or acceptor nucleic acid molecule comprises at least one modified nucleotide. In some instances, the acceptor template or acceptor nucleic acid molecule is engineered to improve template jumping and/or conversion efficiency. In some instances, the acceptor template or acceptor nucleic acid molecule is optimized at the 3'-end. In some instances, the optimization prevents secondary structure formation and/or nucleotide composition.

In some instances, the methods disclosed in the present disclosure may further comprise optimization of the template (e.g. donor template). In some instances, optimization of the template comprises contacting the template (e.g. RNA) with an agent capable of removing the 5' cap structure of the template (e.g., mRNA). In some instances, the removal of the cap structure is performed under conditions permitting the removal of the cap structure by the agent. In some instances, the methods disclosed in the present disclosure further include dephosphorylation of for example, the decapped template. In some instances, the method further includes adding a dephosphorylating agent to the decapped template under conditions permitting dephosphorylation.

In some instances, any method of the present disclosure may further comprise optimization of the template. In some instances, optimization of the template comprises: contacting a sample comprising a template with an agent that removes a 5' cap structure of the template, under conditions permitting the removal of the cap structure by the agent. In some instances, the optimization of the template may further comprise adding a dephosphorylating agent under conditions permitting the dephosphorylation of the decapped template by the agent. In some instances, the template (e.g. RNA molecule) is dephosphorylated after synthesis or isolation. In some instances, the dephosphorylation is achieved by treatment of the nucleic acid (e.g., RNA) molecule with alkaline phosphatase. In some instances, the isolated donor template, such as RNA or mRNA, is decapped and dephosphorylated after isolation. Methods of decapping nucleic acids (e.g., RNAs) include both enzymatic methods (such as by using a pyrophosphatase such as tobacco pyrophosphatase) and chemical methods (such as periodate oxidation and beta elimination). Methods for dephosphorylation of nucleic acid (e.g., RNA) may use alkaline phosphatase. In some instances, the isolated mRNA is decapped (using tobacco acid pyrophosphatase, for example) and dephosphorylated (e.g., by using alkaline phosphatase). In some instances, the removal of the RNA cap structure is by either enzymatic treatment of the mRNA with a pyrophosphatase or chemical decapping (e.g., by periodate oxidation and beta elimination). In some instances, the mRNA is modified with a tag.

In some instances, template jumping is dependent on the concentration of the acceptor nucleic acid molecule.

In some instances, the method of the present disclosure further comprises using the modified reverse transcriptase to subject a template nucleic acid molecule to reverse transcription to yield the nucleic acid molecule. In some instances, the nucleic acid molecule is a cell-free nucleic acid molecule. In some instances, the template nucleic acid molecule is a cell-free nucleic acid molecule.

In some instances, primer extension or elongation reactions are utilized to generate amplified product. Primer extension/elongation reactions may comprise a cycle of incubating a reaction mixture at a denaturation temperature for a denaturation duration and incubating a reaction mixture at an elongation temperature for an elongation duration.

Any type of nucleic acid amplification reaction may be used to amplify a target nucleic acid and generate an amplified product. Moreover, amplification of a nucleic acid may linear, exponential, or a combination thereof. Amplification may be emulsion based or may be non-emulsion based. Non-limiting examples of nucleic acid amplification methods include reverse transcription, primer extension, polymerase chain reaction, ligase chain reaction, helicase-dependent amplification, asymmetric amplification, rolling circle amplification, and multiple displacement amplification (MDA). In some instances, the amplified product may be DNA. In cases where a target RNA is amplified, DNA can be obtained by reverse transcription of the RNA and subsequent amplification of the DNA can be used to generate an amplified DNA product. The amplified DNA product may be indicative of the presence of the target RNA in the biological sample. In cases where DNA is amplified, any DNA amplification may be employed. Non-limiting examples of DNA amplification methods include polymerase chain reaction (PCR), variants of PCR (e.g., real-time PCR, allele-specific PCR, assembly PCR, asymmetric PCR, digital PCR, emulsion PCR, dial-out PCR, helicase-dependent PCR, nested PCR, hot start PCR, inverse PCR, methylation-specific PCR, miniprimer PCR, multiplex PCR, nested PCR, overlap-extension PCR, thermal asymmetric interlaced PCR, touchdown PCR), and ligase chain reaction (LCR). In some cases, DNA amplification is linear. In some cases, DNA amplification is exponential. In some cases, DNA amplification is achieved with nested PCR, which can improve sensitivity of detecting amplified DNA products.

Denaturation temperatures may vary depending upon, for example, the particular biological sample analyzed, the particular source of target nucleic acid (e.g., viral particle, bacteria) in the biological sample, the reagents used, and/or the desired reaction conditions. In some instances, a denaturation temperature may be from about 80° C. to about 110° C. In some instances, a denaturation temperature may be from about 90° C. to about 100° C. In some instances, a denaturation temperature may be from about 90° C. to about 97° C. In some examples, a denaturation temperature may be from about 92° C. to about 95° C. In still other examples, a denaturation temperature may be about 80°, 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., or 100° C.

Denaturation durations may vary depending upon, for example, the particular biological sample analyzed, the particular source of target nucleic acid (e.g., viral particle, bacteria) in the biological sample, the reagents used, and/or the desired reaction conditions. In some instances, a denaturation duration may be less than or equal to about 300 seconds, 240 seconds, 180 seconds, 120 seconds, 90 seconds, 60 seconds, 55 seconds, 50 seconds, 45 seconds, 40 seconds, 35 seconds, 30 seconds, 25 seconds, 20 seconds, 15 seconds, 10 seconds, 5 seconds, 2 seconds, or 1 second. For example, a denaturation duration may be no more than about 180 seconds, 120 seconds, 90 seconds, 60 seconds, 55 seconds, 50 seconds, 45 seconds, 40 seconds, 35 seconds, 30 seconds, 25 seconds, 20 seconds, 15 seconds, 10 seconds, 5 seconds, 2 seconds, or 1 second.

Elongation or extension temperatures may vary depending upon, for example, the particular biological sample analyzed, the particular source of target nucleic acid (e.g., viral particle, bacteria) in the biological sample, the reagents used, and/or the desired reaction conditions. In some instances, an elongation temperature may be from about 30° C. to about 80° C. In some instances, an elongation temperature may be from about 35° C. to about 72° C. In some instances, an elongation temperature may be from about 45° C. to about 68° C. In some instances, an elongation temperature may be from about 35° C. to about 65° C. In some instances, an elongation temperature may be from about 40° C. to about 67° C. In some instances, an elongation temperature may be from about 50° C. to about 68° C. In some instances, an elongation temperature may be about 0° C., 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 34° C., 33° C., 32° C., 31° C., 30° C., 20° C., 21° C., 22° C., 23° C., 24° C., 25° C., 26° C., 27° C., 28° C., 29° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., or 80° C.

Elongation durations may vary depending upon, for example, the particular biological sample analyzed, the particular source of target nucleic acid (e.g., viral particle, bacteria) in the biological sample, the reagents used, and/or the desired reaction conditions. In some instances, an elongation duration may be less than or equal to about 360 seconds, less than or equal to about 300 seconds, 240 seconds, 180 seconds, 120 seconds, 90 seconds, 60 seconds, 55 seconds, 50 seconds, 45 seconds, 40 seconds, 35 seconds, 30 seconds, 25 seconds, 20 seconds, 15 seconds, 10 seconds, 5 seconds, 2 seconds, or 1 second. In some instances, an elongation duration may be no more than about 120 seconds, 90 seconds, 80 seconds, 70 seconds, 65 seconds, 60 seconds, 55 seconds, 50 seconds, 45 seconds, 40 seconds, 35 seconds, 30 seconds, 25 seconds, 20 seconds, 15 seconds, 10 seconds, 5 seconds, 2 seconds, or 1 second.

In some instances, multiple cycles of a primer extension reaction can be conducted. Any suitable number of cycles may be conducted. In some instances, the number of cycles conducted may be less than about 100, 90, 80, 70, 60, 50, 40, 30, 20, 10, or 5 cycles. The number of cycles conducted may depend upon, for example, the number of cycles (e.g., cycle threshold value (Ct)) necessary to obtain a detectable amplified product (e.g., a detectable amount of amplified DNA product that is indicative of the presence of a target RNA in a biological sample). In some instances, the number of cycles necessary to obtain a detectable amplified product (e.g., a detectable amount of DNA product that is indicative of the presence of a target RNA in a biological sample) may be less than about or about 100 cycles, 75 cycles, 70 cycles, 65 cycles, 60 cycles, 55 cycles, 50 cycles, 40 cycles, 35 cycles, 30 cycles, 25 cycles, 20 cycles, 15 cycles, 10 cycles, 8 cycles, 7 cycles, 5 cycles, or 4 cycles. Moreover, in some instances, a detectable amount of an amplifiable product (e.g., a detectable amount of DNA product that is indicative of the presence of a target RNA in a biological sample) may be obtained at a cycle threshold value (Ct) of less than 100, 75, 70, 65, 60, 55, 50, 45, 40, 35, 30, 25, 20, 15, 10, 9, 8, 7, 6, 5, 4, 3, 2, 1.

In some instances, an amplification step (e.g., primer amplification, template amplification, nucleic acid amplification) comprises a PCR step. In some instances, each PCR cycle may comprise a denaturing step, an annealing step, and an extension step. In some instances, each PCR cycle may comprise a denaturing step and an extension step. In some instances, the PCR comprises at least about or about or at most about 1 cycle, at least about or about or at most about 4 cycles, at least about or about or at most about 5 cycles, at least about or about or at most about 10 cycles, at least about or about or at most about 15 cycles, at least about or about or at most about 20 cycles, at least about or about or at most about 25 cycles, at least about or about or at most about 30 cycles, at least about or about or at most about 35 cycles, at least about or about or at most about 40 cycles, at least about or about or at most about 45 cycles, at least about or about or at most about 50 cycles, at least about or about or at most about 55 cycles, at least about or about or at most about 60 cycles, at least about or about or at most about 65 cycles, at least about or about or at most about 70 cycles, at least about or about or at most about 75 cycles, at least about or about or at most about 80 cycles, at least about or about or at most about 90 cycles, at least about or about or at most about 95 cycles, at least about or about or at most about 100 cycles, at least about or about or at most about 110 cycles, at least about or about or at most about 120 cycles, at least about or about or at most about 130 cycles, at least about or about or at most about 140 cycles, at least about or about or at most about 150 cycles, at least about or about or at most about 160. In some instances, the PCR comprises from about 10 cycles to 40 cycles, from about 20 cycles to 40 cycles, from about 20 cycles to 38 cycles, from about 20 cycles to 35 cycles, from about 10 cycles to 35 cycles, from about 10 cycles to 30 cycles, from about 25 cycles to 30 cycles, from about 20 cycles to 30 cycles, from about 4 cycles to 8 cycles, or from about 28 cycles to 32 cycles. In some instances, the reaction is heated to 95° C. for 3 minutes before the PCR cycle begins. In some instances, each PCR cycle comprises 95° C. for 3 seconds and 62° C. for 20 seconds. In some instances, each PCR cycle comprises 95° C. for 3 seconds, 54° C. for 10 seconds, and 64° C. for 20 seconds. In some instances, each PCR cycle comprises 95° C. for 3 seconds and 64° C. for 20 seconds. In some instances, each PCR cycle comprises 95° C. for 3 seconds and 62° C. for 60 seconds. In some instances, each PCR cycle comprises 95° C. for 3 seconds, 54° C. for 10 seconds, and 64° C. for 10 seconds. In some instances, the PCR comprises 30 cycles. In some instances, the reaction is heated to 68° C. after the completion of the PCR cycles. In some instances, the reaction is heated to 68° C. from about 1 second to about 5 seconds, from about 1 second to about 5 minutes, from about 1 minute to about 5 minutes after the completion of the PCR cycles. In some instances, the PCR methods described herein comprises an extension or elongation step that is at least about 5 seconds long, at least about 6 seconds long, at least about 7 seconds long, at least about 8 seconds long, at least about 9 seconds long, at least about 10 seconds long, at least about 11 seconds long, at least about 12 seconds long, at least about 13 seconds long, at least about 14 seconds long, at least about 15 seconds long, at least about 20 seconds long, at least about 30 seconds long, at least about 40 seconds long, at least about 50 seconds long, at least about 60 seconds long, at least about 90 seconds long, at least about 120 seconds long, at least about 150 seconds long, at least about 180 seconds long, at least about 210 seconds long, at least about 240 seconds long, at least about 270 seconds long, at least about 300 seconds long, at least about 330 seconds long, at least about 360 seconds long, at least about 390 seconds long, or more.

The time for which amplification yields a detectable amount of amplified product indicative of the presence of a target nucleic acid amplified can vary depending upon the biological sample from which the target nucleic acid was obtained, the particular nucleic acid amplification reactions to be conducted, and the particular number of cycles of amplification reaction desired. In some instances, amplification of a target nucleic acid may yield a detectable amount of amplified product indicative to the presence of the target nucleic acid at time period of 120 minutes or less; 90 minutes or less; 60 minutes or less; 50 minutes or less; 45 minutes or less; 40 minutes or less; 35 minutes or less; 30 minutes or less; 25 minutes or less; 20 minutes or less; 15 minutes or less; 10 minutes or less; or 5 minutes or less.

In some instances, a biological sample may be preheated prior to conducting a primer extension reaction. The temperature (e.g., a preheating temperature) at which and duration (e.g., a preheating duration) for which a biological sample is preheated may vary depending upon, for example, the particular biological sample being analyzed. In some examples, a biological sample may be preheated for no more than about 60 minutes, 50 minutes, 40 minutes, 30 minutes, 25 minutes, 20 minutes, 15 minutes, 10 minutes, 9 minutes, 8 minutes, 7 minutes, 6 minutes, 5 minutes, 4 minutes, 3 minutes, 2 minutes, 1 minute, 45 seconds, 30 seconds, 20 seconds, 15 seconds, 10 seconds, or 5 seconds. In some examples, a biological sample may be preheated at a temperature from about 80° C. to about 110° C. In some examples, a biological sample may be preheated at a temperature from about 90° C. to about 100° C. In some examples, a biological sample may be preheated at a temperature from about 90° C. to about 97° C. In some examples, a biological sample may be preheated at a temperature from about 92° C. to about 95° C. In some instances, a biological sample may be preheated at a temperature of about 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., or 100° C.

In some instances, reagents necessary for conducting nucleic acid amplification may also include a reporter agent that yields a detectable signal whose presence or absence is indicative of the presence of an amplified product. The intensity of the detectable signal may be proportional to the amount of amplified product. In some cases, where amplified product is generated of a different type of nucleic acid than the target nucleic acid initially amplified, the intensity of the detectable signal may be proportional to the amount of target nucleic acid initially amplified. For example, in the case of amplifying a target RNA via parallel reverse transcription and amplification of the DNA obtained from reverse transcription, reagents necessary for both reactions may also comprise a reporter agent, may yield a detectable signal that is indicative of the presence of the amplified DNA product, and/or the target RNA amplified. The intensity of the detectable signal may be proportional to the amount of the amplified DNA product and/or the original target RNA amplified. The use of a reporter agent also enables real-time amplification methods, including real-time PCR for DNA amplification.

Reporter agents may be linked with nucleic acids, including amplified products, by covalent or non-covalent linkages or interactions. Non-limiting examples of non-covalent linkates or interactions include ionic interactions, Van der Waals forces, hydrophobic interactions, hydrogen bonding, and combinations thereof. In some instances, reporter agents may bind to initial reactants and changes in reporter agent levels may be used to detect amplified product. In some instances, reporter agents may only be detectable (or non-detectable) as nucleic acid amplification progresses. In some instances, an optically-active dye (e.g., a fluorescent dye) may be used as may be used as a reporter agent. Non-limiting examples of dyes include SYBR green, SYBR blue, DAPI, propidium iodine, Hoeste, SYBR gold, ethidium bromide, acridines, proflavine, acridine orange, acriflavine, fluorcoumanin, ellipticine, daunomycin, chloroquine, distamycin D, chromomycin, homidium, mithramycin, ruthenium polypyridyls, anthramycin, phenanthridines and acridines, ethidium bromide, propidium iodide, hexidium iodide, dihydroethidium, ethidium homodimer-1 and -2, ethidium monoazide, and ACMA, Hoechst 33258, Hoechst 33342, Hoechst 34580, DAPI, acridine orange, 7-AAD, actinomycin D, LDS751, hydroxystilbamidine, SYTOX Blue, SYTOX Green, SYTOX Orange, POPO-1, POPO-3, YOYO-1, YOYO-3, TOTO-1, TOTO-3, JOJO-1, LOLO-1, BOBO-1, BOBO-3, PO-PRO-1, PO-PRO-3, BO-PRO-1, BO-PRO-3, TO-PRO-1, TO-PRO-3, TO-PRO-5, JO-PRO-1, LO-PRO-1, YO-PRO-1, YO-PRO-3, PicoGreen, OliGreen, RiboGreen, SYBR Gold, SYBR Green I, SYBR Green II, SYBR DX, SYTO-40, -41, -42, -43, -44, -45 (blue), SYTO-13, -16, -24, -21, -23, -12, -11, -20, -22, -15, -14, -25 (green), SYTO-81, -80, -82, -83, -84, -85 (orange), SYTO-64, -17, -59, -61, -62, -60, -63 (red), fluorescein, fluorescein isothiocyanate (FITC), tetramethyl rhodamine isothiocyanate (TRITC), rhodamine, tetramethyl rhodamine, R-phycoerythrin, Cy-2, Cy-3, Cy-3.5, Cy-5, Cy5.5, Cy-7, Texas Red, Phar-Red, allophycocyanin (APC), Sybr Green I, Sybr Green II, Sybr Gold, CellTracker Green, 7-AAD, ethidium homodimer I, ethidium homodimer II, ethidium homodimer III, ethidium bromide, umbelliferone, eosin, green fluorescent protein, erythrosin, coumarin, methyl coumarin, pyrene, malachite green, stilbene, lucifer yellow, cascade blue, dichlorotriazinylamine fluorescein, dansyl chloride, fluorescent lanthanide complexes such as those including europium and terbium, carboxy tetrachloro fluorescein, 5 and/or 6-carboxy fluorescein (FAM), 5- (or 6-) iodoacetamidofluorescein, 5-{[2 (and 3)-5-(Acetylmercapto)-succinyl] amino}fluorescein (SAMSA-fluorescein), lissamine rhodamine B sulfonyl chloride, 5 and/or 6 carboxy rhodamine (ROX), 7-amino-methyl-coumarin, 7-Amino-4-methylcoumarin-3-acetic acid (AMCA), BODIPY fluorophores, 8-methoxypyrene-1,3,6-trisulfonic acid trisodium salt, 3,6-Disulfonate-4-amino-naphthalimide, phycobiliproteins, AlexaFluor 350, 405, 430, 488, 532, 546, 555, 568, 594, 610, 633, 635, 647, 660, 680, 700, 750, and 790 dyes, DyLight 350, 405, 488, 550, 594, 633, 650, 680, 755, and 800 dyes, or other fluorophores.

In some instances, a reporter agent may be a sequence-specific oligonucleotide probe that is optically active when hybridized with an amplified product. Due to sequence-specific binding of the probe to the amplified product, use of oligonucleotide probes can increase specificity and sensitivity of detection. A probe may be linked to any of the optically-active reporter agents (e.g., dyes) and may also include a quencher capable of blocking the optical activity of an associated dye. Non-limiting examples of probes that may be useful used as reporter agents include TaqMan probes, TaqMan Tamara probes, TaqMan MGB probes, or Lion probes. In some instances, a reporter agent may be a radioactive species. Non-limiting examples of radioactive species include 14C, 123I, 124I, 125I, 131I, 99mTc, 35S, or 3H. In some instances, a reporter agent may be an enzyme that is capable of generating a detectable signal. Detectable signal may be produced by activity of the enzyme with its substrate or a particular substrate in the case the enzyme has multiple substrates. Non-limiting examples of enzymes that may be used as reporter agents include alkaline phosphatase, horseradish peroxidase, I2-galactosidase, alkaline phosphatase, β-galactosidase, acetylcholinesterase, and luciferase.

In some instances, an amplified product (e.g., amplified DNA product, amplified RNA product) may be detected. Detection of amplified product, including amplified DNA, may be accomplished with any suitable detection method. The particular type of detection method used may depend, for example, on the particular amplified product, the type of reaction vessel used for amplification, other reagents in a reaction mixture, whether or not a reporter agent was included in a reaction mixture, and if a reporter agent was used, the particular type of reporter agent use. Non-limiting examples of detection methods include optical detection, spectroscopic detection, electrostatic detection, electrochemical detection, and the like. Optical detection methods include, but are not limited to, fluorimetry and UV-vis light absorbance. Spectroscopic detection methods include, but are not limited to, mass spectrometry, nuclear magnetic resonance (NMR) spectroscopy, and infrared spectroscopy. Electrostatic detection methods include, but are not limited to, gel based techniques, such as, for example, gel electrophoresis, SDS-PAGE gel. Electrochemical detection methods include, but are not limited to, electrochemical detection of amplified product after high-performance liquid chromatography separation of the amplified products.

In some instances, the time required to complete the elements of a method may vary depending upon the particular steps of the method. In some instances, an amount of time for completing the elements of a method may be from about 5 minutes to about 120 minutes. In some instances, an amount of time for completing the elements of a method may be from about 5 minutes to about 60 minutes. In some instances, an amount of time for completing the elements of a method may be from about 5 minutes to about 30 minutes. In some instances, an amount of time for completing the elements of a method may be less than or equal to 120 minutes, less than or equal to 90 minutes, less than or equal to 75 minutes, less than or equal to 60 minutes, less than or equal to 45 minutes, less than or equal to 40 minutes, less than or equal to 35 minutes, less than or equal to 30 minutes, less than or equal to 25 minutes, less than or equal to 20 minutes, less than or equal to 15 minutes, less than or equal to 10 minutes, or less than or equal to 5 minutes.

In some instances, the reaction may have a pH suitable for producing the product, for primer extension, protein expression, PCR amplication, or template jumping. In some instances, the pH of the reaction may range from about 5 to about 9, from about 6 to about 9, from about 7 to about 9, from about 8 to about 9. In some instances, the pH range is from about pH 2 to about pH 10, from about pH 4 to about pH 10, from about pH 2 to about pH 8, from about pH 4 to about pH 8, from about pH 5 to about pH 8, from about pH 5 to about pH 7, from about pH 6 to about pH 11, from about pH 6 to about pH 12, from about pH 5 to pH 13, from about pH 5 to about pH 14. In some instances, the pH is about 2.0, about 2.5, about 3.0, about 3.5, about 4.0, about 4.5, about 5.0, about 5.5, about 6.0, about 6.5, about 7.0, about 7.5, about 8.0, about 8.5, about 9.0, about 9.5, about 10.0, about 10.5, about 11, about 11.5, about 12, about 12.5, about 13, about 13.5, about 14.

In some instances, any method of the present disclosure may comprise a detergent. In some instances, the detergent is non-ionic and/or a zwitterionic detergent. In some instances, a non-ionic detergent is selected from a group consisting of tween, triton, Triton CF-21, Triton CF-32, Triton DF-12, Triton DF-16, Triton GR-SM, Triton N-101 (Polyoxyethylene branched nonylphenyl ether), Triton QS-15, Triton QS-44, Triton RW-75 (Polyethylene glycol 260 monoChexadecyl/octadecyl) ether and 1-Octadecanol), Triton X-100 (Polyethylene glycol tert-octylphenyl ether), Triton X-102, Triton X-15, Triton X-151, Triton X-200, Triton X-207, Triton X-114, Triton X-165, Triton X-305, Triton X-405 (polyoxyethylene(40) isooctylphenyl ether), Triton X-405 reduced (polyoxyethylene(40) isooctylcyclohexyl ether), Triton X-45 (Polyethylene glycol 4-tert-octylphenyl ether), Triton X-705-70, TWEEN in any form including: TWEEN 20 (Polyoxyethylene sorbitan monolaurate), TWEEN 21 (Polyoxyethylene sorbitan monolaurate), TWEEN 40 (polyoxyethylene(20) sorbitan monopalmitate), TWEEN 60 (Polyethylene glycol sorbitan monostearate), TWEEN 61 (Polyethylene glycol sorbitan monostearate), TWEEN 65 (Polyoxyethylene sorbitan Tristearate), TWEEN 80 (Polyoxyethylene sorbitan monooleate), TWEEN 81 (Polyoxyethylene sorbitan monooleate), TWEEN 85 (polyoxyethylene(20) sorbitan trioleate), Brij, Brij 30 (Polyoxyethylene 4 lauryl ether) Brij 35 (Polyoxyethylene 23 lauryl ether), Brij 52 (Polyoxyethylene 2 cetyl ether), Brij56 (Polyoxyethylene 10 cetyl ether), Brij 58 (Polyoxyethylene 20 cetyl ether), Brij 72 (Polyoxyethylene 2 stearyl ether), Brij 76 (Polyoxyethylene 10 stearyl ether), Brij 78 (Polyoxyethylene 20 stearyl ether), Brij 92 (Polyoxyethylene 2 oleyl ether), Brij 97 (Polyoxyethylene 10 oleyl ether), Brij 98 (Polyoxyethylene 20 oleyl ether), Brij700 (Polyoxyethylene 100 stearyl ether, octyl thioglucoside, maltosides, and combinations thereof.

In some instances, any method disclosed herein for producing any molecule according to the present disclosure comprises at least one salt. In some instances, the salt is at least one member selected from the group consisting of NaCl, LiCl, AlCl$_3$, CuCl$_2$, MgCl$_2$, InCl$_3$, SnCl$_4$, CrCl$_2$, CrCl$_3$, KCl, NaI, KI, TMACl (tetramethyl ammonium chloride), TEACl (tetraethyl ammonium chloride), KSCN, CsSCN, KCH$_3$COO, CH$_3$COONa, C$_5$H$_8$KNO$_4$, C$_5$H$_8$NNaO$_4$, CsCl, and any combination thereof. In some instances, any method disclosed herein for producing any molecule according to the present disclosure comprises NaCl. In some instances, the conditions sufficient for producing a molecule or a library comprises NaCl. In some instances, the reaction may have a salt concentration and/or NaCl suitable for producing a product, for primer extension, protein expression, PCR amplication, or template jumping. In some instances, the NaCl concentration is from about 50 mM to about 1000 mM, from about 100 mM to about 500 mM, from about 200 mM to about 300 mM, from about 200 mM to about 600 mM. In some instances, the NaCl concentration is at least about, at most about, or about 50 mM, at least about, at most about, or about 100 mM, at least about, at most about, or about 150 mM, at least about, at most about, or about 200 mM, at least about, at most about, or about 250 mM, at least about, at most about, or about 300 mM, at least about, at most about, or about 350 mM, at least about, at most about, or about 400 mM, at least about, at most about, or about 450 mM, at least about, at most about, or about 500 mM, at least about, at most about, or about 550 mM, at least about, at most about, or at least about, at most about, or about 600 mM, at least about, at most about, or about 650 mM, at least about, at most about, or about 700 mM, at least about, at most about, or about 750 mM, at least about, at most about, or about 800 mM, at least about, at most about, or about 850 mM, at least about, at most about, or about 900 mM, at least about, at most about, or about 950 mM, or at least about, at most about, or about 1000 mM. In some instances, the NaCl may improve enzyme activity and/or template jumping of an enzyme or polypeptide of the present disclosure (e.g., of a reverse transcriptase).

In some instances, the reaction may have a nucleotide (e.g. dNTPs) concentration suitable for producing a product, for primer extension, protein expression, PCR amplification, or template jumping. In some instances, the total dNTP concentration in a reaction may be from about 50 μM to about 1000 μM, from about 100 μM to about 500 μM, from about 200 μM to about 300 μM, from about 200 μM to about 600 μM. In some instances, the total dNTP concentration is at least about, at most about, or about 50 μM, at least about, at most about, or about 100 μM, at least about, at most about, or about 150 μM, at least about, at most about, or about 200 μM, at least about, at most about, or about 250 μM, at least about, at most about, or about 300 μM, at least about, at most about, or about 350 μM, at least about, at most about, or about 400 μM, at least about, at most about, or about 450 μM, at least about, at most about, or about 500 μM, at least about, at most about, or about 550 μM, at least about, at most about, or at least about, at most about, or about 600 μM, at least about, at most about, or about 650 μM, at least about, at most about, or about 700 μM, at least about, at most about, or about 750 μM, at least about, at most about, or about 800 μM, at least about, at most about, or about 850 μM, at least about, at most about, or about 900 μM, at least about, at most about, or about 950 μM, or at least about, at most about, or about 1000 μM. In some instances, the total concentration of each dNTP is at least about, at most about, or about 1 μM; at least about, at most about, or about 2 μM; at least about, at most about, or about 3 μM; at least about, at most about, or about 4 μM; at least about, at most about, or about 5 μM; at least about, at most about, or about 6 μM; at least about, at most about, or about 7 μM; or about 8 μM; at least about, at most about, or about 9 μM; at least about, at most about, or about 10 μM; at least about, at most about, or about 15 μM; at least about, at most about, or about 20 μM; at least about, at most about, or about 25 μM; at least about, at most about, or about 30 μM; at least about, at most about, or about 35 μM; at least about, at most about, or about 40 μM; at least about, at most about, or about 45 μM; at least about, at most about, or about 50 μM; at least about, at most about, or about 55 μM; at least about, at most about, or about 60 μM; at least about, at most about, or about 65 μM; at least about, at most about, or about 70 μM; at least about, at most about, or about 75 μM; at least about, at most about, or about 80 μM; at least about, at most about, or about 85 μM; at least about, at most about, or about 90 μM; at least about, at most about, or about 95 μM; at least about, at most about, or about 100 μM; at least about, at most about, or about 250 μM; at least about, at most about, or about 500 μM; at least about, at most about, or about 1000 μM; at least about, at most about, or about 10000 μM. In some instances, the total concentration of each dNTP is from about 2 μM to about 5 μM, from about 2 μM to about 10 μM, from about 2 µM to about 20 µM, from about 2 µM to about 50 µM, from about 2 µM to about 100 µM, from about 2 µM to about 250 µM, from about 5 µM to about 10 µM, from about 5 µM to about 50 µM, from about 5 µM to about 250 µM, from about 5 µM to about 1000 µM.

In some instances, the concentration of each dNTP may be independent and different from the concentration of one or more dNTP. In some instances, the concentration of each dNTP for example the concentration of each dCTP, dGTP, dTTP, or dATP may be independent and different from the concentration of at least one other dNTP. In some instances, the concentration of one dNTP (e.g., dCTP, dGTP, dTTP, or dATP) may be at least about or at most about or about 1 fold, 2 fold, 3 fold, 4 fold, 5 fold, 7 fold, 10 fold, 20 fold, 35 fold, 50 fold, 75 fold, 90 fold, 100 fold, 200 fold, 500 fold, or 1000 fold different from at least one other dNTP (e.g., dCTP, dGTP, dTTP, or dATP).

In some instances, the reaction mixture includes a pH adjusting agent. pH adjusting agents of interest include, but are not limited to, sodium hydroxide, hydrochloric acid, phosphoric acid buffer solution, tris buffer, citric acid buffer solution, and the like. For example, the pH of the reaction mixture can be adjusted to the desired range by adding an appropriate amount of the pH adjusting agent.

The temperature range suitable for production of a product may vary according to factors such as the particular polymerase employed, the melting temperatures of any optional primers employed, etc. In some instances, the polymerase may include, but it is not limited to, a reverse transcriptase, a Moloney Murine Leukemia Virus (MMLV) reverse transcriptase, an R2 reverse transcriptase, an RNA-directed DNA polymerase, an DNA-directed DNA polymerase, a non-LTR retrotransposon, an R2 non-LTR retrotransposon, a polypeptide having reverse transcriptase activity, or any variant thereof, or any combination thereof.

In some instances, the conditions sufficient to produce a product include bringing the reaction mixture to a temperature ranging from about 4° C. to about 72° C., from about 16° C. to about 70° C., from about 37° C. to about 50° C., from about 40° C. to about 45° C., from about 30° C. to about 42° C., from about 25° C. to about 42° C., from about 25° C. to about 30° C., from about 28° C. to about 32° C., from about 29° C. to about 31° C. In some instances, the temperature is about 15° C., about 16° C., about 17° C., about 18° C., about 19° C., about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., about 50° C., about 51° C., about 52° C., about 53° C., about 54° C., about 55° C., about 56° C., about 57° C., about 58° C., about 59° C., about 60° C., about 61° C., about 62° C., about 63° C., about 64° C., about 65° C., about 66° C., about 67° C., about 68° C., about 69° C., about 70° C., about 71° C., about 72° C., about 73° C., about 74° C., or about 75° C. In some instances, the temperature is about or at most about 42° C. In some instances, the temperature is about or at most about 50° C. In some instances, the temperature is about or at most about 35° C. In some instances, the temperature is about or at most about 25° C. In some instances, the temperature is about or at most about 30° C. In some instances, the reaction is incubated from about 20 minutes to about 3 hours, from about 30 minutes to about 1.5 hours, from about 30 minutes to about 1 hour, from about 30 minutes to about 2 hours, from about 1 hour to about 2 hours, from about 1 hour to about 1.5 hours, from about 30 minutes to about 5 hours, from about 1 hour to about 3 hours, from about 1 hour to about 4 hours, from about 1 hour to about 5 hours. In some instances, the reaction is incubated for about 1 hour. In some instances, the reaction is incubated for about 20 minutes, about 30 minutes, about 40 minutes, about 50 minutes, about 1 hour, about 1.5 hours, about 2 hours, about 2.5 hours, about 3 hours, about 3.5 hours, about 4 hours, about 4.5 hours, or about 5 hours. In some instances, the reaction is incubated for at least at least about 20 minutes, at least about 30 minutes, at least about 40 minutes, at least about 50 minutes, at least about 1 hour, at least about 1.5 hours, at least about 2 hours, at least about 2.5 hours, at least about 3 hours, at least about 3.5 hours, at least about 4 hours, at least about 4.5 hours, or at least about 5 hours. In some instances, the reaction is incubated at about 30° C. for about 1 hour, or at about 42° C. for about 1 hour. In some instances, the conditions sufficient for generating a molecule or a nucleic acid molecule comprises a temperature of about 12° C. to about 42° C. for about 1 minute to about 5 hours. In some instances, the conditions sufficient for generating a molecule or a nucleic acid molecule comprises a temperature of about 8° C. to about 50° C. for about 1 minute to about 24 hours.

In some instances, a primer can be designed to be a certain length. In some instances, a primer can be from about 6 to about 100 nucleotides, from about 6 to about 90 nucleotides, from about 6 to about 80 nucleotides, from about 6 to about 70 nucleotides, from about 6 to about 60 nucleotides, from about 6 to about 50 nucleotides, from about 6 to about 40 nucleotides, from about 6 to about 30 nucleotides, from about 6 to about 20 nucleotides, or from about 6 to about 10 nucleotides in length. In some instances, a primer can be from about 25 to about 80, from about 25 to about 75, from about 25 to about 70, from about 25 to about 65, from about 25 to about 60, from about 25 to about 55, from about 25 to about 50, from about 25 to about 45, from about 25 to about 40, from about 25 to about 35, or from about 25 to about 30 bases in length. In some instances, a primer can be at least about 5, at least about 6, at least about 7, at least about 8, at least about 9, at least about 10, at least about 11, at least about 12, at least about 13, at least about 14, at least about 15, at least about 16, at least about 17, at least about 18, at least about 19, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95 or at least about 100 bases in length. In some instances, a primer can be about 5, about 6, about 7, about 8, about 9, about 10, about 11, about 12, about 13, about 14, about 15, about 16, about 17, about 18, about 19, about 20, about 25, about 30, about 35, about 40, about 45, about 50, about 55, about 60, about 65, about 70, about 75, about 80, about 85, about 90, about 95 or about 100 bases in length. In some instances, a primer can be at least about, no more than about, or about 120, 130, 140, 150, 160, 170, 180, 190, 200, 230, 250, 270, 290, 300, 320, 340, 350, 370, 400, 420, 450, 470, 490, or 500.

In some instances, a primer can be designed to anneal to a target at a given melting temperature (Tm). In some instances, a Tm can be from about 20° C. to about 100° C., about 20° C. to about 90° C., about 20° C. to about 80° C., about 20° C. to about 70° C., about 20° C. to about 60° C., about 20° C. to about 50° C., about 20° C. to about 40° C., or about 20° C. to about 30° C. In some instances, a Tm can be at least about, at most about, or about 20° C., 21° C., 22°

C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 83° C., 84° C., 85° C., 96° C., 97° C., 98° C., 99° C., or 100° C. A plurality of primers can be designed to have Tins within a range, e.g., within a range spanning 15° C., 10° C., 9° C., 8° C., 7° C., 6° C., 5° C., 4° C., 3° C., 2° C., or 1° C. A plurality of primers can be designed to have identical Tins.

In some instances the enzyme, or modified enzyme (e.g., modified reverse transcriptase), or protein, or polypeptide, or a variant, or a PCR product, or a cDNA molecule, or a template, or a nucleic acid molecule, or any component of the present disclosure may be purified. In some instances, the fragmented or degraded nucleic acid (e.g., RNA or DNA) may be purified. In some instances, the reverse transcriptase or a modified reverse transcriptase may be purified. In some instances, the R2 reverse transcriptase or a modified R2 reverse transcriptase may be purified. In some instances, the non-LTR retrotransposon protein or polypeptide having reverse transcriptase activity, or a modified non-LTR retrotransposon protein or a modified polypeptide having reverse transcriptase activity may be further purified. In some instances, the cDNA molecule may be purified. In some instances, the template may be purified. In some instances, the acceptor nucleic acid molecule may be purified.

Purification may comprise precipitation, ultracentrifugation, chromatographic method based on size, charge, hydrophobicity, affinity, metal binding, HPLC. In some instances, the purification comprises column chromatography. In some instances, the column chromatography may be size exclusion (SEC), ion exchange (IEX), affinity chromatography, immobilized metal ion affinity chromatography (IMAC), Ni-IMAC chromatography, and/or hydrophobic interaction (HIC). In some instances, the purification comprises His-tag affinity resin. In some instances, the purification may comprise one step. In some instances, the purification may comprise two steps. In some instances, the two step purification comprises nickel and heparin. In some instances, the two step purification comprises nickel and heparin affinity purifications. In some instances, the two purification steps provide higher activity and/or increased template jumping compared to one step purification. In some instances, the purification comprises heparin-affinity purification. In some instances, purification may include affinity purification, Ni-NTA affinity, fast protein liquid chromatography (FPLC) (e.g., AKTA and Bio-Rad FPLC systems), high-pressure liquid chromatography (HPLC) (e.g., Beckman and Waters HPLC). In some instances, purification may include, but not limited to, ion exchange chromatography (e.g., Q, S), size exclusion chromatography, salt gradients, affinity purification (e.g., Ni, Co, FLAG, maltose, glutathione, protein A/G), gel filtration, reverse-phase, ceramic HYPERD (Registered trademark) ion exchange chromatography, and hydrophobic interaction columns (HIC). Also included are analytical methods such as SDS-PAGE (e.g., coomassie, silver stain), immunoblot, Bradford, and ELISA, which may be utilized during any step of the production or purification process, typically to measure the purity of the protein or enzyme composition.

In some instances, the overall activity of the purified enzyme, protein, polypeptide, the R2 reverse transcriptase, the non-LTR retrotransposon protein or polypeptide having reverse transcriptase activity, the reverse transcriptase, or variants thereof, or products thereof using a two-step purification is at least about 2%, at least about 5%, at least about 7%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99% higher than the overall activity using the one-step purification. In some instances, the overall activity of the purified enzyme, protein, polypeptide, the R2 reverse transcriptase, the non-LTR retrotransposon protein or polypeptide having reverse transcriptase activity, the reverse transcriptase, or variants thereof, or products thereof is at least about 0.5%, at least about 1%, at least about 1.5%, at least about 2%, at least about 5%, at least about 7%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99% higher than the overall activity of the non-purified enzyme, protein, polypeptide, R2 reverse transcriptase, non-LTR retrotransposon protein or polypeptide having reverse transcriptase activity, reverse transcriptase, or variants thereof, or products thereof. In some instances, a purified enzyme, protein, polypeptide, R2 reverse transcriptase, the non-LTR retrotransposon protein, or polypeptide having reverse transcriptase activity, reverse transcriptase, modified enzyme, modified reverse transcriptase, modified polypeptide having reverse transcriptase activity, or variants thereof, or products thereof is at least about 0.5%, at least about 1%, at least about 3%, at least about or about 5%, at least about or about 10%, at least about or about 15%, at least about or about 20%, at least about or about 25%, at least about or about 30%, at least about or about 35%, at least about or about 40%, at least about or about 45%, at least about or about 50%, at least about or about 55%, at least about or about 60%, at least about or about 61%, at least about or about 62%, at least about or about 63%, at least about or about 64%, at least about or about 65%, at least about or about 66%, at least about or about 67%, at least about or about 68%, at least about or about 69%, at least about or about 70%, at least about or about 71%, at least about or about 72%, at least about or about 73%, at least about or about 74%, at least about or about 75%, at least about or about 76%, at least about or about 77%, at least about or about 78%, at least about or about 79%, at least about or about 80%, at least about or about 81%, at least about or about 82%, at least about or about 83%, at least about or about 84%, at least about or about 85%, at least about or about 86%, at least about or about 87%, at least about or about 88%, at least about or about 89%, at least about or about 90%, at least about or about 91%, at least about or about 92%, at least about or about 93%, at least about or about 94%, at least about or about 95%, at least about or about 96%, at least about or about 97%, at least about or about 98%, or at least about or about 99% pure.

In some instances, the purified enzyme, protein, polypeptide, R2 reverse transcriptase, non-LTR retrotransposon protein or polypeptide having reverse transcriptase activity, reverse transcriptase, or variants thereof, or products thereof produces template jumping that is at least about or about one time, at least about or about two times, at least about or about three times, at least about or about four times, at least about or about five times, at least about or about six times, at least about or about seven times, at least about or about eight times, at least about or about nine times, at least about or about ten times, at least about or about fifteen times, at least about or about twenty times, at least about or about twenty five times, at least about or about thirty times, at least about or about forty times, at least about or about fifty times, at least about or about seventy times, at least about or about eighty times, at least about or about ninety times, at least about or about 100 times, at least about or about 150 times, at least about or about 200 times, at least about or about 250 times, at least about or about 300 times, at least about or about 350 times, at least about or about 400 times, at least about or about 500 times, at least about or about 700 times, at least about or about 1000 times, at least about or about 10000 times more and/or higher intensity than the non-purified enzyme, protein, polypeptide, R2 reverse transcriptase, non-LTR retrotransposon protein or polypeptide having reverse transcriptase activity, reverse transcriptase, or variants thereof, or products thereof.

Mutation of Enzymes

In some instances, a modified enzyme, or derivatives and variants may be prepared during synthesis of the peptide or by post-production modification. In some instances, a modified enzyme, or derivatives and variants may be produced by site-directed mutagenesis (e.g. Q5® Site-Directed Mutagenesis Kit Protocol), random mutagenesis, or enzymatic cleavage and/or ligation of nucleic acids. In some instances, the derivatives and variants, or a modified enzyme are produced by random mutagenesis. In some instances, a rational design and/or mutagenesis is based on sequence alignment analysis. In some instances, the rational design/mutagenesis is based on sequence alignment analysis with defined and known enzymes and proteins. In some instances, sequence alignment analysis or homology modeling is performed with enzymes and/or elements with homology to R2, including, but not limited to, non-LTR retrotransposons, telomerase, group II introns, LTR retrotransposons, reverse transcriptase, retroviral reverse transcriptase (e.g., HIV, MMLV), and viral RNA dependent RNA polymerase.

In some instances, variants or modified enzymes of the present disclosure can be produced by, including, but not limited to, for example, site-saturation mutagenesis, scanning mutagenesis, insertional mutagenesis, deletion mutagenesis, random mutagenesis, site-directed mutagenesis, and directed-evolution, as well as various other recombinatorial approaches. Methods for making modified enzymes, polynucleotides and proteins (e.g., variants) include DNA shuffling methodologies, methods based on non-homologous recombination of genes, such as ITCHY (See, Ostermeier et al., 7:2139-44 [1999]), SCRACHY (See, Lutz et al. 98:11248-53 [2001]), SHIPREC (See, Sieber et al., 19:456-60 [2001]), and NRR (See, Bittker et al., 20:1024-9 [2001]; Bittker et al., 101:7011-6 [2004]), and methods that rely on the use of oligonucleotides to insert random and targeted mutations, deletions and/or insertions (See, Ness et al., 20:1251-5 [2002]; Coco et al., 20:1246-50 [2002]; Zha et al., 4:34-9 [2003]; Glaser et al., 149:3903-13 [1992]). In some instances, polynucleotides, polypeptides, proteins, or enzymes of the present disclosure may be altered by being subjected to random mutagenesis by error-prone PCR, random nucleotide insertion or other methods prior to recombination. Polynucleotides, polypeptides, proteins, or enzymes of the present disclosure may be produced by DNA shuffling, gene-shuffling, motif-shuffling, exon-shuffling, and/or codon-shuffling (collectively referred to as "DNA shuffling"). DNA shuffling involves the assembly of two or more DNA segments by homologous or site-specific recombination to generate variation in the polynucleotide sequence. DNA shuffling may be employed to modulate the activities of polynucleotides, polypeptides, proteins, or enzymes of the present disclosure, such methods can be used to generate polypeptides with altered activity. See, generally, U.S. Pat. Nos. 5,605,793; 5,811,238; 5,830,721; 5,834,252; 5,837,458; and 6,444,468; and Patten et al., Curr. Opinion Biotechnol. 8:724-33 (1997); Harayama, Trends Biotechnol. 16(2):76-82 (1998); Hansson, et al., J. Mol. Biol. 287:265-76 (1999); and Lorenzo and Blasco, Biotechniques 24(2): 308-13 (1998). Polynucleotides, polypeptides, proteins, or enzymes of the present disclosure may contain one or more components, motifs, sections, parts, domains, fragments, etc., of a polynucleotide, polypeptide, protein, or enzyme of the present disclosure. In some instances, kits for use in mutagenic PCR, such as, for example, the Diversify PCR Random Mutagenesis Kit (Clontech) or the GeneMorph Random Mutagenesis Kit (Stratagene) may be used.

In some instances, variant proteins differ from a parent protein or modified enzymes differ from a wild-type or unmodified enzyme and one another by a small number of amino acid residues. The number of differing amino acid residues may be one or more, preferably about 1, 2, 3, 4, 5, 10, 15, 20, 30, 40, 50, 60, 70, 80, 90, 100 or more amino acid residues. In some instances, the number of different amino acids between variants is between about 1 and about 10. In some instances, related proteins and particularly variant proteins comprise at least about 35%, 40%, 45%, 50%, 55%, 60%, 65%, 70%, 75%, 80%, 85%, 90%, 95%, 97%, 98%, or 99% amino acid sequence identity. Additionally, a related protein or a variant protein as used herein, refers to a protein that differs from another related protein or a parent protein in the number of prominent regions. For example, in some instances, variant proteins have about 1, 2, 3, 4, 5, 6, 7, 8, 9, or 10 corresponding prominent regions that differ from the parent protein.

In some instances, screening methods can include conventional screening methods such as liquid phase, or microtiter plate based assays. The format for liquid phase assays is often robotically manipulated 96, 384, or 1536-well microtiter plates. Other screening methods include growth selection (Snustad et al., 1988; Lundberg et al., 1993; Yano et al., 1998), colorimetric screening of bacterial colonies or phage plaques (Kuritz, 1999), in vitro expression cloning (King et al., 1997) and cell surface or phage display (Benhar, 2001). In some instances, screening approaches may be a method selected from yeast-2-hybrid, n-hybrid, reverse-2-hybrid, reverse n-hybrid, split two hybrid, bacterial display, phage display, retroviral display, ribosome display, covalent display, in vitro display, or any other display method. In some instances, the library is screened using a phage display method.

Analysis of the sequences derived from template jumps: the band corresponding to the template jump product may be excised from a polyacrylamide gel, eluted with sodium acetate (e.g. 0.3 M sodium acetate, pH 5.2), SDS (e.g. 0.03%) for several hours at room temperature, phenol/chloroform extracted and ethanol precipitated. The isolated cDNA may then be used as a template for PCR amplification using one or more primer(s). The PCR products may then be directly cloned into a vector (Burke et al., "R4, a non-LTR Retrotransposon Specific to the Large Subunit rRNA Gene of Nematodes," Nucleic Acids Res. 23: 4628-4634 (1995)) and individual clones sequenced.

In some instances, the variants or modified enzymes or non-naturally occurring enzymes or modified polypeptides have/has improved enzyme property compared to the unmodified, wild type or naturally occurring enzyme or polypeptide. In some instances, the improved enzyme property is selected from at least one of the following: increased stability (e.g., increased thermostability), increased specific activity, increased protein expression, improved purification, improved processivity, improved strand displacement, increased template jumping, improved ssDNA priming, and improved fidelity. In some instances, the term stability may include, but it is not limited to, thermal stability, storage stability, and pH stability. In some instances, specific activity is a measurement of the enzymatic activity (in units) of the protein or enzyme relative to the total amount of protein or enzyme used in a reaction. In some instances, specific activity is measured based on the ability of the enzyme to produce cDNA molecule. In some instances, the specific activity is measured in U/mg protein determined based on a primer extension reaction. In some instances, the altered or improved property may be characterized by a Performance Index (PI), where the PI is a ratio of performance of the variant, the modified enzyme, or the non-naturally occurring enzyme compared to the wild-type or compared to a naturally occurring enzyme or protein. The term "performance index (PI)" may refer to the ratio of performance of a variant polypeptide to a parent polypeptide or of a modified enzyme to an unmodified enzyme (e.g., reverse transcriptase) or of a non-naturally occurring enzyme to a naturally-occurring enzyme for a specified performance characteristic. In some instances, the specified performance or enzyme property characteristic may include, but is not limited to, stability (e.g., thermostability), specific activity, protein expression, purification, processivity, strand displacement, end-to-end template jumping, improved ssDNA priming, and/or fidelity. In some instances, the PI is greater than about 0.5, while in other instances, the PI is about 1 or is greater than about 1. In some instances, the variant polypeptide, modified enzyme (e.g., modified reverse transcriptase), or the non-naturally occurring enzyme comprises a modification at one or more amino acid positions. In some instances, the modified enzyme or the non-naturally occurring enzyme has a performance index (PI) that is equal to or greater than about 0.1, equal to or greater than about 0.2, equal to or greater than about 0.3, equal to or greater than about 0.4, equal to or greater than about 0.5, equal to or greater than about 0.6, equal to or greater than about 0.7, equal to or greater than about 0.8, equal to or greater than about 0.9, equal to or greater than about 1, equal to or greater than about 1.2, equal to or greater than about 1.5, equal to or greater than about 2, equal to or greater than about 2.5, equal to or greater than about 3, equal to or greater than about 3.5, equal to or greater than about 4, equal to or greater than about 4.5, equal to or greater than about 5, equal to or greater than about 5.5, equal to or greater than about 6, equal to or greater than about 6.5, equal to or greater than about 7, equal to or greater than about 8, equal to or greater than about 9, equal to or greater than about 10, equal to or greater than about 50, equal to or greater than about 75, equal to or greater than about 100, equal to or greater than about 500, equal to or greater than about 1000. In some instances, the variant or modified enzyme has a performance index (PI) from about 0.1 to about 1, from about 0.5 to about 1, from about 0.1 to about 2, from about 1 to about 2, from about 0.5 to about 2, from about 0.5 to about 10, from about 1 to about 10, from about 0.1 to about 10, from about 1 to about 5, from about 0.5 to about 5, from about 0.5 to about 20, from about 0.3 to about 20, from about 5 to about 10, from about 1.5 to about 10, from about 1.5 to about 50, from about 1 to about 50, from about 1.5 to about 100, from about 1.5 to about 75, from about 4 to about 10, from 3 to about 10, from about 3 to about 25, from about 3 to about 50, from about 2 to about 20, from about 2 to about 100, from about 2 to about 1000, from about 1 to about 1000. In some instances, the performance index is determined for protein expression. In some instances, the performance index is determined for at least one characteristic that improves enzyme property. In some instances, the performance index is determined for purification. In some instances, the performance index is determined for stability (e.g., thermostability). In some instances, the performance index is determined for specific activity. In some instances, the performance index is determined for processivity. In some instances, the performance index is determined for strand displacement. In some instances, the performance index is determined for template jumping. In some instances, the performance index is determined for fidelity. In some instances, the characteristic that improves enzyme property is selected from the group consisting of increased thermal stability, increased specific activity, and increased protein expression. In some instances, the performance index is performed at 30° C. In some instances, the enzyme property is analyzed at 30° C. In some instances, the enzyme property, stability (e.g., thermostability), specific activity, protein expression, purification, processivity, strand displacement, template jumping, and/or fidelity is performed at 30° C. In some instances, the performance index for measuring enzyme property, is performed at a specific temperature. In some instances, the temperature is from about 25° C. to about 42° C. In some instances, the temperature is from about 8° C. to about 50° C. In some instances, the performance index for measuring enzyme property may be carried out at a temperature ranging from about from about 8° C. to about 50° C., from about 12° C. to about 42° C., 25° C. to about 42° C., from about 25° C. to about 40° C., from about 28° C. to about 38° C., from about 30° C. to about 38° C., from about 35° C. to about 37° C., from about 27° C. to about 38° C., from about 27° C. to about 37° C., from about 26° C. to about 42° C., from about 25° C. to about 38° C., from about 27° C. to about 38° C., from about 29° C. to about 38° C., from about 29° C. to about 32° C. In some instances, the performance index for measuring enzyme property may be carried out at a temperature that is equal to or lower than about 8° C., equal to or lower than about 12° C., equal to or lower than about 20° C., equal to or lower than about 4° C., equal to or lower than about 55° C., equal to or lower than about 37° C., equal to or lower than about 25° C., equal to or lower than about 28° C., equal to or lower than about 30° C., equal to or lower than about 32° C., equal to or lower than about 34° C., equal to or lower than about 35° C., equal to or lower than about 36° C., equal to or lower than about 33° C., equal to or lower than about 31° C., equal to or lower than about 60° C., equal to or lower than about 38° C., equal to or lower than about 39° C., equal to or lower than about 40° C., equal to or lower than about 41° C., equal to or lower than about 42° C., equal to or lower than about 50° C. In some instances, the temperature may range from about 25° C. to about 80° C.

In some instances, the specific activity of the modified enzyme is from about 5 units/mg to about 140,000 units/mg, from about 5 units/mg to about 125,000 units/mg, from about 50 units/mg to about 100,000 units/mg, from about 100 units/mg to about 100,000 units/mg, from about 250 units/mg to about 100,000 units/mg, from about 500 units/mg to about 100,000 units/mg, from about 1000 units/mg to about 100,000 units/mg, from about 5000 units/mg to about 100,000 units/mg, from about 10,000 units/mg to about 100,000 units/mg, from about 25,000 units/mg to about 75,000 units/mg. In some instances, the ranges of specific activities include a specific activity of from about 20,000 units/mg to about 140,000 units/mg, a specific activity from about 20,000 units/mg to about 130,000 units/mg, a specific activity from about 20,000 units/mg to about 120,000 units/mg, a specific activity from about 20,000 units/mg to about 110,000 units/mg, a specific activity from about 20,000 units/mg to about 100,000 units/mg, a specific activity from about 20,000 units/mg to about 90,000 units/mg, a specific activity from about 25,000 units/mg to about 140,000 units/mg, a specific activity from about 25,000 units/mg to about 130,000 units/mg, a specific activity from about 25,000 units/mg to about 120,000 units/mg, a specific activity from about 25,000 units/mg to about 110,000 units/mg, a specific activity from about 25,000 units/mg to about 100,000 units/mg, and a specific activity from about 25,000 units/mg to about 90,000 units/mg. In some instances, the lower end of the specific activity range may vary from 30,000, 35,000, 40,000, 45,000, 50,000, 55,000, 60,000, 65,000, 70,000, 75,000, and 80,000 units/mg. In some instances, the upper end of the range may vary from 150,000, 140,000, 130,000, 120,000, 110,000, 100,000, and 90,000 units/mg.

Kits

Any of the compositions described herein may be comprised in a kit. In a non-limiting example, the kit, in a suitable container, comprises one or more primer(s). The kit can also comprise reaction components for primer extension and amplification (e.g., dNTPs, polymerase, buffers). The kit can include reagents for library formation (e.g., primers (probes), dNTPs, polymerase, and enzymes). The kit may also comprise approaches for purification, such as a bead suspension. The kit can include reagents for sequencing, e.g., fluorescently labelled dNTPs, sequencing primers, etc.

In some instances, some of the components of the kit may be packaged either in aqueous media or in lyophilized form. The containers of the kits can include at least one vial, test tube, or other containers, into which a component may be placed and suitably aliquoted. Where there is more than one component in the kit, the kit also can contain a second, third or other additional container into which the additional components may be separately placed. When the components of the kit are provided in one or more liquid solutions, the liquid solution can be an aqueous solution. The components of the kit may be provided as dried powder(s). When reagents and/or components are provided as a dry powder, the powder can be reconstituted by the addition of a suitable solvent.

A kit can include instructions for employing the kit components as well the use of any other reagent not included in the kit. Instructions may include variations that can be implemented.

In some instances, a kit may be used for the preparation of cDNA from a template (e.g. RNA template). Such a kit may include a carrier device compartmentalized to receive one or more containers, such as vials, tubes, and the like, each of which includes one of the separate elements used to prepare cDNA from RNA. For example, there may be provided a first container, the contents of which include a reverse transcriptase (e.g. non-retroviral reverse transcriptase, non-LTR retrotransposon, R2 reverse transcriptase) or variants thereof, in a liquid solution, powder form, or lyophilized form. Further, any number of additional containers can be provided, the contents of which independently include suitable buffers, substrates for nucleotide synthesis such as the deoxynucleotide triphosphates (e. g., dATP, dCTP, dGTP, and dTTP) either individually or collectively in a suitable solution, a template (e.g. template RNA), one or more primer(s), and acceptor nucleic acid molecule (e.g. acceptor RNA), and optionally a terminal transferase in solution. In some instances, a kit may comprise a fragment or degraded nucleic acid, DNA, RNA, or a combination thereof, one of more primer(s), an acceptor nucleic acid molecule (e.g., an acceptor nucleic acid molecule comprising a modified nucleotide), a reverse transcriptase (e.g., non-retroviral reverse transcriptase, non-LTR retrotransposon, R2 reverse transcriptase) or variants thereof, suitable buffers, substrates for nucleotide synthesis such as the deoxynucleotide triphosphates (e. g., dATP, dCTP, dGTP, and dTTP). Any combinations of the above components can be provided. Any of the above components may be excluded from the kit. In some instances, the one or more primer(s) may be one or more random primer(s). In some instances, any of the components may be individually packed.

The present disclosure relates to a kit of producing a nucleic acid molecule (e.g., cDNA molecule) comprising: one or more primer(s), nucleotides, at least one modified reverse transcriptase, a template, and instructions for performing any of the methods disclosed in the present disclosure. In some instances, a kit can be used for detecting nucleic acid comprising a nucleic acid template (e.g., a DNA template), at least one modified reverse transcriptase, nucleotides, and instructions for performing any of the methods disclosed in the present disclosure. In some instances, the modified reverse transcriptase present in the kit or to be used with the kit has activity and/or is capable of template jumping at a temperature equal to or less than about or more than about 4° C., 8° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 45° C., 46° C., 47° C., 48° C., 49° C., 50° C., 52° C., 55° C., or 60° C. In some instances, the nucleic acid and/or the template (e.g., nucleic acid template, DNA, or RNA) is present at a concentration as low as about 50 femtomolar, as low as about 60 femtomolar, as low as about 70 femtomolar, as low as about 75 femtomolar, as low as about 80 femtomolar, as low as about 90 femtomolar, as low as about 100 femtomolar, as low as about 120 femtomolar, as low as about 150 femtomolar, as low as about 200 femtomolar, as low as about 250 femtomolar, as low as about 300 femtomolar, as low as about 350 femtomolar, as low as about 400 femtomolar, as low as about 500 femtomolar, as low as about 550 femtomolar, as low as about 600 femtomolar, as low as about 700 femtomolar, or as low as about 800 femtomolar. In some instances, the nucleic acid and/or the template (e.g., nucleic acid template, DNA, or RNA) is present at a concentration as high as 1 micromolar. In some instances, a kit may comprise one or more primer(s), and/or a template annealed to a primer. The present disclosure also relates to a kit of producing modified enzymes, modified reverse transcriptases, or modified polypeptides. In some instances, the kit includes a PCR step and/or components to use for PCR.

In some instances, the present disclosure relates to a kit for detecting nucleic acid comprising a template, at least one modified reverse transcriptase, nucleotides, and instructions to perform the method of the present disclosure. In some instances, the nucleic acid is present at a concentration of at least about 50 femtomolar, at least about 20 femtomolar, at least about 100 femtomolar, or greater than about 1000 femtomolar.

Sequencing

In some instances, determining the number of different labeled nucleic acids may comprise determining the sequence of the labeled nucleic acid or any product thereof (e.g., labeled-amplicons, labeled-cDNA molecules). In some instances, an amplified target nucleic acid may be subjected to sequencing. Determining the sequence of the labeled nucleic acid or any product thereof may comprise conducting a sequencing reaction to determine the sequence of at least a portion of the sample tag, molecular identifier label, at least a portion of the labeled nucleic acid, a complement thereof, a reverse complement thereof, or any combination thereof. In some instances, only the sample tag or a portion of the sample tag is sequenced. In some instances, only the molecular identifier label or a portion of the molecular identifier label is sequenced.

Determining the sequence of the labeled nucleic acid or any product thereof may be performed by sequencing methods such as Helioscope (Registered Trademark) single molecule sequencing, Nanopore DNA sequencing, Lynx Therapeutics' Massively Parallel Signature Sequencing (MPSS), 454 pyrosequencing, Single Molecule real time (RNAP) sequencing, Illumina (Solexa) sequencing, SOLiD sequencing, Ion Torrent, Ion semiconductor sequencing, Single Molecule SMRT (Registered Trademark) sequencing, Polony sequencing, DNA nanoball sequencing, and VisiGen Biotechnologies approach. Alternatively, determining the sequence of the labeled nucleic acid or any product thereof may use sequencing platforms, including, but not limited to, Genome Analyzer IIx, HiSeq, and MiSeq offered by Illumina, Single Molecule Real Time (SMRT (Registered Trademark)) technology, such as the PacBio RS system offered by Pacific Biosciences (California) and the Solexa Sequencer, True Single Molecule Sequencing (tSMS (Registered Trademark)) technology such as the HeliScope (Registered Trademark) Sequencer offered by Helicos Inc. (Cambridge, Mass.).In some instances, the sequencing reaction can occur on a solid or semi-solid support, in a gel, in an emulsion, on a surface, on a bead, in a drop, in a continuous follow, in a dilution, or in one or more physically separate volumes.

Sequencing may comprise sequencing at least about 10, 20, 30, 40, 50, 60, 70, 80, 90, 100 or more nucleotides or base pairs of the labeled nucleic acid. In some instances, sequencing comprises sequencing at least about 200, 300, 400, 500, 600, 700, 800, 900, 1000 or more nucleotides or base pairs of the labeled nucleic acid. In other instances, sequencing comprises sequencing at least about 1500; 2,000; 3,000; 4,000; 5,000; 6,000; 7,000; 8,000; 9,000; or 10,000 or more nucleotides or base pairs of the labeled nucleic acid.

Sequencing may comprise at least about 200, 300, 400, 500, 600, 700, 800, 900, 1000 or more sequencing reads per run. In some instances, sequencing comprises sequencing at least about 1500; 2,000; 3,000; 4,000; 5,000; 6,000; 7,000; 8,000; 9,000; or 10,000 or more sequencing reads per run. Sequencing may comprise less than or equal to about 1,600,000,000 sequencing reads per run. Sequencing may comprise less than or equal to about 200,000,000 reads per run.

Cells

The cell as described in the present disclosure may be a cell from an animal (e.g., human, rat, pig, horse, cow, dog, mouse). In some instances, the cell may be a single cell. In some instances, the cell is a human cell. The cell may be a fetal human cell. The fetal human cell may be obtained from a mother pregnant with the fetus. The cell may be a cell from a pregnant mother. The cell may be a cell from a vertebrate, invertebrate, fungi, archaea, or bacteria. The cell may be from a multicellular tissue (e.g., an organ (e.g., brain, liver, lung, kidney, prostate, ovary, spleen, lymph node, thyroid, pancreas, heart, skeletal muscle, intestine, larynx, esophagus, and stomach), a blastocyst). The cell may be a cell from a cell culture. The cell may be a HeLa cell, a K562 cell, a Ramos cell, a hybridoma, a stem cell, an undifferentiated cell, a differentiated cell, a circulating cell, a CHO cell, a 3T3 cell, and the like.

Circulating diseased cells that can be used in the methods of the present disclosure include all types of circulating cells that may be affected by a disease or condition or infected by an infectious agent. A circulating cell refers to a cell present in the bodily fluid. A circulating cell may not necessarily circulate throughout the entire body or in the circulatory system. For example, a circulating cell may be present locally, such as in synovial fluid, or cerebrospinal fluid, or lymph fluid. A circulating diseased cell may also be detached from a tissue or organ that has been affected by a disease or condition or infected by an infectious agent. In other instances, the circulating diseased cells can be a mixture of different types of circulating diseased cells.

In some instances, the cell is a cancerous cell. Non-limiting examples of cancer cells may include a prostate cancer cell, a breast cancer cell, a colon cancer cell, a lung cancer cell, a brain cancer cell, and an ovarian cancer cell. In some instances, the cell is from a cancer (e.g., a circulating tumor cell). Non-limiting examples of cancers may include, adenoma, adenocarcinoma, squamous cell carcinoma, basal cell carcinoma, small cell carcinoma, large cell undifferentiated carcinoma, chondrosarcoma, and fibrosarcoma.

In some instances, the cell is a rare cell. A rare cell can be a circulating tumor cell (CTC), circulating epithelial cell (CEC), circulating stem cell (CSC), stem cells, undifferentiated stem cells, cancer stem cells, bone marrow cells, progenitor cells, foam cells, fetal cells, mesenchymal cells, circulating endothelial cells, circulating endometrial cells, trophoblasts, immune system cells (host or graft), connective tissue cells, bacteria, fungi, or pathogens (for example, bacterial or protozoa), microparticles, cellular fragments, proteins and nucleic acids, cellular organelles, other cellular components (for example, mitochondria and nuclei), and viruses.

In some instances, the cell is from a tumor. In some instances, the tumor is benign or malignant. The tumor cell may comprise a metastatic cell. In some instances, the cell is from a solid tissue that comprises a plurality of different cell types (e.g., different genotypes).

Samples

In some instances, the sample that includes the template nucleic acid, e.g. DNA and/or RNA, may be combined into the reaction mixture in an amount sufficient for producing a product. In some instances, the sample is combined into the reaction mixture such that the final concentration of DNA and/or RNA in the reaction mixture is from about 1 fg/µL to about 10 µg/µL, from about 1 µg/µL to about 5 µg/µL, from about 0.001 µg/µL to about 2.5 µg/µL, from about 0.005 µg/µL to about 1 µg/µL, from about 0.01 µg/µL to about 0.5 µg/µL, from about 0.1 µg/µL to about 0.25 µg/µL. In some instances, the sample that includes the template is isolated from a single cell. In some instances, the sample that includes the template is isolated from about 2, 3, 4, 5, 6, 7, 8, 9, 10, 20, 50, 100, 500 or more cells.

In some instances, the template is DNA, RNA, or a combination of DNA and RNA. In some instances, the template is a fragment or degraded DNA, a fragment or degraded RNA, or a combination of fragment or degraded DNA and fragment or degraded RNA. In some instances, the total amount of template is the total amount of template in a sample. In some instances, the total amount of template is the total amount of template in a reaction mixture. In some instances, the total amount of template is the total amount of template in one pot or a single vessel. In some instances, the total amount of template is the total amount of template in one pot or a single vessel reaction. In some instances, the total amount of the template is from about 1 femtomolar (fM) to about 100 micromolar, from about 0.0001 micromolar to about 0.01 micromolar, from about 0.0001 micromolar to about 0.1 micromolar, from about 40 femtomolar to about 0.01 micromolar, from about 50 femtomolar to about 500 femtomolar, from about 50 femtomolar to about 0.01 micromolar, from about 50 femtomolar to about 0.1 micromolar, from about 50 femtomolar to about 500 picomolar, from about 50 femtomolar to about 500 nanomolar, from about 50 femtomolar to about 500 micromolar, from about 50 femtomolar to about 1 picomolar, from about 40 femtomolar to about 1 nanomolar, from about 1 femtomolar to about 1 picolomar. In some instances, the total amount of template is equal to or at least about or lower than about 1000 micromolar, equal to or at least about or lower than about 500 micromolar, equal to or at least about or lower than about 250 micromolar, equal to or at least about or lower than about 100 micromolar, equal to or at least about or lower than about 50 micromolar, equal to or at least about or lower than about 25 micromolar, equal to or at least about or lower than about 10 micromolar, equal to or at least about or lower than about 1 micromolar, equal to or at least about or lower than about 0.1 micromolar, equal to or at least about or lower than about 0.01 micromolar, equal to or at least about or lower than about 0.001 micromolar, equal to or at least about or lower than about 0.0001 micromolar, equal to or at least about or lower than about 2000 nanomolar, equal to or at least about or lower than about 500 nanomolar, equal to or at least about or lower than about 250 nanomolar, equal to or at least about or lower than about 200 nanomolar, equal to or at least about or lower than about 50 nanomolar, equal to or at least about or lower than about 25 nanomolar, equal to or at least about or lower than about 20 nanomolar, equal to or at least about or lower than about 2 nanomolar, equal to or at least about or lower than about 0.2 nanomolar, equal to or at least about or lower than about 0.01 nanomolar, equal to or at least about or lower than about 0.001 nanomolar, equal to or at least about or lower than about 0.0001 nanomolar, equal to or at least about or lower than about 3000 picomolar, equal to or at least about or lower than about 500 picomolar, equal to or at least about or lower than about 250 picomolar, equal to or at least about or lower than about 300 picomolar, equal to or at least about or lower than about 50 picomolar, equal to or at least about or lower than about 25 picomolar, equal to or at least about or lower than about 30 picomolar, equal to or at least about or lower than about 3 picomolar, equal to or at least about or lower than about 0.3 picomolar, equal to or at least about or lower than about 0.01 picomolar, equal to or at least about or lower than about 0.001 picomolar, equal to or at least about or lower than about 0.0001 picomolar, equal to or at least about or lower than about 5000 femtomolar, equal to or at least about or lower than about 500 femtomolar, equal to or at least about or lower than about 250 femtomolar, equal to or at least about or lower than about 50 femtomolar, equal to or at least about or lower than about 25 femtomolar, equal to or at least about or lower than about 10 femtomolar, equal to or at least about or lower than about 1 femtomolar, equal to or at least about or lower than about 0.1 femtomolar, equal to or at least about or lower than about 0.01 femtomolar, equal to or at least about or lower than about 0.001 femtomolar, equal to or at least about or lower than about 0.0001 femtomolar.

In some instances, the sample may be obtained from a biological sample obtained from a subject. In some instances, a sample comprises circulating tumor DNA sample and/or a tissue sample. In some instances, the biological sample comprises a cell-free biological sample. In some instances, the biological sample comprises a circulating tumor DNA sample. In some instances, the biological sample comprises a biopsy sample. In some instances, the biological sample comprises a tissue sample. In some instances, the biological sample comprises liquid biopsy. In some instances, the biological sample comprises cell-free DNA. In some instances, the biological sample can be a solid biological sample, e.g., a tumor sample. In some instances, a sample from a subject can comprise at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or at least about 100% tumor cells or nucleic acid from a tumor. The solid biological sample can be processed by fixation in a formalin solution, followed by embedding in paraffin (e.g., a FFPE sample). The solid biological sample can be processed by freezing. Alternatively, the biological sample can be neither fixed nor frozen. The unfixed, unfrozen sample can be stored in a solution configured for the preservation of nucleic acid. The solid biological sample can optionally be subjected to homogenization, sonication, French press, dounce, freeze/thaw, which can be followed by centrifugation.

In some instances, the sample can be a liquid biological sample. In some instances, the liquid biological sample can be a blood sample (e.g., whole blood, plasma, or serum). A whole blood sample can be subjected to separation of cellular components (e.g., plasma, serum) and cellular components by use of a Ficoll reagent. In some instances, the liquid biological sample can be a urine sample. In some instances, the liquid biological sample can be a perilymph sample. In some instances, the liquid biological sample can be a fecal sample. In some instances, the liquid biological sample can be saliva. In some instances, the liquid biological sample can be semen. In some instances, the liquid biological sample can be amniotic fluid. In some instances, the liquid biological sample can be cerebrospinal fluid. In some instances, the liquid biological sample can be bile. In some instances, the liquid biological sample can be sweat. In some instances, the liquid biological sample can be tears. In some instances, the liquid biological sample can be sputum. In some instances, the liquid biological sample can be synovial fluid. In some instances, the liquid biological sample can be vomit. In some instances, the liquid biological sample can be a cell-free sample. In some specific instances, the cell-free sample can be a cell-free plasma sample.

Polynucleotides in a sample (which can be referred to as input nucleic acid or input) can comprise DNA. The input nucleic acid can be complex DNA, such as double-stranded DNA, genomic DNA or mixed nucleic acids from more than one organism. Polynucleotides in the sample can comprise RNA. The RNA can be obtained and purified. RNA can include RNAs in purified or unpurified form, which include, but are not limited to, mRNAs, tRNAs, snRNAs, rRNAs, retroviruses, small non-coding RNAs, microRNAs, polysomal RNAs, pre-mRNAs, intronic RNA, viral RNA, cell-free RNA and fragments thereof. The non-coding RNA, or ncRNA may include snoRNAs, microRNAs, siRNAs, piRNAs and long nc RNAs.

Polynucleotides in the sample can comprise cDNA. The cDNA can be generated from RNA, e.g., mRNA. The cDNA can be single or double stranded. The input DNA can be mitochondrial DNA. The input DNA can be cell-free DNA. The cell-free DNA can be obtained from, e.g., a serum or plasma sample. The input DNA can be from more than one individual or organism. The input DNA can be double stranded or single stranded.

In some instances, samples can be collected over a period of time. Samples can be collected over regular time intervals, or can be collected intermittently over irregular time intervals. Nucleic acids from different samples can be compared, e.g., to monitor progression or recurrence of a condition or disease.

In some instances, a sample can be collected by core biopsy. In some instances, a sample can be collected as a purified nucleic acid. Examples of such purified samples can include precipitated nucleic acid affixed to filter paper, phenol-chloroform extractions, nucleic acid purified by kit purification (e.g. Quigen Miniprep (Registered Trademark) and the like), or gel purified nucleic acid as exemplary examples.

The sample of the disclosure may be a sample from an animal (e.g., human, rat, pig, horse, cow, dog, mouse). In some instances, the sample is a human sample. The sample may be a fetal human sample. The sample may be from a multicellular tissue (e.g., an organ (e.g., brain, liver, lung, kidney, prostate, ovary, spleen, lymph node, thyroid, pancreas, heart, skeletal muscle, intestine, larynx, esophagus, and stomach), a blastocyst). The sample may be a cell from a cell culture.

The sample may comprise a plurality of cells. The sample may comprise a plurality of the same type of cell. The sample may comprise a plurality of different types of cells. The sample may comprise a plurality of cells at the same point in the cell cycle and/or differentiation pathway. The sample may comprise a plurality of cells at different points in the cell cycle and/or differentiation pathway. A sample may comprise a plurality of samples.

The plurality of samples may comprise one or more malignant cell. The one or more malignant cells may be derived from a tumor, sarcoma or leukemia.

The plurality of samples may comprise at least one bodily fluid. The bodily fluid may comprise blood, urine, lymphatic fluid, saliva. The plurality of samples may comprise at least one blood sample.

The plurality of samples may comprise at least one cell from one or more biological tissues. The one or more biological tissues may be a bone, heart, thymus, artery, blood vessel, lung, muscle, stomach, intestine, liver, pancreas, spleen, kidney, gall bladder, thyroid gland, adrenal gland, mammary gland, ovary, prostate gland, testicle, skin, adipose, eye or brain.

The biological tissue may comprise an infected tissue, diseased tissue, malignant tissue, calcified tissue or healthy tissue.

In some instances, the characteristic that improves enzyme property is selected from the group consisting of increased stability (e.g., increased thermostability), increased specific activity, increased protein expression, increased processivity, increased strand displacement, increased end-to-end template jumping, and increased fidelity.

EXAMPLES

The following specific examples are illustrative and non-limiting. The examples described herein reference and provide non-limiting support to the various embodiments described in the preceding sections.

Example 1: Expression and Purification

Small and medium scale: Expression vector pET-45b caring modified R2 non-long terminal repeat (LTR) retrotransposon or one of the modified R2 reverse transcriptases of SEQ ID Nos: 1-20 was transformed into *E. coli* BL21 (DE3). TABLE 1 below shows examples of non-naturally occurring R2 enzyme variants of the present disclosure. For expression, pre-culture can be setup in 2 ml LB with 100 μM Corbenicillin and grown overnight for about 8 to 12 hours at room temperature. After about 8 h to 12 h, 200 μL of the pre-culture can be transferred to 25 mL of an auto-induction expression media, Overnight Express TB (Novagen), and shaker-incubated at room temperature for 36 hours to 48 hours. Cells were harvested by centrifugation at 8000×g for 10 min at 4-8° C. The biomass-pellet was frozen at −20° C. for a minimum of 1 h.

Purification: pellet can be re-suspended in 0.5 mL lysis buffer (0.5 mL lysis buffer per ⅙ of the biomass) and incubated for 30 minutes at room temperature. Lysis buffer composition: 1×BugBuster, 100 mM Sodium Phosphate, 0.1% Tween, 2.5 mM TCEP, 3 μL Protease inhibitor mix (Roche), 50 μg lysozyme, 0.5 μL DNaseI (2,000 units/ml, from NEB). After incubation, the lysate can be mixed with equal volume (0.5 mL) of His-binding buffer (50 mM Sodium Phosphate pH 7.7, 1.5M Sodium Chloride, 2.5 mM TCEP, 0.1% Tween, 0.03% Triton X-100, and 10 mM Imidazole) and incubated at room temperature for about 10-15 minutes. After incubation, the lysate can be centrifuged at 10000×g for about 15 min at a temperature from about 4° C. to about 8° C. Pellet can then mixed with 250 μL of His-Affinity Gel (His-Spin Protein Miniprep by Zymo Research) according to manufacturer's protocol. After the binding step, the His-Affinity Gel was washed three times with Washing buffer (50 mM Sodium Phosphate pH 7.7, 750 mM Sodium Chloride, 0.1% Tween, 0.03% Triton X-100, 2.5 mM TCEP, and 50 mM Imidazole). The R2 reverse transcriptase (RT) (e.g., non-naturally occurring enzyme) can be eluted with 150 μL of elution buffer (50 mM Sodium Phosphate pH 7.7, 300 mM Sodium Chloride, 2.5 mM TCEP, 0.1% Tween, and 250 mM Imidazole) and either used directly or frozen in 30% glycerol. This protocol can be adjusted for expression and purification of mutagenesis and for screening. For example, a similar protocol can be adjusted to a plate format, such as 2 mL of the Overnight Express TB (Novagen) instead of 25 mL can be used, and the purification step can comprise 96 well spin plates with nickel-immobilized resin.

Result: After purification, samples can be analyzed using sodium dodecyl sulfate polyacrylamide gel electrophoresis (SDS-PAGE), 4-12% polyacrylamide, Bis-Tris.

Example 2: Surrogate/Diagnostic Assays

Example of reverse transcriptase (RT) activity assay: activity assay can be used to compare enzyme activity, active fraction, stability (e.g., thermostability), and robustness of the non-naturally occurring enzymes. RT activity and active fraction(s) can be estimated based on primer extension assay by comparing fraction(s) of extended to non-extended DNA primer using various template/primer and enzyme concentrations. Extension assays can be conducted with and without the addition of a DNA trap.

Example protocol: annealed 0.2 µM template/primer with fluorescently labeled primer can be pre-incubated with various concentrations of R2 RT (relative to template/primer 0.1 to 4-fold) at room temperature for 20 minutes. Pre-incubation conditions can include 40 mM Tris pH 7.5, 200 mM NaCl, 5 mM TCEP, and 0.1% Tween. Extension can start with the addition of $MgCl_2$ (5 mM, final) and dNTPs (25 µM of each, final) and optionally a DNA trap (unlabeled DNA oligo duplex at 3 µM, final, or heparin). The addition of trap DNA helps to estimate RT active fraction(s). The reaction can then be incubated for 10 minutes and stopped with EDTA (50 mM, final) or formamide (50%, final). The product of the reaction can then be analyzed with 15% PAGE-Urea. An example of a template sequence used is rCrArG rUrCrA rGrUrC rArGrU rCrArG rUrCrA rGrUrG rCrCrA rArArU rGrCrC rUrCrG rUrCrA rUrC and of a primer is /56-FAM/ TGATGACGAGGCATTTGGC.

Example of end-to-end template jumping assay: Primer extension assay with two templates where one template is annealed to a fluorescently labeled primer (donor template) and the other is primer-free (acceptor nucleic acid).

Example protocol: annealed 0.1 µM template/primer with fluorescently labeled primer (alternatively the product of the reaction can be stained with Syber Gold) can be pre-incubated with various concentrations of R2 RT (relative to template/primer 0.1 to 4-fold) at room temperature for 20 minutes. Pre-incubation conditions can include 40 mM Tris pH 7.5, 200 mM NaCl, 5 mM TCEP, and 0.1% Tween. Extension can start with the addition of $MgCl_2$ (5 mM, final), dNTPs (50 µM of each, final) and the acceptor nucleic acid at various concentrations (range from about 0.01 µM to about 5 µM). The reaction can then be incubated for 30 min-1 h and stopped with EDTA (50 mM, final) or formamide (50%, final). The product of the reaction can be analyzed with 15% PAGE-Urea.

Templates: the templates can be generated by in vitro RNA synthesis with T7 RNA polymerase based on the DNA template generated in a PCR reaction with two primers, one of which included a T7 promoter sequence (i.e., a first primer). The second primer can also be used as a DNA primer in the donor template/primer protocol. The product of the reaction can then be analyzed with 15% PAGE-Urea. Example of materials used: template for PCR amplification pUC18 with T7 primer CTGCAGTAATACGACTCAC-TATAGGATCCTCTAGAGTCGACCTGC (SEQ ID NO: 24); donor primer GCCATTCGCCATTCAGGCTGC (SEQ ID NO: 102)(used for both PCR amplification and priming at the donor RNA template); RNA template (~190 nucleotides); acceptor nucleic acid—G-block PCR template ACGGCCAGTGAATTGTAATACGACTCAC-TATAGGGCGAATTGGGTACCGCCTCGAG GTCGACGGTATCGATAAGCTTGATATCGAAT-TCCTGCAGCGGATCCACTAGTTCTAG AGCGGCCGCCACCGCGGTG-GAGCTCCAGCTTTTGTTCCCTTTAGTGAGGGT-TAATTT CGAGCTTGGCGTAATCATGGTCAT-AGCTGTTTCC (SEQ ID NO: 103); two primers for PCR amplification (a T7 primer ACGGCCAGTGAAT-TGTAATACGAC (SEQ ID NO: 104) and a second primer GGAAACAGCTATGACCATG (SEQ ID NO: 105)).

Example of processivity assay: processivity of each non-naturally occurring enzyme can be analyzed based on primer extension and product formation using a 15% PAGE-Urea, or a 1.2% agarose gel, or a 2% agarose gel. Product length distribution can be analyzed with densitometry.

Example protocol: annealed 0.05-0.1 µM template/primer with fluorescently labeled primer (alternatively product of the reaction can be stained with Syber Gold) can be pre-incubated with various concentration of R2 RT (0.1 to 4-fold relative to template/primer) for 20 minutes at room temperature. Pre-incubation conditions: 40 mM Tris pH 7.5, 200 mM NaCl, 5 mM TCEP, and 0.1% Tween. Extension can start with addition of $MgCl_2$ (5 mM, final), dNTPs (50 µM of each, final), and optionally a DNA trap (unlabeled DNA oligo duplex at 3 µM, final). The reaction can then be incubated for 30 min-1 h and stopped with EDTA (50 mM, final) or formamide (50%, final).

Templates: the templates can be generated by in vitro RNA synthesis with T7 RNA polymerase based on the DNA template generated in a PCR reaction with two primers, one of which included a T7 promoter sequence. The second primer can also be used as a DNA primer in the donor template/primer protocol. The product of the reaction was analyzed with a 15% PAGE-Urea, or a 1.2% agarose gel, or a 2% agarose gel. Materials included: template for PCR amplification pUC18 with T7 primer CTGCAGTAATACGACTCACTATAG-GATCCTCTAGAGTCGACCTGC, RT primer CAGGGTT-ATTGTCTCATGAGCG (SEQ ID NO: 101)(used for both PCR amplification and priming at the donor RNA template), and RNA template (~600 nucleotides).

Example of Random priming: Longer RNA template(s) with several primers with adapters or random primers with adapters; product analysis is performed after PCR amplification to compare product's length distribution (one primer is specific to the 5'-end of the template and the second primer is complementary to the adapter sequence).

Example 3: Activity and Template Jumping Experiment Using Synthetic RNA

Non-naturally occurring R2 enzymes can have template jumping properties.

Example protocol: reactions containing 0.25 mM of dNTPs, R2 buffer, 0.4 µM template/primer, acceptor nucleic acid (0 to 1 µM), non-naturally occurring R2, and $H_2O$ can be used to detect template jumping. The reactions containing the R2 enzyme or the R2 buffer can be incubated at 30° C. for 1 hour. Products can be analyzed using 15% PAGE-Urea gel.

Sequences of templates, primers, and acceptors that can be used to test template jumping are shown below:

| | |
|---|---|
| P173 (RNA template) | CAGUCAGUCAGUCAGUCAGUGCCAAAUGCCUCGUCAUC (SEQ ID NO: 98) |
| P174 (fluorescently labeled primer) | /56-FAM/TGATGACGAGGCATTTGGC (SEQ ID NO: 99) |
| P181 (acceptor nucleic acid) | GTTAATAACGAAATGAGCAGCCrGrGrG (SEQ ID NO: 100) |

Example 4: DNA Fragments can be Captured and Tagged with Non-Naturally Occurring R2 Enzyme This experiment can be used to show that a 200 bp DNA fragment (typical size for cfDNA) can be captured and tagged in a 1-pot (single vessel) reaction using the methods of the present disclosure. Some facts of this experiment: no prior knowledge of the sequence is required and the data provided by this experiment may meet the sensitivity requirement (a typical liquid biopsy sample has between about 10-30 ng of DNA, a required sensitivity of 0.1% (~10-30 pg)).

This experiment can be used to show that 1-pot (single vessel) reaction containing DNA fragments (200 bp PCR product prepared by heat denaturation and quick cooling of PCR product) can be captured and tagged using a non-naturally occurring R2 enzyme (P8 variant R2 enzyme). In brief, this experiment can include two approaches: 1) capture of DNA fragment with RNA priming; and 2) capture of DNA fragment using RNA donor. Briefly, the reactions per the first approach (RNA priming) can include H$_2$O, 5×R2 buffer, 0.25 mM dNTPs, 200 bp DNA fragment (0 ng (no DNA template control (NTC)), 160 pg, 32 pg, or 6 pg of DNA template), enzyme (e.g., 0.023 µg/µL P8 variant R2 enzyme), and 0.5 µM of P173. The reactions per the second approach (RNA donor) can include H$_2$O, 5×R2 buffer, 0.25 mM dNTPs, 200 bp DNA fragment (0 ng (no DNA template control (NTC)), 160 pg, 32 pg, or 6 pg), enzyme (e.g., 0.023 µg/µL P8 variant R2 enzyme), and 0.2 µM RNA donor (P173+P174). The reactions can then be incubated at 30° C. for about 1 hour. The reactions can then be diluted 1:10 and supplemented with PCR reagents including amplification primers and hot-start polymerase. The PCR amplification reactions for the first approach (RNA priming) can include H$_2$O, 1× taq master mix with 1×SYBR Green, 0.5 µM of P169, 0.5 µM of P186, and 1× template (10 µL RT reaction in 100 µL total volume for PCR). The PCR amplification reactions for the second approach (RNA donor) can include H$_2$O, 1× Taq Mastermix with 1× sybr green, 0.5 µM of P169, 0.5 µM of P186, and 1× template (10 µL RT reaction in 100 µL total volume for PCR). The PCR conditions for the reactions were 95° C. for 3 minutes and 30 cycles of 95° C. for 3 seconds, 54° C. for 10 seconds, and 64° C. for 10 seconds. The reactions can then be increased to 68° C. for 2'. The length of the PCR products can be confirmed on an acrylamide gel. The results can be used to show that the DNA fragment (~200 bp) can be captured using either the RNA priming or the donor RNA mechanism without prior knowledge of the DNA sequence.

Sequences:

| | |
|---|---|
| 200 bp DNA fragment (PCR product) | CTGCAGTAATACGACTCACTATAGGATCCTCTAGAGTCGACCTG CAGGCATGCAAGCTTGGCACTGGCCGTCGTTTTACAACGTCGTG ACTGGGAAAACCCTGGCGTTACCCAACTTAATCGCCTTGCAGCA CATCCCCCTTTCGCCAGCTGGCGTAATAGCGAAGAGGCCCGCAC CGATCGCCCTTCCCAACAGTTGCGCAGCCTGAATGGCGAATGGC (SEQ ID NO: 23) |
| P169 | CTGCAGTAATACGACTCACTATAGGATCCTCTAGAGTCGACCTG C (SEQ ID NO: 24) |
| P186 | CAGTCAGTCAGTCAGTCAGTGCCA (SEQ ID NO: 25) |
| P173 (RNA template) | CAGUCAGUCAGUCAGUCAGUGCCAAAUGCCUCGUCAUC (SEQ ID NO: 26) |
| P174 | TGATGACGAGGCATTTGGC (SEQ ID NO: 27) |

Example 5: Template Concatemerization

This experiment was designed to demonstrate a method for converting short DNA fragments into a concatemer. Concatemers may contain about 2, 3, 4, 5, 6, 7, 8, 9, 10, 20, 30, 40, 50, 60, 70, 80, 90, 100, 500, 1000, or more copies of the starting nucleic acid. In brief, the initial PCR protocol for template preparation can include H₂O, 2× Q5 master mix, P316 (0.5 μM), P317 (0.5 μM), and pUC18 (0.05 ng/μL). The PCR condition can be 98° C. for 30 seconds followed by 30 cycles of: 98° C. for 10 seconds, 66° C. for 15 seconds, and 72° C. for 10 seconds. At the end of the 30 cycles, the reaction can be kept at 72° C. for 2 minutes and then, it can be reduced to 4° C. The adaptor annealing reaction can include H₂O, Tris pH 8.0 (20 mM), NaCl (100 mM), and two primers (25 μM each; (P312+P313) or (P314+P315) or (P320+P321)). The reaction can be incubated at 90° C. for 1 minute, followed by 0.1° C./second ramp to 25° C. (20 seconds) and then, it can be reduced and kept at 4° C. The first adaptor ligation reaction can include H₂O (30 μL), fragmented DNA (20 μL), end repair and T-tailing buffer (7 μL), and end repair and T-tailing enzyme mix (3 μL). The reaction can be incubated at 20° C. for 30 minutes and then increased to 65° C. for 30 minutes. H₂O (5 μL) can then added to the reaction (50 μL) along with 2.5 μL of 20 μM adaptor (P312+P313), 2.5 μL of 20 μM adaptor (P314+P315), ligation buffer (30 μL), and DNA ligase (10 μL). The reaction can then be incubated at room temperature for 15 minutes, followed by a reaction clean-up. SPRI beads can then be added and the reaction can be eluted. The adaptor ligated library (10 μL) can be incubated with H₂O (40 μL) and 2× Kappa HiFi master mix (50 μL) and it can be subjected to PCR (98° C. for 45 seconds; 5 cycles of 98° C. for 15 seconds, 60° C. for 30 seconds, and 72° C. for 30 seconds; 72° C. for 1 minute; and kept at 4° C.). This protocol can then be modified in order to increase the number of cycles (e.g., from 5 cycles to 25 cycles). The second adaptor ligation reaction comprises of a similar protocol as the one described for the first adaptor ligation reaction; the difference being that 5 μL of 20 μM adaptor (P320+P321) can be used instead of 2.5 μL of 20 μM adaptor (P312+P313) and 2.5 μL of 20 μM adaptor (P314+P315).

Sequences:

| | | | |
|---|---|---|---|
| P312 | ACACTCTTTCCCTACACGACGCT (SEQ ID NO: 28) | | Right adaptor |
| P313 | /5Phos/GCGTCGTGTAGGGAAAGAGTGT (SEQ ID NO: 29) | | Right adaptor |
| P314 | /5Phos/CACTCTTTCCCTACACGACGCT (SEQ ID NO: 30) | | Left adaptor |
| P315 | AGCGTCGTGTAGGGAAAGAGTGT CACTCTTTCCCTACACGACGCT (SEQ ID NO: 31) | | Left adaptor |
| P316 | ACACTTTATGCTTCCGGCTC CACTCTTTCCCTACACGACGCT (SEQ ID NO: 32) | | Amp pUC18 for 200 bp frag with KpnI in middle |
| P317 | TAAGTTGGGTAACGCCAGG CACTCTTTCCCTACACGACGCT (SEQ ID NO: 33) | | Amp pUC18 for 200 bp frag with KpnI in middle |
| P318 | ACACTCTTTCC CACTCTTTCCCTACACGACGCT (SEQ ID NO: 34) | | Invasion primers |
| P319 | AGCGTCGTG CACTCTTTCCCTACACGACGCT (SEQ ID NO: 35) | | Invasion primers |
| P320 | TTCCAATGATACGGCGACCACCGAUACUGUCA UAGCTAGCTCCTCACTCTTTCCCTACACGACGC T (SEQ ID NO: 36) | | Outside adaptor - can use P5 primer USER compatible |
| P321 | /5Phos/GGAGCTAGCTATGACAGTATCGGTGGTC GCCGTATCATTACTT CACTCTTTCCCTACACGACGCT (SEQ ID NO: 37) | | Outside adaptor - can use P5 primer |

Example 5: Improved Conversion Efficiency (RNA Sample to Next-Generation Sequence (NGS) Library) after 3'-Phosphate, 2'-Phosphate and 2', 3'-Cyclic Phosphate Removal Some of the proposed or demonstrated techniques of the present disclosure require free 3'-hydroxyl at the 3'-end of an RNA sample. For example, 3'-OH is required for RNA poly(A) tailing with a polymerase (e.g., poly-A polymerase), and/or for DNA poly-tailing with terminal deoxynucleotidyl transferase (TdT), and/or for ligation. Endogenous RNA usually contains a 3'-hydroxyl or a 2',3'-cyclic phosphate or a 3'-phosphate. The 3'-hydroxyl can be a product of transcription, poly(A) tail synthesis, or enzymatic cleavage (enzymes with catalytic mechanism similar to RNase H). The 2',3'-cyclic phosphate can be a product of enzymatic cleavage (enzymes like RNase A) or spontaneous hydrolysis (non-enzymatic intramolecular transphosphorylation). For example, RNA can be cleaved by intramolecular transesterification.

The 2',3'-cyclic phosphate is very common due to natural RNA phosphodiester bond instability and can occur naturally (cell free RNA degradation) or as a result of sample treatment or storage. RNA samples bearing 2',3'-cyclic phosphate or 3'-phosphate cannot be subsequently poly-tailed or ligated because the presence of a free 3'-hydroxyl group is required for both. For this reason, RNA samples with 2',3'-cyclic phosphate or 3'-phosphate can be treated with a phosphatase (e.g., T4 polynucleotide kinase (PNK) enzyme) to generate a 3'-hydroxyl group. Other examples of phosphatases are disclosed in TABLE 1 below (Ushati Das and Stewart Shuman, Mechanism of RNA 2',3'-cyclic phosphate end healing by T4 polynucleotide kinase-phosphatase, Nucleic Acids Research, 2013, vol. 41, No. 1, 355-365).

TABLE 1

Comparison of RNA repair enzymes that heal 2',3'-cyclic phosphate ends

| Enzyme | Family | Metal | End-product | CPDase product | 3'-Pase | 2'-Pase |
|---|---|---|---|---|---|---|
| T4 Pnkp | Acylphosphatase | $Mg^{2+}$ | 3'-OH, 2'-OH | 3'-PO$_4$, 2'-OH | Yes | Yes |
| CthPnkp | Binuclear metallophosphoesterase | $Mn^{2+}$ $Ni^{2+}$ | 3'-OH, 2'-OH | 3'-OH, 2'-PO$_4$ | Yes | Yes |
| Yeast and plant tRNA ligase | 2 H phosphoesterase | None | 3'-OH, 2'-PO$_4$ | 3'-OH, 2'-PO$_4$ | No | No |
| RtcB | RtcB | $Mn^{2+}$ | 3'-PO$_4$, 2'-OH | 3'-PO$_4$, 2'-OH | No | ? |

T4 polynucleotide kinase (PNK) enzyme includes both kinase and phosphatase enzymatic activities. Thus, to optimize the T4 PNK, the kinase enzymatic activity can be removed by substituting at least one of the catalytically essential amino acids. This results in the phosphatase being the only enzymatic activity present. Removing the kinase activity helps with subsequent reactions such as poly-A tailing using ATP for example, because ATP is also a kinase substrate. Examples of cell free RNA NGS library preparation protocols including de-phosphorylation are disclosed herein. Also disclosed herein are comparison reactions (e.g., reactions not treated with T4 PNK).

Additional potential benefits: the unique properties of the 3'end of RNA particles depending on the type of process used to generate the RNA particles, allow one to focus and/or manipulate the sequencing library. For example, if one does not wish to sequence RNA fragments generated due to process degradation (e.g., incomplete RNA fragments bearing 2',3'-cyclic phosphate), one can avoid treating the sample with T4 PNK. In this way, the library will include full mRNAs and miRNAs (3'-hydroxyl).

Example 7: RNA Sample Fragmentation is Part of the NGS Library Preparation Workflow; Enzymatic and Nonenzymatic Methods Major DNA sequencing technologies, such as illumina or ion torrent, are limited in regards to sequencing read-length (meaning that a limited number of bases can be sequenced in each individual read). Both technologies have a read range of up to about 100 bp-500 bp, making it impractical to use a library that significantly exceeds this range. Cell free RNA usually ranges from about 20 to 2000 bases, formalin-fixed paraffin-embedded (FFPE) RNA ranges from about 20 to 500 bases and mRNA is usually around 2000 bases. For practical reasons, samples are usually fragmented, so effective library size is no more than about 400 bp. Sample loading library fragments longer than 1000 bp is very inefficient compared to shorter fragments. Disclosed herein are two general methods of RNA sample fragmentation; enzymatic and non-enzymatic. The enzymatic method can use enzymes with RNase activity (e.g., RNase A, RNase P, RNase H, RNase III, RNase T1, RNase T2, RNase U2, RNase V1, RNase I, RNase L, RNase PhyM, RNase V, dicer, or argonaute). The non-enzymatic method disclosed herein takes advantage of the natural chemical instability of RNAs. RNA can undergo spontaneous non-enzymatic fragmentation as a result of internal transphosphorylation. Breaking of phosphodiester bonds of RNA can be brought about by various conditions (e.g., metals, such as Mg, Mn, Pb, or polyamines, or cofactors, such as PVP or PEG). An increase in the transphosphorylation rate can be achieved, for example, with high pH or with high(er) temperature. Non-enzymatic hydrolysis preferentially happens in single stranded portions of RNA particles, preferentially between bases UA or CA. The advantages of using a non-enzymatic method includes: simplicity and reliability (independent of enzyme activity or shelf life), and the fact that the reaction can be conducted in conditions compatible with the majority of the subsequent steps. TABLE 2 below shows a workflow of both a fragmentation protocol and a no-fragmentation protocol. The libraries were prepared using cell free RNA sample.

TABLE 2

Workflow

| Work flow: | No Fragmentation | | With Fragmentation |
|---|---|---|---|
| STEP_1 | PNK Treatment | STEP_1 | RNA fragmentation by heat treatment |
| STEP_2 | Poly Adenylation using Poly-A Polymerase | STEP_2 | PNK Treatment |
| | | STEP_3 | Poly Adenylation using Poly-A Polymerase |
| STEP_3 | Poly T Primer annealing | STEP_4 | Poly T Primer annealing |
| STEP_4 | 2D-RT & Tagging reaction | STEP_5 | 2D-RT & Tagging reaction |
| STEP_5 | primer-adapter excess and non-specific priming product cleaning with Magnetic beads with immobilized oligoA | STEP_6 | primer-adapter excess and non-specific priming product cleaning with Magnetic beads with immobilized oligoA |
| STEP_6 | SPRI cleanup | STEP_7 | SPRI cleanup |
| STEP_7 | Sample Index PCR | STEP_8 | Sample Index PCR |
| STEP_8 | SPRI cleanup | STEP_9 | SPRI cleanup |

In short, the no-fragmentation protocol can include 6.5 μL of H$_2$O, 2 μL of 10× T4 PNK buffer, 0.5 μL of 10× RNase inhibitor, 1 μL of 10 U/μL T4 PNK enzyme, and 10 μL sample (e.g., cell free RNA sample). The reaction can then be incubated at 37° C. for 20 minutes, 70° C. for 4 minutes, and then placed on ice. 3.25 μL of H$_2$O, 10 μL of 5×2D PNK buffer, 1.25 μL of 10× RNase inhibitor, 7.5 μL of 10 mM ATP, and 1.25 μL of 5 U/μL E. coli PolyA Pol can then be added to the reaction. The reaction can be incubated at 16° C. for 5 minutes and can then be placed on ice. 0.5 μL of 100× dNTPs, 1 μL of 10 μM P334 Primer, 0.25 μL of 100 μM P423 DNA ter acc can then be added to the reaction. The reaction can be incubated at 70° C. for 2 minutes, and can then be placed on ice for 2 minutes. 1.25 μL of 10× RNase inhibitor, 3.75 μL of P2 (e.g., R2 variant at 1 μg/μL can be added to the reaction (for a total of 50 μL reaction). The reaction can be incubated at 34° C. for 1 hour, pulled down, spri 1.6×, then eluted in 50 μL. In some instances, a reverse transcriptase or a modified reverse transcriptase, or an enzyme that has similar function to a reverse transcriptase can be used instead of P2.

In short, the fragmentation protocol can include 1 μL of 10× buffer A and 9 μL of sample (e.g., cell free RNA sample). The reaction can be incubated at 94° C. for 4 minutes and can then be placed on ice. 14.75 μL of H$_2$O, 3 μL of 10× buffer B, 0.75 μL of 10× RNase inhibitor, and 1.5 μL of 10 U/μL T4 PNK enzyme can be added to the reaction. The reaction can be incubated at 37° C. for 30 minutes, at 72° C. for 3 minutes and can then be placed on ice. 5 μL of 10× buffer C, 1.25 μL of 10× RNase inhibitor, 7.5 μL of 10 mM ATP, and 1.25 μL of 5 U/μL E. coli PolyA Pol can then be added to the reaction. The reaction can be incubated at 16° C. for 5 minutes and can then be placed on ice. 0.5 μL of 100× dNTPs, 1 μL of 10 μM P334 Primer, 0.25 μL of 100 μM P423 DNA ter acc can then be added to the reaction. The reaction can be incubated at 70° C. for 2 minutes, and can then be placed on ice for 2 minutes. 1.25 μL of 10× RNase inhibitor and 3.75 μL of P2 (e.g., R2 variant at 1 μg/μL (e.g., an R2 RT N-truncation, such as SEQ ID NO: 50)) (can be added to the reaction (for a total of 50 μL reaction). The reaction can be incubated at 34° C. for 1 hour, pulled down, spri 1.6×, then eluted in 50 μL. In some instances, a reverse transcriptase or a modified reverse transcriptase, or an enzyme that has similar function to a reverse transcriptase can be used instead of P2.

In short, the 5×2D PNK buffer can include 645 μL of H$_2$O, 10 μL of 1000 mM Tris-HCl pH 7.5, 300 μL of 5000 mM NaCl$_2$, 5 μL of 1000 mM MgCl$_2$, 25 μL of 10% tween, and 15 μL of 1000 mM DTT. The buffer A stock can include 60 μL of H$_2$O, 10 μL of 1000 mM Tris-HCl pH 8.3, and 30 μL of 1000 mM MgCl$_2$. The buffer B stock can include 45 μL of H$_2$O, 50 μL of 1000 mM Tris-HCl pH 7.5, and 5 μL of 1000 mM DTT. The buffer C stock can include 36 μL of H$_2$O, 60 μL of 5000 mM NaCl$_2$, 2.5 μL of 10% tween, and 1.5 μL of 1000 mM DTT. The 10×PNK buffer can include 150 μL of H$_2$O, 700 μL of 1000 mM Tris-HCl pH 7.5, 100 μL of MgCl$_2$, and 50 μL of 1000 mM DTT. The 100× balanced dNTPs can include 100 μL of H$_2$O, 75 μL of 100 mM dATP, 75 μL of 100 mM of dTTP, 375 μL of 100 mM dGTP, and 375 μL of 100 mM dCTP. The 5× R2 buffer+ dNTPs can include 430 μL of H$_2$O, 150 μL of 1000 mM Tris-HCl pH 7.5, 300 μL of 5000 mM NaCl$_2$, 25 μL of 1000 mM MgCl$_2$, 25 μL of 10% tween, 25 μL of 1000 mM DTT, 3.75 μL of 100 mM dATP, 3.75 μL of 100 mM of dTTP, 18.75 μL of 100 mM dGTP, and 18.75 μL of 100 mM dCTP. The streptavidin magnetic beads can include 160 μL of streptavidin magnetic beads (NEB) saturated with biotinylated oligo AAAAAAAAAAAAAAAAAAAAAAAAAAAAAAAAA AA/3BioTEG/; beads can be resuspended in 10 mM Tris pH7.5, 300 mM NaCl$_2$. The primer sequences used can be:

P334

(SEQ ID NO: 93)
(A/iSp9/CCGTGACTGGAGTTCAGACGTGTGCTCTTCCGATCTNNNNN

NNNTTTTTTTTTTTTTTTT);

P423

(SEQ ID NO: 94)
(AA/iSp9/ACACTCTTTCCCTACACGACGCTCTTCCGATCT/3ddC/);

P399

(SEQ ID NO: 95)
(AATGATACGGCGACCACCGAGATCTACACGTACTGACACACTCTTTCC

CTACACGACGC);

P400

(SEQ ID NO: 96)
(CAAGCAGAAGACGGCATACGAGATATTACTCGGTGACTGGAGTTCAGA

CGTGT)

Example 9: Robust Mechanism of R2 RT Jumping

R2 RT jumping is a very efficient mechanism. It is much less sensitive to the acceptor-adapter sequences compared to template switching mechanisms (e.g., methods that use MMLV). This low sensitivity allows for optimal utilization of sequencing adapters in the Illumina sequencing for example. In this experiment, a variety of acceptors can be tested. This experiment can be used to show efficiency similarities between RNA and DNA acceptors. The use of DNA acceptors allow for cheaper and more reliable and/or stable technology. This experiment can be used to show that the conversion efficiency is not sensitive to the 3'-end of the acceptor sequences. Thus, this mechanism allows for flexibility regarding acceptor sequences and it is relevant for both RNA and DNA samples. Examples of acceptors used:

```
                                      (SEQ ID NO: 80)
1) AA/iSp9/ACACTCTTTCCCTACACGACGCTCTTCCGA
TCTAGGG/3ddC/;

(SEQ ID NO: 81)
2) AA/iSp9/ACACTCTTTCCCTACACGACGCTCTTCCGA
TCTCAGGG/3ddC/;

(SEQ ID NO: 82)
3) AA/iSp9/ACACTCTTTCCCTACACGACGCTCTTCCGA
TCTTCTGGG/3ddC/;

(SEQ ID NO: 83)
4) AA/iSp9/ACACTCTTTCCCTACACGACGCTCTTCCGA
TCTG/3ddC/;

(SEQ ID NO: 84)
5) AA/iSp9/ACACTCTTTCCCTACACGACGCTCTTCCGA
TCT/3ddC/;

(SEQ ID NO: 85)
6) AA/iSp9/ACACTCTTTCCCTACACGACGCTCTTCCGA
TCTrGrGrG/3ddC/;

(SEQ ID NO: 86)
7) AAAA/iSp9/ACACTCTTTCCCTACACGACGCTCTTCC
GATCTrGrGrG;

(SEQ ID NO: 87)
8) AA/iSp9/ACACTCTTTCCCTACACGACGCTCTTCCGA
TCTN/3ddC/;

(SEQ ID NO: 88)
9) AA/iSp9/ACACTCTTTCCCTACACGACGCTCTTCCGA
TCTNN/3ddC/;
```

-continued

```
                                      (SEQ ID NO: 89)
10) AA/iSp9/ACACTCTTTCCCTACACGACGCTCTTCCG
ATCT*/3ddC/;

(SEQ ID NO: 90)
11) AA/iSp9/ACACTCTTTCCCTACACGACGCTCTTCCG
ATCTN/ideoxyI//3ddC/;

(SEQ ID NO: 91)
12) AA/iSp9/ACACTCTTTCCCTACACGACGCTCTTCCG
ATC/iSuper-dT//3ddC/;
and (SEQ ID NO: 92)
13) A/iSp9/CCGTGACTGGAGTTCAGACGTGTGCTCTTC
CGATCT/3ddC/.
```

Example 10: Poly-A Tail Length Control, Method with Non-Extendable Nucleotide

PolyA polymerase is an RNA polymerase used frequently to generate a poly-A tail on the 3' end of an RNA (e.g., poly-A polymerase form E. coli or yeast). Poly-A polymerase has enzymatic activity that allows for the generation of an RNA chain (i.e., extension of the 3'end of an RNA) without an RNA or DNA template. Although, poly-A polymerase preferably synthesizes a poly-A tail, poly-A polymerase also has activity with other ribonucleotides (e.g., CTP, GTP and UTP). Controlling the poly-A tail length is important for sequencing quality and yield. Typically, ATP concentration and reaction time and/or temperature are used to control the poly-A tail length. Alternative methods can be used, such as using a blocking (un-extendable) nucleotide (e.g., 3'-Deoxyadenosine-5'-Triphosphate (an ATP analog)). Once a blocking nucleotide, 3'-Deoxyadenosine-5'-Triphosphate, is incorporated to an RNA chain analog, it cannot be further extended due to a lack of a 3' hydroxyl group. Various concentrations of ATP and 3'-Deoxyadenosine-5'-Triphosphate can be used. Poly-A tail length can be controlled based on the concentration/ratio of ATP and 3'-Deoxyadenosine-5'-Triphosphate, which is independent of reaction time and/or enzyme concentration. This method provides for significant protocol advantage when applied to high throughput or automated processes.

Example 11: Library Preparation, Depletion of Ribosomal RNA (rRNA) and Transfer RNA (tRNA) to Maximize Sequencing Throughput Approximately 80% of the total RNA in cells is rRNA and 15% is tRNA. Ribosomal RNA rarely serves as a diagnostic target. Therefore, because of that, the practice is to remove/deplete rRNA and tRNA from sequencing libraries. The amount of rRNA and tRNA in sequencing libraries can be controlled at various stages of library preparation. For example, depletion of rRNA and tRNA can occur during the early stages, e.g., after total RNA isolation (RNA level), or after PCR amplification (dsDNA level). Two general methods to remove rRNA and tRNA is described herein: 1) pulling rRNA/tRNA or PCR products using complementary oligonucleotide attached to magnetic beads or solid support; and 2) oligonucleotide-guided degradation of the rRNA/tRNA or PCR products.

Method 1: In this method, amplified dsDNA can be denatured and hybridized to a pool of strategically designed oligonucleotides. Oligonucleotides are complementary to one or both DNA strands with rDNA sequence. For Illumina library, only one strand may be depleted as only one polarity is used in bridge amplification. Each oligonucleotide includes biotin modification. Ribosomal sequences (including DNA fragments) can be depleted/removed using straptvidin-immobilized magnetic beads or solid support. In some cases, depletion can be performed after PCR library amplification in order to mitigate losses of rare and low represented sequences. Depletion can also be performed during the early stages of library preparation (e.g., RNA level).

Example 12: A Method to Express the R2 Retrotransposon

Described herein are two methods of expressing the R2 retrotransposon enzyme: the first, involves the removal of the N-terminal domain, and the second, involves tag-fusion stabilization.

Method 1: N-terminal domain removal. This method can be used to transform the R2 retrotransposon, while increasing its protection, leading to increase expression in E. Coli and improved stability. It is important to note, however, that due to its eukaryotic origin as well as the structure and complexity of its R2 retroelements, a high level of expression, and thus, production is difficult to achieve. These R2 retroelements are multi-domain elements with a molecular mass that is usually over 100 kD. These elements are composed of three major domains (see, FIG. 1C): (1) the N-terminal domain, which usually includes DNA binding motifs zinc-finger and c-myb (see, FIG. 1A and FIG. 1B). This domain contributes to the ability of the R2 retrotransposon to have specific recognition and to bind to target DNA through the target primed reverse transcription mechanism (TPRT); (2) reverse transcriptase, which is responsible for copying the R2 RNA template; and (3) the endonuclease domain, which is responsible for the specific cleavage of target DNA.

This method, based on the underlying principle that the presence of the N-terminal domain interferes with the expression and stability of the R2 retroelement, focuses on the full or partial removal of the N-terminal domain. The removal method can be focused on either the full N-terminal domain, only a part of it, thus, a partial N-terminal domain removal. This method improves the expression and stability of the R2 protein without negatively affecting the enzyme's performance in the downstream process of library preparation (see, FIGS. 1A, B, and C).

Method 2: Tag-fusion stabilization. This method involves the extension of Method 1, whereby the N-terminal domain is removed, in combination with fusion-tags. These tags include: Fh8, MBP, NusA, Trx, SUMO, GST, SET, GB1, ZZ, HaloTag, SNUT, Skp, T7PK, EspA, Mocr, Ecotin, CaBP, ArsC, IF2-domain I, an expressivity tag, an expressivity tag that is part of 1F2-domain I, RpoA, SlyD, Tsf, RpoS, PotD, Crr, msyB, yjgD, rpoD, His6, His-tag, His6-tag, Calmodulin-tag, CBP, CYD (covalent yet dissociable NorpD peptide), Strep II, FLAG-tag, HA-tag, Myc-tag, S-tag, SBP-tag, Softag-1, Softag-3, V5-tag, Xpress-tag, Isopeptag, SpyTag, B, HPC (heavy chain of protein C) peptide tags, GST, MBP, biotin, biotin carboxyl carrier protein, glutathione-S-transferase-tag, green fluorescent protein-tag, maltose binding protein-tag, Nus-tag, Strep-tag, and thioredoxin-tag.

Example 13: Mutagenesis of R2 Retrotransposon Motif −1, Motif 0, and Thumb Domain Mutagenesis of motif −1 and motif 0. The reverse transcriptases (RTs) that are the most studied and best described in the literature are those of retroviral and long terminal repeats (LTR)-retrotransposon origin. This family of reverse transcriptases shares seven highly conservative amino acid sequence motifs. RTs encoded by non-LTR retroelements as well as those encoded by telomerases include additional conservative motifs located at the N-terminal of the RT. These are referred to in the literature as motif −1 and motif-0. It was hypothesized that the non-LTR retroelement motifs −1 and 0 retain functional similarity to telomerase motif CP and T (part of RNA-Binding Domain (TRBD), see FIG. 3). Some reports also demonstrate the involvement of motif −1 and motif 0 in interactions with specific R2 RNA templates as well as other templates, contributing to the R2 jumping mechanism. This method focuses on the mutagenesis of motif −1 and motif 0 (see, FIG. 2). This mutagenesis results in an increase in jumping efficiency, single-stranded priming efficiency and processivity, as well as a significant reduction in bias toward RNA with similar sequences.

Mutagenesis of thumb domain. The thumb domain is mostly responsible for holding and/or interacting with the primer or the primer/template. R2 RTs possess a unique capability to use a single-stranded primer compared to other retroviral enzymes. More specifically, using defined sequences of single-stranded DNA primer, R2 RTs can prime the reverse transcription at the 3'-end of random RNA templates. This reaction does not require base pairing with the RNA template (see, FIG. 10). This property of R2 is perhaps linked to Target Primed Reverse Transcription (TPRT). In this mechanism, the R2 retrotransposon recognizes a specific double stranded DNA (dsDNA) sequence than endonuclease domain of R2 and cleaves one of the strands. The cleaved strand can then be transferred to the RT catalytic center and the 3'-end of the strand can be used as a primer. In this method, the R2 thumb domain can be mutagenized to improve single-stranded priming efficiency and processivity (see, FIG. 4).

Example 14: Method to Prepare RNA Library for Single Cell and Low Input Samples

Methods for single cell library preparation include, but are not limited to, confinement techniques focused on emulsion and nanofabrication. Other methods include cell sorting and serial dilution. Library preparation involving single cells and/or low RNA sample inputs (5-50 μg) have many challenges, and as such, limitations. Due to the small sample size, the possible presence of artifacts, and the presence of excess reaction reagents like oligo adapters and primers (in this case, outnumbering the RNA sample), one of the many challenges is the risk of artifact amplification. To ensure high quality library preparation, two major conditions must be met: the first being high conversion efficiency, thus, input RNA to DNA library, and the second, is a low oligo adapter-adapter product. The enzymatic platform of the present disclosure provides the possibility to use a simple technique that results in the necessary high RNA-sample-library conversion efficiency while ensuring relatively small sample loss. This small sample loss is mainly due to the shorter protocol, hence, less number of total steps in the method. Unlike current methods, which are limited to target Poly-adenylated RNA from the cells, the method described in the present disclosure can also capture non-polyadenylated RNA, like miRNA, and ncRNA lincRNA.

Example 15: Method to Anneal rRNA Fragments Using DNA-Sponge

A large majority of the RNA in cells consists of ribosomal RNA (rRNA), whereby 80% of the cell's RNA is rRNA.

Another 15% consists of transfer RNA (tRNA) and other translational RNA machinery. Various methods have been developed to deplete rRNA and tRNA. These methods are based on two general ideas: the first, pulling rRNA using specific oligonucleotide probes attached to solid support, and the second, a specific probe guided degradation of the rRNA sequences, which is usually enzymatic. This depletion can be executed before library preparation, at the RNA level, or after library preparation, at the dsDNA level. In most current approaches, however, rRNA sequence depletion is an entirely separate and distinct protocol, thus, adding to the process of sample preparation.

In this method, rRNA sequence depletion can be integrated into the process of sample preparation. Briefly, during or right after RNA sample fragmentation ssDNA that is complementary to rRNA, referred to as the DNA-sponge, can be included in the library preparation reaction. The DNA-sponge consists of complete or large DNA fragments covering sequences of rRNA subunits. The length of the DNA-sponge is a multiplex of the length of average RNA sample after the fragmentation and can have a linear form with blocked 3'end, or a circular form, or it can be concatemerized. The main function of the DNA-sponge is to anneal to rRNA fragments. The annealing of the rRNA fragments to large complementary ssDNA make the 3'-end of the rRNA fragment not available to poly A polymerase (in a method with polyA tailing) or to 3'-priming by R2 enzyme (method with random 3'-end priming with ssDNA adapter). As such, rRNA fragments with no available 3'-end are not converted to the sequencing library (see, FIG. 5 and FIG. 6).

Example 16: Direct RNA and ssDNA Sequencing with R2 Enzyme

The non-naturally occurring R2 reverse transcriptase (RT) of the present disclosure can be used directly for RNA or ssDNA sequencing focused on single-molecule sequencing technology whereby confinement methods can be optic, microscopy-based, nanopore-based or field-effect transistors-based.

In this method, the R2 enzyme can be used as a tool for direct RNA sequencing using single-molecule technology, which as described above can be optic, microscopy-based, nanopore-based or field-effect transistors-based. These single-molecule sequencing methods require a processive enzyme since the essential property of these techniques is the enzyme/protein processivity. Direct RNA sequencing can be conducted with either Reverse transcriptase (RT) or RNA-directed-RNA polymerase. RTs of retroviral origin may be low processivity polymerases with polymerase-template complex lifetime of ~30s. The R2-template complex, on the other hand, has a lifetime that is in the range of ~30 min. In this method, this enzyme can be used for direct RNA sequencing. The direct sequencing has a main advantage, which is that there is no need for conversion to DNA and the additional possibilities to detect RNA modifications, such as methylation.

Example 17: R2 Based Method for In Situ RNAseq

RNA-sequencing profiles gene expression over the whole transcriptome, but it lacks spatial context. In situ RNAseq allowed genome-wide profiling of gene expression in situ in fixed cells and tissues (see, FIG. 6). These cells and tissues can be from any animal which may benefit from the methods of the disclosure, including, e.g., humans and non-human mammals, such as primates, rodents, horses, dogs and cats. Subjects include without limitation a eukaryotic organism, a mammal such as a primate, e.g., chimpanzee or human, cow; dog; cat; a rodent, e.g., guinea pig, rat, mouse; rabbit; or a bird; reptile; or fish. Subjects specifically intended for treatment using the methods described herein include humans. A subject may be an individual or a patient.

In this method, RNA from fixed cells and/or tissues can be converted into cDNA and directly sequenced using single-molecule methods or by tagging the with barcode information including spatial-information. This cDNA can then be converted to sequencing library. One of the methods of spatial-specific barcoding can be by using a glass plate with printed in spatial-specific manner oligonucleotide primer (FIG. 6). The cDNA is generated using a slice of tissue.

In the methods of the present disclosure, the non-naturally occurring R2 enzyme and the jumping method can be used for spatial specific library generation. The primer can be specifically barcoded with poly T oligonucleotides (see, FIG. 6) and applied modification of the poly A based library preparation protocol. This method is highly efficient and the high conversion efficiency is critical for this application. Due to the nature of the samples (single cells, small tissue, etc), this method needs to be very sensitive and thus, operate with very low sample input. For this method, either a specific primer or a random primer can be used.

Example 18: RNA-Sequencing Library Preparation: A Poly-A-Based Method for Total-RNA, mRNA, miRNA, and cfRNA The methods described below require a poly A tail at the 3'-end of the RNA sample. A natural poly A can be used for the mRNA protocol. For the protocols for total-RNA, miRNA, and cfRNA, the poly A that is used can be synthesized with poly A polymerase or alternatively, poly U polymerase. Depending on which sequencing technology is used after sample preparation (either a long-read or short-read); RNA sample fragmentation can also be applied.

Figure 7:
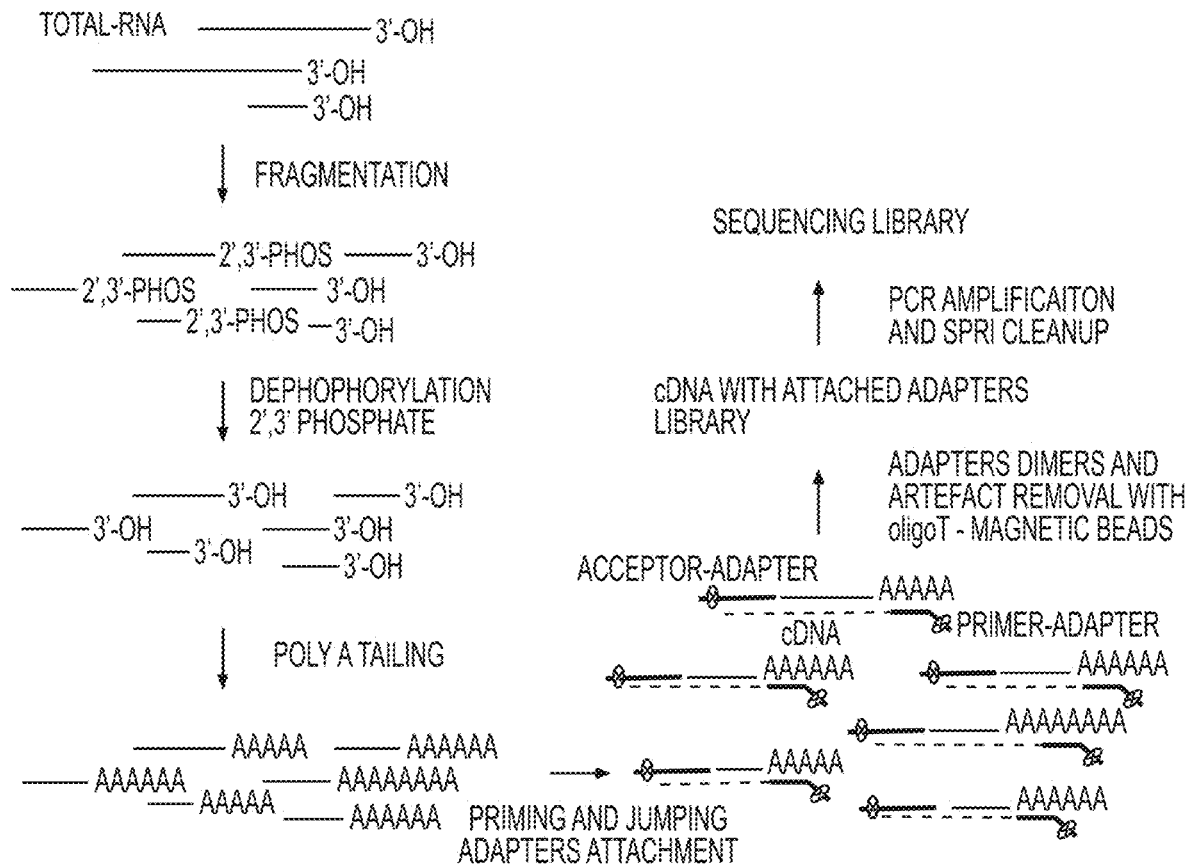
FIG. 7 illustrates the general Poly A based method of RNA-sequencing library prep. This figure illustrates the different steps starting with RNA fragmentation. The methods for fragmentation include spontaneous RNA magnesium induced degradation or enzymatic cleavage. This figure illustrates that depending on which method is used, the cleavage may result in 3'-OH or cyclic 2', 3'-phosphate at the 3'-end of the RNA fragment.
Figure 8:
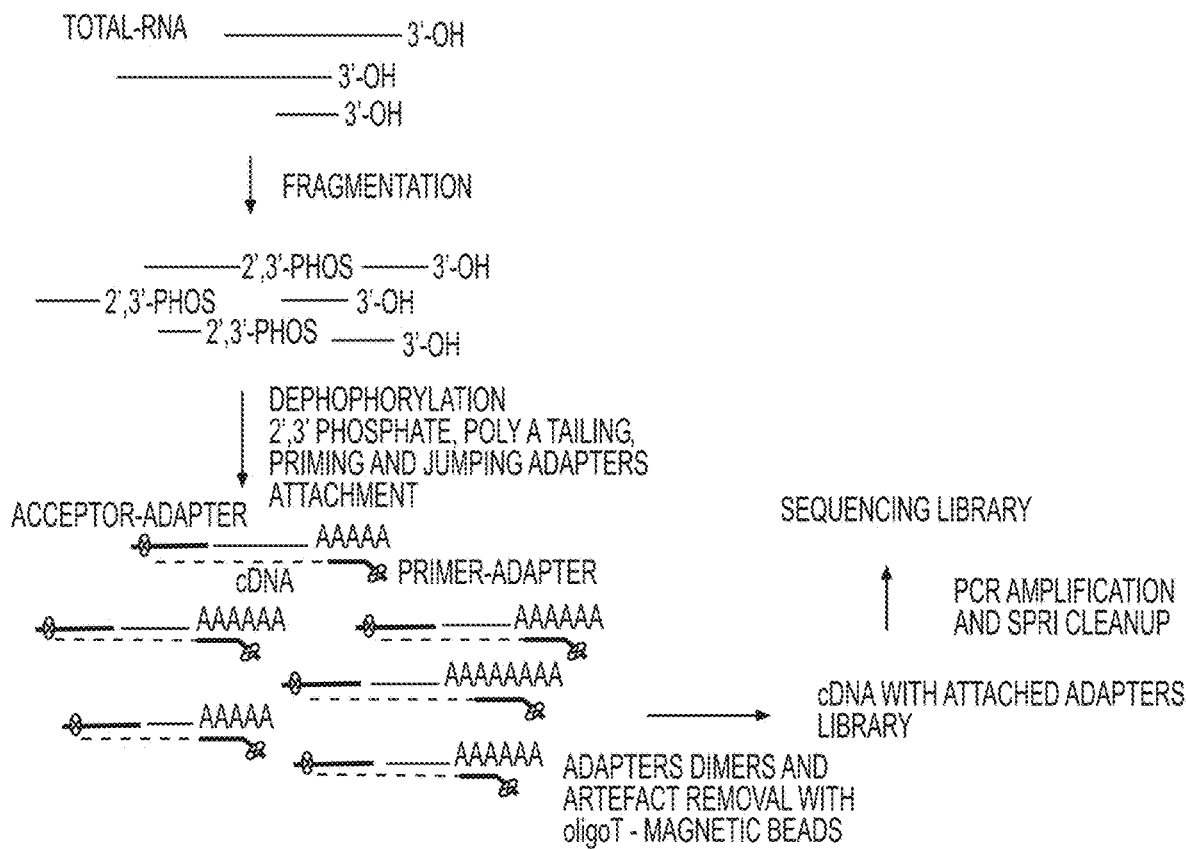
FIG. 8 illustrates a shorter version of the Poly A based method of RNA sequence library prep described in FIG. 7. This figure illustrates a method whereby engineered T4 PNK is used, thus, allowing the simultaneous use of both enzyme T4 PNK and Poly A polymerase without breaking the protocol into two steps as in FIG. 7.

General Poly-A based method. In a first step, the RNA sample can be fragmented. Several methods for fragmentation can be used, including but not limited to spontaneous RNA-magnesium-induced degradation or enzymatic cleavage (see, FIG. 7). Depending on the fragmentation method that is used, the cleavage may generate 3'-OH or cyclic 2',3'-phosphate at the 3'-end of the RNA fragment. For example, the method with spontaneous magnesium-catalyzed hydrolysis can produce 2', 3'-phosphate, which needs to be removed in order to generate 3' poly A tail with poly A polymerase. To remove the phosphate from the 3'-end, an enzymatic reaction where T4 polynucleotide kinase (PNK) is applied. It is important to note that T4 PNK includes two enzymatic activities: 5' kinase and cyclic 2',3'-phosphatase. After de-phosphorylation, the PNK can be temperature inactivated and RNA 3'-end can be poly A tailed with poly-A polymerase or alternatively, poly-U polymerase. Following the poly A polymerase temperature inactivation, poly A tailed RNA can be mixed with primer-adapter, including oligo-T sequences, acceptor-adapter, and R2 enzyme. Annealed to RNA poly-A tail oligo-T adapter can be used as a primer in an extension reaction catalyzed by R2 enzyme (reverse transcription). After reaching the 5'end of the RNA template, the R2 extension complex jumps to the 3'-end of the acceptor-adapter, and continues the extension. Extension can then be paused on the nucleotide analog, also referred to as the blocker, which is strategically incorporated in the adapter toward the 5'-end of the adapter. Blocking the analog prevent the R2 extension complex from second jumping (both primer-adapter and acceptor-adapter includes blocker nucleotide, blocker nucleotide analog here is Spacer 9). During the reaction, artifacts can be generated including primer-adapter-acceptor-adapter dimers or homogenous dimers (see, FIG. 9). The adapter dimers artifacts including acceptor extension are prevented by 3'-dideoxy nucleotide at the acceptor-adapter 3'-end. Alternatively, different extension blockers can be applied, such as 3'phospho-dNTP, 3'amino-dNTP. The artifacts primed by primer-adapter, including poly-T sequence, can be removed from the reaction with oligo-A attached to magnetic beads. The artifacts can be primed without annealing (template primer duplex formation) so the primer sequence remains single-stranded (see, FIG. 9). After pulling with oligo-A immobilized magnetic beads, additional cleanup with solid phase reverse immobilization (SPRI) can be conducted. The last step is polymerase chain reaction (PCR) amplification using primers that are complementary to both the primer- and the acceptor-adapter. The primers may include additional sequences for additional applications, such as barcodes, or adapter sequences that are compatible with/recommended by major sequencing technologies, such as Illumina, Ion Torrent, and PacBio, and Roche 454.

Shorter poly-A based method. In this method, engineered T4 PNK can be used. The modified enzyme retains only one enzymatic activity cyclic 2',3'-phosphatase and kinase activity can be removed. This change can allow the simultaneous use of both enzymes T4 PNK and poly-A polymerase without breaking the protocol into two separate steps. Both enzymes use the same substrate, ATP. As such, PNK mutation can be used to prevent the depletion of ATP and the 5'-end phosphorylation of the sample.

In a first step, the RNA sample can be fragmented (for long read sequencing; miRNA application fragmentation is not required). Depending on the method that is used, cleavage may generate 3'-OH or cyclic 2',3'-phosphate at the 3'-end of the RNA fragment. To remove phosphate from 3'-end, enzymatic de-phosphorylation with T4 polynucleotide kinase can be applied (engineered T4 PNK—only cyclic 2',3'-phasphatase activity). De-phosphorylation can be conducted simultaneously with sample RNA 3'-end poly-A tailing with poly-A polymerase, or alternatively poly-U polymerase. After a short incubation, the reaction can be stopped by temperature inactivation. All subsequent steps are the same as the ones for the general poly-A based method described above.

TABLE 3

Protocol for Total RNA

Library Prep: Total RNA

| | [stock] | Reagent | vol | [final] | |
|---|---|---|---|---|---|
| PNK MM | | H2O | 0 | | |
| | 10 | X T4 PNK buffer | 2 | 1 | |
| | 10 | X Rnase Inhibitor | 0.5 | 0.25 | |
| | 10 | U/ul T4 PNK enz | 1 | 0.5 | |
| | | Sample | 16.5 | 0 | |
| | | Total | 20 | | |
| | | 37 C., 20' --> 70 C., 4' --> on Ice | | | |
| Poly A Pol MM | | H2O | 8.5 | | |
| | 5 | X 2 D PNK buffer | 10 | 1 | |
| | 10 | X Rnase Inhibitor | 1.25 | 0.25 | |
| | 10 | mM ATP | 2 | 0.4 | |
| | 5 | U/uL Ecoli PolyA Pol | 1.25 | 0.125 | |
| | | 16 C. for 5 mins and then move to ice | | | |
| P/A MM | | H2O | 1.15 | | |
| | 100 | X dNTPs | 0.5 | 1 | |
| | 100 | uM P334 Primer | 0.1 | 0.2 | |
| | 100 | uM P423 DNA ter acc | 0.25 | 0.5 | |
| | | Incubate at 70 C., 2 mins --> On ice for 2' | | | |
| Enz MM | 10 | X Rnase Inhibitor | 1.25 | 0.25 | |
| | 40 | P2 enzyme (1 mg/mL) | 3.75 | 3 | |
| | | Total | 50 | | |
| | | 34 C., 1 hr --> Pull down --> spri 1.6x --> Elute in 50 uL | | | |
| Before PCR cleanup | Pull down with pre-prepared beads | | 30 mins | | |
| | | SPRI | 80 ul | | |
| | | Elution | 25 uL | | |

| | [stock] | Reagent | vol | [final] | Thermocycling | |
|---|---|---|---|---|---|---|
| 2 D Library amp PCR | | H2O | 0 | 0 | 95 C.-3 min | |
| | 2 | x Kapa Hifi MM | 25 | 1 | 98 C.-20 sec | 14 |
| | 10 | uM SI primer P5 + P7 | 1.25 | 0.25 | 61 C.-15 sec | cycles |
| | | Template | 23.75 | 0 | 72 C.-20 sec | |
| | | Total | 50 | | 72 C.-1 min | |
| | | | | | 4-forever | |
| Post PCR cleanup | | SPRI | 60 ul | | | |
| | | Elution | 25 uL | | | |

TABLE 4

| | | Protocol for miRNA | | | |
|---|---|---|---|---|---|
| | | Library Prep: miRNA | | | |
| | | | Template | | |
| | [stock] | Reagent | vol | [final] | |
| PolyA rxn | | H2O | 0.00 | | |
| | | H2O | 11.2 | | |
| | 10 | X Poly(A) Pol Rxn Buffer | 2 | 1 | |
| | 10 | X Rnase Inhibitor | 0.5 | 0.25 | |
| | 10 | mM ATP | 0.8 | 0.4 | |
| | 5 | U/uL Ecoli PolyA Pol | 0.5 | 0.125 | |
| | | Sample | 5 | | |
| | | Total | 20 | | |
| | | 32 C. for 20 mins and then move to ice | | | |
| dNTP/P/A | 5 | X 2 D miRNA buffer | 4 | 0.4 | |
| | | dNTP/Accep/Primer Mix | 2 | | |
| | | Incubate at 70 C., 2 mins --> On ice for 2' | | | |
| Enz | 10 | X Rnase Inhibitor | 1.25 | 0.25 | |
| | 40 | P2 enzyme (1 mg/mL) | 3.75 | 3 | |
| | | Total | 50 | | |
| | | 34 C., 1 hr --> Pull down | | | |
| Pull down with pre-prepared beads | | | 30 | mins | |
| Before PCR | | SPRI | 80 | ul | |
| cleanup | | Elution | 25 | uL | |
| | [stock] | Reagent | vol | [final] | 12 cycles |
| 2 D Library | | H2O | 0 | 0 | |
| amp | 2 | x Kapa Hifi MM | 25 | 1 | |
| PCR | 10 | uM SI primer P5 + P7 | 1.25 | 0.25 | |
| | | Template | 23.75 | 0 | |
| | | Total | 50 | | |
| Post PCR | | SPRI | | 60 ul | |
| cleanup | | Elution | | 25 uL | |

| [stock] | [final] | 5 × miRNA Buffer | Vol (uL) |
|---|---|---|---|
| | | H2O | 695 |
| 1000 | 50 | mM Tris-HCl pH 7.5 | 50 |
| 5000 | 1000 | mM NaCl2 | 200 |
| 1000 | 5 | mM MgCl2 | 5 |
| 10 | 0.25 | % Tween | 25 |
| 1000 | 25 | mM DTT | 25 |
| | | Total | 1000 |
| | | dNTP/Accep/Primer Mix | |

| [stock] | | vol (uL) | [final] |
|---|---|---|---|
| | H2O | 1.15 | |
| 100 | X dNTPs | 0.5 | 1 |
| 100 | uM P334 Primer | 0.1 | 0.2 |
| 100 | uM P423 DNA ter acc | 0.25 | 0.5 |
| | Total | 2 uL/rxn | |

TABLE 5

Protocol for mRNA temp ng 10

1

| [stock] | Reagent | Vol | [final] |
|---|---|---|---|
| 5 | H2O | 15.25 | |
| 5 | X 2D buffer + dNTPs | 10 | 1 |
| 10 | X Rnase Inhibitor | 1.25 | 0.25 |
| 10 | uM P334 Primer | 1 | 0.2 |
| 10 | uM P423 terminated acceptor | 2.5 | 0.5 |
| 5 | ng/uL | 15 | |
| | Total Human Brain RNA + ERCC | | |
| | Incubate at Temperature, varying mins --> On ice for 2' | | |
| 10 | X Rnase Inhibitor | 1.25 | 0.25 |
| 40 | P2 enzyme (1 mg/mL) | 3.75 | 3 |
| | Total | 50 | |
| | 34 C., 30 min --> spri 0.8x | | |

TABLE 6

Protocol for 2D library amplification PCR

Library amp PCR

| [stock] | Reagent | Vol | [final] | Thermocycling 95 c.-3 min | |
|---|---|---|---|---|---|
| | H2O | 0 | 0 | 98 c.-20 sec | 15 |
| 2 | x Kapa Hifi MM | 50 | 1 | 61 c.-15 sec | cycles |
| 10 | uM SI primer P5 + P7 | 2.5 | 0.25 | 72 c.-20 sec | |
| | Template | 47.5 | 0 | 72 c.-1 min | |
| | Total | 100 | | 4-forever | |

| Cleanup SPRI 1.2X [stock] | [final] | 5X R2 Buffer + dNTPs | vol (uL) |
|---|---|---|---|
| | | H2O | 430 |
| 1000 | 150 | mM Tris-HCl pH 7.5 mM | 150 |
| 5000 | 1500 | NaCl2 mM | 300 |
| 1000 | 25 | MgCl2 | 25 |
| 10 | 0.25 | % Tween | 25 |
| 100 | 0.375 | mM dATP | 3.75 |
| 100 | 0.375 | mM dTTP | 3.75 |
| 100 | 1.875 | mM dGTP | 18.75 |
| 100 | 1.875 | mM dCTP | 18.75 |
| 1000 | 25 | mM DTT | 25 |
| | | Total | 1000 |

Example 19: RNA-Sequencing Library Preparation: A Method Using Random Fragmentation for Total-RNA, mRNA, miRNA, and cfRNA This method focuses on random priming using the random fragmentation of the RNA samples in combination with the unique properties of the R2 enzyme. Here, the R2 enzyme is capable of priming the extension reaction without template-primer annealing. In this mechanism, extension can be primed on the 3'-end of the template by a ssDNA primer without a complementary sequence annealing to the template strand (R2 3'-end priming, see, FIG. 10). In contrast to random priming with a random oligonucleotide primer, the R2 3'-end priming efficiency is less template-length dependent and as such, library products are a full length copy of the template strand.

In a first step, the RNA sample can be fragmented. Here, several fragmentation methods can be used for this first step, including but not limited to spontaneous RNA hydrolysis with magnesium, or enzymatic cleavage (see, FIG. 11). After this first fragmentation step, the RNA sample can be mixed with primer-adapter (ssDNA), R2 enzyme, and acceptor-adapter (ssDNA or RNA). With dNTP present, the R2 enzyme can prime the extension at the template RNA 3'-end using ssDNA primer-adapter. Once the extension reaches the 5'end of the RNA template, the R2 enzyme can jump to the acceptor-adapter and can continue the reaction, pausing on the nucleotide analog, or blocker, which is strategically incorporated to the adapter toward the 5'-end of the adapter. The blocker nucleotide analog here is Spacer 9. The blocking of the analog prevents the R2 extension complex from a second jumping mechanism (both primer-adapter and acceptor-adapter include blocker nucleotide). In the next step, the reaction can be cleaned with solid phase reverse immobilization (SPRI). Similarly, size selection can be used to remove some adapter-adapter dimer artifacts. The last step is polymerase chain reaction (PCR) amplification whereby primers complementary to both the primer- and the acceptor-adapter can be used. These primers may include additional sequences for applications such as barcoding and/or adapter sequences that are compatible with/recommended by major sequencing technologies, such as Illumina, Ion Torrent, PacBio, and Roche 454.

TABLE 7

Protocol for miRNA

Random libraries

| [stock] | Reagent | vol | [final] |
|---|---|---|---|
| | H2O | 14.7 | |
| 5 | X 2 D nmer frag buffer | 4 | 1 |
| 100 | uM nMer Primer P591 | 0.1 | 0.5 |
| 100 | ng/ul Total Human Brain RNA | 1.25 | |
| | Total | 20 | |
| | Incubate at 94 C., 3 mins --> On ice for 2' | | |
| | H2O | 12 | |
| 5 | X 2 d nmer buff2 | 10 | 1 |
| 10 | X Rnase Inhibitor | 1.25 | 0.25 |
| 40 | P2 enzyme (1 mg/mL) | 3.75 | 3 |
| | Incubate at RT, 5 mins | | |
| 100 | X dNTPs | 0.5 | 1 |
| 10 | uM P423 DNA ter acc | 2.5 | 0.5 |
| | Total | 50 | |
| | 30 C., 60 mins -> spri 0.7x (x2) --> Elute in 50 uL | | |

| [stock] | Reagent | Vol | [final] | Thermocycling | |
|---|---|---|---|---|---|
| | H2O | 0 | 1 | 95 C.-3 min | |
| 2 | x Kapa Hifi MM | 25 | 1 | 98 C.-20 sec | 15 |
| 10 | uM SI primer P5 + P7 | 2.5 | 0.5 | 61 C.-15 sec | cycles |
| | Template | 22.5 | 0 | 72 C.-20 sec | |
| | Total | 50 | | 72 C.-1 min 4-forever | |

| [stock] | [final] | 5 × 2 D nmer frag buffer | vol (uL) |
|---|---|---|---|
| | | H2O | 875 |
| 1000 | 100 | mM Tris-HCl pH 8.5 | 100 |

TABLE 7-continued

Protocol for miRNA

Random libraries

| | | | |
|---|---|---|---|
| 5000 | 0 | mM NaCl2 | 0 |
| 1000 | 25 | mM MgCl2 | 25 |
| 10 | 0 | % Tween | 0 |
| 1000 | 0 | mM DTT | 0 |
| | | Total | 1000 vol |

| [stock] | [final] | 5 × 2 d nmer buff2 | (uL) |
|---|---|---|---|
| | | H2O | 765 |
| 1000 | 110 | mM Tris-HCl pH 7.5 | 110 |
| 5000 | 300 | mM NaCl2 | 60 |
| 1000 | 15 | mM MgCl2 | 15 |
| 10 | 0.25 | % Tween | 25 |
| 1000 | 25 | mM DTT | 25 |
| | | Total | 1000 |

Example 20: Method for Abundant RNA Depletion from Full Length and Fragmented Sample Using Streptavidin-Magnetic-Beads to Remove RNA Comprising Biotin-Labeled Primers About 80% of the total RNA in cell is composed of ribosomal RNA (rRNA), another 15% is a transfer RNA (tRNA) and other translation RNA machinery. This example describes a method for depletion of abundant ribosomal sequent subsequent to cDNA synthesis and incorporation of both 3'- and 5' sequencing adapters.

In this method, cDNA comprising sequencing adapters is first pre-amplified with few PCR cycles, such as 1 single PCR cycle, but in some instances less than 10 or less than 5 PCR cycles using primers complementary to the adapter sequence. After the aforementioned pre-amplification step, the sample is mixed with strategically designed probes complementary to ribosomal sequence (both PCR product polarity) and subjected to single cycle PCR.

Figure 21:
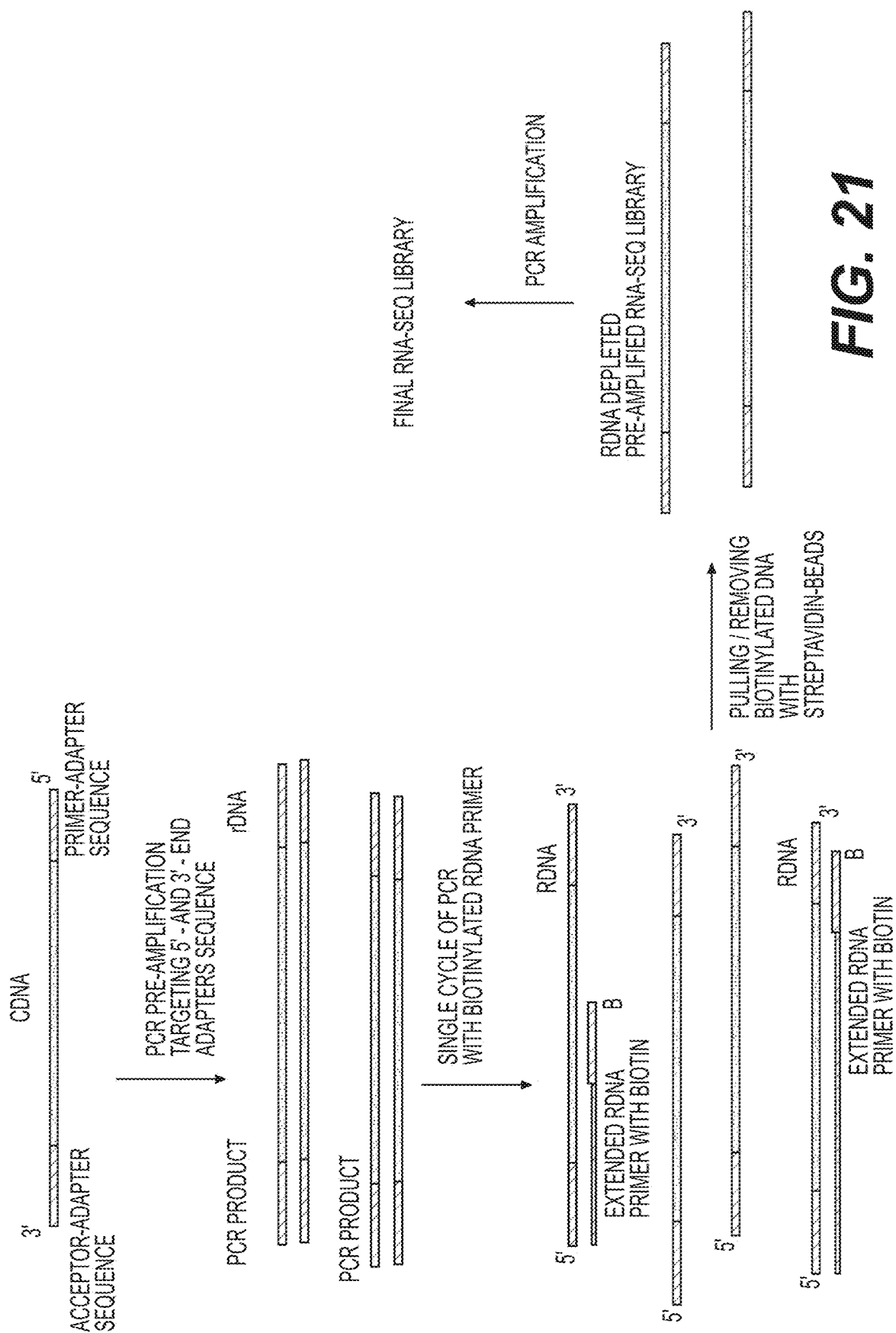
FIG. 21 illustrates the steps of a method for abundant (rRNA) sequence depletion with PCR extension and biotinylated oligo-primers.

The primers include nucleotide modification that allow for the binding/immobilization to a solid support, such as a primer comprising a biotin modification that allows for the binding to a streptavidin solid support. After the aforementioned PCR cycles the cDNA product that incorporated the primer is allowed to bind to the solid support and is thus removed from the liquid phase of the reaction. This product is subsequently removed from the reaction using magnetic beads coated with streptavidin. See FIG. 21.

Example 21: Method for Abundant RNA Depletion from Full Length and Fragmented Sample Using 5'-End Protected Oligo (PCR Primer)

Figure 22:
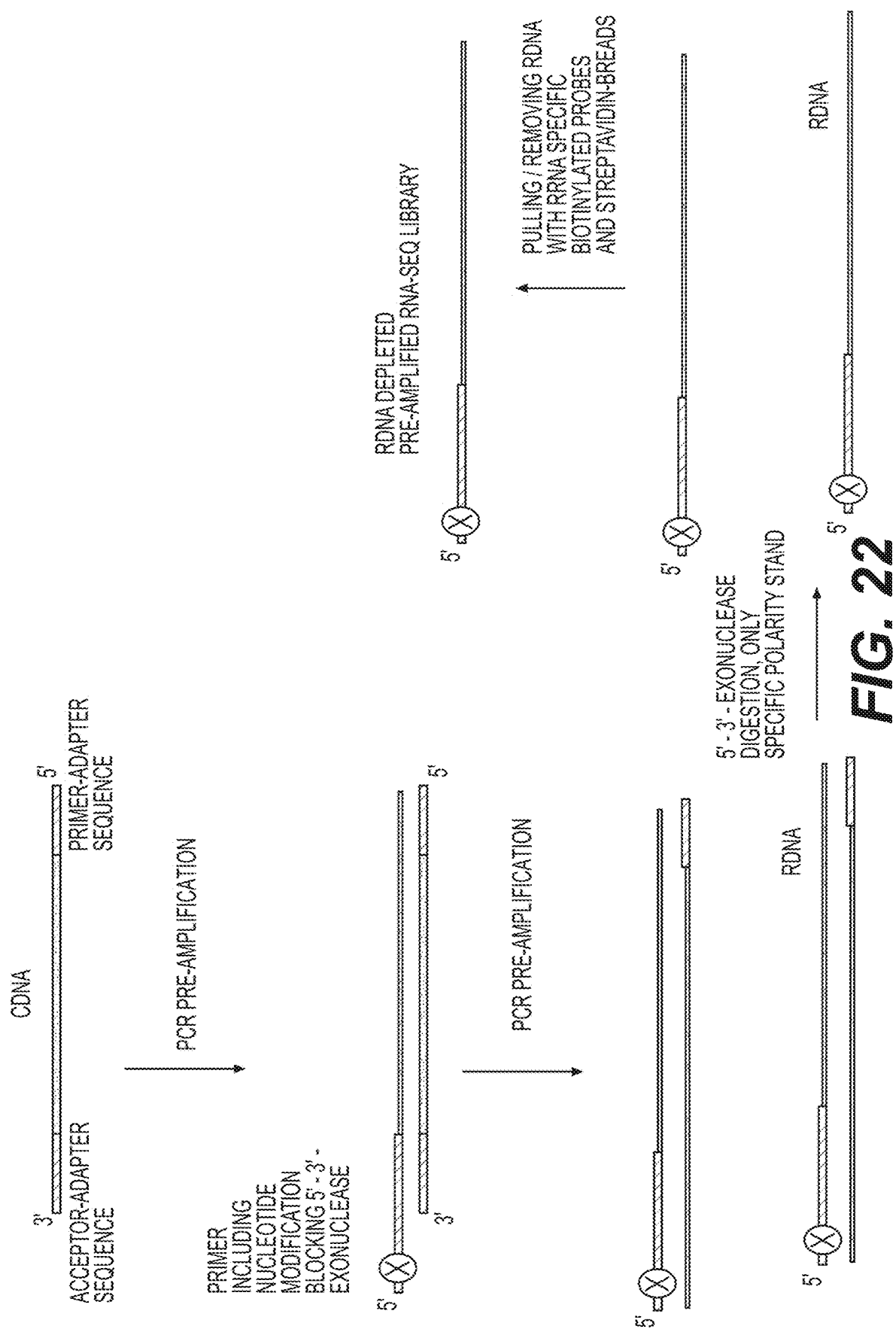
FIG. 22 illustrates the steps of a method for abundant (rRNA) sequence depletion with 5'-end protected oligos (PCR primer).

About 80% of the total RNA in cell is composed of ribosomal RNA (rRNA), another 15% is a transfer RNA (tRNA) and other translation RNA machinery. This example describes a method for the depletion of abundant ribosomal sequent after cDNA synthesis and incorporation of both 3'- and 5' modified sequencing adapters (See FIG. 22). These modified adapters have a modification at their 5'-end that prevents enzymatic degradation by an 5'- to 3'-exonuclease.

In this method a cDNA product including 3'- and 5' partial sequence adapters is subjected to PCR amplification using oligo primers where one of the primers include nucleotide modification(s) at the 5'-end preventing enzymatic degradation by 5'- to 3'-exonuclease, such as lambda exonuclease. These modified primers may be selected to have the same polarity as the RNA strands that they are designed to hybridize. Alternatively, the primers may be designed to have the opposite polarity.

After amplification the PCR product is digested with 5'-to-3'-exonuclease. During enzymatic digestion, the unprotected strand(s) is/are removed from the PCR product, and only ssDNA PCR product with one particular polarity is retained. Subsequently, rRNA depletion can be used by using, for instance, a commercial kit such as LexoGen RiboCop.

Figure 23:
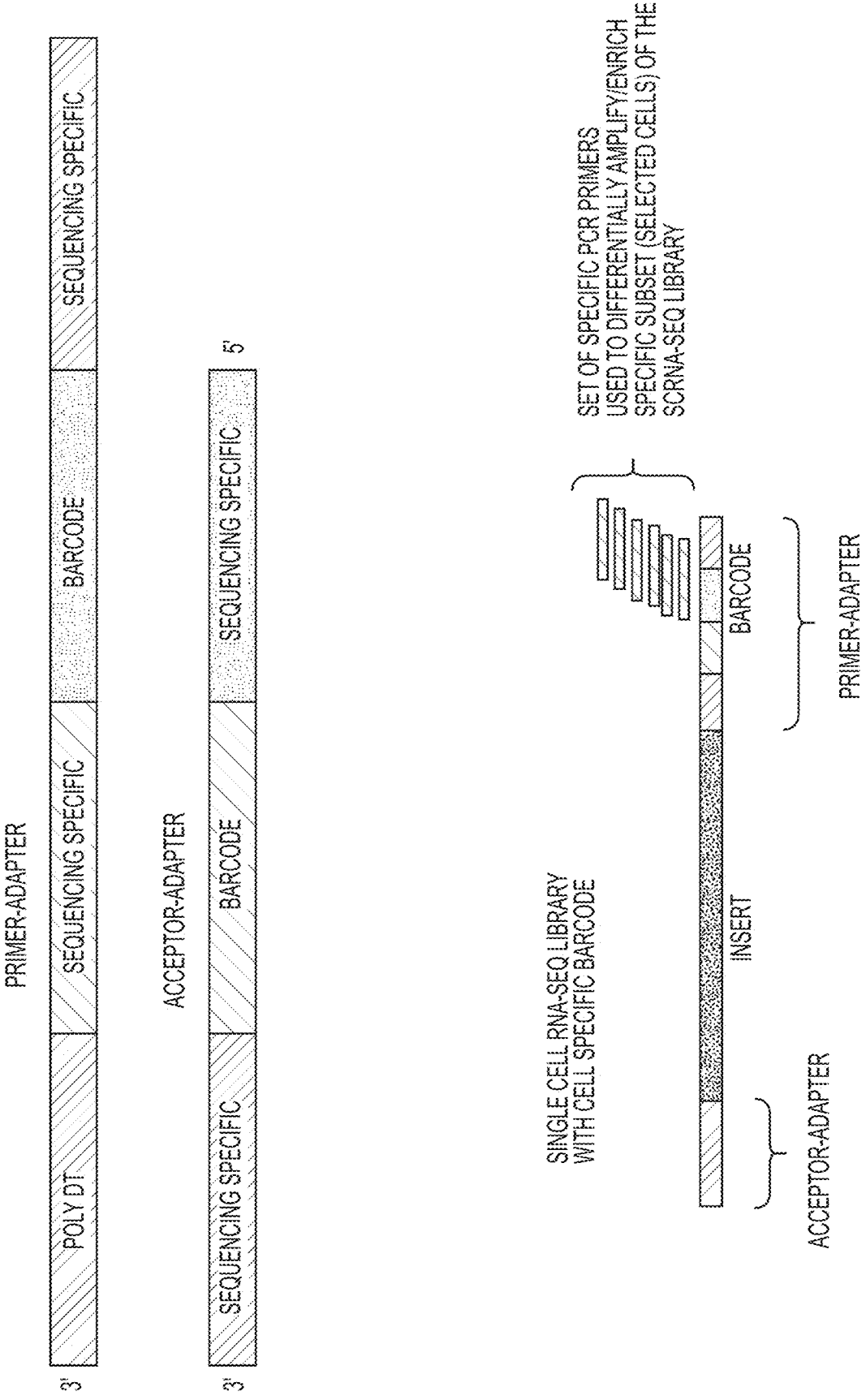
FIG. 23 illustrates the steps of a method for sequencing a pool of single cells where each single cell is labeled with a unique barcode as a selective target for PCR amplification.

Example 22: Method for Enrichment and Deep Sequencing of the Selected Single Cell Libraries Using a Barcode as a Selective Target for PCR Amplification This example describes the preparation of RNA-seq library(ies) from a multiplicity of single cells (single cell library) where each unique single cell is individually barcoded. Each unique barcode is configured to serve as a template for a specific PCR primer. The barcode design is to optimize for PCR specificity with individual specific primers. (See FIG. 23).

This library can be subsequently sequenced with moderate or low sequencing deepness (number of reads per cell). Based on complete or partial results from the sequencing, a single cell of interest may be selected from the single cell library. The barcode associated with such single cells can be identified. These barcodes may then be used to enrich and amplify a pool of nucleic acids derived from a selected single cell.

Example 23: Method for Direct RNA-Seq Library Preparation from Tissue/Cells Biomass without RNA Purification Step This example describes the preparation of nucleic acid libraries from tissue/cell biomass without RNA purification. Briefly, natural tissue is homogenized in a master mix that is insensitive to cell components inhibition. The mix includes collagenasis, estalases and other enzymes/protein promoting cell/tissue lysis, also a component library prep and reagents for converting RNA to RNA-seq library, including one or more enzymes described herein. Because the R2 derived enzymes described herein are resistant to the homogenizing reagents, the RNA-seq library preparation can proceed without RNA purification step. The cell dissociation and lysis reagents may include enzymes from a group of Collagenase, Hyaluronidase, DNase, Elastase, Papain, protease Type XIV, Trypsin, Lipase, alpha-hemolysin, and detergents.

Figure 24:
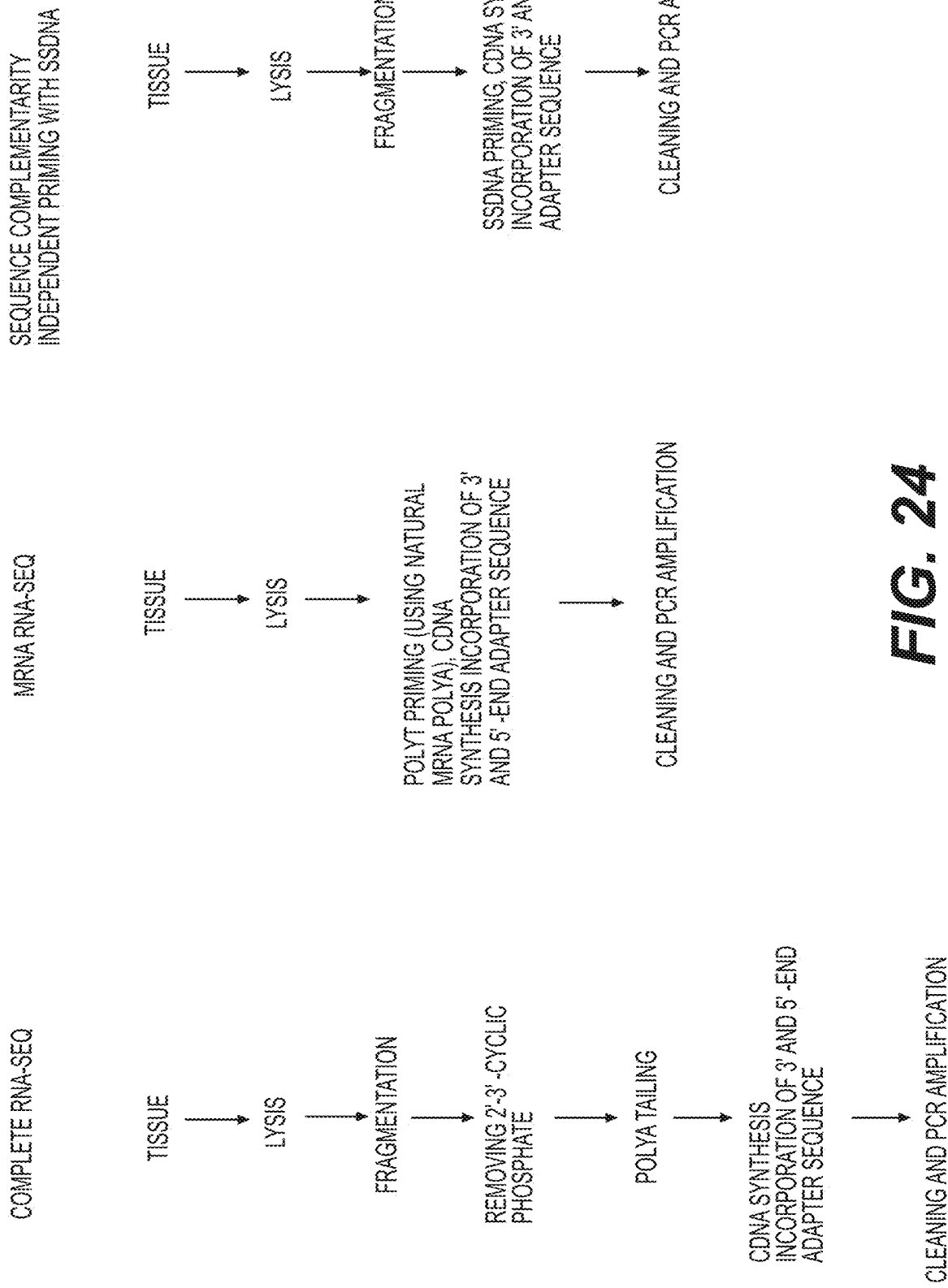
FIG. 24 illustrates the steps of a method for direct RNA-seq library preparation from tissue/cell biomass without RNA purification.

After lysis anyone of the protocols described above can be used for cDNA synthesis. (See FIG. 24).

Example 24: Method for Direct RNA-Seq Library Preparation from Tissue/Cells Biomass without RNA Purification Step This example describes the preparation of nucleic acid libraries from tissue/cell biomass without RNA purification by selecting a small of the tissue with a selected morphology or a different sub-substructure of the tissue. The selected tissue may be then collected separately or it may be collected together with a larger biopsy fragment. In this example, the selected tissue is labeled with a unique barcode on the adapter that may be used to retain the spatial information of the nucleic acids being analyzed, alternatively post library lysis/library prep mix can be collected by allowing the tissue slice to interact with surface (solid support) with immobilized oligonucleotide primer/adapter, where this primer-adapter is labeled to preserve the spatial information.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

Example 25: Total RNA

Library preparation was performed by bringing sample volume up to 18 uL, adding 2 µl of nA (see Table 8) and mixing. The sample was fragmented, incubated at 94° C. for 6 minutes and placed on ice for 2 minutes. 25 µL of nB (see Table 8) was added and mixed followed by 5 µL of nC (see Table 8) with mixing. The sample was incubated at 30° C. for 1 hour and stored at 4° C.

A 0.7×SPRI cleanup standard protocol was performed. A double SPRI cleanup can be performed in cases of low sample input. The sample was eluted in 24 µL EB and transferred to new PCR tubes (22.5 µL).

A sample index PCR was performed (see Table 10) by adding 25 µL of 'Amp' mix to the cleaned sample. 2.5 µL of SI primer mix was added and mixed well. A PCR thermocycler program was run with the following protocol: 95° C. for 3 minutes; followed by n-cycles (dependent on input amount) of 98° C. for 20 seconds, 61° C. for 15 seconds, and 72° C. for 20 seconds; followed by 72° C. for 1 minute.

Another 0.7×SPRI cleanup was performed using standard protocols. The sample was then eluted in 20 µL EB and 18.5 µL transferred into new PCR tubes.

Library QC and sequencing were performed.

TABLE 8

Materials and Reaction Compositions 1

| [stock] | Reagent | vol | |
|---|---|---|---|
| | Template | 18 | |
| 10 | X Fragmentation Buffer | 2 | Tube nA |
| | Total | 20 | |
| | Incubate at 94 C., 4 mins --> On ice, 2' | | |
| | H2O | 14.15 | Tube nB |

TABLE 8-continued

Materials and Reaction Compositions 1

| [stock] | Reagent | vol | |
|---|---|---|---|
| 5 | X 2d nmer buff2 | 10 | |
| 100 | uM nMer Primer P591 | 0.1 | |
| 100 | X dNTPs | 0.5 | |
| 100 | uM P423 DNA ter acc X | 0.25 | |
| 10 | X Rnase Inhibitor | 1.25 | Tube nC |
| 40 | R2 Enzyme (R2 Reverse transcriptase) | 3.75 | |
| | Total | 50 | |

Incubate at 30 C. for 60 mins --> spri 0.7x --> Elute in 24 uL

TABLE 9

Materials and Reaction Compositions 2

| [stock] | 5X 2d nmer buff2 | vol (uL) |
|---|---|---|
| | H2O | 885 |
| 1000 | mM Tris-HCl pH 7.5 | 10 |
| 5000 | mM NaCl2 | 60 |
| 1000 | mM MgCl2 | 5 |
| 10 | % Tween | 25 |
| 1000 | mM DTT | 15 |
| | Total | 1000 |

The 10× Fragmentation Buffer was made up of 700 mM Tris-HCl, 100 mM MgCl$_2$, and 50 mM DTT at a pH of 7.6.

TABLE 10

Sample Index PCR

| [stock] | Reagent | vol | 95 c.-3 min | |
|---|---|---|---|---|
| | H2O | 0 | 98 c.-20 sec | cycle |
| 2 | x Kapa Hifi MM | 25 | Tube Amp 61 c.-15 sec | |
| 10 | uM SI primer P5 + P7 | 2.5 | 72 c.-20 sec | |
| | Template | 22.5 | 72 c.-1 min | |
| | Total | 50 | 4-forever | |

The oligo primers used in the PCR were:

P423

(SEQ ID NO: 76)
AA/iSp9/ACACTCTTTCCCTACACGACGCTCTTCCGATCT/3ddC/

P591

(SEQ ID NO: 77)
/5Sp9/GTGACTGGAGTTCAGACGTGTGCTCTTCCGATCT

Sample Index P5 Primers:

P551

SEQ ID NO: 78)
AATGATACGGCGACCACCGAGATCTACACTAATCTTAAC

ACTCTTTCCCTACACGA

Sample Index P7 Primers:

P559
(SEQ ID NO: 79)
CAAGCAGAAGACGGCATACGAGATATTACTCGG
TGACTGGAGTTCAGACG

Figure 26:
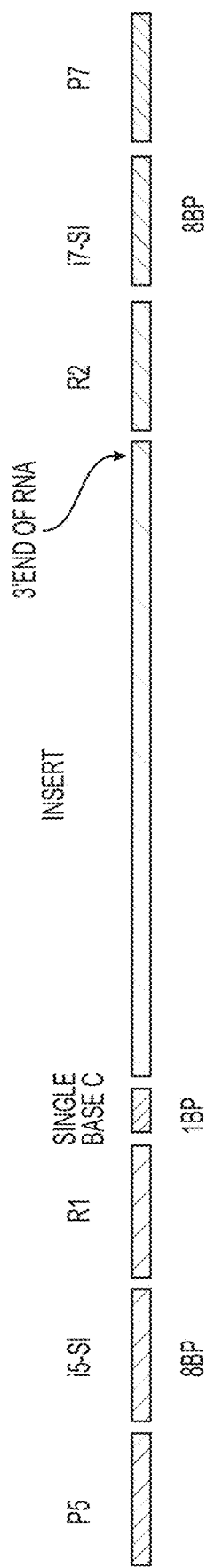
FIG. 26 illustrates library molecule structure in Example 25.

Bioanalyzer traces of the fragmentation are shown in FIG. 25 and the library molecule structure is illustrated in FIG. 26.

The sequencing results, using Illumina hiseq, are shown in Table 11. In the experiment with rRNA depletion before sample preparation, the sample was rRNA depleted using NEB Next rRNA Depletion (accordingly to NEB protocol). The sequencing results showed good RNA-seq library quality including percentage of the aligned reads, number of genes and coverage CV as shown in Table 11.

tubes were transferred to the magnetic rack and the solution was allowed to clear. Once the solution was clear, 23 μL of it was transferred to a fresh PCR tube and the amplification reaction was set up.

Sample index PCR was performed using the following protocol: The reaction was placed on a thermocycler and the following thermocycling protocol was run:
Step 1: 98° C. —1 min
Step 2: 98° C. —20 sec
Step 3: 61° C. —15 sec
Step 4: 72° C. —20 sec
Step 5: Repeat Step 2-Step 4 for 6 cycles
Step 6: 72° C. —2 min
Step 7: 4° C. —HOLD PCR cleanup was then performed (0.8×SPRI cleanup using Ampure beads). The library was eluted in 20 μL EB and 18 μL of the library was transferred for storage, QC, and

TABLE 11

Sequencing Data

| RNA Template | Ribo Depletion | # of reads | RL | RNA input | % aligned | % abundant | % unaligned | % IG |
|---|---|---|---|---|---|---|---|---|
| Human Brain mRNA | None | 22056690 | 2 × 100 | 100 ng | 93 | 9 | 7 | 4 |
| Universal Human Reference | NEB Next rRNA Depletion | 27949188 | 2 × 100 | 200 ng | 92 | 9 | 8 | 4 |

| RNA Template | Ribo Depletion | # of genes (0.1 FPKM) | Coverage CV | % stranded | % Exons | % Intron |
|---|---|---|---|---|---|---|
| Human Brain mRNA | None | 22681 | 0.58 | 99 | 51 | 49 |
| Universal Human Reference | NEB Next rRNA Depletion | 23237 | 0.58 | 99.3 | 51 | 45 |

Example 26: Ribo Depletion

Exemplary Protocol:

A template was prepared by starting with 5 ng of library material, diluting the 5 ng of library material in a total of 10 μL of volume using 10 mM Tris pH 8.0. The diluted library material was transferred to a PCR tube for PCR.

A 1 cycle PCR was performed for pull down. To the 10 μL of library (5 ng), 1.5 μL of Ribo depletion Primer Mix (stock concentration of 25 uM) was added. To that, 13.5 uL of 2× Kapa Hifi Mastermix was added. The reaction was kept on ice during setup. The reaction was then placed on a thermocycler and the following thermocycling protocol was run: 98° C. —1 min→62° C. —2 mins→72° C. —2 mins→1 cycle→hold at 20° C.

Pull Down Bead Preparation:

During the above PCR protocol, the pull down beads were prepared in following way. Ribo depletion pull down beads were vortexed to uniformly suspend. 50 μl for each reaction was transferred into separate PCR tubes. The PCR tubes were spun down briefly and placed on a magnetic rack until the 1 cycle PCR was done. Once the PCR was done, the buffer was removed from the beads and discarded. 25 μL of the PCR reaction product was added to the beads and vortexed to mix and incubated at room temperate for 15 minutes with mixing every 5 minutes. After 15 minutes the sequencing. The exemplary RiboDepletion Protocol is also shown in Table 12 and the bead washing protocol used is shown in Table 13. The wash buffer and resuspension buffer compositions are shown in Tables 14 and 15 respectively.

TABLE 12

RiboDepletion Protocol
Set up Biotin (18S) PCR

| [stock] | reagent | vol (uL) | [final] |
|---|---|---|---|
|  | H2O | 0 |  |
| 2 | x KapaHifi MM | 13.5 | 1.08 |
| 25 | uM Primers Biotin Mix | 1.5 | 1.5 |
|  | Template | 10 |  |
|  | Total | 25 |  |

Do 1 PCR cycle
Pull down with step beads - 50 uL ready beads
Final PCR

|  | h2o | 32 |  |
| 2 | x Kapa Hifi MM | 40 | 0.8 |
| 10 | uM P5-P7 | 5 | 0.5 |
|  | Template | 23 |  |
|  | Total | 100 |  |

Do 6 PCR cycle
0.8x SPRI cleanup --> 20 ul Elute

TABLE 13

Bead Washing Protocol

| Step | Bead washing protocol |
|---|---|
| 1 | NEB streptavedin beads |
| 2 | 1 ml, put them against the magnet |
| 3 | wait till solution is clear, discard the buffer |
| 4 | respend the beads with 1 mL of wash buffer |
| 5 | wait till solution is clear, discard the buffer |
| 6 | Repeat step 4 & 5 for 3 times |
| 7 | Resuspend beads in 0.5 ml of Final resuspension buffer Store it at 4 C. |

TABLE 14

Wash Buffer Composition
Wash buffer

| [stock] | [final] | reagent | volume |
|---|---|---|---|
|  |  | H2O | 93850 |
| 1000 | 10 | mM Tris pH 8.3 | 1000 |
| 1000 | 50 | mM KCl | 5000 |
| 1000 | 1.5 | mM MgCl2 | 150 |
| 50 | 0 | % Glyceraol | 0 |
|  |  | Total | 100000 |

TABLE 15

Final Resuspension Buffer Composition
Final resuspension buffer

| [stock] | [final] | reagent | volume |
|---|---|---|---|
|  |  | H2O | 6770 |
| 1000 | 10 | mM Tris pH 8.3 | 200 |
| 1000 | 50 | mM KCl | 1000 |
| 1000 | 1.5 | mM MgCl2 | 30 |
| 50 | 30 | % Glyceraol | 12000 |
|  |  | Total | 20000 |

The sequencing results (using a illumina sequencer) showed a 3.6-times reduction in a number of sequencing reads mapping to 18S rRNA sequence and are summarized in Table 16.

TABLE 16

Sequencing Results

|  | 18S rRNA no depletion | 18S rRNA depleted |
|---|---|---|
| Number of input reads | 263367 | 263198 |
| Number of quality reads | 262927 | 262586 |
| Reads mapped to 18S | 96692 | 27142 |
| All rRNA (%) | 36.8% | 10.3% |

The probe sequences used were as follows:

| Name | SEQ ID NO: | Sequence |
|---|---|---|
| P600 | 38 | /5Biosg/TACCTGGTTGATCCTGCCAGTAGCATATG |
| 18S_1 | 39 | /5Biosg/CCGTGCGTACTCAGACATGCATG |
| 18S_2 | 40 | /5Biosg/CAGTTATGGTTCCTTTGGTCGCTCGC |
| 18S_3 | 41 | /5Biosg/GCCCGTCGGCATGTATTAGCTCTAGAATTAC |
| 18S_4 | 42 | /5Biosg/CGTGCATTTATCAGATCAAAACCAACCCG |
| 18S_5 | 43 | /5Biosg/GCCCGAGGTTATCTAGAGTCACCAAAGC |
| 18S_6 | 44 | /5Biosg/CGACCCATTCGAACGTCTGCC |
| 18S_7 | 45 | /5Biosg/CGTGGTCACCATGGTAGGCAC |
| 18S_8 | 46 | /5Biosg/CGGAGAGGGAGCCTGAGAAAC |
| 18S_9 | 47 | /5Biosg/GGTCGGGAGTGGGTAATTTGCG |
| 18S_10 | 48 | /5Biosg/CTCTTTCGAGGCCCTGTAATTGGAATGAG |
| 18S_11 | 49 | /5Biosg/GCACCAGACTTGCCCTCCAATG |
| 18S_12 | 50 | /5Biosg/GTTGCTGCAGTTAAAAAGCTCGTAGTTGGATC |
| 18S_13 | 51 | /5Biosg/GGGACACTCAGCTAAGAGCATCGAG |
| 18S_14 | 52 | /5Biosg/GAGTGTTCAAAGCAGGCCCGAG |
| 18S_15 | 53 | /5Biosg/CCCTCTTAATCATGGCCTCAGTTCCG |
| 18S_16 | 54 | /5Biosg/GAGGTGAAATTCTTGGACCGGCG |
| 18S_17 | 55 | /5Biosg/CGTCTTCGAACCTCCGACTTTCGTTC |
| 18S_18 | 56 | /5Biosg/ATGCGGCGGCGTTATTCCC |
| 18S_19 | 57 | /5Biosg/CCCGGAACCCAAAGACTTTGGTTTC |
| 18S_20 | 58 | /5Biosg/GAATTGACGGAAGGGCACCACC |

| Name | SEQ ID NO: | Sequence |
| --- | --- | --- |
| 18S_21 | 59 | /5Biosg/GAGCTATCAATCTGTCAATCCTGTCCGTGTC |
| 18S_22 | 60 | /5Biosg/GTTCTTAGTTGGTGGAGCGATTTGTCTGG |
| 18S_23 | 61 | /5Biosg/GTCGCGTAACTAGTTAGCATGCCAG |
| 18S_24 | 62 | /5Biosg/CAGCCACCCGAGATTGAGCAATAACA |
| 18S_25 | 63 | /5Biosg/AGTCAGTGTAGCGCGCGTG |
| 18S_26 | 64 | /5Biosg/TCAGCGTGTGCCTACCCTACG |
| 18S_27 | 65 | /5Biosg/GCACTTACTGGGAATTCCTCGTTCATGG |
| 18S_28 | 66 | /5Biosg/GCTTGCGTTGATTAAGTCCCTGCC |
| 18S_29 | 67 | /5Biosg/CGAGGGCCTCACTAAACCATCCAATC |
| 18S_30 | 68 | /5Biosg/GCTGAGAAGACGGTCGAACTTGACTATC |
| P601 | 69 | /5Biosg/TAATGATCCTTCCGCAGGTTCACCTACG |
| RiboHill-1 | 70 | /5Biosg/GGGGATTGCAATTATTCCCCATGAACGAG |
| RiboHill-2 | 71 | /5Biosg/GCTTATGACCCGCACTTACTGGGA |
| RiboHill-3 | 72 | /5Biosg/TGCGTTGATTAAGTCCCTGCCCT |
| RiboHill-4 | 73 | /5Biosg/TAGCGACGGGCGGTGTGTAC |
| RiboHill-5 | 74 | /5Biosg/TGGATGGTTTAGTGAGGCCCTCG |
| RiboHill-6 | 75 | /5Biosg/CTTCTCAGCGCTCCGCCA |

Sequences:

SEQ ID NO: 1
CEPKRHQSPPPPKKRTTEEPKNRRQKIRSKYAQMQSLFKRDPKRVAAHL
IKNQPLCNVSCPIDAAESALRQRLSQRPGVDAAPFTSKCPQYSKNILDP
IFPEEVTLHLQKIKIHTLEGPDGIKVSHLRSCDPDCRTTLIPKTDDPHP
DAEDYRPITVASCLYRLFSKVVTRRLEDSLSLHPRQKAFRSGTDGAFDN
TSTLMTVIREAHNCGEELNIVSIDLAKAFDNVNHTSITRALRMHGLDDD
SRTLITQMVTGSSTIIKDGGALSNRIEINQGVRQGDPISPLLFNAVMDE
LVERLQLTGEGFKLKGVEVTTLAFADDVTLISRSHRGIEKLLSITLDFL
NERGLKLNINKCKGIRLVRTPKTKSLVEDTSKPFTVPSYGEENQHIPMV
PPGDLIKFLGVDITLNGKPHFDLAPLECTLERIRKAPLKPTQKLATVRD
YLIPSLEYRLGVPGISRKILESVDGAIRSAVKRFLHPTTGMNSMFLSM
PIKKGGLGLRPLTTQHMARVAVGANNMMTSMDCLSRVVADTTTLRKPLL
SALEHFAVPAATKSAIREGKQNLLREEIAQLSETYHGSCLPSFKKGSLV
NSWLRGTGGMRSRDYITGLKLRFGVIETRSQKWKGRTPQNPDALLCRHC
GHLSGHRETAAHISQKCPTTQATIIQRHNKIVNLVGDRAKREGFAVHVE
PAIKSGDAVYKPDLVLVKDDTAHILDVAAPWEKGTTMHEKHERKISKYT
VLTEDVKALFDVQTCTVGAIIIGASSSWCPSNNRSLKACGLHMPKKFKR
LLCRVALEGTCKIFQNFFTLT

SEQ ID NO: 2
CESKSHQPPPPRKKRTREEPKNRRQKIRSKYAQMQTLFKRDPKRVAAHL
IRNQPLCNVSCPIDAAESALRQRLSQRPGVDAAPITSKCPQNSKNILDP
IFPEEVTLHLQKMKIHTSAGPDGIKVSHLRSCDPVCLAKAFNLFLLARH
IPQQLKDCRTTLIPKTDDPRPDAEDYRPITVASCLYRLFSKIVTRRLED
SLSLHPRQKAFRSGTDGAFDNTSTLMTVIREAHNCGKELNIVSIDLAKA
FDTVNHTSITRALRMHGLDDESRTLITEMVTGSSTIIKGDGGALSNRIE
INQGVRQGDPISPLLFNAVMDELVERLERTGEGFKLKGVEVTTLAFADD
VTLISRSHRGMEKLLSITLDFLNERGLQLNINKCKGIRLVRTPKTKSLV
EDTSKPFRVPSFGEENQHIPMVLPGDLIKFLGIDITLNGKPHFDLAPLE
DTLERIRKAPLKPAQKLATVRDYLIPSLEYRLGVPGISRKLLESVDGAI
RLTVKRFLHLPLTGMNSMFLSMPVKEGGLGLRSLSTQHIARLAVGTNSM
SISTDTVSRVVADTTTLRKPLLSALEHFAVPTATKSAIREGKRNLLRAE
IAQLSETYQGSCLPSFKHGSLVNTWLRGTSGMRSRDYITGLKLRFGVIE
TRSQKWRGRTPQNPDALLCRHCGHSSGNRETAAHVSQKCLVTHALIVQR
HNKIVRLVGDRAKDEGFAVHVETAVKSGEEVYKPDLILIKADTAHIIDV
AVPWEKGTNMHEKHERKTNKYAQLVDDVKALFGVQNCTVGALVIGARSS
WCTSNDGSLKACGLHLPKKTGEDLTTEADDSDAEPWQKPEHSPPHAKE
NTEDRNTEEQSEPYTTPQTLRTSENPEIQRRRRLHRTTTRRDCARRTDH
NWTPERGTTHPQKQGP

SEQ ID NO: 3
NCDGRNPPAPTNRRKRLPPPARNRSERKRCNYASFQSLFKRDPKRIAAH
LIKNQPLRNVSCPIDVAESALRQRLSQRPGIDAAPFKFKRPPNSECILS
PISADEVTLHLKLMSAETSAGLDGVQVSHLRQCDPMCLAKAFNCFLLAR
YIPPQLKDCRTTLIPKTDNPRPDADDYRPITIASCIYRLFSKIVTRRLE
NCISLHPRQKAFRSGTDGAFDNITTLTTIVRDAHKSGKELNIVCVDLAK
AFDTVNHSSIDRALRMHGLDANSRALIAQMVTGSTTVIKGDGGVLSHKI
EINQGVRQGDPISPLLFNSVMDELIERLEQSGVGYKINNTEVVTLAFAD
DVTLVSSSHRGMEKLLSITHDFINERGLKLNIRKCKGIRFVRTPKTKSL
VQDTSKAFKVRGSGEESSCIPMAGPGEFIKILGVPIAPNGKPSFDIDTL
EGTLERIRKAPLKPAQKLAIVRDYLIPSLEYKLGVPGVGRRVLDEVDAS
IRQTVKRFLHLPHTGMNSMFLTMPIKDGGLGLRSLRTQHLARVAVGTNS
MMSSADPTSHTIASMPQHQKPLHAALQHFSVPAATKDALKKGKRQLLCA
EIAELTETYQGSCLPTFRKRPVGNSWLSGLNGMRSRDFITGLKLRFGVI
ETRSQKWRGRTPQNPAVLLCRHCGHSTGKRETAAHISQKCPQTKNLNIQ
RHNKIVHLVAEHARREGFTVHVEHALKSDGQVYKPDLILTKGNAAHVLD
VAVPWETGTDMHEHHERKVTKYCMISDDVKAHFGVDSCTVGAIVVGARS
SWCASNKTTLKACNTHFTKRFKRLLCRVALEGTCRPLLSALEHFAVPAA
TKSAIREDKQNLLREEIGQLSETYRSSCLPSFKKASLVNSWLRGTSGMR
SRDYIAGLKLRFGVIKTRSQKWRG

SEQ ID NO: 4
GAMRPEEERGPKKGRKKKKPEPSVPLNSKQRKRMAYRKVQQAYHKDPKR
VVAHLFHSQPLENVSCPVESGEKALQARLGKRPPADRAPFLPKRAPLKN
HLLSPISAKEVSEHLKQMNLASASGPDGVKVSHLRDIGPQCLSKIFNTF
LLERHIPQVLKDCRTTLIPKVDNPRPDAEDFRPITIGSCIYRLFSKIVT
SRLSQLTPLNPRQKAFRSGTDGAFDNITTVASLLKLARKTGKEINLACI
DLAKAFDTVNHTSITRALHRHGVDSASIELVESMVGEATTVIINSDGTR
SNVIKFNRGVRQGDPISPLLFNLVLDELIDNLDQARCGFSITKEIQVSC
VAFADDITLVSGSREGMNNLLTITREFLGERGLGINHSKCKGIRFTKVP
KSKSLIIDTNPNCFLIRNQQGTPEPIPMAKPGEPLKTLGINLTLEGNPT
FNYPELTRILNTIKHAPLKPHQKVQIIRDHLIPLLQYKLGVPTFYRATL
NNIDKSIRLTVKEILHLPTTGLHNSYLYLPLKEGGLGLKRLATQYASRV
GLGLSNMATSDDAVSRAVAGLHLSLMDKAKNCLGLSEISKEAIKKAKEK
LVQAEIRTLLQCHLGRSHSSFTNDTISNSWMRYPTFLSARNYIMGIKLR
AGIIETRAQKWRGRSPPHPTMLLCRHCGARSRTRETDIHVSQKCLHNKK
LILRRHNCVVSTLGRRATQQGFAVYYEPCIKHGETVLKPDLVIIKGDTA
TIIDVAVPWEQGTNLREHNSRKISKYQCLEREAAKYFNVKTVKTGSLVV
GARGKWSAGNDSTLKSCGLHCSKRLKKLLCTIALEGTCAVFKH

SEQ ID NO: 5
LEPNRRRRGYAKATRIALNAPGKVRRRAEYAAMQRQWKTKRGLCAREAL
EGTWKIPARTVSLSDQEAFWRPLMESQSKNDLREPAKVGETLWGLLDPI
TPDEVRQILGSMSSKAPGPDGHRLSDLRSIPIDQICSHFNLWLLAGYQP
KALRMGESCLIPKVKDASRPQQFRPITLGSYVGRCLHKCLASRFERDLP
ISIRQKAFRCMDGVAENVMILRSVLDDHKKRLAELNLVFLDVSKAFDSV
SHRSILHAVKRLGVPPPLLKYVEELYADSETFLRGSGELSPSIKVRRGV
KQGEPLSPHLFNAVIDWALSSLDQSFGVTVGEARVNHLAFADDIVLLSS
SQPGLQRLIDQLTTHLGESGLRVNSTKSASIRIAVDGKNKRWVVDPRDS
VHVGGVRIPAVAVSGSYRYLGVNISAAGMRVDAADSLASKLANLSRAPL
KPQQRLYILCTHLLPSIYHQLVLSSTSKKFLKYLDRCVRVAVRRWLRLP
KDTPKAYFHAKCNDGGLGVPELQRVIPLQKAGRWLKMTRSQDPVVQAAV
GLEYFQKLLERWSTPELYQWGGGGITTSGHLAVAQARSLYSSVNGRGLR
QSGLVSTQFDWVRSGCSLLSGRNFIGAMQLRGNLLATKLRASRGRPRVD
ISCDCCRTPESSGHILQVCPRTSWGARIGRHDNVAKLVARESAKRHWKV
IREPAIPTPAGIRRPDLVFSKGDTAIVVDVTIVPDNAELSDAHSSKVSY
YDNGAIRGWVALNTGASHITFSSVNNNWSDCMAEESKRMLKLGLGLPNS
IRGTISAVVLEKGFHMYLCFKRGTFRASY

SEQ ID NO: 6
NHERTTKQVPENNTPARRPFKRRLHRVERYKRFQRMYDLQRKRLAEEIL
DGREAVTCNLKKEEIKDHYDQVYGVSNDRVSLDDCPRPPGANNTDLLKP
FTPTEVMDSLQGMKNGAPGPDKITLPFLQKRLKNGIHVSLANVFNLWQF
SGRIPECMKSNRSVLIPKGKSNLRDVRNWRPITISSIVLRLYTRILARR
LERAVQINPRQRGFVPQAGCRDNIFLLQSAMRRAKRKGTLALGLLDLSK
AFDTVGHKHLLTSLERFAVHPHFVRIVEDMYSGCSTSFRVGSQSTRPIV
LMRGVKQGDPMSPILFNIALDPLLRQLEEESRGFMFREGQAPVSSLAYA
DDMALLAKDHASLQSMLGTVDKFCSGNGLGLNIAKSAGLLIRGANKTFT
VNDCPSWLVNGETLPMIGPEQTYRYLGASICPWTGINSGPVKPTLEKWI
ANITESPLKPHQRVDILCKYALPRLFYQLELGTLNFKELKELDSMVKQA
VKRWCHLPACTADGLLYSRHRDGGLAVVKLESLVPCLKIKTNLRLVHST
DPVISSLAESDGLVGAIEGIAQKAGLPIPTPDQRSGTYHSNWRDMERRS
WERLALHGQGVELFKGSRSANHWLPRPVGMKPHHWVKCLAMRANVYPTK
RGLSRGNLSKNKDSAKCRGCTSMRETLCHLSGQCPKLKSMRIRRHNKIC
EHLIAEASFKGWKVLQEPTLVTDNGERRRPDLIFHRDDKAVVVDVTVRY
EISKDTLREAYASKVRRYGCLTEQIKDLTGATSVVFHGFPMGARGAWFP
ESSDVMADLNIRSKYFEEFLCRRTILYTLDLLWKSNNEQYLERLAP

SEQ ID NO: 7
NEGLQGNQRLPKEKPMTARAKMRHLRLLRYRRLQELYKKDRSLAAKQVL
QDMLDSKPGRNPEAVKYWAETMGKESTGIDVSVMTGRPRYRDNVWSPIY
PGEVSAAVKLMDSSGATGPDGFSVRSLKCTPSRVLAKVFNLFLLEEKLP

AFLMTSRTVLVPKVKEPKAPTDYRPISVSSTLVRLFHKILARRLTLASG
LDSRQRGFVPVDGCAENLVVLESAIRSAKNYKRSLFVASMDIKNAFGSV
AHEAIFEALSKSGAPDSFVTYVRNCYDGFASVVKLGRDTAQTTVRQGVL
QGDPLSPILFNLVIDQIIRSLPETVGVQLDANTKLNSMAFADDLILLSS
SEAGMRRMLGVLAGVSSKFGLIFHPGKCKYLAMIWAGKQKKMKIATDLS
FEIGGGFMTPVGVTETWKYLGAYLGQIGIQPARLSLQTFLERIAKSPLK
PQQKLYLIRVHLLPKLIYPLVMAPIRASMLNKLDRMVRVALTGKDGILH
LPQSVPSAFFYAPIGEGGLGLMELRTSIPAMVKARFERMMNSTCHHVRA
AAKGAANSNRIALANRFLRKTADGIPVTSAKLVKEYQAAKLHGSFDGKP
LSEAGRVKGIHSWTCDGRMVMTGQAFCEALKIRINALPCLSRYNRGTEK
PRECRAGCKTTESLNHVLQVCPRTHDMRVARHDKLVNRLGGYLSQKGFE
IHTEPRIITSLGLRKPDIIAIKGEKGVVLDAQIGGAANLNAAHDAKMCY
YSSSPEIKEWVTGKGAPDVSYGACIVSPQGIMSEESWKTLRGLGFSKGM
LNSLVVTVMEQSTYVWHVFNRSTASYGWKRRRKRKWD

SEQ ID NO: 8
MAQNPCPKPPPPAKNSRERRDREYSRVQNFYKKNRSACINSILDGNTRS
QNVIPGLTKFWTETFEKNSPPDDEAPDQFVADEPRDMYKWITFYEMSQD
YLDSSTAPGVDGFSAKQLRSMSPRVLNKILNLLLLSENLPNSFKMHKTV
LIPKIDDPKSPGDFRPITISPVLARLLNKILAARLSKLVPISQRQKAFL
PVDGCGENIFLLDYILRSSKKSSKSVAMAVLDVKKAFDSVSHHSILRAL
NEAKCPINFINFVRNSYDGCTTKLTCGGTSFPDSVRMNRGVKQGDPLSP
VLFNLIIDSAIRKLPDSIGYVIRDGLKINCLAYADDLILVASSRAGLKT
LLNIVAEHLSLRGLDLNAAKCHGLSIIASGKAKTTYVSAADSLDLDGQP
IKNLGVLDTWTYLGIPFSHLGRAEKVSPDLTNLLNKLQKAPLKLQQKLY
AVRNFVIPRALHGLILSKTNLKELNTLDRAIRVFLRTLLYLPKDTPLGF
FHSPIKSGGLGITCFRTSVLKCRLQRIARMRSSCDGVIQAVAESDIFAD
EYAKLRDLIRINGNVLDTTESIKRYWAQRLHSSVDGKTLAYMDYFPQGN
LWMSEDKVSQRSYVFADCVKLRINAIPTRVRVSRGRPNKEMCCRAKCFD
SQRMPAFESLNHITQVCPRTHGSRIQRHDKIAKFLFKNLNNCPSRSVLY
EPHFVTVDGLRKPDIIIYDDSHMVVLDVQVVSDSANLEKEFECKAKKYA
NDVALRSAMLIKYPFIKSFSFVAATYNNRGLIAKSSVQVLRQLGLSPRS
IMVSILICLEGTLETWRIFNQSTMNAH

SEQ ID NO: 9
SDLEVTGRKRVARGPRAIPVLSKRKARRIEYRRMQQLWRTNMTKAAHKV
LDGDAGSLPHPTLAAQLGFWKPVLEAESVDLAWPFAVGHPGVAVGDLWS
PITEGEVINIRLPRTSSPGLDGLTVHRWFTEVPAILRATILNIFMATGW
VPPRFRHSRTVLIPKSSDLMDPAYYRPISVSSVILRHFHKILARRVAAC
ELLDVRQRAFIAADGCAENVAVLSAILFDARTNRRQLHVITLDVRKAFD
TVSHNAIRYVLSKHGMPQIMVEYLSTLYRTAAVRLEVDGEFSDEILPGR

GVRQGDPLSPLLFNLIMNEILAEVPDQVGYCMMDRNVNALAFADDLVLI
GATRDGAQRSLERVMAALYRFGLELAPAKCAAFSLVPCGKTKRIKILTD
PQFVAGDRPIPQLGVLHTVRYLGVRFGETGPVIQGVELLPLLERITRAP
LKPQQRLKILRTYLIPRYTHNLVLGRVSYSMLRKLDKQTRAAVRRWLVL
PDDVPVAFFHCPIKQGGLGIQSFETAIPRLTLLRLNRLKDSQYEMARVV
GSSAWADRRMRWCRFARRRDEDWPSELHAKVDGFELREAGNVSVSTRWL
DDAMVHIPSSDWLQYVKVWINALPTRIRTTRGSRRLREDVNCRGGCGVQ
ETAAHVVQQCFRTHGGRIMRHDAVASALAGELQRGGYNVHRERVFRTRE
GVRKPDILAAKGTHGHVLDVQIISGARPLSDGHDRKRSYYANNADLLAR
ISALLQVPVRNLDVSTVTLSWRGVWARESAAVLTSLGVSKAVLRGITTR
VLKGSYMNFSRFNQTTATCRGRANLRMSGWGPP

SEQ ID NO: 10
NTAKCPKGPRFRKTATHSGTNKQQRQQRYARVQKLYKMNRKVAAKMVLE
ETDKIQIKLPDHDPMFKFWESEFKEGEGMPERMPKDLKESPDLKAIWDP
VTEEEVRKAKVANNTAAGPDGIQPKSWNRISLKYKTLIYNLLLYYEKVP
HKLKVSRTVFIPKKKDGSSDPGEFRPLTICSVVLRGFNKILVQRLVSLY
KYDERQTAYLPIDGVGTNIHVLAAILNDSNTKLSELHVALLDITKAFNR
LHHTSIIKSLVGKGFPYGFITFIRRMYTGLQTMMQFEGHCKMTQVNRGV
YQGDPLSGPIFLLAIEKGLQALDKEVGYDIGDVRVNAGAYADDTDLVAG
TRLGLQDNINRFSSTIKQVGLEVNPRKSMTLSLVPSGKEKKMKVETGKP
FRANDVPLKELSINDFWRYLGISYTNEGPERLSLTIEQDLERLTKAPLK
PQQRIHMLNAYVIPKYQDKLVLSKTTAKGLKRTDRQIRQYVRRWLKLPH
DVPIAYLHAPVKSGGLNIPCLQYWIPLLRVNRVNKITESQRSVLAAVGK
DDTAHIVDVQVARCSKLNESHVRKRSKYDKKEIEVEVKSRYRVSKVMYE
ATALLTSTVYKCNQSLATLGGNPTMLAYRTYWEKELYAKVDGKDLQNAR
DDKASTRWNGMLHSDISGEDYLNYHKLRTNSVPTKVRTARGRPQKETSC
RGGCKSTETLQHVVQQCHRTHGGRTLRHDRIVGLLQHELRRDYNVLAKQ
ELKTGIGLRKPDLVLIKCTISYKGIWDKQSVMSMRRLGVSEYCLFKIVT
STLRGTWLCWKRFNMITSVRS

SEQ ID NO: 11
FWKPLTPNLARVSLPSKDKVSRRRLRRADYGRVQRAWKRNRNTCLRDLL
RDKRTESAPPEELXVPYWESVLRSGSSCTPGQRGRTAERTELWDPVSSK
EVEQALPPLGTAPGPDSFTPKDFRAVPSAVWACIFNIFMLCGRLPDYLL
ESRTTLIPKRDGACNPEDFRPITVSSVVVRCFHKVIANRMSRHIQLDPR
QKAFRSLDGCSEGVFLLDFILGHARRNHRPVHLASLDVAKAFDSVSHAA
ILDVLRSFGVPDQMVEYIASVYAGSRTRLQGDGWQSHAIHPTCGVKQGD
PLSPMIFNMVIDRLFTLFPRDTGVSVGDTVLNGMGYADDLVLFATTPVG
LQQLLDITAEYLSQCGLRVNAAKCFSVSLAIVPHEKKVVVATKHRFKCL
GQPIPALKRSDQWKYLGVPFSPEGRLKIDPLGRLKDELEKLRRAPLKPQ

QRLYALRTVVVPGLYHLLVLGGTTISSLNRLDIAVRSTVRKWLSLPHDV
PNAYIHADARDGGLSIPSYRWTVPRLRFHRLKALSVLCDGGGPDEMVAC
VGDEIKRASARLQDHGMNINTRNTYRVRFARLLHTSNDGAPLKGSKKVE
GQHRWVTDGSLMLSGRDYIACNWVRINSIPLRKRTARGRVRDTRCRAGC
DSTETLHHVLQQCHRTHDMRIKRHNACVKYLLDRQRSRGKTVFWEPHFH
TAGGLLKPDSVILHDASTAVVVDALVAGERSDLDREHDRKVSKYEPLVD
LVKDRYSVDKVIFSSLIISARGVWGGRSFRHLSKLRLLDISDAKVLSTR
VLLGGMGAVRVFNRRTAVSGRVNGW

SEQ ID NO: 12:
EVFPAPPPRRERRRKKTPNPAPMRKREARRCEYGAAQSLWKRDRRHCIT
NILNEMGPVNQPPRETMEPYWTRMMTTDGRTSPPSDKVPIKEDIWTPIT
GNDIKRSRIPRASAPGPDGISARLYRSIPTTVIIRLFNLLLWCERLPED
LLLSRTIFLPKKTNASEPGDFRPITIPPVLVRGLHKILAKRLETALDID
PRQRAFRSMDGCADNTLLLDTLLRYHRKQYKSLYMASIDVSKAFDAVTH
PTIESTLISLGVPPPMIRYLGQVYANSRTRIEGDGWTSKPVHPKRGVRQ
GDPLSPILFNAVTHRLLQRLPREVGARLGNIPINAAAYADDLLLFASTS
MGLQQMIDTMTDYLAECGMTINVEKSMTVAIRAAPHLKKTAVDASLSFS
CGGRQLPSLKRTNKWRYLGVVFTPEGRAQCRPAEVVAPLLGALTKAPLK
PQQRLYALRTVVIPKLYHQLALGAVTIGTLNKTDRLVRGALRKWLAPH
DTPNAYFHTSVRDGGLGIPAIRWTAPVQRRGRLLGVMKALGQQGLDRFI
QDELNTCKKRLTDHGVLLGTPEMVAKRWAQQLYGSIDGAGLKDSAKTPH
QHQWIADGSKFLTGKDFINCNRARIGALPTRSRTTGRPQDRRCRGGCL
AQETLNHVLQHCHRTHGQRIKRHDAVVKYIARNMPRSGYEVHQEPHYKT
ELGLRKPDLVAVLGQTAIIIDAQVVSEQTNLDDAHTRKVAYYNEPATIR
AIKAEHGVRTVKVTSATLSWKGVWSPRSAEELRKLGFIRAGDAKVVATR
VLIGNIAAFRTFNATTSVEHRAGIG

SEQ ID NO: 13
SKEPAAHPPLPFGARRPPDKKRARRRWEYAAVQRAFRKNAARCVNGLLD
GTLLHQPPSIPGLVEFWKDLFTAPCASSRPRSKEGLSPMLLASSQPVSF
RDLWAPITSEEAAAALPPRNSAAGPDALTPAQLRRLPHPVFLKILNLFL
LARSLPSRLLRARTTLLPKKTSPASPADFRPITVCSVLARAFHKVLAGR
LMRYCVLDGRQRAFIPQDGMLHNSFLLDLAMAHSRRTACSLYVASLDVS
KAFDSLDHGALSPVLRAHGLPVEFVEYVRGCYQASTTVICGGGSSSDLV
RPSKGVRQGDPLSPILFNLSIDLLLSRLPGYIGARIFSRRVNAAAFADD
ILLFAETKGGLQELLSTATSALGDLGLEVNPFKCFSLALVASGREKKVK
VDNSVIFRAGNKNIPALAMGDTFRYLGLQFSTSGLSQFHPRQEVQEQLD
IIKRAPLKPQQRLFALRSVILPGTYHGLALGRTRLGALKSLDVCVRAAV
RAWLRLPDDTPIGYFHAPVIYGGLGIPATRWLGPLLRRRRLASMEGLGV
IVDEPSQDILKREICRLDNYLKWDGDVIKTSYQLGRFWALRLHSSVDGA

ALRRSAQTPGQHSWVSNTRLMLSGRDFLACVRARISALPSRARLLRGRE
GDTRCRAGCNASETNNHVIQHCWRSHEARVERHDAVALYMVRGLRRRGY
DVHRELHLRTSQGLKKPDIVAVSGTTAFVIDAQVIGDHLDADRCHREKV
EVYDQQPVHTEIKRMFPEVQMITTTSATLNWRGVWSPASAKALIGIGFN
SNHLSTMATRALLGSIMAARRFDSMTAPRRRMMPRTGVG

SEQ ID NO: 14
NRNDRPSSATVPARRPRNRRISRRQQYARCIKSLLDGTDESALPNQSIM
EPYWRQVMTQPSPSLCSNTVPRKGNMQEGVWSPITSRDLQVHKVPLTSS
PGPDGITSQTARSIPIGIMLRIVNLILWCGDLPVPFRMARTIFIPKTVR
ANRPQDFRPISVPSIVVRQLNAILASRLTAAVSWDPRQRGFLPTDGCAD
NATIVDLVLRDHHKRYASCYIATLDVSKAFDSVAHDAVFNTVTAYGAPK
SFVDYVRRWYSGGGTYFNGGDWRSEEFVPARGVKQGDPLSPVLFNLIID
RLLRSLPKDIGVHVGNAKVNACAFADDLMLFASTPKGLQELLNTTVKFL
SSVGLTLNADKCFTISIKGQPKQKVTVVEQRTFCIGRARVQLKRSEEWK
YLGIHFTADGRARYNPSEDIGPKLERLMQSPLKPQQKLFALRTVLVPQL
YHKLTLGSVALGVLRKCDKLVRSFARKLLGLPLDVSVAFYHAPHSCGGL
GIPSVRWIAPMLRTKRLAGINWPHLEQSEVASAFLSEELRRARDRAKAG
VNELLSQPKIDTYWADRLYTSVDGNGLREARRYAPQHGWVSQPTRLMSG
KAYRTGIQLRINALPTRSRTTGRHEMNRQCRAGCDAPSHNHVLQRCHR
THGSRVSRHNGVVSYLKKGLETRGYTVYSEQSLHGQNRVYKPDIVAFRH
DSTIVVDAQVVTDGLDLDRAHQSKVEIYNRQDLLTTLRSVYRARENIEV
VSATLNWRGIWSFQSITRLRTLGILTAGDSNVISSRVVSGRVYSFKTFM
FHAGFHRGMA

SEQ ID NO: 15
SSGRKLPVKSRGARETVQKKMANPRVAKYKRFQRLFRSNRRKLASHIFD
KASLEQFGGSIDEASDHLEKFLSRPRLESDSYSVINGNKSIGVAHPILA
EEVELELKASRPTAVGPDGIALEDIKKLNSYDLASLFNLWLKAGDLPES
VKASRTIFLPKSDGTTDISNCRPITIASALYRLFSKIITRRLAARLELN
VRQKAFRPEMNGVFENSAILYALIKDAKARSKEICITTLDLAKAFDTVP
HSRIVRALRKNNVDPESVDLISKMLTGTTYAEIKGLQGKPITIRNGVRQ
GDPLSPLLFSLFIDEIIGRLQACGPAYDFHGEKICILAFADDLTLVADN
AAGMKILLKAACDFLEESGMSLNAEKCRTLCISRSPRSRKTFVNPAAKF
NISDWKTGISSEIPSLCATDTFRFLGHTFDGEGKIHIDMEEIRSMLKSV
RSAPLKPEQKVALIRSHLLPRLQFLFSTAEADSRKAWLIDSIIRGCVKE
ILHSVKAGMCTEIFYIPSRDGGLGLTSLGEFSLFSRQKALAKMAGSSDP
LSKRVAEFFMERWNIARDPKVTEAARRVYQKKRYQRFFQTYQSGGWNEF
SGNTIGNAWLTNGRARGRNYVMAVKFRSNTAATRAENLRGRPGMKECRF
CKSATETLAHICQKCPANHGLVIQRHNAVVSFLGEVARKEGYQVMIEPK
VSTPVGALKPDLLLIKADTAFIVDVGIAWEGGRPLKLVNKMKCDKYKIA

IPAILETFHVGHAETYGVILGSRGCWLKSNDKALASIGLNITRKMKEHL

SWLTFENTIRIYNSFMKN

SEQ ID NO: 16

TKWRPSKPRLPPTYRANTSRKHLRRLQYGHIQTLYNRCRRDAANTVLDG

RWRSPHTSSPFSIPEFETFWKTIFTTPSTPDNRPVVPVLPTCPALLDPI

TPDEITWALKDMRNSAPGVDRLSAQHFLNFDVPSLAGYLNMVLAFKFLP

TNLSISRVTFIPKGASPQQPNDFRPISIAPVITRCLHKILAKRWMPLFP

SSKLQFAFLQRDGCFEAINLLHSLLRHAHERHSGCSIALLDISRAFDSV

SHHSILRAAHRFGAPDGLCQYLQRVYNGSTSLFNTVDCAPSRGVKQGDP

LSPLLFIMSLDEALESIETVSPVIVDGLPISYIAYADDLVILAPNADLL

QKKLDKLASLLQRSGLIINTSKSMSIDLIAGGHSKLTALKPTVFKIDGN

QLQRLNVSDHFDFLGISFDYKGRSKMDHVETLSAYLLNLTQAPLKPQQR

MSILRENLEPRLLYPLTIGVVHKCTLRQMDCLIRSSVRKWLRLPSDTPT

SFFHSSISTGGLGIPHLSSIIPLHRRKRAAKLLLSPCPIIRWVSQSPSF

SNFLRICNLPINVHRDLIHSFDEARCSWSKQLHSTCDGRGLSMSSRNTV

SHLWLRYPEHIFPRLYINAIKLRGGLLSTKVRRSRGRQENADLLCRGRC

GHHESIQHILQHCSLTHDIRCRRHNDICRLVASRLRRNNIRFFQEPCIP

TPVSFCKPDFIIIRDSIAYVLDVSVCDDANVHLSRQLKINKYGCSTVVS

SIYNFLNATGLRISSVRQTPLIITYRGLIDPLSTTSLRRLSFSSRDISD

LCVASIQGSMRIYNTYMRGTSPQDP

SEQ ID NO: 17

QHALDCFPRLWAPSRPRPNHPQPRSYRALRKAQYASLQRILHTSPKDAA

THVLDGSWRLLHQNRALPPDLHSFWTNVFRIPSFSDNRPVSATQPELSL

ISPITCEEVKKAIAGMGGTAPGLDRLTPANLKSFGLKPLTGYLNLILCY

GCPASLAAARVTLIPKVPDATRPEQYRPLAVSSVIVRCLHKILAFRWAS

VLKLSSLQLAFMQRDGCLEATTILQGVFRDAHSRRRPIAMAFLDVSKAF

DTVLHDSVFRAAAMYGAPPLLLRYLRKLYSQGTVTLGDIDILPKRGVRQ

GDPLSPLLFILAMEEILMAANPNDGYQLPSSTISTLAYADDLVLFAHSP

GALGLKLERVAAALRLAGMEINAAKSITFTISANTHNKNLCLENIAYTL

DGVSIAAADTETRVKYLGLHFNWKGQISYKDTARLAGYCQELTSAPLKP

QQRIHILRQVALPKLHHQLVLSSIHRRTLKAMDISCRHYVRRWLKLPQD

TSTAFFHAKIGDGGLGLTSLATSIPLWRRTRLTKLITSEHPVVRDVVSI

CLTKALAVANEPVFVMGTVVSDKDEAAMAWKLAMYATLDCADLQTIHET

PESSNWVVRPLRMTPSLYIRGLQLRAGTLGTKSRQQRGRAQMDKLCRRG

CGQTETLPHILQSCPAAHAARCVRHNRVAKSIAVSLRRKGYRVYEEPII

RTGTTYCKPDIIACQDGLGFVIDVAVVSGHRLHESWDLKIAKYDTDFIN

TAIIDCLPEDVEILSLIHQPAIISFKGVWFPPSAKRLKTLGLSADCLAG

LGLVTIKGSLACFDMFMMGSNG

SEQ ID NO: 18

KENLKKRACKTLTRRIKPKKSKKHEYWKMQQMYHRDRAGLAKLILEGEA

RDICPIPLTRLTTAFKEKWEKEDRFVSLGQFKSSCKAVNDIFASPISPE

EVCKIRSKMKNKAATGLDGISKTCLMRGDPKGINLANLFTAILLNGYIP

RALKKNRTTLLPKTQDKRKLSDTSQWRPITIGSTIQRLLSGVINDRLKE

ACEIHPRQRGFISSPGCAENLMLLRELIALSKRELKPLAVIFIDFAKAF

DTVSHKHIKAVLQQRGVDKMIIDLISNSYEGRTTILKAKGSYSREIRLK

MGVKQGDPLSPLLFNLAIDPLLCKLDKVGEGAIVDGIEITSLAFADDIV

LLSNSWSGMRKNLKILEVFCELTGLTLNVMKCHGFFIDSMNRCLAINEC

PPWRLQQNDLHMIGSKEKEKYLGMEISPWLGIIEPNIQKMINIMLNNLT

ASLLKPSQKLELLRTYAVPKLTYMADNGMVTQTTLITTDRKIRMTIKKW

FHLNHATTDGLLYTGCKSGGMGLVKLARVIPRIQVNRILGLCNSEDSCT

RTMARKAHRPSEFRKIWKMGMGKGGETTIQGASDIRTPYWNTPKIHSDW

RINELDKWKKMKTQGEGIEVFENDKISNSWLRHPTLSNFSERDYILALK

LRTNTYPMKAILARGRMAKNKGTKCRLCGYIKKTTKHVLGSCIGTRPNR

MQRHNKICALLAKAARQLGWETLTEHHLKMDNGKTLVPDLIMMKDTRAI

VADVTICYETNQYSLRKAYEVKVKKYAPLELPIKERWPGIKDVRIHGFP

LGTRGKWPSLNWRLLEELDMDKSKRRKFASLLSKRSLLYTIDILKWFSK

N

SEQ ID NO: 19

TRSAPSSTSSGKSTRNAKRLEKLKKYGYYQHLYYNNKKKLVAEILDGET

SGAKPPPMNLVEDYYKNIWSRSTIDDSPVNNIKTVNSDSIFAPISRDEI

KLALSNTKKDSAAGPDSVTIKEAKAIIDNLYVAYNIWLGVQGIPEQLKL

NKTILIPKGNSDLSLLKNWRPITISSIILRVYNRLLAYRMNKVFKTNDK

QVGFKPVNGCGINISWLHSLLKHARLNKNPIYACLVDVSKAFDSVSHQS

IVRALTMNGAPSLLVKLIMDQYTNINTIITCSGSISNKININSSGVKQGD

PLSSLLFNMVIDELFDVIKDQYGYTIDNIGTTNARCFADDLTLISSSRM

GMNKLLELTTEFFKERGLNVNPSKCMSIGMSKGYKGKKSKIESEPLFSI

ADAQIPMLGYIDKTTRYLGVNFTSIGAIDAKRIKKDLHDTLDKLEHLKL

KAQCKMDLRTYMIPRFMFQLIHTELYPKLLIKMDILIRKLAKRILHLP

ISTSSEFFYLPFKEGGLQLTSLKEAVGLAKIKLHKKIMSSNDPMLCYLI

ESQRSRIIEHFMKDLKLGDSLTLNEMDNIKECFMKEKRISFAQKIHGVG

FEVFSSSPLTNQWINGEIKTMTTRTYINSIKLRTNTLETRVTTSRGLNI

IKTCRRCHVADESLMHVLQYCSSTKGLRYSRHHRICAKVANKLMKNGYG

VYREKSYPDPNNSGSYLRPDLIAVKDGHVIVLDVTVVYEVTGATFINAY

QTKVNKYNTIMVQIEQMFNCVSGVLHGLVIGSRGSIHHSQLHIWHQMGF

SSTELKYVAIGCMEDSLRIMSTFSKAIL

SEQ ID NO: 20

KSKSLPRLKRTGRAFHRREKYAICQKSLDKDFSGTISKILDGVEISEAE

VRPEMAKIEEVYQQRLGNTSGALPENTDTPVVEGLRFERKTAPFDAQEV

-continued

TRAIRESNKSTAAGPDRWFNGRCLKNLDCETVAALFNLWRFKQKIPSAL
RENRTILLPKGGDLTDANNWRPLTIGSLLLRLYAKSLTTRWSDAPICER
QKAFRPVDGCWENINLLLGALKSAHKKRRQINLISIDLAKAFDNIQHGA
IFNAMRRFGFSPSEISVVKDLYTNVWTKISIGNEISGPINISRGVKQGC
PLSPFLFNLVLDELINELQSSGYGYPVEGFKVPVLAYADDLILCGATDY
ETKRMVEITEKFFARQMLAVNLKKCKALRLLPVKGKRTLKVSSDPMLWK
GEQLPMVKSIDDFISYLGVKVSVTGKVIWSVDQLRLWLDRVMKAPLKPD

-continued

QKIKGIKEVLIGRLTYQLRLSEARVCELRRVTRMVRKACKQILHMQLGA
PNAWAHLPLRKCGLGLPDFELTIPLMRRAACEKMKSSPDPVVANISEKI
PIYESGLTRGLDVRAAKRAIQDKYEQAYLSTQRGKLMNARWISAVKPYW
LHGGTGVVKAGEYVSINKLVTRTIETRQFIHPGVTDFETLKCRRCGKAV
ETDLHVLNECPFTRLAQCRRHNFIADYLGKVLVDHGWEVWRERLVKKDL
ENFKPDLICRKGAEGAIIDVTVPYESNEAVLQSKERFKEAKYAGLKGQV
AELLNINGGVKVVGIAVGALGTILTSTLEKAKGLGLDPVKVGKSLQISA
LRGSGHVWKAFRS

---

What is claimed is:

1. A method for preparing a complementary deoxyribonucleic acid (cDNA) molecule comprising:
   (a) partitioning a cell and a non-naturally occurring reverse transcriptase having at least 95% identity to SEQ ID NO: 20 in a partition, which cell comprises ribonucleic acid (RNA) molecules;
   (b) releasing said RNA molecules from said cell in said partition; and
   (c) in said partition, using said non-naturally occurring reverse transcriptase to synthesize a complementary deoxyribonucleic acid (cDNA) library from said RNA molecule, which non-naturally occurring transcriptase synthesizes said cDNA library at a processivity of 20 nucleotides or longer.

2. The method of claim 1, wherein said non-naturally occurring reverse transcriptase has at least 100% identity to SEQ ID NO: 20.

3. The method of claim 1, wherein said partition further comprises one or more acceptor nucleic acid molecules.

4. The method of claim 1, further comprising performing said method on a heterogeneous plurality of template nucleic acid molecules comprising a plurality of distinct ribonucleic acid (RNA) molecules.

* * * * *